US009822373B2

(12) United States Patent
Znameroski et al.

(10) Patent No.: US 9,822,373 B2
(45) Date of Patent: Nov. 21, 2017

(54) MUTANT CELLS FOR PROTEIN SECRETION AND LIGNOCELLULOSE DEGRADATION

(71) Applicant: The Regents of the University of California, Oakland, CA (US)

(72) Inventors: Elizabeth A. Znameroski, Berkeley, CA (US); James H. Doudna Cate, Berkeley, CA (US); N. Louise Glass, Orinda, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/714,165

(22) Filed: May 15, 2015

(65) Prior Publication Data

US 2015/0247152 A1   Sep. 3, 2015

Related U.S. Application Data

(62) Division of application No. 14/005,245, filed as application No. PCT/US2012/029293 on Mar. 15, 2012, now abandoned.

(60) Provisional application No. 61/453,086, filed on Mar. 15, 2011.

(51) Int. Cl.

| | | |
|---|---|---|
| *C12N 15/80* | (2006.01) | |
| *C12N 9/04* | (2006.01) | |
| *C12N 9/18* | (2006.01) | |
| *C12N 9/24* | (2006.01) | |
| *C12N 9/42* | (2006.01) | |
| *C12P 19/02* | (2006.01) | |
| *C12P 19/14* | (2006.01) | |
| *C12P 21/00* | (2006.01) | |

(52) U.S. Cl.
CPC ........... *C12N 15/80* (2013.01); *C12N 9/0006* (2013.01); *C12N 9/18* (2013.01); *C12N 9/24* (2013.01); *C12N 9/2402* (2013.01); *C12N 9/2437* (2013.01); *C12N 9/2445* (2013.01); *C12P 19/02* (2013.01); *C12P 19/14* (2013.01); *C12P 21/00* (2013.01); *C12Y 302/01021* (2013.01); *C12Y 101/99018* (2013.01); *C12Y 302/01004* (2013.01)

(58) Field of Classification Search
None
See application file for complete search history.

(56) References Cited

U.S. PATENT DOCUMENTS

| | | |
|---|---|---|
| 6,022,725 A | 2/2000 | Fowler et al. |
| 2006/0258554 A1 | 11/2006 | Dunn-Coleman et al. |
| 2008/0095889 A1 | 4/2008 | Dunn-Coleman et al. |

FOREIGN PATENT DOCUMENTS

| | | |
|---|---|---|
| WO | 2004/081201 A1 | 9/2004 |
| WO | 2011/123715 A1 | 10/2011 |

OTHER PUBLICATIONS

Ziv et al. Fungal Gen. Biol. (2008) 45(2) 103-116.*
Meyer, V. 2008 Biotechnology Advances 26: 177-185.*
International Search Report and Written Opinion received for PCT Patent Application No. PCT/US2012/029293, dated Jul. 24, 2012, 16 pages.
Invitation to Pay Additional Fees received for PCT Patent Application No. PCT/US2012/029293, dated May 18, 2012, 6 pages.
International Preliminary Report on Patentability received for PCT Patent Application No. PCT/US2012/029293 dated Sep. 17, 2013, 9 pages.
Office Action received for Chinese Patent Application No. 201280023229.6, dated Dec. 11, 2014, 9 pages (3 pages of English Translation and 6 pages of Official Copy).
Non Final Office Action received for U.S. Appl. No. 14/005,245, dated Nov. 17, 2014, 13 pages.
Bohlin et al., "A Comparative Study of Activity and Apparent Inhibition of Fungal Beta-Glucosidases.", Biotechnology and Bioengineering, vol. 107, No. 6, 2010, pp. 943-952.
Cantarel et al., "The Carbohydrate-Active EnZymes Database (CAZy): An Expert Resource for Glycogenomics", Nucleic Acids Research, vol. 37, Database issue, 2009, pp. D233-D238.
Dementhon et al., "VIB-1 is Required for Expression of Genes Necessary for Programmed Cell Death in Neurospora Crassa", Eukaryotic Cell, vol. 5, No. 12, Dec. 2006, pp. 2161-2173.
Fritscher et al., "Cellobiose Metabolism and Cellobiohydrolase I Biosynthesis by Trichoderma Reesei", Experimental Mycology, vol. 14, 1990, pp. 405-415.
Galazka et al., "Cellodextrin Transport in Yeast for Improved Biofuel Production", Science, vol. 330, Oct. 1, 2010, pp. 84-86.
Gielkens et al., "Two Cellobiohydrolase-Encoding Genes from Aspergillus Niger Require D-Xylose and the Xylanolytic Transcriptional Activator XlnR for their Expression", Applied and Environmental Microbiology, vol. 65, No. 10, Oct. 1999, pp. 4340-4345.
Goncalves et al., "A Genome-Wide Screen for Neurospora Crassa Transcription Factors Regulating Glycogen Metabolism", Molecular & Cellular Proteomics, vol. 10, No. 11, 2011, pp. M111.007963-1-M111.007963-13.
Ha et al., "Engineered *Saccharomyces cerevisiae* Capable of Simultaneous Cellobiose and Xylose Fermentation", Proceedings of the NationaL Academy of Sciences, vol. 108, No. 2, Jan. 11, 2011, pp. 504-509.
Ilmen et al., "Regulation of Cellulase Gene Expression in the Filamentous Fungus Trichoderma Reesei", Applied and Environmental Microbiology, vol. 63, No. 4, Apr. 1997, pp. 1298-1306.

(Continued)

*Primary Examiner* — Marsha Tsay
(74) *Attorney, Agent, or Firm* — Richard Aron Osman

(57) ABSTRACT

The present disclosure provides mutant cells for the secretion of proteins and for the degradation of lignocellulosic biomass. Methods for the use of these cells are also provided. Specifically, the utility of combined genetic deletions of β-glucosidases and the catabolite repressor gene creA/cre-1 for protein secretion in fungal and yeast cells is disclosed.

23 Claims, 36 Drawing Sheets

(56) References Cited

OTHER PUBLICATIONS

Kubicek et al., "Triggering of Cellulase Biosynthesis by Cellulose in Trichoderma Reesei; Involvement of a Constitutive, Sophorose-Inducible, Glucose-Inhibited Beta-Diglucoside Permease", The Journal of Biological Chemistry, vol. 268, No. 26, Sep. 15, 1993, pp. 19364-19368.

Levine et al., "A Mechanistic Model for Rational Design of Optimal Cellulase Mixtures", Biotechnology and Bioengineering, vol. 108, No. 11, Nov. 2011, pp. 2561-2570.

Ilmen et al., Mol. Gen. Genet., 1996, pp. 251-460.

Maddi et al., "Trifluoromethanesulfonic Acid-Based Proteomic Analysis of Cell Wall and Secreted Proteins of the Ascomycetous Fungi *Neurospora crassa* and *Candida albicans*", Fungal Genetics and Biology, vol. 46, 2009, pp. 768-781.

Messner et al., "Differential Regulation of Synthesis of Multiple Forms of Specific Endoglucanases by Trichoderma Reesei QM9414", Journal of Bacteriology, vol. 170, No. 8, Aug. 1988, pp. 3689-3693.

Nakari-Setälä et al., "Genetic Modification of Carbon Catabolite Repression in Trichoderma Reesei for Improved Protein Production", Applied and Environmental Microbiology, vol. 75, No. 14, Jul. 2009, pp. 4853-4860.

Noguchi et al., "Genes Regulated by AoXlnR, the Xylanolytic and Cellulolytic Transcriptional Regulator, in Aspergillus Oryzae", Applied Microbiology Biotechnology, vol. 85, No. 1, 2009, pp. 141-154.

Phillips et al., "A Quantitative Proteomic Approach for Cellulose Degradation by Neurospora Crassa", Journal of Proteome Research, vol. 10, 2011, pp. 4177-4185.

Portnoy et al., "Differential Regulation of the Cellulase Transcription Factors XYR1, ACE2, and ACE1 in Trichoderma Reesei Strains Producing High and Low Levels of Cellulase", Eukaryotic Cell, vol. 10, No. 2, Feb. 2011, pp. 262-271.

Portnoy et al., "The CRE1 Carbon Catabolite Repressor of the Fungus Trichoderma Reesei: A Master Regulator of Carbon Assimilation", BMC Genomics, vol. 12, 2011, 12 pages.

Seiboth et al., "Lactose Metabolism and Cellulase Production in Hypocrea Jecorina: The gal7 Gene, Encoding Galactose-1-Phosphate Uridylyltransferase, is Essential for Growth on Galactose but not for Cellulase Induction", Mol. Genet. Genomics, vol. 267, 2002, pp. 124-132.

Sun et al., "Identification of the CRE-1 Cellulolytic Regulon Neurospora Crassa", PLOS One, vol. 6, No. 9, Sep. 2011, pp. 1-14.

Suzuki et al., "Cellotriose and Cellotetraose as Inducers of the Genes Encoding Cellobiohydrolases in the Basidiomycete Phanerochaete Chrysosporium", Applied and Environmental Microbiology, vol. 76, No. 18, Sep. 2010, pp. 6164-6170.

Tamayo et al., "CreA Mediates Repression of the Regulatory Gene XlnR which Controls the Production of Xylanolytic Enzymes in Aspergillus Nidulans", Fungal Genetics and Biology, vol. 45, 2008, pp. 984-993.

Tian, et al., "Systems Analysis of Plant Cell Wall Degradation by the Model Filamentous Fungus *Neurospora crassa*", PNAS, vol. 106, No. 52, Dec. 29, 2009, pp. 22157-22162.

Ulmer et al., "Possible Induction of the Ligninolytic System of Phanerochaete Chrysosporium", Journal of Biotechnology, vol. 1, 1984, pp. 13-24.

Woodward et al., "The Inhibition of Beta-Glucosidase Activity in Trichoderma Reesei C30 Cellulase by Derivatives and Isomers of Glucose". Biotechnology and Bioengineering, vol. XXIII, 1981, pp. 1553-1562.

Znameroski et al., "Induction of Lignocellulose-Degrading Enzymes in Neurospora Crassa by Cellodextrins", PNAS, vol. 109, No. 16, Apr. 17, 2012, pp. 1-6.

* cited by examiner

| NCU ID | GH FAMILY | WILD TYPE AVICEL | | | Δ3βG CELLOBIOSE | | | Δ3βGΔcre CELLOBIOSE | | |
|---|---|---|---|---|---|---|---|---|---|---|
| | | WHOLE SUPERNATANT | PASC BOUND | PASC UNBOUND | WHOLE SUPERNATANT | PASC BOUND | PASC UNBOUND | WHOLE SUPERNATANT | PASC BOUND | PASC UNBOUND |
| NCU04952 | 3 | + | | | | | | | | |
| NCU00762 | 5 | + | | + | + | | | + | + | |
| NCU08412 | 5 | + | + | + | + | + | | + | + | + |
| NCU07190 | 6 | + | | + | | | | | | |
| NCU09680 | 6 | + | + | | | | | | | |
| NCU05057 | 7 | + | | + | + | | | + | | + |
| NCU07340 | 7 | + | + | + | + | + | | + | | + |
| NCU05924 | 10 | + | | + | | | | | | |
| NCU08189 | 10 | + | | + | | | | | | |
| NCU02855 | 11 | + | | | | | | | | |
| NCU07225 | 11 | + | | | | | | + | + | |
| NCU04431 | 16 | | + | | | | | | | |
| NCU05686 | 16 | + | | | + | + | + | + | | |
| NCU05974 | 16 | + | | + | + | + | + | + | | + |
| NCU01517 | 17 | | | | + | | + | | | + |
| NCU09175 | 17 | + | | | + | + | + | + | | + |
| NCU04395 | 30 | | | | | | + | | | |
| NCU04265 | 32 | + | | + | + | + | + | | | |
| NCU07326 | 43 | | | | | | + | | | |
| NCU05121 | 45 | | | | | | | | | |
| NCU02343 | 51 | | | | | | | | | |
| NCU09775 | 54 | + | + | + | + | | + | + | + | |
| NCU07523 | 55 | + | + | + | + | + | | + | + | |
| NCU00836 | 61 | + | + | + | | | | | | |
| NCU01050 | 61 | + | + | + | | | | + | + | + |
| NCU02240 | 61 | + | + | + | | | | + | + | + |
| NCU07898 | 61 | + | + | + | | | | + | + | + |
| NCU08760 | 61 | + | + | + | + | + | + | | | |

FIG. 22A

MUTANT CELLS FOR PROTEIN SECRETION AND LIGNOCELLULOSE DEGRADATION

CROSS-REFERENCE TO RELATED APPLICATIONS

This application is a Divisional of U.S. application Ser. No. 14/005,245, which is a U.S. National Phase of PCT/US2012/029293, filed Mar. 15, 2012, which claims the benefit of U.S. Provisional Application No. 61/453,086, filed Mar. 15, 2011, each of which is hereby incorporated by reference, in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 677792001610SEQLIST.TXT, date recorded: May 13, 2015, size: 262 KB).

FIELD

The present disclosure relates to mutant cells for the production of proteins, such as cellulases, and for the degradation of lignocellulosic biomass. In particular, mutant cells and methods for the production of proteins, such as cellulases, are provided.

BACKGROUND

Lignocellulosic biomass is an abundant and renewable raw material for biofuel production. However, the initial conversion of insoluble lignocellulosic biomass into cell-permeable and readily fermentable sugars presents a significant technical challenge and major bottleneck in the biofuel production process. Improved means to overcome this bottleneck are therefore needed to unlock the full potential of lignocellulosic biomass as a versatile energy source.

The natural degradation of biomass is achieved by fungal microorganisms through their secretion of lignocellulolytic enzymes. For example, the filamentous fungus and laboratory model organism *Neurospora crassa* (*N. crassa*) is often found in the wild growing upon recently burnt plant matter, where it secretes cellulases and thereby initiates the depolymerization of plant cell walls. Based on their natural role in lignocellulose degradation, filamentous fungi and their lignocellulolytic enzymes have great potential as catalysts of biomass degradation in biotechnological production processes.

However, whereas cellulase secretion in filamentous fungi is effectively induced by insoluble plant cell wall components, such as cellulose, hemicellulose, or xylan, soluble inducers are much less effective. For example, cellobiose, the main soluble end product of cellulases, induces cellulases in several species of filamentous fungi, including *Hypocrea jecorina* (*Trichoderma reesei; T. reesei*) and *Aspergillus* species (*A. niger, A. nidulans, A. oryzae*) but at much lower levels than cellulose itself. However, one problem with insoluble inducers is that cellulase can adhere to insoluble inducers, resulting in reduced yields of secreted enzyme activity.

The processing of insoluble biomass matter is a heterogeneous process and access to biomass surfaces is limiting for fungal cells. In rich fungal cultures therefore, a large population of cells will be free-floating and not secreting high levels of active cellulase enzymes, due to their lack of contact with inducing plant surfaces. To optimize the production of proteins, including cellulase enzymes, in such cell suspensions and thereby facilitate biomass degradation, cellular systems are needed that secrete high levels of active proteins after induction with soluble small molecules, such as cellodextrin.

BRIEF SUMMARY

Provided herein are mutant cells for increasing secretion of proteins and for the degradation of lignocellulosic biomass. Also provided are methods for increasing secretion of proteins and for degrading lignocellulosic biomass using the mutant cells described herein. Moreover, the present disclosure is based, at least in part on the surprising discovery that mutating β-glucosidase genes and/or the catabolite repressor gene, cre-1, in filamentous fungi, such as *Neurospora crassa*, results in an increase in the secretion of proteins when induced by cellulosic biomass, such as cellobiose. Without wishing to be bound by theory, it is believed that the activity of β-glucosidase genes and the cre-1 is involved in the transcriptional regulation of proteins (FIG. 1).

Accordingly, one aspect of the present disclosure provides a method for increasing secretion of a protein from a cell, by: (a) providing a mutant cell, where the mutant cell contains inactivating mutations in two or more β-glucosidase genes; and (b) contacting the mutant cell with cellulosic biomass, where the cellulosic biomass induces the mutant cell to secrete the protein. In certain embodiments, the mutant cell further contains an inactivating mutation in a cre-1 gene in the cell. Another aspect of the present disclosure provides a method for increasing secretion of a protein from a cell, by: (a) providing a mutant cell, where the mutant cell contains an inactivating mutation in a cre-1 gene in the cell; and (b) contacting the mutant cell with a cellulosic biomass, where the cellulosic biomass induces the mutant cell to secrete the protein. In certain embodiments, the mutant cell further contains inactivating mutations in two or more (3-glucosidase genes. In certain embodiments that may be combined with any of the preceding embodiments, the cellulosic biomass includes one or more of a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the cellulosic biomass includes cellobiose.

Accordingly, one aspect of the present disclosure provides a method for increasing secretion of a protein from a cell, by: (a) providing a mutant cell, where the mutant cell contains inactivating mutations in two or more β-glucosidase genes; and (b) contacting the mutant cell with a saccharide, where the saccharide induces the mutant cell to secrete the protein. In certain embodiments, the mutant cell further contains an inactivating mutation in a cre-1 gene in the cell. Another aspect of the present disclosure provides a method for increasing secretion of a protein from a cell, by: (a) providing a mutant cell, where the mutant cell contains an inactivating mutation in a cre-1 gene in the cell; and (b) contacting the mutant cell with a saccharide, where the saccharide induces the mutant cell to secrete the protein. In certain embodiments, the mutant cell further contains inactivating mutations in two or more β-glucosidase genes. In certain embodiments that may be combined with any of the preceding embodiments, the saccharide is selected from a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the saccharide is cellobiose.

In certain embodiments that may be combined with any of the preceding embodiments, the secreted protein is a cellulose-induced protein. In certain embodiments that may be combined with any of the preceding embodiments, the secreted protein is selected from a cellulase, a GH61 enzyme, a cellobiose dehydrogenase, a lactonase, a carbohydrate esterase, a polysaccharide lyase, and a cellulose binding domain-containing protein, and combinations thereof. In certain embodiments that may be combined with any of the preceding embodiments, the secreted protein is a cellulase. In certain embodiments that may be combined with any of the preceding embodiments, the secreted protein is encoded by a gene selected from NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, and NCU05137. In certain embodiments that may be combined with any of the preceding embodiments, the mutant cell further contains an inactivating mutation in at least one β-mannosidase gene. In certain embodiments that may be combined with any of the preceding embodiments, the mutant cell further contains an inactivating mutation in at least one phospholipase gene or phospholipase-like gene. In certain embodiments that may be combined with any of the preceding embodiments, the inactivating mutations are deletions. In certain embodiments that may be combined with any of the preceding embodiments, the cell is a recombinant cell. In certain embodiments that may be combined with any of the preceding embodiments, the cell is a fungal or yeast cell. In certain embodiments that may be combined with any of the preceding embodiments, the cell is a fungal or yeast cell. In certain embodiments that may be combined with any of the preceding embodiments, the cell is selected from *Neurospora crassa* (*N. crassa*) cells, *Aspergillus nidulans* cells, *Trichoderma reesei* cells, *Phanerochaete chrysosporium* cells, *Sporotrichum thermophile* (*Myceliophthora thermophila*) cells, *Gibberella zeae* cells, *Sclerotinia sclerotiorum* cells, *Botryotinia fuceliana* cells, *Aspergillus niger* cells, *Penicillium chrysogenum* cells, *Schizophyllum commune* cells, *Postia placenta* cells, *Aspergillus oryzae* cells, and *Acremonium cellulolyticus* cells. In certain embodiments that may be combined with any of the preceding embodiments, the two or more β-glucosidase genes are three or more β-glucosidase genes. In certain embodiments that may be combined with any of the preceding embodiments, the two or more β-glucosidase genes are four or more β-glucosidase genes. In certain embodiments that may be combined with any of the preceding embodiments, the two or more β-glucosidase genes are five or more β-glucosidase genes. In certain embodiments that may be combined with any of the preceding embodiments, the two or more β-glucosidase genes are six or more β-glucosidase genes. In certain embodiments that may be combined with any of the preceding embodiments, the two or more β-glucosidase genes are seven or more β-glucosidase genes. In certain embodiments that may be combined with any of the preceding embodiments, the three or more β-glucosidase genes, four or more β-glucosidase genes, five or more β-glucosidase genes, six or more β-glucosidase genes, or seven or more β-glucosidase genes include NCU00130, NCU04952, and NCU08755. In certain embodiments that may be combined with any of the preceding embodiments, at least one of the β-glucosidase genes encodes an intracellular β-glucosidase. In certain embodiments that may be combined with any of the preceding embodiments, at least one of the β-glucosidase genes encodes an extracellular β-glucosidase. In certain embodiments that may be combined with any of the preceding embodiments, the at least one β-mannosidase gene is NCU00890. In certain embodiments that may be combined with any of the preceding embodiments, the at least one phospholipase gene or phospholipase-like gene is NCU06650.

Another aspect of the present disclosure provides a method for increasing secretion of a protein from a cell, by: (a) providing a recombinant cell, where the recombinant cell exhibits reduced expression of at least two β-glucosidase genes compared to the expression of the at least two β-glucosidase genes in a corresponding non-recombinant cell; and (b) contacting the recombinant cell with cellulosic biomass, where the cellulosic biomass induces the recombinant cell to secrete the protein. In certain embodiments, the recombinant cell further exhibits reduced expression of a cre-1 gene compared to the expression of the expression of the cre-1 gene in a corresponding non-recombinant cell. Another aspect of the present disclosure provides a method for increasing secretion of a protein from a cell, by: (a) providing a recombinant cell, where the recombinant cell exhibits reduced expression of a cre-1 gene compared to the expression of the expression of the cre-1 gene in a corresponding non-recombinant cell; and (b) contacting the recombinant cell with cellulosic biomass, where the cellulosic biomass induces the recombinant cell to secrete the protein. In certain embodiments, the recombinant cell further exhibits reduced expression of at least two β-glucosidase genes compared to the expression of the at least two β-glucosidase genes in a corresponding non-recombinant cell. In certain embodiments that may be combined with any of the preceding embodiments, the cellulosic biomass includes one or more of a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the cellulosic biomass includes cellobiose.

Another aspect of the present disclosure provides a method for increasing secretion of a protein from a cell, by: (a) providing a recombinant cell, where the recombinant cell exhibits reduced expression of at least two β-glucosidase genes compared to the expression of the at least two β-glucosidase genes in a corresponding non-recombinant cell; and (b) contacting the recombinant cell with a saccharide, where the saccharide induces the recombinant cell to secrete the protein. In certain embodiments, the recombinant cell further exhibits reduced expression of a cre-1 gene compared to the expression of the expression of the cre-1 gene in a corresponding non-recombinant cell. Another aspect of the present disclosure provides a method for increasing secretion of a protein from a cell, by: (a) providing a recombinant cell, where the recombinant cell exhibits reduced expression of a cre-1 gene compared to the expression of the expression of the cre-1 gene in a corresponding non-recombinant cell; and (b) contacting the recombinant cell with a saccharide, where the saccharide induces the recombinant cell to secrete the protein. In certain embodiments, the recombinant cell further exhibits reduced expression of at least two β-glucosidase genes compared to the expression of the at least two β-glucosidase genes in a corresponding non-recombinant cell. In certain embodiments that may be combined with any of the preceding embodiments, the saccharide is selected from a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the saccharide is cellobiose.

In certain embodiments that may be combined with any of the preceding embodiments, the secreted protein is a cellulose-induced protein. In certain embodiments that may be combined with any of the preceding embodiments, the secreted protein is selected from a cellulase, a GH61 enzyme, a cellobiose dehydrogenase, a lactonase, a carbohydrate esterase, a polysaccharide lyase, and a cellulose binding domain-containing protein, and combinations thereof. In certain embodiments that may be combined with any of the preceding embodiments, the secreted protein is a cellulase. In certain embodiments that may be combined with any of the preceding embodiments, the secreted protein is encoded by a gene selected from NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, and NCU05137. In certain embodiments that may be combined with any of the preceding embodiments, the function of creA/cre-1 is reduced by overexpression of a dominant negative mutant or a protein inhibitor. In certain embodiments that may be combined with any of the preceding embodiments, the recombinant cell further exhibits reduced expression of at least one β-mannosidase gene compared to the expression of the at least one β-mannosidase genes in a corresponding non-recombinant cell. In certain embodiments that may be combined with any of the preceding embodiments, the recombinant cell further exhibits reduced expression of at least one phospholipase gene or phospholipase-like gene compared to the expression of the at least one phospholipase gene or phospholipase-like gene in a corresponding non-recombinant cell. In certain embodiments that may be combined with any of the preceding embodiments, gene expression is reduced by siRNA, antisense DNA, quelling, or meiotic silencing. In certain embodiments that may be combined with any of the preceding embodiments, the two or more β-glucosidase genes are three or more β-glucosidase genes. In certain embodiments that may be combined with any of the preceding embodiments, the two or more β-glucosidase genes are four or more β-glucosidase genes. In certain embodiments that may be combined with any of the preceding embodiments, the two or more β-glucosidase genes are five or more β-glucosidase genes. In certain embodiments that may be combined with any of the preceding embodiments, the two or more β-glucosidase genes are six or more β-glucosidase genes. In certain embodiments that may be combined with any of the preceding embodiments, the two or more β-glucosidase genes are seven or more β-glucosidase genes. In certain embodiments that may be combined with any of the preceding embodiments, the three or more β-glucosidase genes, four or more β-glucosidase genes, five or more β-glucosidase genes, six or more β-glucosidase genes, or seven or more β-glucosidase genes include NCU00130, NCU04952, and NCU08755. In certain embodiments that may be combined with any of the preceding embodiments, at least one of the β-glucosidase genes encodes an intracellular β-glucosidase. In certain embodiments that may be combined with any of the preceding embodiments, at least one of the β-glucosidase genes encodes an extracellular β-glucosidase. In certain embodiments that may be combined with any of the preceding embodiments, the at least one β-mannosidase gene is NCU00890. In certain embodiments that may be combined with any of the preceding embodiments, the at least one phospholipase gene or phospholipase-like gene is NCU06650. In certain embodiments that may be combined with any of the preceding embodiments, the cell is a stable cell line or a transiently transfected cell. In certain embodiments that may be combined with any of the preceding embodiments, the cell is a fungal or yeast cell. In certain embodiments that may be combined with any of the preceding embodiments, the cell is a filamentous fungus of the ascomycete or basidiomycete species. In certain embodiments that may be combined with any of the preceding embodiments, the cell is selected from *Neurospora crassa* (*N. crassa*) cells, *Aspergillus nidulans* cells, *Trichoderma reesei* cells, *Phanerochaete chrysosporium* cells, *Sporotrichum thermophile* (*Myceliophthora thermophila*) cells, *Gibberella zeae* cells, *Sclerotinia sclerotiorum* cells, *Botryotinia fuceliana* cells, *Aspergillus niger* cells, *Penicillium chrysogenum* cells, *Schizophyllum commune* cells, *Postia placenta* cells, *Aspergillus oryzae* cells, and *Acremonium cellulolyticus* cells.

Another aspect of the present disclosure provides a mutant cell containing inactivating mutations in two or more β-glucosidase genes, where cellulosic biomass induces the cell to secrete higher levels of a protein than a corresponding cell lacking said mutation in the two or more β-glucosidase genes. In certain embodiments, the mutant cell further contains an inactivating mutation in a cre-1 gene in the cell, where cellulosic biomass induces the cell to secrete higher levels of a protein than a corresponding cell lacking the mutation in the cre-1 gene. In certain embodiments that may be combined with any of the preceding embodiments, the mutant cell further contains an inactivating mutation in at least one β-mannosidase gene, where cellulosic biomass induces the cell to secrete higher levels of a protein than a corresponding cell lacking the mutation in the at least one β-mannosidase gene. In certain embodiments that may be combined with any of the preceding embodiments, the mutant cell further contains an inactivating mutation in at least one phospholipase gene or phospholipase-like gene, where cellulosic biomass induces the cell to secrete higher levels of a protein than a corresponding cell lacking the mutation in the at least one phospholipase gene or phospholipase-like gene. In certain embodiments that may be combined with any of the preceding embodiments, the cellulosic biomass includes one or more of a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the cellulosic biomass includes cellobiose.

Another aspect of the present disclosure provides a mutant cell containing inactivating mutations in two or more β-glucosidase genes, where a saccharide induces the cell to secrete higher levels of a protein than a corresponding cell lacking said mutation in the two or more β-glucosidase genes. In certain embodiments, the mutant cell further contains an inactivating mutation in a cre-1 gene in the cell, where a saccharide induces the cell to secrete higher levels of a protein than a corresponding cell lacking the mutation in the cre-1 gene. In certain embodiments that may be combined with any of the preceding embodiments, the mutant cell further contains an inactivating mutation in at least one β-mannosidase gene, where a saccharide induces the cell to secrete higher levels of a protein than a corresponding cell lacking the mutation in the at least one β-mannosidase gene. In certain embodiments that may be combined with any of the preceding embodiments, the mutant cell further contains an inactivating mutation in at least one phospholipase gene or phospholipase-like gene, where a saccharide induces the cell to secrete higher levels of a protein than a corresponding cell lacking the mutation in the at least one phospholipase gene or phospholipase-like gene. In certain embodiments that may be combined with any of the preceding embodiments, the saccharide is selected from a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the saccharide is cellobiose.

In certain embodiments that may be combined with any of the preceding embodiments, the secreted protein is a cellulose-induced protein. In certain embodiments that may be combined with any of the preceding embodiments, the secreted protein is selected from a cellulase, a GH61 enzyme, a cellobiose dehydrogenase, a lactonase, a carbohydrate esterase, a polysaccharide lyase, and a cellulose binding domain-containing protein, and combinations thereof. In certain embodiments that may be combined with any of the preceding embodiments, the secreted protein is a cellulase. In certain embodiments that may be combined with any of the preceding embodiments, the secreted protein is encoded by a gene selected from NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, and NCU05137. In certain embodiments that may be combined with any of the preceding embodiments, the inactivating mutations are deletions. In certain embodiments that may be combined with any of the preceding embodiments, the cell is a recombinant cell. In certain embodiments that may be combined with any of the preceding embodiments, the cell is a fungal or yeast cell. In certain embodiments that may be combined with any of the preceding embodiments, the cell is a filamentous fungus of the ascomycete or basidiomycete species. In certain embodiments that may be combined with any of the preceding embodiments, the cell is selected from *Neurospora crassa* (*N. crassa*) cells, *Aspergillus nidulans* cells, *Trichoderma reesei* cells, *Phanerochaete chrysosporium* cells, *Sporotrichum thermophile* (*Myceliophthora thermophila*) cells, *Gibberella zeae* cells, *Sclerotinia sclerotiorum* cells, *Botryotinia fuceliana* cells, *Aspergillus niger* cells, *Penicillium chrysogenum* cells, *Schizophyllum commune* cells, *Postia placenta* cells, *Aspergillus oryzae* cells, and *Acremonium cellulolyticus* cells. In certain embodiments that may be combined with any of the preceding embodiments, the two or more β-glucosidase genes are three or more β-glucosidase genes. In certain embodiments that may be combined with any of the preceding embodiments, the two or more β-glucosidase genes are four or more β-glucosidase genes. In certain embodiments that may be combined with any of the preceding embodiments, the two or more β-glucosidase genes are five or more β-glucosidase genes. In certain embodiments that may be combined with any of the preceding embodiments, the two or more β-glucosidase genes are six or more β-glucosidase genes. In certain embodiments that may be combined with any of the preceding embodiments, the two or more β-glucosidase genes are seven or more β-glucosidase genes. In certain embodiments that may be combined with any of the preceding embodiments, the three or more β-glucosidase genes, four or more β-glucosidase genes, five or more β-glucosidase genes, six or more β-glucosidase genes, or seven or more β-glucosidase genes include NCU00130, NCU04952, and NCU08755. In certain embodiments that may be combined with any of the preceding embodiments, at least one of the β-glucosidase genes encodes an intracellular β-glucosidase. In certain embodiments that may be combined with any of the preceding embodiments, at least one of the β-glucosidase genes encodes an extracellular β-glucosidase. In certain embodiments that may be combined with any of the preceding embodiments, the at least one β-mannosidase gene is NCU00890. In certain embodiments that may be combined with any of the preceding embodiments, the at least one phospholipase gene or phospholipase-like gene is NCU06650.

Another aspect of the present disclosure provides a recombinant cell exhibiting reduced expression of at least two β-glucosidase genes compared to the expression of the at least two β-glucosidase genes in a corresponding non-recombinant cell, where the expression is reduced by siRNA, antisense DNA, quelling, or meiotic silencing, and where cellulosic biomass induces the cell to secrete higher levels of a protein than the corresponding non-recombinant cell in which the expression of the at least two β-glucosidase genes is not reduced In certain embodiments, the cell further exhibits reduced expression of a cre-1 gene compared to the expression of the cre-1 gene in a corresponding non-recombinant cell, where the expression is reduced by siRNA, antisense DNA, quelling, or meiotic silencing, and where cellulosic biomass induces the cell to secrete higher levels of a protein than the corresponding non-recombinant cell in which the expression of the cre-1 gene is not reduced. In certain embodiments, the function of creA/cre-1 is reduced by overexpression of a dominant negative mutant or a protein inhibitor, where cellulosic biomass induces the cell to secrete higher levels of a protein than a corresponding cell in which the dominant negative mutant is not overexpressed. In certain embodiments that may be combined with any of the preceding embodiments, the cell further exhibits reduced expression of at least one β-mannosidase gene compared to the expression of the at least one β-mannosidase gene in a corresponding non-recombinant cell, where expression is reduced by siRNA, antisense DNA, quelling, or meiotic silencing, and where cellulosic biomass induces the cell to secrete higher levels of a protein than the corresponding non-recombinant cell in which the expression of the least one β-mannosidase gene is not reduced. In certain embodiments that may be combined with any of the preceding embodiments, the cell further exhibits reduced expression of at least one phospholipase gene or phospholipase-like gene compared to the expression of the at least one phospholipase gene or phospholipase-like gene in a corresponding non-recombinant cell, where expression is reduced by siRNA, antisense DNA, quelling, or meiotic silencing, and where cellulosic biomass induces the cell to secrete higher levels of a protein than the non-recombinant cell in which the expression of the least one phospholipase gene or phospholipase-like gene is not reduced. In certain embodiments that may be combined with any of the preceding embodiments, the cellulosic biomass includes one or more of a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the cellulosic biomass includes cellobiose.

Another aspect of the present disclosure provides a recombinant cell exhibiting reduced expression of at least two β-glucosidase genes compared to the expression of the at least two β-glucosidase genes in a corresponding non-recombinant cell, where the expression is reduced by siRNA, antisense DNA, quelling, or meiotic silencing, and where a saccharide induces the cell to secrete higher levels of a protein than the corresponding non-recombinant cell in which the expression of the at least two β-glucosidase genes is not reduced In certain embodiments, the cell further exhibits reduced expression of a cre-1 gene compared to the expression of the cre-1 gene in a corresponding non-recombinant cell, where the expression is reduced by siRNA, antisense DNA, quelling, or meiotic silencing, and where a saccharide induces the cell to secrete higher levels of a protein than the corresponding non-recombinant cell in which the expression of the cre-1 gene is not reduced. In certain embodiments, the function of creA/cre-1 is reduced by overexpression of a dominant negative mutant or a protein inhibitor, where a saccharide induces the cell to secrete higher levels of a protein than a corresponding cell in which the dominant negative mutant is not overexpressed. In certain embodiments that may be combined with any of the preceding embodiments, the cell further exhibits reduced expression of at least one β-mannosidase gene compared to the expression of the at least one β-mannosidase gene in a corresponding non-recombinant cell, where expression is reduced by siRNA, antisense DNA, quelling, or meiotic silencing, and where a saccharide induces the cell to secrete higher levels of a protein than the corresponding non-recombinant cell in which the expression of the least one β-mannosidase gene is not reduced. In certain embodiments that may be combined with any of the preceding embodiments, the cell further exhibits reduced expression of at least one phospholipase gene or phospholipase-like gene compared to the expression of the at least one phospholipase gene or phospholipase-like gene in a corresponding non-recombinant cell, where expression is reduced by siRNA, antisense DNA, quelling, or meiotic silencing, and where a saccharide induces the cell to secrete higher levels of a protein than the non-recombinant cell in which the expression of the least one phospholipase gene or phospholipase-like gene is not reduced. In certain embodiments that may be combined with any of the preceding embodiments, the saccharide is selected from a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the saccharide is cellobiose.

In certain embodiments that may be combined with any of the preceding embodiments, the secreted protein is a cellulose-induced protein. In certain embodiments that may be combined with any of the preceding embodiments, the secreted protein is selected from a cellulase, a GH61 enzyme, a cellobiose dehydrogenase, a lactonase, a carbohydrate esterase, a polysaccharide lyase, and a cellulose binding domain-containing protein, and combinations thereof. In certain embodiments that may be combined with any of the preceding embodiments, the secreted protein is a cellulase. In certain embodiments that may be combined with any of the preceding embodiments, the secreted protein is encoded by a gene selected from NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, and NCU05137. In certain embodiments that may be combined with any of the preceding embodiments, the two or more β-glucosidase genes are three or more β-glucosidase genes. In certain embodiments that may be combined with any of the preceding embodiments, the two or more β-glucosidase genes are four or more β-glucosidase genes. In certain embodiments that may be combined with any of the preceding embodiments, the two or more β-glucosidase genes are five or more β-glucosidase genes. In certain embodiments that may be combined with any of the preceding embodiments, the two or more β-glucosidase genes are six or more β-glucosidase genes. In certain embodiments that may be combined with any of the preceding embodiments, the two or more β-glucosidase genes are seven or more β-glucosidase genes. In certain embodiments that may be combined with any of the preceding embodiments, the three or more β-glucosidase genes, four or more β-glucosidase genes, five or more β-glucosidase genes, six or more β-glucosidase genes, or seven or more β-glucosidase genes include NCU00130, NCU04952, and NCU08755. In certain embodiments that may be combined with any of the preceding embodiments, at least one of the β-glucosidase genes encodes an intracellular β-glucosidase. In certain embodiments that may be combined with any of the preceding embodiments, at least one of the β-glucosidase genes encodes an extracellular β-glucosidase. In certain embodiments that may be combined with any of the preceding embodiments, the at least one β-mannosidase gene is NCU00890. In certain embodiments that may be combined with any of the preceding embodiments, the at least one phospholipase gene or phospholipase-like gene is NCU06650. In certain embodiments that may be combined with any of the preceding embodiments, the cell is a stable cell line or a transiently transfected cell. In certain embodiments that may be combined with any of the preceding embodiments, the cell is a fungal or yeast cell. In certain embodiments that may be combined with any of the preceding embodiments, the cell is a filamentous fungus of the ascomycete or basidiomycete species. In certain embodiments that may be combined with any of the preceding embodiments, the cell is selected from *Neurospora crassa* (*N. crassa*) cells, *Aspergillus nidulans* cells, *Trichoderma reesei* cells, *Phanerochaete chrysosporium* cells, *Sporotrichum thermophile* (*Myceliophthora thermophila*) cells, *Gibberella zeae* cells, *Sclerotinia sclerotiorum* cells, *Botryotinia fuceliana* cells, *Aspergillus niger* cells, *Penicillium chrysogenum* cells, *Schizophyllum commune* cells, *Postia placenta* cells, *Aspergillus oryzae* cells, and *Acremonium cellulolyticus* cells.

Another aspect of the present disclosure relates to a method for the degradation of biomass, by: (a) providing lignocellulosic biomass; (b) providing the cell of any of the preceding embodiments, or a cell containing an inactivating mutation in the cre-1 gene; (c) inducing the cell to secrete a protein by contacting the cell with a cellulosic biomass; and (d) contacting the induced cell with the lignocellulosic biomass, where the secreted protein degrades the lignocellulosic biomass. In certain embodiments that may be combined with any of the preceding embodiments, the cellulosic biomass includes one or more of a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the cellulosic biomass includes cellobiose. Another aspect of the present disclosure relates to a method for the degradation of biomass, by: (a) providing lignocellulosic biomass; (b) providing the cell of any of the preceding embodiments, or a cell containing an inactivating mutation in the cre-1 gene; (c) inducing said cell to secrete a protein by contacting the cell with a saccharide; and (d) contacting the induced cell with the lignocellulosic biomass, where the secreted protein degrades the lignocellulosic biomass. In certain embodiments that may be combined with any of the preceding embodiments, the saccharide is selected from a polysaccharide, an oligosaccharide, cellulose, microcrystalline cellulose, cellodextrin, cellobiose, cellotriose, cellotetraose, cellopentose, and cellohexose. In certain embodiments that may be combined with any of the preceding embodiments, the saccharide is cellobiose. In certain embodiments that may be combined with any of the preceding embodiments, the secreted protein is a cellulose-induced protein. In certain embodiments that may be combined with any of the preceding embodiments, the secreted protein is selected from a cellulase, a GH61 enzyme, a cellobiose dehydrogenase, a lactonase, a carbohydrate esterase, a polysaccharide lyase, and a cellulose binding domain-containing protein, and combinations thereof. In certain embodiments that may be combined with any of the preceding embodiments, the secreted protein is a cellulase. In certain embodiments that may be combined with any of the preceding embodiments, the secreted protein is encoded by a gene selected from NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, and NCU05137.

BRIEF DESCRIPTION OF THE DRAWINGS

FIG. 2A shows the cellobiohydrolase I (cbh-1, NCU07340) time course. FIG. 2B shows the endoglucanase 2 (gh5-1, NCU00762) time course. Expression levels for all genes were normalized to 1 when induced with 2% sucrose. Strains were grown in minimal media with 2% sucrose for 16 hours followed by 4 hours growth in minimal media with 2% Avicel®. Actin (NCU04173) gene expression levels were used as an endogenous control in all samples. Each reaction was done in triplicate and error bars indicate a 95% confidence interval.

FIG. 6A shows results for the wild type. FIG. 6B shows results for the Δ4952Δ8755Δ130 deletion mutant. FIG. 6C shows results for Δ4952Δ8755Δ130Δcre-1 deletion mutant. Expression levels for all genes were normalized to 1 when induced with 2% sucrose. Strains were grown in minimal media with 2% sucrose for 16 hrs followed by 4 hrs growth in minimal media with 1 mM cellobiose, 10 mM cellobiose, or 2% sucrose. Actin (NCU04173) gene expression levels were used as an endogenous control in all samples. Each reaction was done in triplicates and error bars indicate a 95% confidence interval.

FIG. 7A shows the production of cellulases in a bioreactor using Δ3βG induced with cellobiose. FIG. 7B shows the production of cellulases in a bioreactor using Δ3βGΔcre induced with cellobiose. FIG. 7C shows the production of cellulases in a bioreactor using WT induced with cellobiose. FIG. 7D shows the production of cellulases in a bioreactor using WT grown 5 days on Avicel®. Cellobiose-induced strains were pre-grown in minimal media with 1% sucrose for 24 hours before induction with 0.2% cellobiose for 36 hours. The concentration of sucrose, glucose, fructose (in glucose equivalents; triangle) cellobiose (circle), protein production (square), and biomass accumulation (diamond) were measured. FIG. 7E shows 24-hour induced supernatant activity from 7A, 7B, and 7D towards Avicel®. Cellulase activity of culture supernatant from Δ3βG (squares) and Δ3βGΔcre (triangle) induced with cellobiose for 24 hours compared to culture supernatants from WT grown on Avicel® for 5 days (diamond). Error bars are 1 standard deviation. FIG. 7F shows Azo-CMC (endoglucanase) activity time course from bioreactor culture supernatants in 7A and 7B. Azo-CMC activity is expressed as a percentage of activity from WT culture supernatant grown on 2% Avicel® for 5 days.

FIG. 8A shows MuLac activity expressed as a percentage of the wild type activity on Avicel® after 4 days on Avicel®. FIG. 8B shows MuLac activity expressed as μg purified recombinant Cbh-1 equivalents. Strains were grown in 2% sucrose for 16 hrs followed by 4 days in 2% sucrose, 2% cellobiose, or 2% Avicel® with time points taken at both 2 and 4 days. Exoglucanase activity in the culture supernatant was measured using a 4-Methylumbelliferyl-β-D-cellobioside (MuLac) assay.

FIG. 10A shows an SDS-PAGE analysis of secreted proteins in culture filtrates from WT and Δcre-1 strains grown on Avicel® for 7 days. Protein bands representing β-glucosidase (NCU04952), cellobiohydrolase 1 (cbh-1, NCU07340) and 2 (cbh-2, NCU09680), and endoglucanase 2 (gh5-1, NCU00762) are marked. FIG. 10B compares the endoglucanase activity on Azo-CMC, protein concentrations, and glucose and cellobiose concentrations as determined by Avicelase assays of 7-day culture supernatants from WT and Δcre-1 strains.

Figure 13C:
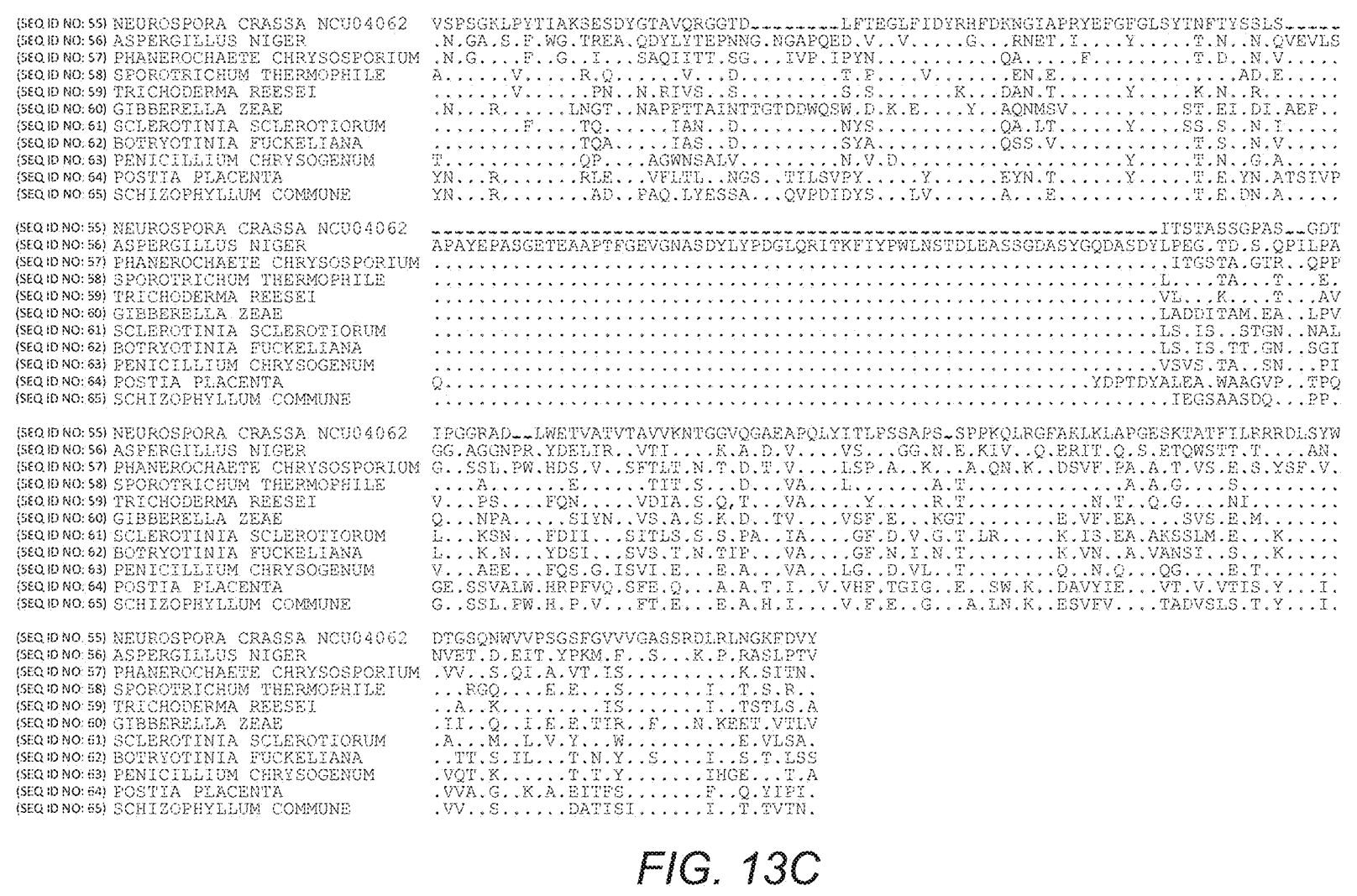
Figure 13E:
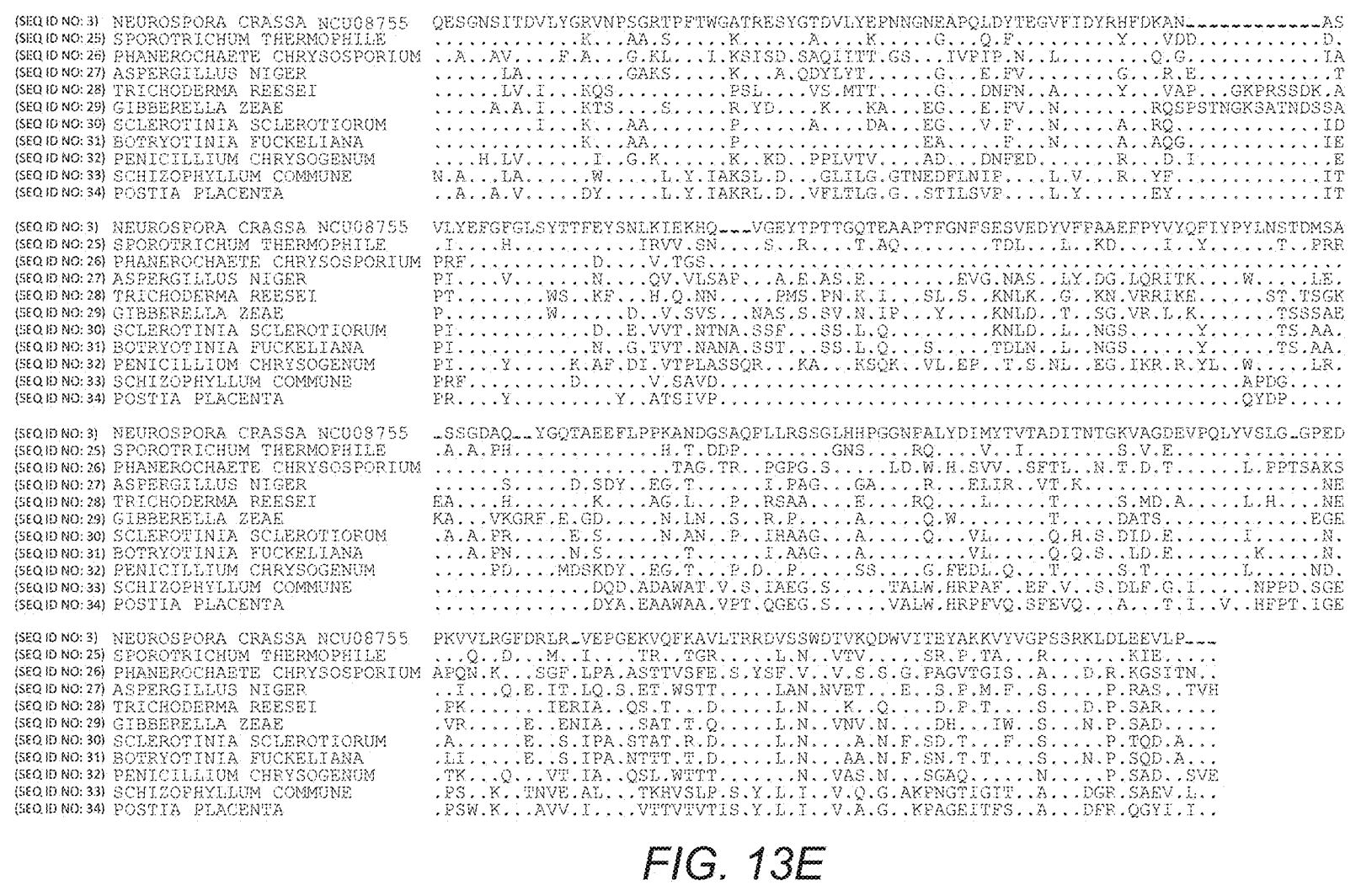

FIGS. 13AA and 13AB show ClustalW alignments for NCU00130 (SEQ ID NO: 1), FIGS. 13BA, 13BB and 13C show ClustalW alignments for NCU04952 (SEQ ID NO: 2), and FIGS. 13DA, 13DB and 13E show ClustalW alignments for NCU08755 (SEQ ID NO: 3) orthologues in closely related fungi. The aligned sequence is provided for each N. crassa gene with orthologues displaying only divergent amino acids. A "." indicates an identical residue and "-" indicates an insertion or deletion.

FIG. 17A shows cbh-1, gh5-1, and gh6-2 expression in WT after a 4-hour induction with Avicel®, cellobiose, cellotriose, or cellotetraose. FIG. 17B shows cbh-1, gh5-1, and gh6-2 expression in Δ3βG after a 4-hour induction with Avicel®, cellobiose, cellotriose, or cellotetraose. Gene expression levels of cbh-1, gh5-1 and gh6-2 were normalized to 1 when induced with 1% sucrose. Actin (NCU04173) gene expression levels were used as an endogenous control in all samples. Error bars indicate 1 standard deviation.

FIG. 18A shows an SDS-PAGE analysis of secreted proteins in culture filtrates from WT, Δ3βG, and Δ3βGΔcre strains. Protein bands representing CBH-1, GH6-2, and GH5-1 are marked. In addition, the absence of the extracellular β-glucosidase (NCU04952) is marked in the triple knockout. The presence of glucoamylase I (NCU01517) correlates with the deletion of the cre-1 gene. Cultures were grown in 1% sucrose for 24 hours followed by the addition of 2% sucrose or 0.2% cellobiose. Supernatant was harvested after 24 hours (WT, Δ3βG and Δ3βGΔcre) or 72 hours (Δ3βG). The WT Avicel® culture was grown for 5 days on 2% Avicel®, Δ3βG was grown in 1% sucrose for 24 hours followed by 48 hours in 1% Avicel® and Δ3βGΔcre was grown in 1% sucrose for 24 hours followed by 24 hours in 1% Avicel®. FIG. 18B shows activity of supernatant from 18A towards Avicel®. Glucose (dark grey) and cellobiose (light grey) were measured after 24 hours of incubation with 1% Avicel® at 50° C. Error bars are 1 standard deviation.

FIG. 19A shows cbh-1 expression in WT and Δ3βG after a 4 hour induction with 1 mM sophorose, 1 mM lactose or 1 mM D-(+)-galactose. FIG. 19B shows gh6-2 expression in WT and Δ3βG after a 4 hour induction with 1 mM sophorose, 1 mM lactose or 1 mM D-(+)-galactose. Gene expression levels of cbh-1 and gh6-2 were normalized to 1 when induced with 1% sucrose. Actin (NCU04173) gene expression levels were used as an endogenous control in all samples. Error bars indicate 1 standard deviation.

FIG. 20A shows hierarchical clustering analysis of 318 genes differentially induced in WT N. crassa by Avicel®, compared to induction by cellobiose. Light color indicates higher relative expression and dark color indicates lower relative expression. FIG. 20B shows cellulase expression in FPKMs (fragments per kilobase of exon per million fragments mapped) for the WT induced with cellobiose or Avicel® compared to Δ3βG induced with cellobiose. All strains were grown for 16 hours on 2% sucrose, followed by a transfer to no carbon source (Vogels salt solution only), 0.2% cellobiose or 1% Avicel® for 4 hours.

FIG. 21A shows the 24-hour induced supernatant activity towards Avicel®. Cellulase activity of culture supernatant from Δ3βG (square) and Δ3βGΔcre (diamond) strains when induced with cellobiose for 24 hours compared to culture supernatants from WT grown on Avicel® for 5 days (triangle). FIG. 21B shows breakdown of cellobiose (light grey) and glucose (dark grey) produced in the Avicel® hydrolysis assay (from A) after 36 hours. Error bars are 1 standard deviation.

FIGS. 22A-22B summarize the proteins identified by Mass Spectrometry in wild type (Avicel®), Δ3βG (cellobiose), and Δ3βGΔcre (cellobiose) Neurospora crassa strains.

DETAILED DESCRIPTION

Overview

Figure 1:
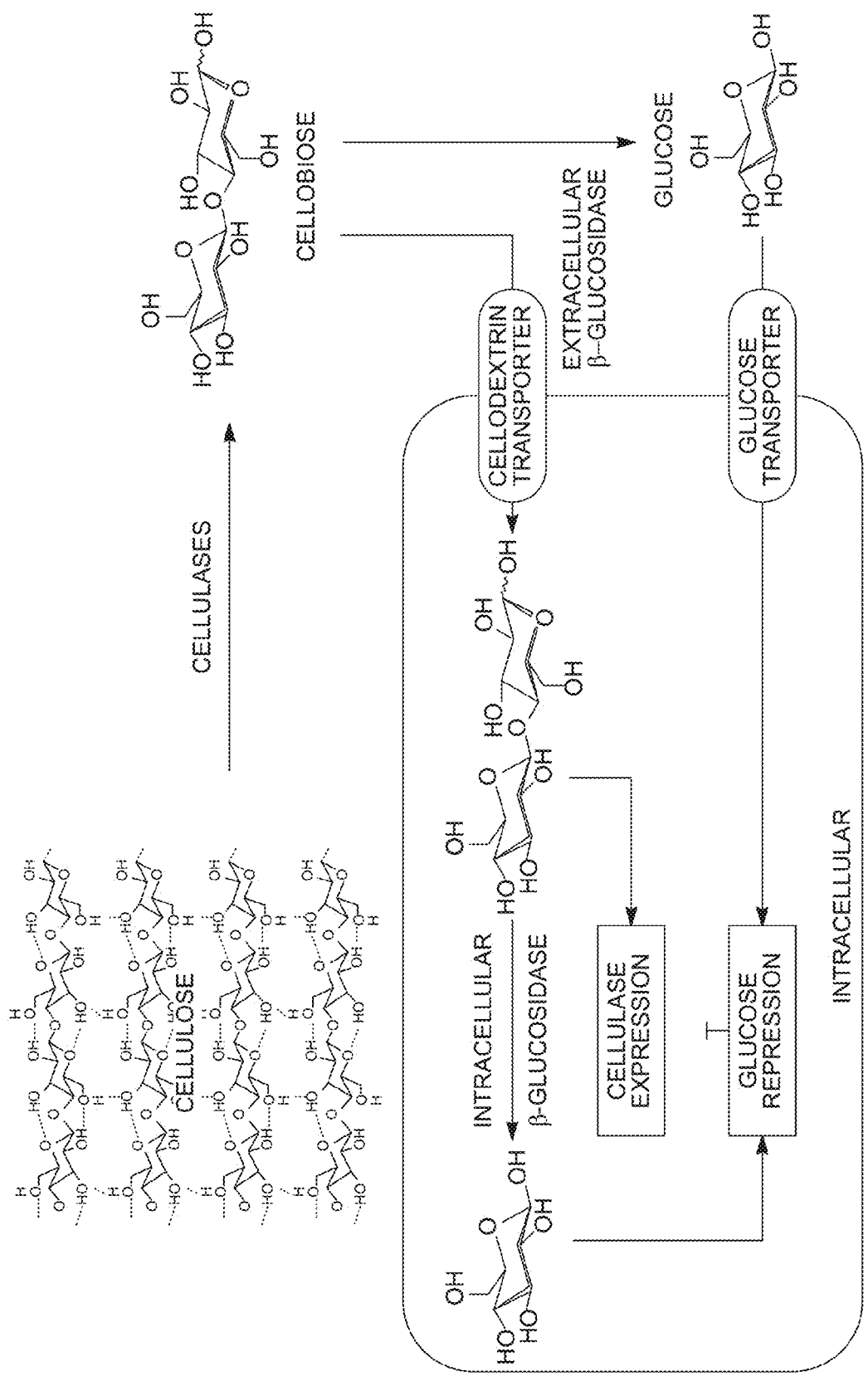
FIG. 1 shows a model for transcriptional regulation of cellulases in β-glucosidase deletion strains of *N. crassa*. Both transcriptional de-repression and specific induction are required to achieve maximal transcriptional activation of cellulase gene expression. Arrows indicate possible pathways for cellulose metabolites. Blue lines indicate pathways believed to be minimized in the Δ3βG and Δ3βGΔcre deletion strains; and red lines indicate pathways believed to be most active in the Δ3βG and Δ3βGΔcre deletion strains.

The present disclosure relates to mutant cells and recombinant cells that exhibit increased secretion of a protein, such as a cellulase, in response to induction by cellulosic biomass or a saccharide; and to methods of using such cells to increase secretion of a protein. The secreted proteins may find use in degrading lignocellulosic biomass. As disclosed herein, mutant cells of the present disclosure contain inactivating mutations in at least one gene, such as a β-glucosidase gene, a cre-1 gene, a β-mannosidase gene, or a phospholipase or phospholipase-like gene. As disclosed herein, recombinant cells of the present disclosure exhibit reduced expression of at least one gene, such as a β-glucosidase gene, a cre-1 gene, a β-mannosidase gene, or a phospholipase or phospholipase-like gene, compared to the expression of the at least one gene in a corresponding non-recombinant cell.

Inducers of Protein Secretion

Cellulosic biomass is mass obtained from living matter, such as plants, algae, fungi, bacteria, and bacterial biofilms that contains polysaccharides and polysaccharide components. Cellulose is the predominant polysaccharide in cellulosic biomass. Cellulose is a homopolymer of anhydrocellobiose (a linear beta-(1-4)-D-glucan), and includes glucose units linked together in β-1,4-glycosidic linkages. Although generally polymorphous, cellulose is found in plant tissue primarily as an insoluble crystalline matrix of parallel glucan chains. Cellulosic biomass may be raw biomass, pre-treated biomass, or processed biomass. Cellulosic biomass may also include one or more saccharides.

Suitable cellulosic biomass of the present disclosure may include, without limitation, saccharides, polysaccharides, oligosaccharides, purified cellulose, and cellulose derivatives. Purified celluloses include holocelluloses, such as Solka Flok, and microcrystalline celluloses, such as Avicel® and Sigmacell®. Cellulose derivatives include, without limitation, cellodextrins, β-methylumbelliferyl-oligosaccharides, p-nitrophenol-oligosaccharides, long chain cellulose derivatives, carboxymethyl cellulose (CMC), and hydroxyethyl cellulose (HEC).

As used herein, "cellodextrin(s)" refers to a β(1→4) glucose polymers of varying length and includes, without limitation, cellobiose (2 glucose monomers), cellotriose (3 glucose monomers), cellotetraose (4 glucose monomers), cellopentose (5 glucose monomers), and cellohexose (6 glucose monomers). Advantageously, short-chain cellodextrins, such as cellobiose are soluble. Moreover, secreted proteins of the present disclosure do not adhere to short-chain cellodextrins, such as cellobiose.

In certain aspects, cellulosic biomass of the present disclosure may be raw biomass material that is degraded by the cells of the present disclosure. The degraded biomass may include, without limitation, polysaccharides, such as cellulose and microcrystalline cellulose; or oligosaccharides, such as cellodextrin and cellobiose. In other aspects, cellulosic biomass of the present disclosure may include purified polysaccharides, such as cellulose and microcrystalline cellulose; or oligosaccharides, such as cellodextrin and cellobiose. In still other aspects, biomass of the present disclosure may include a mixture of polysaccharides, such as cellulose and microcrystalline cellulose; and oligosaccharides, such as cellodextrin and cellobiose.

In certain aspects, cellulosic biomass of the present disclosure is directly added to mutant cells or recombinant cells of the present disclosure to induce secretion of a protein.

In other aspects, secretion of a protein is induced from mutant cells or recombinant cells of the present disclosure by one or more cellulose derivatives, such as cellodextrin or cellobiose, that are generated in situ by the cells via degradation of the cellulosic biomass. In certain aspects, a sufficient amount of the cellulosic biomass to generate cellulose derivatives that induce secretion from the cell, but that does not adhere to or otherwise sequester the one or more types of proteins secreted from the cell.

Additionally, saccharides may be used to induce secretion of a protein from a mutant cell or recombinant cell of the present disclosure. Suitable saccharides include, without limitation, polysaccharides, oligosaccharides, sophorose, cellulose, microcrystalline cellulose, cellodextrin, cellobiose, cellotriose, cellotetraose, cellopentose, and cellohexose.

Secreted Proteins

In certain aspects, mutant cells and recombinant cells of the present disclosure exhibit increased secretion of at least one, at least two, at least three, at least four, at least five, or more types of proteins in response to induction by cellulosic biomass or a saccharide.

As used herein, increased secretion refers to increased levels of secretion of a protein of the present disclosure. Secretion involves the movement of the protein from inside the cell to outside of the cell. The increased levels of secretion may be the result of increasing expression or production of the protein of interest. Alternatively, the increased levels of secretion may be the result of increasing transport of the protein of interest from the cell. The methods of the present disclosure may also increase level of secretion of a protein by altering a pathway involved in the production and secretion of a protein that results in overall increased levels of secretion of the protein.

Types of proteins of the present disclosure that may be secreted include, without limitation, endogenous proteins and heterologous proteins. Endogenous proteins of the present disclosure are proteins endogenous to a cell of the present disclosure, or naturally produced by a cell of the present disclosure. Heterologous proteins of the present disclosure are proteins that are not normally expressed in a cell of the present disclosure. Heterologous proteins may be recombinantly expressed in the cell by any method known in the art. Generally, the recombinant nucleic acid encoding a heterologous protein is operably linked to a regulatory sequence, such as a promoter. Any suitable regulatory sequence known in the art may be used. Suitable promoters include, without limitation, constitutive promoters or inducible promoters. Additionally, the heterologous protein may contain a secretion peptide that directs its secretion from the cell. Any secretion peptide known in the art suitable for use in the methods of the present disclosure may be used.

In certain aspects, the secreted protein is a cellulose-induced protein. As used herein, "cellulose-induced protein" refers to a protein whose expression and secretion in a wild-type cell (e.g., non-mutant or non-recombinant cell) is induced by cellulose. For example, cellulose-induced proteins are described in C. M. Phillips et al., 2011 (Phillips, C M et al., *Proteome Res.* 2011 Sep. 2; 10(9):4177-85. Epub 2011 Aug. 1).

Secreted cellulose-induced proteins of the present disclosure include, without limitation, cellulases, GH61 enzymes, cellobiose dehydrogenases, lactonases, carbohydrate esterases, polysaccharide lyases, and cellulose binding domain-containing proteins.

As used herein, a "cellulase" or "cellulase polypeptide" refers to a polypeptide having enzymatic activity that catalyzes the hydrolysis of cellulose, lichenin, and cereal β-D-glucans. For example, cellulases may have hydrolyze 1,4-β-D-glucosidic linkages in cellulose. Ccellulases of the present disclosure include, without limitation, endocellulases, endoglucanases, endo-1,4-β-glucanases, endo-1,4-β-D-glucanases, carboxymethyl cellulases (CMCases), β-1,4-glucanases, β-1,4-endoglucan hydrolases, and celludextrinases; exocellulases, such as exoglucanases; cellobiases; cellobiohydrolases; oxidative cellulases, such as cellobiose dehydrogenases; and cellulose phosphorylases.

As used herein, "GH61 enzyme(s)" refers to Glycoside Hydrolase Family 61 enzymes. GH61 enzymes of the present disclosure are capable of enhancing cellulase activity. Examples of GH61 enzymes include, without limitation, polysaccharide monooxygenases. In certain aspects, a GH61 hydrolase of the present disclosure is encoded by a GH61-1 gene, a GH61-2 gene, a GH61-5 gene, the NCU07898 gene, the NCU08760 gene, homologues thereof, and orthologues thereof.

Cellobiose dehydrogenases are enzymes with oxidoreductase activity, and include enzymes having EC 1.1.99.18 activity. In certain aspects, a cellobiose dehydrogenase of the present disclosure is encoded by NCU00206, the cdh-1 gene, homologues thereof, and orthologues thereof.

Lactonases are enzymes that can hydrolyze the ester bond of the homoserine lactone ring of acylated homoserine lactones. In certain aspects, a lactonase of the present disclosure is encoded by NCU07143, the lac-2 gene, homologues thereof, and orthologues thereof.

Carbohydrate esterases are enzymes that have EC 3.1.1.- and EC 3.1.2-activity. Examples of carbohydrate esterases include, without limitation, acetyl xylan esterases, cinnamoyl esterases, feruloyl esterases, carboxylesterases, and S-formylglutathione hydrolases. In certain aspects, a carbohydrate esterase of the present disclosure is encoded by NCU09491, NCU09664, homologues thereof, and orthologues thereof.

Polysaccharide lyases are enzymes that have EC 4.2.2-activity. In certain aspects, a polysaccharide lyase of the present disclosure is encoded by NCU05598, homologues thereof, and orthologues thereof.

As used herein, "cellulose binding domain-containing protein(s)" refers to a protein that contains a cellulose binding domain. A cellulose binding domain is a protein domain found in cellulose-active enzymes, such as glycoside hydrolases. Generally, cellulose binding domains have carbohydrate-binding activity. In certain aspects, a cellulose binding domain-containing protein of the present disclosure is encoded by NCU09764, homologues thereof, and orthologues thereof.

In certain aspects, a secreted cellulose-induced protein of the present disclosure is a protein encoded by NCU05137, homologues thereof, and orthologues thereof.

Mutant Cells

One aspect of the present disclosure relates to mutant cells exhibiting increased secretion of a protein in response to cellulosic biomass or a saccharide; and to methods of using such cells to increase secretion of a protein from the cell, and to degrade lignocellulosic biomass. As disclosed herein, mutant cells of the present disclosure contain inactivating mutations in at least one gene. Examples of suitable inactivating mutations include, without limitation, deletions, point mutations, loss-of-function mutations, truncations, duplications, amplifications, translocations, and/or inversions that result inhibit the function of the protein encoded by the gene. Methods of generating one or more inactivating mutations in a gene of interest are well known in the art and include, without limitation, PCR mutagenesis, insertional mutagenesis, chemical mutagenesis, and irradiation.

In one aspect of the present disclosure the mutant cells are fungal or yeast cells. In another aspect of the present disclosure the mutant cells may be ascomycete or basidiomycete fungal cells, *Neurospora crassa* (*N. crassa*) cells, *Aspergillus nidulans* cells, *Trichoderma reesei* cells, *Phanerochaete chrysosporium* cells, *Sporotrichum* thermophile (*Myceliophthora thermophila*) cells, *Gibberella zeae* cells, *Sclerotinia sclerotiorum* cells, *Botryotinia fuckeliana* cells, *Aspergillus niger* cells, *Penicillium chrysogenum* cells, *Schizophyllum commune* cells, *Postia placenta* cells, *Aspergillus oryzae* cells, or *Acremonium cellulolyticus* cells. Preferably, the mutant cells are mutant *N. crassa* cells. In another aspect of the present disclosure the mutant cells are recombinant cells. Preferably, the mutant, recombinant cells are *N. crassa* mutant, recombinant cells.

β-Glucosidase Mutant Cells

β-Glucosidase genes encode β-glucosidase enzymes. As used herein, "β-glucosidase(s)" refers to a β-D-glucoside glucohydrolase that catalyzes the hydrolysis of terminal non-reducing β-D-glucose residues with the release of glucose. β-Glucosidases are highly conserved enzymes.

In one aspect a mutant cell of the present disclosure contains inactivating mutations in at least two β-glucosidase genes, which cause a loss of the β-glucosidase function encoded by the at least two genes. Inactivating mutations of the at least two β-glucosidase genes include, without limitation, deletion mutations, point mutations, nonsense mutations, truncations, and insertions. Inactivating mutations may completely abolish β-glucosidase activity or inhibit β-glucosidase activity by at least 75%, at least 80%, at least 85%, at least 90%, at least 91%, at least 92%, at least 93%, at least 94%, at least 95%, at least 96%, at least 97%, at least 98%, at least 99%, or more. Inactivating mutations may affect the expression levels of mutated genes or affect the functional activity of proteins or RNAs encoded by mutated genes. Inactivating mutations may also be cis- or trans-acting. Inactivating mutations may be introduced by random mutagenesis, including irradiation or exposure to mutagenic chemicals, or they may be introduced in a targeted manner, including homologous recombination and crossing of strains that include inactivating mutations.

β-Glucosidases of the present disclosure that contain inactivating mutations may be intracellular β-glucosidases or extracellular (i.e., secreted) β-glucosidases. Examples of suitable fl-glucosidases containing inactivating mutations include, without limitation, those encoded by the *N. crassa* genes NCU00130, NCU04952, NCU08755, homologues thereof, and orthologues thereof. Examples of NCU00130 orthologues, NCU04952 orthologues, and NCU08755 orthologues include, without limitation, those listed in FIGS. 13A-16.

In one specific aspect of the present disclosure, cellulosic biomass or a saccharide may induce the mutant cell to transcribe 10, 50, 100, 500, 1,000, 5,000, 10,000, 50,000 or 100,000-fold higher levels of at least one type of protein compared to that of a cell lacking the inactivating β-glucosidase mutations.

In one specific aspect of the present disclosure, cellulosic biomass or a saccharide may induce the mutant cell to secrete 1.2, 1.4, 1.6, 1.8, 2, 4, 6, 8, 10, 50, 100, 500, 1,000, 5,000, or 10,000-fold higher levels of at least one type of protein after a two day induction compared to that of a cell lacking the inactivating β-glucosidase mutations.

In another specific aspect of the present disclosure, cellulosic biomass or a saccharide may induce the mutant cell to secrete 1.2, 1.4, 1.6, 1.8, 2, 3, 4, 5, 6, 7, 8, 9, or 10-fold higher levels of total protein after a two day induction compared to that of a cell lacking the inactivating β-glucosidase mutations.

In another specific aspect of the present disclosure, the mutant cells may transcribe 10, 50, 100, 500, 1,000, 5,000, 10,000, 50,000 or 100,000-fold higher levels of at least one type of protein after induction with at least 1 nM, at least 5 nM, at least 10 nM, 15 nM, at least 20 nM, at least 25 nM, 30 nM, at least 35 nM, at least 40 nM, 45 nM, at least 50 nM, at least 55 nM, 60 nM, at least 65 nM, at least 70 nM, at least 75 nM, 80 nM, at least 85 nM, 90 nM, at least 95 nM, at least 100 nM, at least 125 nM, 150 nM, at least 175 nM, 200 nM, at least 225 nM, at least 250 nM, at least 275 nM, 300 nM, at least 325 nM, 350 nM, at least 375 nM, at least 400 nM, at least 425 nM, at least 450 nM, at least 475 nM, 500 nM, at least 525 nM, at least 550 nM, at least 575 nM, 600 nM, at least 625 nM, 650 nM, at least 675 nM, at least 700 nM, at least 725 nM, at least 750 nM, at least 775 nM, 800 nM, at least 825 nM, at least 850 nM, at least 875 nM, 900 nM, at least 925 nM, 950 nM, at least 975 nM, at least 1 µM, at least 2 µM, at least 3 µM, at least 4 µM, at least 5 µM, at least 6 µM, at least 7 µM, at least 8 µM, at least 9 µM, at least 10 µM, at least 15 µM, at least 20 µM, at least 25 µM, at least 30 µM, at least 35 µM, at least 40 µM, at least 45 µM, at least 50 µM, at least 55 µM, at least 60 µM, at least 65 µM, at least 70 µM, at least 75 µM, at least 80 µM, at least 85 µM, at least 90 µM, at least 95 µM, at least 100 µM, at least 125 µM, at least 150 µM, at least 175 µM, at least 200 µM, at least 225 µM, at least 250 µM, at least 275 µM, at least 300 µM, at least 325 µM, at least 350 µM, at least 375 µM, at least 400 µM, at least 425 µM, at least 450 µM, at least 475 µM, at least 500 µM, at least 525 µM, at least 550 µM, at least 575 µM, at least 600 µM, at least 625 µM, at least 650 µM, at least 675 µM, at least 700 µM, at least 725 µM, at least 750 µM, at least 775 µM, at least 800 µM, at least 825 µM, at least 850 µM, at least 875 µM, at least 900 µM, at least 925 µM, at least 950 µM, at least 975 µM, at least 1 mM, at least 2 mM, at least 3 mM, at least 4 mM, at least 5 mM, at least 6 mM, at least 7 mM, at least 8 mM, at least 9 mM, at least 10 mM, at least 11 mM, at least 12 mM, at least 13 mM, at least 14 mM, at least 15 mM, at least 16 mM, at least 17 mM, at least 18 mM, at least 19 mM, at least 20 mM, or more cellulosic biomass or saccharide compared to a cell lacking the inactivating β-glucosidase mutations.

In another specific aspect of the present disclosure the at least two β-glucosidase genes are at least three β-glucosidase genes, at least four β-glucosidase genes, at least five β-genes, at least six β-glucosidase genes, at least seven β-glucosidase genes or more β-glucosidase genes.

In one preferred embodiment of the present disclosure the β-glucosidase genes NCU00130, NCU04952, and NCU08755 are deleted in a *N. crassa* cell.

In another aspect of the present disclosure, the mutant cell including inactivating mutations that reduce the activities of at least two β-glucosidases further includes an inactivating mutation in the cre-1 gene, where cellulosic biomass or a saccharide induces the cell to secrete higher levels of at least one protein than a cell lacking a mutation in the cre-1 gene. Inactivating mutations may affect the expression levels of mutated genes or affect the functional activity of proteins or RNAs encoded by mutated genes. Inactivating mutations may be cis- or trans-acting. Inactivating mutations may be introduced by random mutagenesis, including irradiation or exposure to mutagenic chemicals, or they may be introduced in a targeted manner, including homologous recombination and crossing of strains that include single or multiple inactivating mutations.

In one specific aspect of the present disclosure, cellulosic biomass or a saccharide may induce the mutant cell to transcribe 2, 4, 6, 8, 10, 50, 100, 500, 1,000, 5,000, 10,000, 50,000, or 100,000-fold higher levels of at least one type of protein compared to that of a cell lacking the inactivating creA/cre-1 mutation.

In one specific aspect of the present disclosure, cellulosic biomass or a saccharide may induce the mutant cell to secrete 1.2, 1.4, 1.6, 1.8, 2, 4, 6, 8, 10, 50, 100, 500, 1,000, 5,000, or 10,000-fold higher levels of at least one type of protein compared to that of a cell lacking the β-glucosidase mutations or the cre-1 mutation.

In another specific aspect of the present disclosure, cellulosic biomass or a saccharide may induce the mutant cell to secrete 1.2, 1.4, 1.6, 1.8, 2, 3, 4, 5, 6, 7, 8, 9, or 10-fold higher levels of total protein after a two-day induction than a cell lacking the β-glucosidase mutations or the cre-1 mutation.

In another specific aspect of the present disclosure, the mutant cell may transcribe 10, 50, 100, 500, 1,000, 5,000, 10,000, 50,000 or 100,000-fold higher levels of at least one type of protein after induction with 1 nM, at least 5 nM, at least 10 nM, 15 nM, at least 20 nM, at least 25 nM, 30 nM, at least 35 nM, at least 40 nM, 45 nM, at least 50 nM, at least 55 nM, 60 nM, at least 65 nM, at least 70 nM, at least 75 nM, 80 nM, at least 85 nM, 90 nM, at least 95 nM, at least 100 nM, at least 125 nM, 150 nM, at least 175 nM, 200 nM, at least 225 nM, at least 250 nM, at least 275 nM, 300 nM, at least 325 nM, 350 nM, at least 375 nM, at least 400 nM, at least 425 nM, at least 450 nM, at least 475 nM, 500 nM, at least 525 nM, at least 550 nM, at least 575 nM, 600 nM, at least 625 nM, 650 nM, at least 675 nM, at least 700 nM, at least 725 nM, at least 750 nM, at least 775 nM, 800 nM, at least 825 nM, at least 850 nM, at least 875 nM, 900 nM, at least 925 nM, 950 nM, at least 975 nM, at least 1 µM, at least 2 µM, at least 3 µM, at least 4 µM, at least 5 µM, at least 6 µM, at least 7 µM, at least 8 µM, at least 9 µM, at least 10 µM, at least 15 µM, at least 20 µM, at least 25 µM, at least 30 µM, at least 35 µM, at least 40 µM, at least 45 µM, at least 50 µM, at least 55 µM, at least 60 µM, at least 65 µM, at least 70 µM, at least 75 µM, at least 80 µM, at least 85 µM, at least 90 µM, at least 95 µM, at least 100 µM, at least 125 µM, at least 150 µM, at least 175 µM, at least 200 µM, at least 225 µM, at least 250 µM, at least 275 µM, at least 300 µM, at least 325 µM, at least 350 µM, at least 375 µM, at least 400 µM, at least 425 µM, at least 450 µM, at least 475 µM, at least 500 µM, at least 525 µM, at least 550 µM, at least 575 µM, at least 600 µM, at least 625 µM, at least 650 µM, at least 675 µM, at least 700 µM, at least 725 µM, at least 750 µM, at least 775 µM, at least 800 µM, at least 825 µM, at least 850 µM, at least 875 µM, at least 900 µM, at least 925 µM, at least 950 µM, at least 975 µM, at least 1 mM, at least 2 mM, at least 3 mM, at least 4 mM, at least 5 mM, at least 6 mM, at least 7 mM, at least 8 mM, at least 9 mM, at least 10 mM, at least 11 mM, at least 12 mM, at least 13 mM, at least 14 mM, at least 15 mM, at least 16 mM, at least 17 mM, at least 18 mM, at least 19 mM, at least 20 mM, or more cellulosic biomass or saccharide compared to that of a cell lacking the β-glucosidase mutations or the cre-1 mutation.

In another specific aspect of the present disclosure the at least two β-glucosidases are at least three β-glucosidases.

In another preferred embodiment of the present disclosure the β-glucosidase genes NCU00130, NCU04952, and NCU08755 and the cre-1 gene are deleted in a *N. crassa* cell.

CreA/cre-1 Mutant Cells

In one aspect, a mutant cell of the present disclosure contains an inactivating mutation in the creA/cre-1 gene, which causes a loss of the CreA/CRE-1 function encoded by the gene. Inactivating mutations of the creA/cre-1 gene include, without limitation, deletion mutations, point mutations, nonsense mutations, truncations, and insertions. Inactivating mutations may completely abolish CreA/CRE-1 activity or inhibit CreA/CRE-1 activity by at least 75%, at least 80%, at least 85%, at least 90%, at least 91%, at least 92%, at least 93%, at least 94%, at least 95%, at least 96%, at least 97%, at least 98%, at least 99%, or more. Inactivating mutations may affect the expression levels of mutated genes or affect the functional activity of proteins or RNAs encoded by mutated genes. Inactivating mutations may also be cis- or trans-acting. Inactivating mutations may be introduced by random mutagenesis, including irradiation or exposure to mutagenic chemicals, or they may be introduced in a targeted manner, including homologous recombination and crossing of strains that include inactivating mutations. As used herein, "cre-1 gene" and "creA/cre-1 gene" are used interchangeably.

In one specific aspect of the present disclosure, cellulosic biomass or a saccharide may induce the mutant cell to transcribe 2, 4, 6, 8, 10, 50, 100, 500, 1,000, 5,000, 10,000, 50,000, or 100,000-fold higher levels of at least one type of protein compared to that of a cell lacking the inactivating cre-1 mutation.

In one specific aspect of the present disclosure, cellulosic biomass or a saccharide may induce the mutant cell including the inactivating mutation of cre-1 to secrete 1.2, 1.4, 1.6, 1.8, 2, 4, 6, 8, 10, 50, 100, 500, 1,000, 5,000, or 10,000-fold higher levels of at least one type of protein compared to that of a cell lacking the inactivating cre-1 mutation.

In another specific aspect of the present disclosure, the mutant cells exhibit elevated basal levels of expression of genes involved in C-compound/carbohydrate metabolism, extracellular metabolism, proteins with binding function or cofactor requirement, C-compound/carbohydrate transport, transport facilities, and protein synthesis relative to a cell lacking the cre-1 mutation.

In one preferred example of the present disclosure the cre-1 gene is deleted in a N. crassa cell.

In another aspect of the present disclosure, the mutant cell including an inactivating mutation in the cre-1 gene further includes inactivating mutations, which abolish the β-glucosidase activity encoded by the at least two β-glucosidase genes. Inactivating mutations of the at least two β-glucosidase genes include deletions, point mutations, nonsense mutations, truncations, and insertions. Inactivating mutations may completely abolish β-glucosidase activity or inhibit the activity by at least 75%, at least 80%, at least 85%, at least 90%, at least 91%, at least 92%, at least 93%, at least 94%, at least 95%, at least 96%, at least 97%, at least 98%, at least 99%, or more. Inactivating mutations may affect the expression levels of mutated genes or affect the functional activity of proteins or RNAs encoded by mutated genes. Inactivating mutations may be cis- or trans-acting. Inactivating mutations may be introduced by random mutagenesis, including irradiation or exposure to mutagenic chemicals, or they may be introduced in a targeted manner, including homologous recombination and crossing of strains that include inactivating mutations. The β-glucosidases may be intracellular or extracellular (i.e., secreted) β-glucosidases.

In one specific aspect of the present disclosure, cellulosic biomass or a saccharide may induce the mutant cell to transcribe 2, 4, 6, 8, 10, 50, 100, 500, 1,000, 5,000, 10,000, 50,000, or 100,000-fold higher levels of at least one type of protein compared to that of a cell lacking the inactivating β-glucosidase mutations.

In one specific aspect of the present disclosure, cellulosic biomass or a saccharide may induce induces the mutant cell to secrete 1.2, 1.4, 1.6, 1.8, 2, 4, 6, 8, 10, 50, 100, 500, 1,000, 5,000, or 10,000-fold higher levels of at least one type of protein compared to that of a cell lacking the inactivating mutations in the at least two β-glucosidase mutations.

In another specific aspect of the present disclosure, the at least two β-glucosidases are three β-glucosidases.

In one preferred embodiment of the present disclosure the mutant cell is a N. crassa cell including deletions of the β-glucosidases genes NCU00130, NCU04952, and NCU08755 and a deletion of cre-1.

β-Mannosidase Mutant Cells

In another aspect of the present disclosure, mutant cells containing inactivating mutations that reduce the activities of at least two β-glucosidases of the present disclosure; mutant cells containing an inactivating mutation in the cre-1 gene of the present disclosure; and/or mutant cells containing inactivating mutations that reduce the activities of at least two β-glucosidases and an inactivating mutation in the cre-1 gene further include a mutation that reduces the activity of at least one β-mannosidase gene.

β-Mannosidase genes of the present disclosure encode β-mannosidase enzymes. As used herein, "β-mannosidase," "mannan endo-1,4-β-mannosidase," "endo-1,4-β-mannanase," "endo-β-1,4-mannase," "β-mannanase B," "β-1,4-mannan 4-mannanohydrolase," "endo-β-mannanase," "β-D-mannanase," and "1,4-β-D-mannan mannanohydrolase" are used interchangeably and refer to an enzymes capable of the random hydrolysis of 1,4-β-D-mannosidic linkages in mannans, galactomannans and glucomannans (EC 3.2.1.78). In certain aspects, the at least one β-mannosidase gene is NCU00890, T. reesei protein ID 62166, T. reesei protein ID 57857, homologues thereof, and orthologues thereof.

In one aspect a mutant cell of the present disclosure contains inactivating mutations in at least one β-mannosidase gene, which causes a loss of the β-mannosidase function encoded by the gene. Inactivating mutations of the at least one β-mannosidase gene include, without limitation, deletion mutations, point mutations, nonsense mutations, truncations, and insertions. Inactivating mutations may completely abolish β-mannosidase activity or inhibit β-mannosidase activity by at least 75%, at least 80%, at least 85%, at least 90%, at least 91%, at least 92%, at least 93%, at least 94%, at least 95%, at least 96%, at least 97%, at least 98%, at least 99%, or more. Inactivating mutations may affect the expression levels of mutated genes or affect the functional activity of proteins or RNAs encoded by mutated genes. Inactivating mutations may also be cis- or trans-acting. Inactivating mutations may be introduced by random mutagenesis, including irradiation or exposure to mutagenic chemicals, or they may be introduced in a targeted manner, including homologous recombination and crossing of strains that include inactivating mutations.

In one specific aspect of the present disclosure, cellulosic biomass or a saccharide may induce the mutant cell further containing the inactivating mutation of at least one β-mannosidase gene to transcribe 2, 4, 6, 8, 10, 50, 100, 500, 1,000, 5,000, 10,000, 50,000, or 100,000-fold higher levels of at least one type of protein compared to that of a cell lacking the inactivating mutation of the at least one β-mannosidase gene.

In one specific aspect of the present disclosure, cellulosic biomass or a saccharide may induce the mutant cell further containing the inactivating mutation of at least one β-mannosidase gene to secrete 1.2, 1.4, 1.6, 1.8, 2, 4, 6, 8, 10, 50, 100, 500, 1,000, 5,000, or 10,000-fold higher levels of at least one type of protein compared to that of a cell lacking the inactivating mutation of the at least one β-mannosidase gene.

In one preferred example of the present disclosure the at least one β-mannosidase gene is deleted in a N. crassa cell.
Phospholipase Mutant Cells In another aspect of the present disclosure, mutant cells containing inactivating mutations that reduce the activities of at least two β-glucosidases of the present disclosure; mutant cells containing an inactivating mutation in the creA/cre-1 gene of the present disclosure; mutant cells containing inactivating mutations that reduce the activities of at least two β-glucosidases and an inactivating mutation in the creA/cre-1 gene; and/or mutant cells containing inactivating mutations that reduce the activities of at least two β-glucosidases, an inactivating mutation in the creA/cre-1 gene, and an inactivating mutation that reduces the activity of at least one β-mannosidase gene of the present disclosure further contain an inactivating mutation that reduces the activity of at least one phospholipase gene or phospholipase-like gene.

As used here, a "phospholipase-like gene" is a gene having sequence homology to a phospholipase gene, or a gene encoding a protein having amino acid sequence homology to a phospholipase. For example, a phospholipase-like gene of the present disclosure may be NCU06650. While NCU06650 has not been shown to encode a protein having phospholipase activity, the closest related homologues of the encoded amino acid sequence are phospholipases.

Phospholipase genes of the present disclosure encode phospholipase enzymes. As used herein, phospholipase enzymes include, without limitation, any enzyme that hydrolyzes phospholipids into, for example, fatty acids and other lipophilic molecules. Phospholipase-encoding genes may include, without limitation, genes that encode a phospholipase A1, a phospholipase A2, a phospholipase B, a phospholipase C, a phospholipase D, or a phosphodiesterase.

Accordingly, in certain aspects, the at least one phospholipase gene or phospholipase-like gene is NCU06650, *T. reesei* protein ID 67579, homologues thereof, and orthologues thereof.

In one aspect a mutant cell of the present disclosure contains inactivating mutations in at least one phospholipase gene or phospholipase-like gene, which causes a loss of the protein function encoded by the gene. Inactivating mutations of the at least one phospholipase gene or phospholipase-like gene include, without limitation, deletion mutations, point mutations, nonsense mutations, truncations, and insertions. Inactivating mutations may completely abolish phospholipase activity or inhibit phospholipase activity by at least 75%, at least 80%, at least 85%, at least 90%, at least 91%, at least 92%, at least 93%, at least 94%, at least 95%, at least 96%, at least 97%, at least 98%, at least 99%, or more. Inactivating mutations may affect the expression levels of mutated genes or affect the functional activity of proteins or RNAs encoded by mutated genes. Inactivating mutations may also be cis- or trans-acting. Inactivating mutations may be introduced by random mutagenesis, including irradiation or exposure to mutagenic chemicals, or they may be introduced in a targeted manner, including homologous recombination and crossing of strains that include inactivating mutations.

In one specific aspect of the present disclosure, cellulosic biomass or a saccharide may induce the mutant cell further containing the inactivating mutation of at least one phospholipase gene or phospholipase-like gene to transcribe 2, 4, 6, 8, 10, 50, 100, 500, 1,000, 5,000, 10,000, 50,000, or 100,000-fold higher levels of at least one type of protein compared to that of a cell lacking the inactivating mutation of the at least one phospholipase gene or phospholipase-like gene.

In one specific aspect of the present disclosure, cellulosic biomass or a saccharide may induce the mutant cell further containing the inactivating mutation of at least one phospholipase gene or phospholipase-like gene to secrete 1.2, 1.4, 1.6, 1.8, 2, 4, 6, 8, 10, 50, 100, 500, 1,000, 5,000, or 10,000-fold higher levels of at least one type of protein compared to that of a cell lacking the inactivating mutation of the at least one phospholipase gene or phospholipase-like gene.

In one preferred example of the present disclosure the at least one phospholipase gene or phospholipase-like gene is deleted in a *N. crassa* cell.

Recombinant Cells

Another aspect of the present disclosure relates to recombinant cells exhibiting reduced expression of at least two β-glucosidase genes or a cre-1 gene in the cell, that also exhibit increased secretion at least one, at least two, at least three, at least four, at least five, or more types of proteins in response to cellulosic biomass or a saccharide; and to methods of using such cells to increase secretion of a protein from the cell, and to degrade lignocellulosic biomass. Recombinant cells of the present disclosure may be stable cell lines or transiently transfected cells.

Recombinant cells of the present disclosure exhibiting reduced expression of a gene of interest (e.g., a β-glucosidase gene, a cre-1 gene, a β-mannosidase gene, or a phospholipase gene or phospholipase-like gene) may contain a mutation that reduces expression of the gene of interest. Methods for generating and characterizing mutations are well known in the art, such as mutational screening. Alternatively, recombinant cells of the present disclosure may be transgenic cells that contain a recombinant construct, such as an inhibitory oligonucleotide, that targets and reduces expression of the gene of interest. Non-limiting examples of inhibitory oligonucleotides include siRNA, miRNA, antisense DNA. Additionally, the expression of a gene of interest may be reduced by gene silencing techniques, such quelling and meiotic silencing. Gene silencing techniques can target the gene of interest, RNA of the gene of interest, a regulator protein of the gene of interest.

Types of proteins that may be secreted by recombinant cells of the present disclosure include, without limitation, cellulose-induced proteins. Non-limiting examples of cellulose-induced proteins include, without limitation, cellulases, GH61 enzymes, cellobiose dehydrogenases, lactonases, carbohydrate esterases, polysaccharide lyases, and cellulose binding domain-containing proteins. In certain aspects, a secreted protein of the present disclosure is encoded by NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, or NCU05137. In certain aspects, recombinant cells of the present disclosure have increased secretion of at least one, at least two, at least three, at least four, at least five, or more types of proteins.

In certain aspects, a recombinant cell of the present disclosure exhibits reduced expression of at least two β-glucosidase genes compared to the expression of the at least two β-glucosidase genes in a corresponding non-recombinant cell. In other embodiments, a recombinant cell of the present disclosure exhibits reduced expression of a cre-1 gene compared to the expression of the cre-1 gene in a corresponding non-recombinant cell.

As used herein, a "corresponding non-recombinant cell" refers to a cell that is of the same species as the recombinant cell and has been cultured under the same conditions as the recombinant cell, but lacks the modification of the recombinant cell that results in reduced gene expression in the recombinant cell. "Reduced expression" of a gene of the present disclosure refers to decreased levels of expression of a gene in a modified cell as compared to the levels of expression of the gene in a corresponding non-modified cell.

In certain aspects, the expression of the at least two β-glucosidase genes may be reduced by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In other aspects, the expression of the cre-1 gene may be reduced by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In a specific aspect of the present disclosure, the recombinant cell exhibiting reduced expression of at least two β-glucosidase genes further exhibits reduced expression of the gene creA/cre-1. Means for the reduction of creA/cre-1 expression may be gene silencing techniques, including siRNA, miRNA, antisense DNA, quelling or meiotic silencing. Gene silencing techniques may target creA/cre-1 or a creA/cre-1 regulator protein or RNA. CreA/cre-1 expression may be reduced by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another specific aspect of the present disclosure, the recombinant cell exhibiting reduced expression of at least two β-glucosidase genes may also be a cell in which the functional activity of the CreA/CRE-1 transcription factor has been reduced by overexpression of a dominant negative mutant or protein inhibitor. CreA/CRE-1 function may be reduced by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another specific aspect of the present disclosure, the recombinant cell exhibiting reduced expression of at least two β-glucosidase genes, and/or the recombinant cell exhibiting reduced expression levels of at least two β-glucosidase genes and reduced expression levels of the gene creA/cre-1, may further exhibit reduced expression of at least one β-mannosidase gene of the present disclosure. Means for the reduction of the β-mannosidase expression include, without limitation, gene silencing techniques, including siRNA, miRNA, antisense DNA, quelling or meiotic silencing. Gene silencing techniques may target the at least one β-mannosidase gene or a β-mannosidase gene regulator protein or RNA. β-Mannosidase gene expression may be reduced by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In certain aspects, expression of the β-mannosidase gene NCU00890 is reduced in a recombinant N. crassa cell.

In another specific aspect of the present disclosure, the recombinant cell exhibiting reduced expression of at least two β-glucosidase genes; the recombinant cell exhibiting reduced expression of at least two β-glucosidase genes and reduced expression of the gene creA/cre-1; and/or the recombinant cell exhibiting reduced expression of at least two β-glucosidase genes, reduced expression of the gene creA/cre-1, and reduced expression of at least one β-mannosidase gene may further exhibit reduced expression of at least one phospholipase gene or phospholipase-like gene of the present disclosure. Means for the reduction of the phospholipase expression include, without limitation, gene silencing techniques, including siRNA, miRNA, antisense DNA, quelling or meiotic silencing. Gene silencing techniques may target the at least one phospholipase gene or phospholipase-like gene or a gene regulator protein or RNA. Phospholipase gene or phospholipase-like gene expression may be reduced by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In certain aspects, expression of the gene NCU06650 is reduced in a recombinant N. crassa cell.

In a preferred embodiment of the present disclosure, expression of the β-glucosidase genes NCU00130, NCU04952, and NCU08755 is reduced in a recombinant N. crassa cell. In another preferred embodiment of the present disclosure, expression of the β-glucosidases genes NCU00130, NCU04952, and NCU08755, and expression of the cre-1 gene is reduced in a recombinant N. crassa cell. In still another preferred embodiment of the present disclosure, expression of the β-glucosidases genes NCU00130, NCU04952, and NCU08755, expression of the cre-1 gene, and expression of the β-mannosidase gene NCU00890 is reduced in a recombinant N. crassa cell. In a further preferred embodiment of the present disclosure, expression of the β-glucosidases genes NCU00130, NCU04952, and NCU08755, expression of the cre-1 gene, expression of the β-mannosidase gene NCU00890, and expression of the gene NCU06650 is reduced in a recombinant N. crassa cell.

In one aspect of the present disclosure, the recombinant cell exhibits reduced expression of the cre-1 gene. Means for the reduction of cre-1 expression include, without limitation, gene silencing techniques, including siRNA, miRNA, antisense DNA, quelling or meiotic silencing. Gene silencing techniques may target cre-1 or a cre-1 regulator protein or RNA. Cre-1 expression may be reduced in recombinant cells by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another aspect of the present disclosure, the functional activity of the CreA/CRE-1 transcription factor has been reduced in a recombinant cell by overexpression of a dominant negative mutant or a protein inhibitor. CreA/cre-1 function may be reduced by at least 10%, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

Variants, Sequence Identity, and Sequence Similarity

Methods of alignment of sequences for comparison are well-known in the art. For example, the determination of percent sequence identity between any two sequences can be accomplished using a mathematical algorithm. Non-limiting examples of such mathematical algorithms are the algorithm of Myers and Miller (1988) CABIOS 4:11 17; the local homology algorithm of Smith et al. (1981) Adv. Appl. Math. 2:482; the homology alignment algorithm of Needleman and Wunsch (1970) J. Mol. Biol. 48:443 453; the search-for-similarity-method of Pearson and Lipman (1988) Proc. Natl. Acad. Sci. 85:2444 2448; the algorithm of Karlin and Altschul (1990) Proc. Natl. Acad. Sci. USA 872264, modified as in Karlin and Altschul (1993) Proc. Natl. Acad. Sci. USA 90:5873 5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237 244 (1988); Higgins et al. (1989) CABIOS 5:151 153; Corpet et al. (1988) Nucleic Acids Res. 16:10881 90; Huang et al. (1992) CABIOS 8:155 65; and Pearson et al. (1994) Meth. Mol. Biol. 24:307 331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the present disclosure. BLAST protein searches can be performed with the BLASTX program, score=50, wordlength=3, to obtain amino acid sequences homologous to a protein or polypeptide of the present disclosure. To obtain gapped alignments for comparison purposes, Gapped BLAST (in BLAST 2.0) can be utilized as described in Altschul et al. (1997) Nucleic Acids Res. 25:3389. Alternatively, PSIBLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used. Alignment may also be performed manually by inspection.

As used herein, sequence identity or identity in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical and often differ by conservative amino acid substitutions, where amino acid residues are substituted for other amino acid residues with similar chemical properties (e.g., charge or hydrophobicity), do not change the functional properties of the molecule. When sequences differ in conservative substitutions, the percent sequence identity may be adjusted upwards to correct for the conservative nature of the substitution. Sequences that differ by such conservative substitutions are said to have sequence similarity or similarity. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

The nucleic acids may be synthesized, isolated, or manipulated using standard molecular biology techniques such as those described in Sambrook, J. et al. 2000. Molecular Cloning: A Laboratory Manual (Third Edition). Techniques may include cloning, expression of cDNA libraries, and amplification of mRNA or genomic DNA.

The nucleic acids of the present disclosure, or subsequences thereof, may be incorporated into a cloning vehicle including an expression cassette or vector. The cloning vehicle can be a viral vector, a plasmid, a phage, a phagemid, a cosmid, a fosmid, a bacteriophage, or an artificial chromosome. The viral vector can include an adenovirus vector, a retroviral vector, or an adeno-associated viral vector. The cloning vehicle can include a bacterial artificial chromosome (BAC), a plasmid, a bacteriophage P1-derived vector (PAC), a yeast artificial chromosome (YAC), or a mammalian artificial chromosome (MAC).

The nucleic acids may be operably linked to a promoter. The promoter can be a viral, bacterial, mammalian or plant promoter. The promoter can be a constitutive promoter, an inducible promoter, a tissue-specific promoter, or an environmentally regulated or a developmentally regulated promoter.

Methods for Increasing Secretion of a Protein

Other aspects of the present disclosure relate to methods for increasing secretion of a protein from a cell by providing any of the cells of the present disclosure capable of secreting at least one, at least two, at least three, at least four, at least five, or more types of proteins in response to cellulosic biomass or a saccharide; and inducing the cell to secrete the at least two, at least three, at least four, at least five, or more types of proteins by contacting the cell with cellulosic biomass or a saccharide.

Cellulosic biomass that may be used with the methods of the present disclosure may include, without limitation, one or more of a polysaccharide, an oligosaccharide, cellulose, microcrystalline cellulose, cellodextrin, cellobiose, cellotriose, cellotetraose, cellopentose, and cellohexose. In certain preferred embodiments, the cellulosic biomass includes cellobiose.

Saccharides that may be used with the methods of the present disclosure include, without limitation, a polysaccharide, an oligosaccharide, cellulose, microcrystalline cellulose, cellodextrin, cellobiose, cellotriose, cellotetraose, cellopentose, cellohexose, and sophorose. In certain preferred embodiments, the saccharide is cellobiose Types of proteins that may be secreted by recombinant cells of the present disclosure include, without limitation, cellulose-induced proteins. Non-limiting examples of cellulose-induced proteins include, without limitation, cellulases, GH61 enzymes, cellobiose dehydrogenases, lactonases, carbohydrate esterases, polysaccharide lyases, and cellulose binding domain-containing proteins. In certain aspects, a secreted protein of the present disclosure is encoded by NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, or NCU05137.

Accordingly, certain aspects of the present disclosure provide methods for increasing secretion of a protein from a cell by: providing a mutant cell, where the mutant cell contains inactivating mutations in two or more β-glucosidase genes, or contains an inactivating mutation in a cre-1 gene in the cell; and contacting the mutant cell with cellulosic biomass or a saccharide, where the cellulosic biomass or saccharide induces the mutant cell to secrete the protein. In certain aspects, the cellulosic biomass or saccharide induces the cell to secrete at least two, at least three, at least four, at least five, or more types of proteins.

In some aspects the method for increasing secretion of a protein from a cell includes the step of inducing the secretion of the protein in the presence of β-glucosidase inhibitors. Preferably, the β-glucosidase inhibitor is nojirimycin.

Other aspects of the present disclosure provide methods for increasing secretion of a protein from a cell, by: providing a recombinant cell, where the recombinant cell exhibits reduced expression of two or more β-glucosidase genes compared to the expression of the at least two β-glucosidase genes in a corresponding non-recombinant cell, or exhibits reduced expression of a cre-1 gene compared to the expression of the cre-1 gene in a corresponding non-recombinant cell; and contacting the recombinant cell with cellulosic biomass or a saccharide, where the cellulosic biomass or saccharide induces the recombinant cell to secrete the protein. In certain aspects, the cellulosic biomass or saccharide induces the cell to secrete at least two, at least three, at least four, at least five, or more types of proteins.

Methods for Degrading Lignocellulosic Biomass

Further aspects of the present disclosure relate to methods for the degradation of biomass by providing lignocellulosic biomass; providing any of the mutant or recombinant cells of the present disclosure; inducing the cell to secrete at least one, at least two, at least three, at least four, at least five, or more types of proteins by contacting the cell with cellulosic biomass or a saccharide; and contacting the induced cell with the lignocellulosic biomass, where the secreted at least one, at least two, at least three, at least four, at least five, or more types of proteins degrade the lignocellulosic biomass.

Lignocellulosic biomass generally refers to plant biomass containing cellulose and other carbohydrate polymers that are tightly bound to lignin. Examples of suitable lignocellulosic biomass include, without limitation, plant material, municipal solid waste, municipal paper waste, wood residues, sawmill and paper mill discards, and agricultural residues. Examples of suitable plant material includes, without limitation, *Miscanthus*, energy grass, elephant grass, switchgrass, cord grass, rye grass, reed canary grass, common reed, wheat straw, barley straw, canola straw, oat straw, corn stover, soybean stover, oat hulls, oat spelt, sorghum, rice hulls, sugarcane bagasse, corn fiber, barley, oats, flax, wheat, linseed, citrus pulp, cottonseed, groundnut, rapeseed, sunflower, peas, lupines, palm kernel, coconut, konjac, locust bean gum, gum guar, soy beans, Distillers Dried Grains with Solubles (DDGS), Blue Stem, corncobs, pine, conifer softwood, eucalyptus, birchwood, willow, aspen, poplar wood, hybrid poplar, energy cane, short-rotation woody crop, crop residue, yard waste, and combinations thereof.

Cellulosic biomass that may be used with the methods of the present disclosure may include, without limitation, one or more of a polysaccharide, an oligosaccharide, cellulose, microcrystalline cellulose, cellodextrin, cellobiose, cellotriose, cellotetraose, cellopentose, and cellohexose. In certain preferred embodiments, the cellulosic biomass includes cellobiose.

Saccharides that may be used with the methods of the present disclosure include, without limitation, a polysaccharide, an oligosaccharide, cellulose, microcrystalline cellulose, cellodextrin, cellobiose, cellotriose, cellotetraose, cellopentose, cellohexose, and sophorose. In certain preferred embodiments, the saccharide is cellobiose Types of proteins that may be secreted by recombinant cells of the present disclosure include, without limitation, cellulose-induced proteins. Non-limiting examples of cellulose-induced proteins include, without limitation, cellulases, GH61 enzymes, cellobiose dehydrogenases, lactonases, carbohydrate esterases, polysaccharide lyases, and cellulose binding domain-containing proteins. In certain aspects, a secreted protein of the present disclosure is encoded by NCU07340, NCU09680, NCU07898, NCU00762, NCU08760, NCU05057, NCU02240, NCU07190, NCU07898, NCU08760, NCU00206, NCU07143, NCU09491, NCU09664, NCU05598, NCU09764, or NCU05137.

In one aspect of the present disclosure, the method for degrading lignocellulosic biomass includes the step of contacting lignocellulosic biomass with mutant cells of the present disclosure as described above in the presence of β-glucosidase inhibitors. Preferably, the β-glucosidase inhibitor is nojirimycin.

Applications

The methods described herein can be practiced in combination with other methods useful for degrading lignocellulosic biomass.

For example, lignocellulosic biomass may be subjected to pretreatment including ammonia fiber expansion (AFEX), steam explosion, treatment with alkaline aqueous solutions, acidic solutions, organic solvents, ionic liquids (IL), electrolyzed water, phosphoric acid, and combinations thereof. Pretreatments that remove lignin from the plant material may increase the overall amount of sugar released from the hemicellulose.

EXAMPLES

The following Examples are merely illustrative and are not meant to limit any aspects of the present disclosure in any way.

Example 1

The following example relates to the characterization of the cellulase transcription and cellulolytic enzyme production induced in the *N. crassa* triple fl-glucosidase gene deletion strain and the triple β-glucosidase and cre-1 gene deletion strain.

Materials and Methods

Strains

Strains were obtained from the Fungal Genetics Stock Center (FGSC) including the *Neurospora crassa* wild-type (WT) (FGSC 2489), the cre-1 gene deletion (Δcre-1) (FGSC 10372), and deletion strains for the intracellular β-glucosidase NCU00130 (FGSC 11822 and FGSC 11823), and extracellular β-glucosidases: NCU08755 (FGSC 18387 and FGSC 18388) and NCU04952 (FGSC 13731 and FGSC 13732).

The quadruple deletion produced by performing sequential crosses of the single deletions using the method described by the Fungal Genetics Stock Center (FGSC) The genotype of all deletion strains was confirmed by using a gene-specific primer and a common primer for the hygromycin (hph) cassette. The forward primer for hph was:

```
hph Middle FWD:
                                      [SEQ ID NO: 4]
    5'-CGA CAG ACG TCG CGG TGA GTT CAG-3'
```

Reverse Primers Were:

```
                                      [SEQ ID NO: 5]
    NCU00130:    5'-TAG TGT ACA AAC CCC AAG C-3'

[SEQ ID NO: 6]
    NCU004953:   5'-AAC ACA CAC ACA CAC ACT GG-3'

[SEQ ID NO: 7]
    NCU08755:    5'-ACA GTG GAG GTG AGA AAG G-3'

[SEQ ID NO: 8]
    NCU08807:    5'-GTA CTT ACG CAG TAG CGT GG-3'
```

Transcriptional Studies Growth

Strains were inoculated at an OD595 equal to 0.05 in 50 ml Vogel's salts with 2% (wt/vol) sucrose in a 250 ml Erlenmeyer flask and grown under constant light at 200 rpm for 16 hours. The biomass was then spun at 4000 rpm for 10 minutes and washed in Vogel's twice to remove any excess sucrose. The biomass was then added to a new 50 ml culture with 2% (wt/vol) sucrose, cellobiose (Sigma) or Avicel® PH 101 (Avicel®). Cultures were induced for 4 hours under constant light at 200 rpm. The culture biomass was then harvested by filtration over a Whatman glass microfiber filter (GF/F) on a Buchner funnel and washed with 50 ml Vogel's, biomass was flash frozen in liquid Nitrogen and stored at −80° C.

RNA Isolation

Total RNA from frozen samples was isolated using Zirconia/Silica beads (0.2 g, 0.5 mm diameter; Biospec) and a Mini-Beadbeater-96 (Biospec) with 1 mL TRIzol reagent (Invitrogen) according to manufacturer's instructions. Total RNA was further purified by digestion with TURBO DNA-free (Ambion) and an RNeasy kit (Qiagen). RNA integrity was checked by Nanodrop and agarose gel electrophoresis.

Quantitative Real-Time RT-PCR

Quantitative RT-PCR was performed using the EXPRESS One-Step SYBR GreenER Kit (Invitrogen) and the StepOnePlus Real-Time PCR System (Applied Biosystems). Reactions were performed in triplicate with a total reaction volume of 10 ul including 300 nM each forward and reverse primers and 75 ng template RNA. Data Analysis was performed by the StepOne Software (Applied Biosystems) using Relative Quantitation/Comparative CT ($\Delta\Delta$CT). Data was normalized to the endogenous control actin with expression on sucrose as the reference sample. Error bars indicate a 95% confidence interval. The RT-PCR primers were used as described in (Tian et al., 2009).

```
Actin:
                                      [SEQ ID NO: 9]
5'-TGA TCT TAC CGA CTA CCT-3'

[SEQ ID NO: 10]
5'-CAG AGC TTC TCC TTG ATG-3'

CBHI (NCU07340)
                                      [SEQ ID NO: 11]
5'-ATC TGG GAA GCG AAC AAA G-3'

[SEQ ID NO: 12]
5'-TAG CGG TCG TCG GAA TAG-3'

CBHII (NCU09680)
                                      [SEQ ID NO: 13]
5'-CCC ATC ACC ACT ACT ACC-3'

[SEQ ID NO: 14]
5'-CCA GCC CTG AAC ACC AAG-3'

Endoglucanase 2
(NCU00762)
                                      [SEQ ID NO: 15]
5'-GAG TTC ACA TTC CCT GAC A-3'

[SEQ ID NO: 16]
5'-CGA AGC CAA CAC GGA AGA-3'

GH61 (NCU07898)
                                      [SEQ ID NO: 17]
5'-TCA AGC CCG GTT ACT ATC-3'

[SEQ ID NO: 18]
5'-AAC CTG TCA CCT GCA ACT-3'

CRE-1
                                      [SEQ ID NO: 19]
5'-CTACTGCCATGTCCTCTC-3'

[SEQ ID NO: 20]
5'-TATCAGGACCACTTTGGCTTC-3'

B-Glucosidase
(NCU00130)
                                      [SEQ ID NO: 21]
5'-GTTCGGCGTTACCTATGT-3'

[SEQ ID NO: 22]
5'-AGAGTCAAAGAGCGGCTTC-3'
```

Protein Secretion/Enzyme Activity Studies

Strains were inoculated at an OD595 equal to 0.05 in 100 ml Vogel's salts with 1% (wt/vol) sucrose in a 250 ml Erlenmeyer flask and grown under constant light at 200 rpm for 24 hours. Cultures were then induced with 2% sucrose, 2% cellobiose, 1% sucrose/1% cellobiose, or 1% sucrose/1% Avicel®. Cultures continued to grow under constant light at 200 rpm for 5 days with supernatant collected at 1, 2, 3, 4 and 5 day. The collected supernatant was filtered through a 0.2 μm PES filter to remove biomass before being stored at −20° C. until all samples were collected. To visualize the secreted proteins, 15 μl of unconcentrated supernatant was run on a Criterion 10% Tris-HCL polyacrylamide gel and stained with Thermo Scientific GelCode Blue Stain Reagent.

Endo-1,4-β-Glucanase activity was measured using Azo-CM-Cellulose (Megazyme) according to the manufacturers suggested method. Briefly, 100 μl Azo-CM-Cellulose substrate solution pre-heated to 37° C. was mixed with 96.5 μl culture supernatant and 3.5 μl 3M sodium acetate pH5.0 in a deep-well 96-well plate. Following mixing, the plate was incubated for 10 minutes at 37° C. The reaction was stopped by the addition of 0.5 ml Precipitant Solution and centrifuged for 10 minutes at 1000 g. 50 μl sample was transferred to a flat-bottom 96-well assay plate in triplicate and the absorbance was read in a Beckman Coulter Paradigm plate reader at an optical density of 590 nm. The data is presented as a percentage of the wild type activity on Avicel® after 4 days.

Exoglucanase (Cellobiohydrolase I) activity was measured using a 4-Methylumbelliferyl β-D-cellobioside (MuLac) assay. This assay mainly measures the activity of CBH-1 and activity is expressed as the change in fluorescence over time resulting in the slope of a best-fit line as an indication of enzyme activity. Prior to performing this assay, any excess sugars in the culture supernatant were removed by passing the supernatant over a 5,000 Dalton concentrator (sartorius stedim Vivaspin 500). Retained proteins were washed twice with 50 mM sodium acetate pH 5 and diluted to 2 μg/μl to assure that the assay remained in the linear range. The assay was performed in a total volume of 100 μl containing 10 μg total protein and had a final concentration of 1.0 mM MuLac and 50 mM sodium acetate pH 5. The assay was performed in a Beckman Coulter Paradigm plate reader set at 40° C. with excitation/emission wavelengths of 360/465 nm with readings every 30 seconds for 10 minutes. The slope of the best-fit line represents the MuLac activity for an individual culture supernatant. The MuLac activity is normalized to the initial dilution required to obtain a 2 μg/μl concentration in order to represent the undiluted activity. The activity of recombinant cellobiohydrolase-1 was used as a standard and data is presented as a percentage of the wild type activity on Avicel® after 4 days.

Avicelase activity was determined according to Tian et al. (Tian et al, 2009) as a measure for glucose and cellobiose concentrations in 7-day culture supernatants from WT, Δcre-1 and other deletion strains. In brief, one volume of 7-day culture supernatants from WT and Δcre-1 strains were mixed with one volume of substrate solution containing 5 mg/ml Avicel® and 50 mM NaAc buffer, pH 5.0 at 37° C. After 5 hours of shaking glucose and cellobiose concentrations were measured by coupled enzyme assays.

Results

Induction of Cellulase Transcription in Triple β-Glucosidase Gene Deletion

Figure 2A:
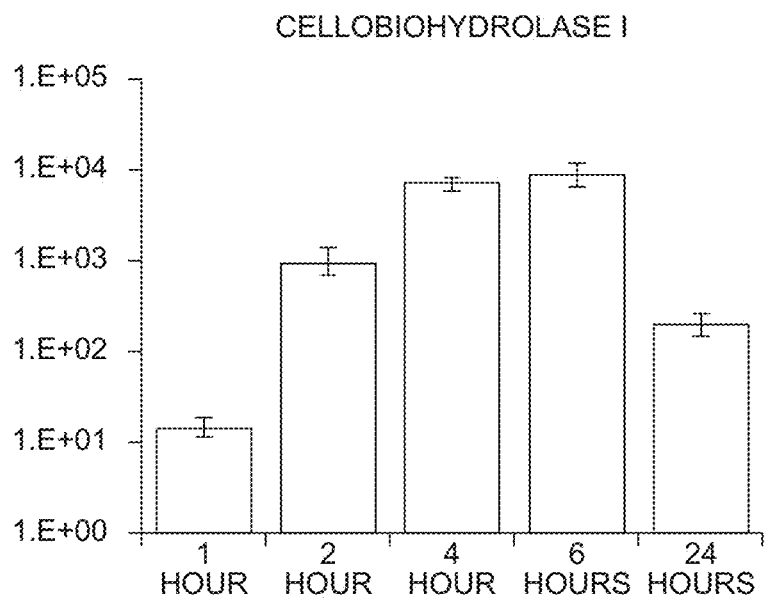
FIGS. 2A-2B show gene expression time courses for cellulase enzymes in *N. crassa*.
Figure 2B:
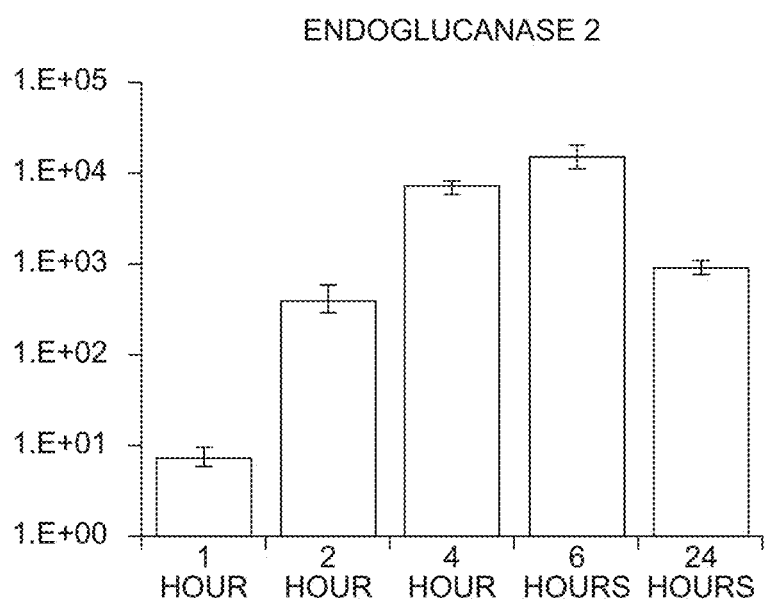

In order to study early time points of cellulase induction in *N. crassa*, cultures were first grown for 16-hours on sucrose to produce a significant amount of biomass and subsequently transferred to a fresh culture containing an alternate carbon source. An initial time course on the WT strain demonstrated that a four-hour induction period provides a maximal difference in gene expression on sucrose versus Avicel® for the cellobiohydrolase I gene cbh-1 and the endoglucanase 2 gene gh5-1 (FIGS. 2A-2B).

Three β-glucosidases (NCU08755, NCU04952, and NCU00130) have been shown to be significantly increased at the transcriptional level during growth of WT *N. crassa* on Avicel® or *Miscanthus* (Tian et al, 2009). Additionally, NCU04952 was identified as a secreted protein by mass spectrometry (Tian et al, 2009). To determine whether these three β-glucosidases play a role in the induction of cellulases on cellobiose, three strains containing deletions of single β-glucosidases were screened by qRT-PCR for cellobiose-mediated induction of cellulases. However, no single β-glucosidase deletion mutant showed a significant effect. To overcome the problem of redundancy of β-glucosidase activities and the possibility of strong catabolite repression at minimal glucose concentrations, a triple β-glucosidase deletion strain was constructed.

Figure 3:
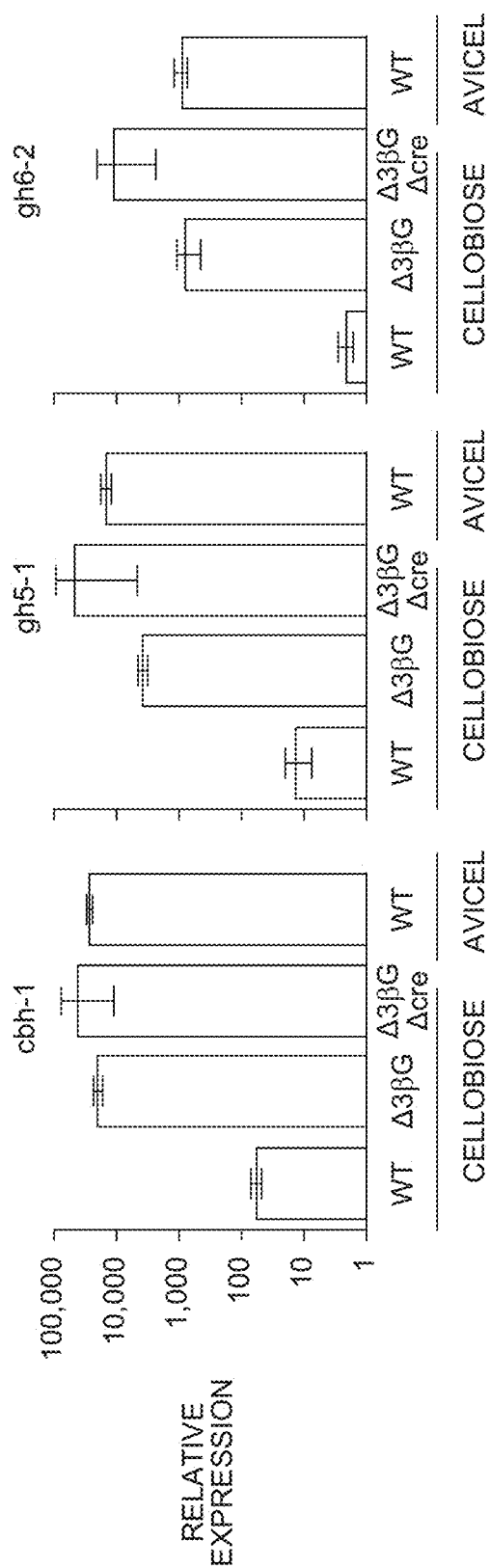
FIG. 3 shows gene expression of select cellulases after 4 hours induction with 0.2% cellobiose or 1% Avicel® in WT, Δ3βG and Δ3βGΔcre. Gene expression levels of cbh-1, gh6-2, and gh5-1 were normalized to 1 when induced with 1% sucrose. Actin was used as an endogenous control in all samples. Each strain was grown in triplicate and error bars indicate 1 standard deviation.

On Avicel®, the triple β-glucosidase deletion strain showed a similar induction phenotype as the WT strain for the three cellulases examined (FIG. 3). However, on 2% cellobiose, while the WT strain only shows a 20-fold induction for cbh-1, and no change for cbh-2 or eg-2 compared to their relative expression on sucrose, the triple β-glucosidase mutant shows a very different picture: cbh-1 has a 6,500-fold increase in relative expression over expression on sucrose; cbh-2 has a 2,100-fold increase in relative expression and eg-2 has a 2,200-fold increase in relative expression (FIG. 3).

Induction of Cellulase Transcription in Triple β-Glucosidase and Cre-1 Gene Deletion By crossing the triple β-glucosidase deletion with the Δcre-1 strain a mutant was generated that transcriptionally responds to cellobiose in the same way as the WT strain responds to Avicel®. Induction of this mutant with either cellobiose or Avicel® shows similar transcriptional induction of cbh-1, cbh-2 and eg-2 as the triple β-glucosidase deletion on cellobiose or Avicel® and as the WT strain on Avicel® (FIG. 3). These results demonstrate that cre-1 acts as a general cellulolytic regulon and that cre-1 deletion causes the permanent de-repression of *N. crassa* cellulases.

Figure 4:
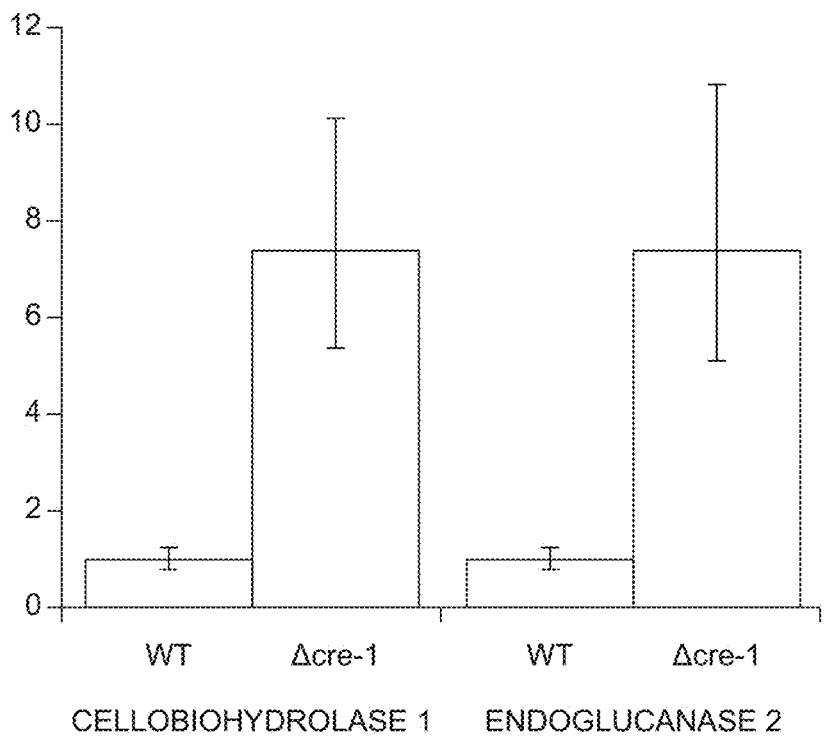
FIG. 4 shows gene expression levels of cellulases cellobiohydrolase I (cbh-1, NCU07340) and endoglucanase 2 (gh5-1, NCU00762) in Δcre-1 at 4 hrs post transfer to minimal media with 2% sucrose. Expression levels for both genes were normalized to 1 for wild type induction with 2% sucrose. Actin (NCU04173) gene expression levels were used as an endogenous control. Each reaction was done in triplicate and error bars indicate a 95% confidence interval.

Cre-1 deletion is known to moderately increase the transcription and secretion of cellulases on Avicel®. Similarly, Cre-1 is known to allow for approximately 7-fold increases in the basal level of transcription for cbh-1 and eg-2 on sucrose compared to WT expression on sucrose (FIG. 4). When induced with cellobiose, Δcre-1 shows a 600-fold increase in transcription of cbh-1 and an 80-fold increase in eg-2 above their expression on sucrose in the same strain (FIG. 3). While this increase in expression is significant relative to expression on sucrose, it is dwarfed by the 11,000-fold increase in cbh-1 and the 8000-fold increase in eg-2 seen when Δcre-1 is induced with Avicel® (FIG. 3).

In order to show that the transcriptional response to cellobiose is specific and not due to a general starvation effect, a no carbon control experiment was performed. After an initial 16-hour pre-growth phase on sucrose a gentle wash was conducted with minimal media to remove any remaining sucrose and finally the biomass was transferred to a culture containing minimal media without any added carbon source. Because these cultures were processed in the same way as the cultures with added sucrose, cellobiose or Avicel®, the transcriptional data obtained through RT-PCR will show the general affect of starvation on cellulase transcription.

Figure 5:
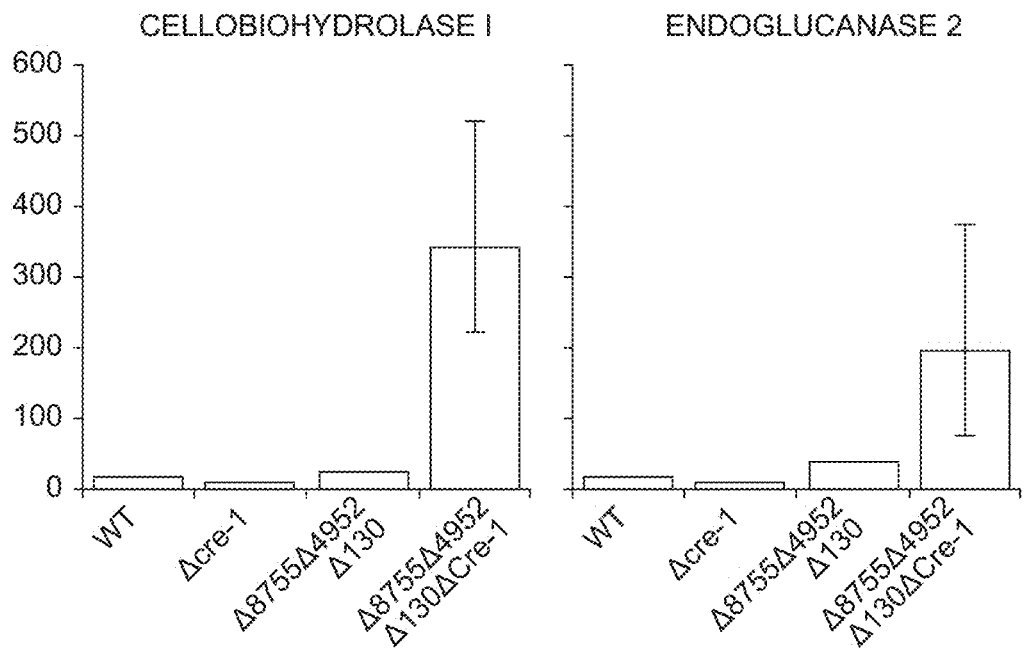
FIG. 5 shows gene expression levels of cellulases cellobiohydrolase I (cbh-1, NCU07340) and endoglucanase 2 (gh5-1, NCU00762) under starvation conditions in wild type (WT), Δcre-1, Δ4952Δ8755Δ130, and Δ4952Δ8755Δ130Δcre-1. Expression levels for all genes were normalized to 1 when induced with 2% sucrose. Strains were grown in minimal media with 2% sucrose for 16 hrs followed by 4 hrs growth in minimal media with no carbon source added. Actin (NCU04173) gene expression levels were used as an endogenous control in all samples. Each reaction was done in triplicates and error bars indicate a 95% confidence interval.

FIG. 5 shows that while the WT strain, Δcre-1, and the triple β-glucosidase deletion show a slight induction due to starvation (three to thirty-fold increases), the triple β-glucosidase/cre-1 deletion has a larger increase in transcription of cbh-1 and eg-2 under these conditions. Relative to triple β-glucosidase/cre-1 deletion growth on sucrose, its response to starvation is a 340 and 200-fold induction of cbh-1 and eg-2 respectively. These effects are minor compared to the 10,000 to 20,000-fold induction of cbh-1 and eg-2 observed on Avicel® or cellobiose. These results therefore demonstrate that the transcriptional response of these *N. crassa* cellulases on Avicel® and cellobiose is specific and not a general response to starvation.

Figure 6A:
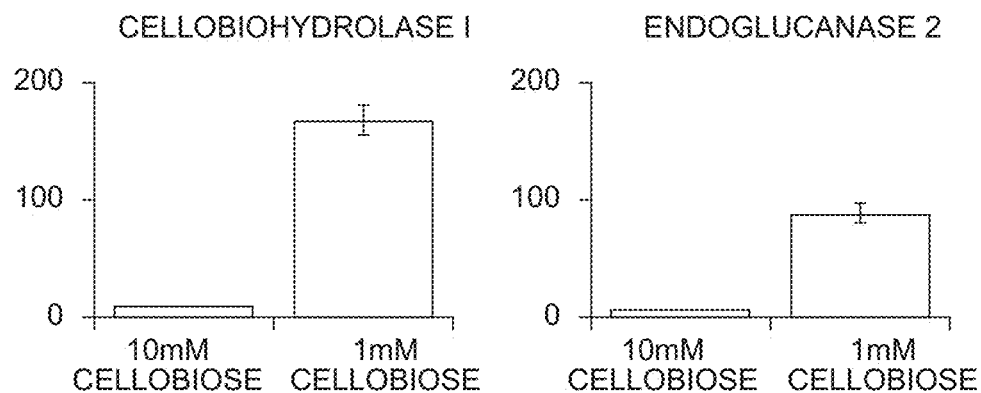
FIGS. 6A-6C show gene expression levels of cellulases cellobiohydrolase I (cbh-1, NCU07340) and endoglucanase 2 (gh5-1, NCU00762) after 4 hour induction with either 10 mM or 1 mM cellobiose.
Figure 6B:
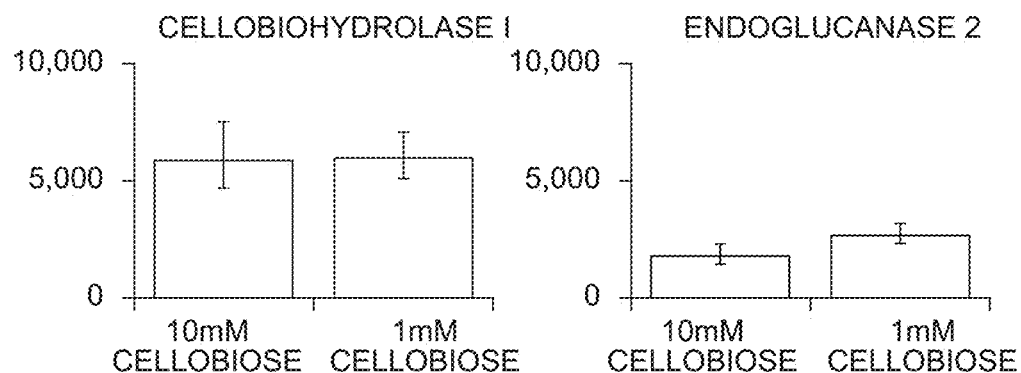
Figure 6C:
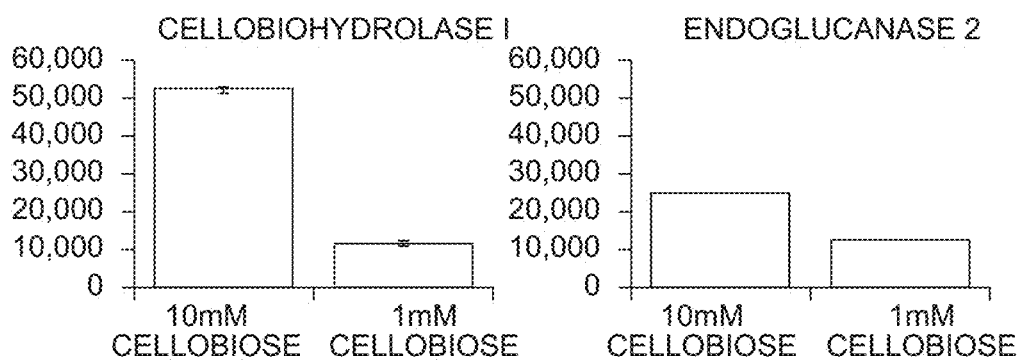

During cellulose hydrolysis in nature cellobiose and glucose do not accumulate to levels high enough to cause significant glucose repression. This phenomenon can be reproduced in vitro by varying the experimental concentrations of cellobiose. FIGS. 6A-6C shows that while induction of cellulases in the wild type strain is significantly reduced relative to the deletion strains, the WT cellulase expression is concentration dependent, with the lower 1 mM cellobiose concentration acting as a better inducer than the higher 10 mM concentration. By removing the activity of the major β-glucosidases, a 25-fold increase over wild type induction is achieved at either cellobiose concentration. Moreover, after deleting the catabolite repressor CRE-1, increasing cellobiose concentrations no longer limit enzyme induction (FIGS. 6A-6C).

Figure 7A:
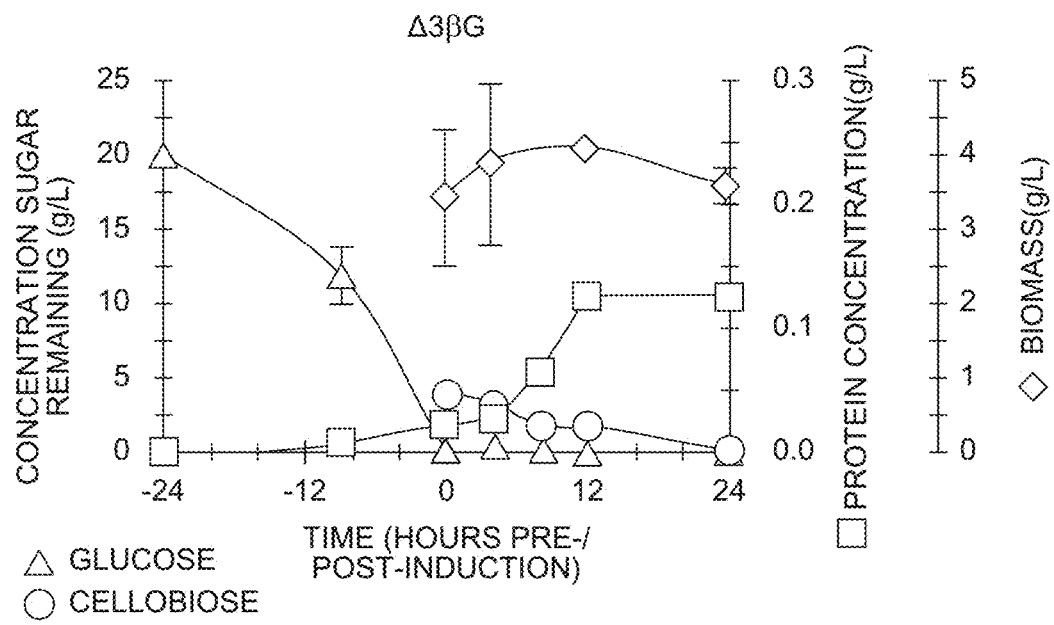
FIGS. 7A-7F summarize protein production and enzyme activity in WT, Δ3βG, and Δ3βGΔcre strains after induction with cellobiose or Avicel®.
Figure 7B:
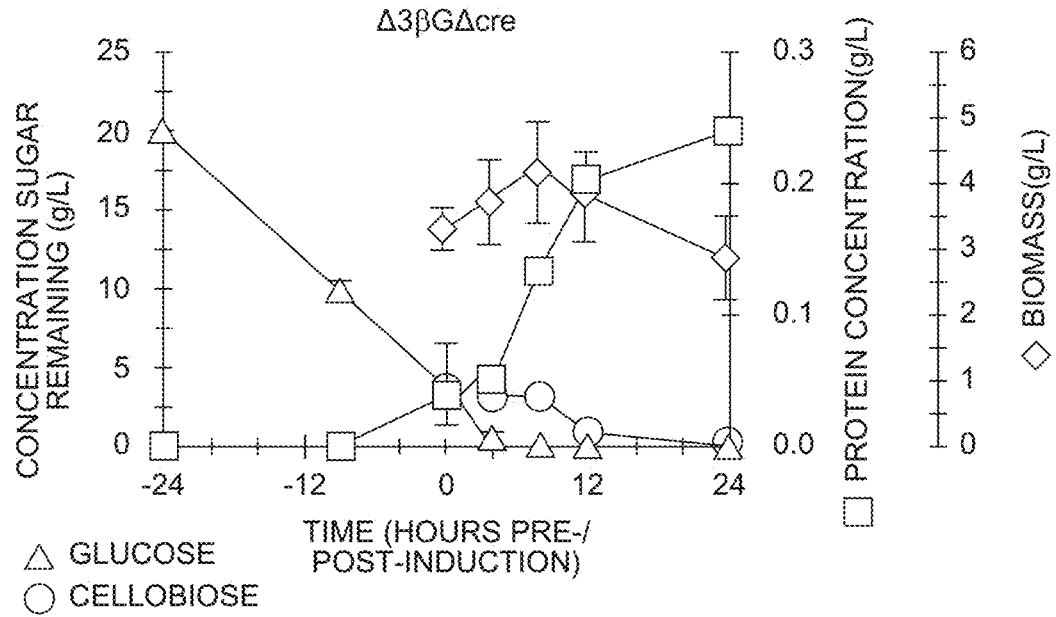
Figure 7C:
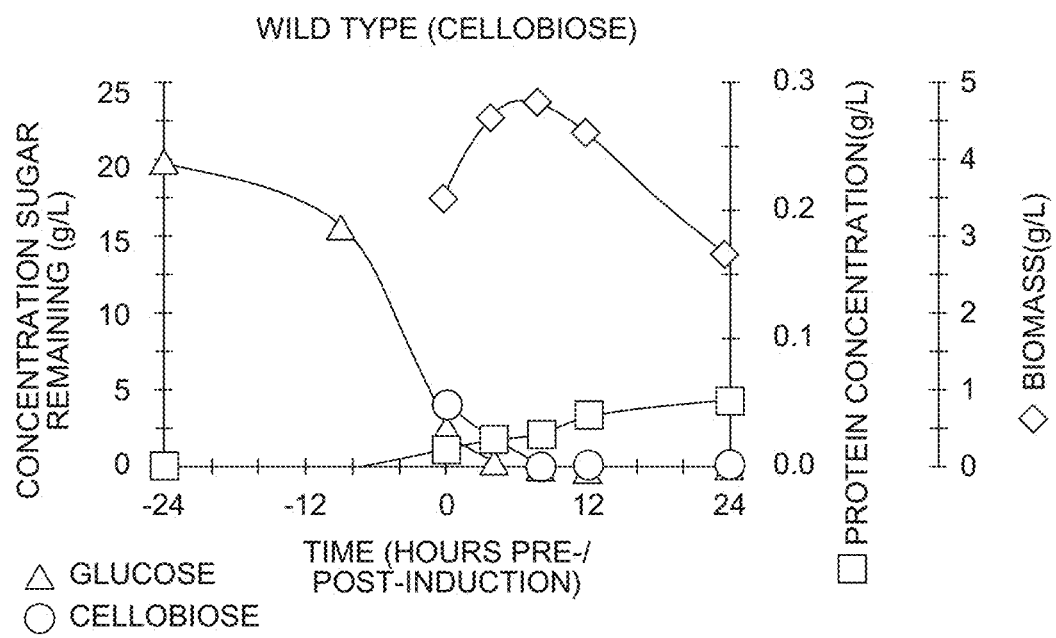
Figure 7D:
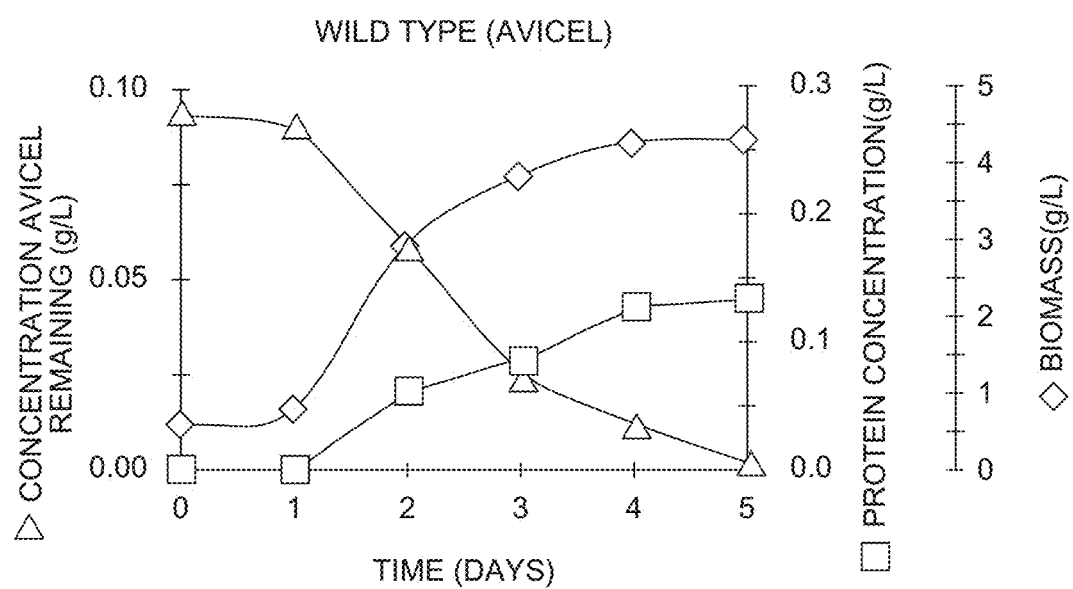
Figure 7E:
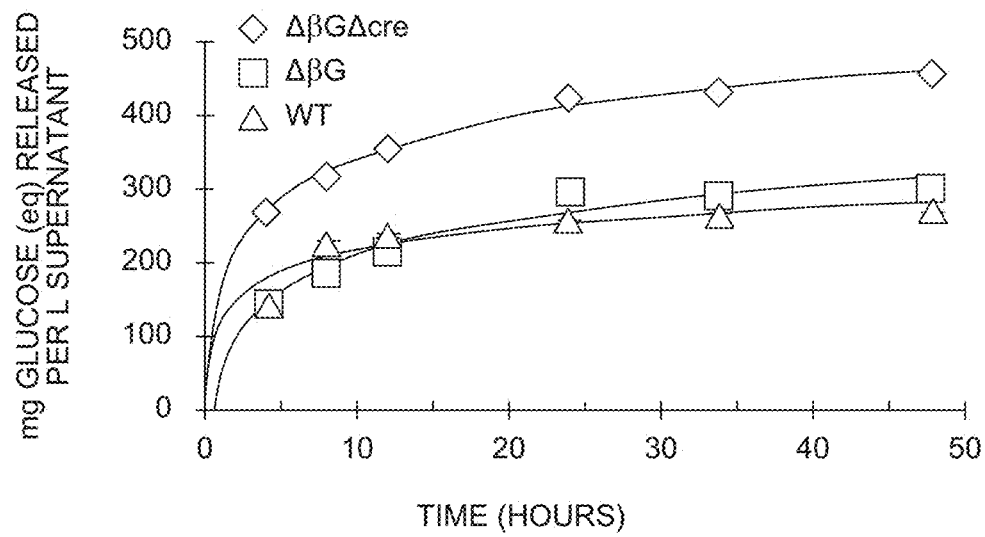
Figure 7F:
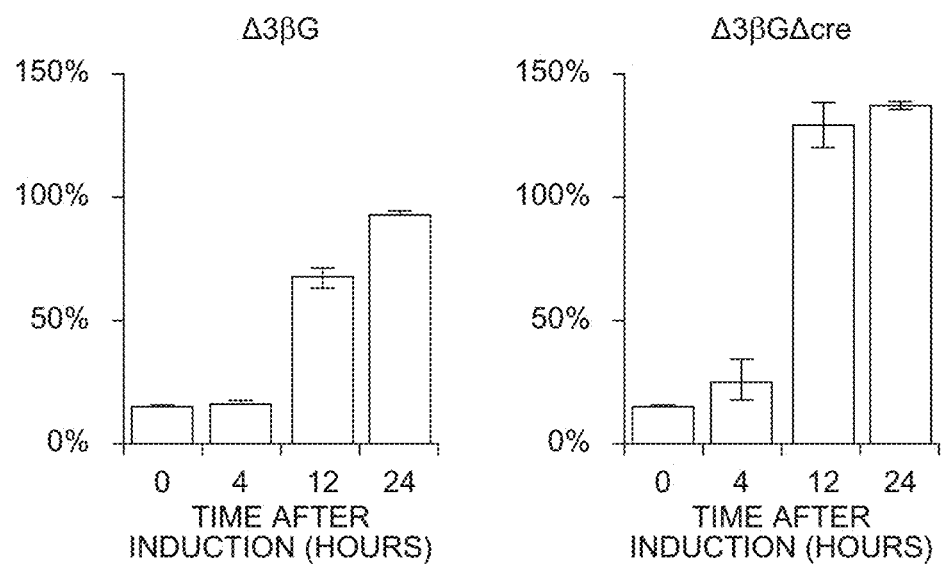
Figure 8A:
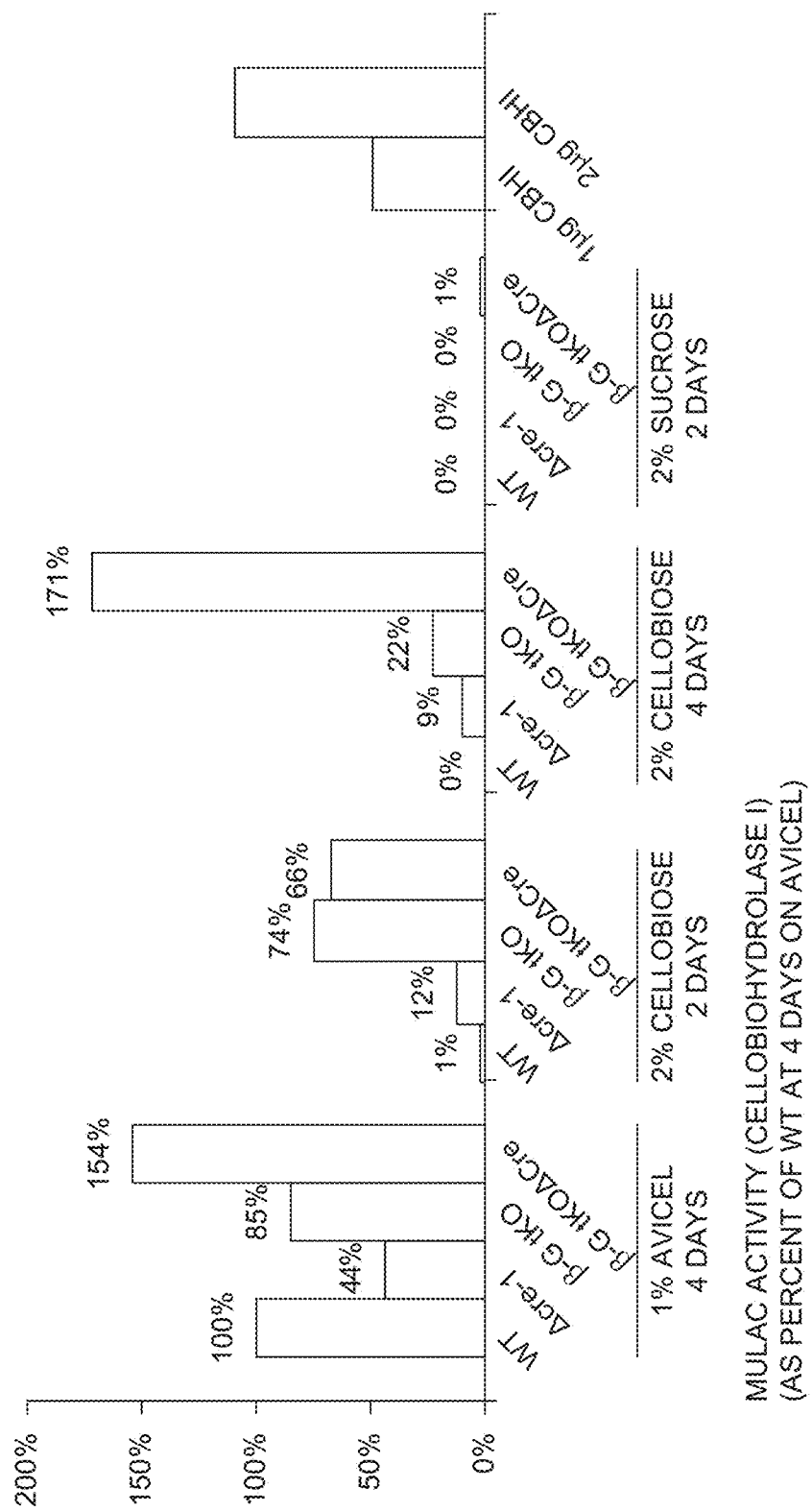
FIGS. 8A-8B compare MuLac activities (cellobiohydrolase I) in culture filtrates from wild type (WT), Δcre-1, Δ4952Δ8755Δ130, and Δ4952Δ8755Δ130Δcre-1.
Figure 8B:
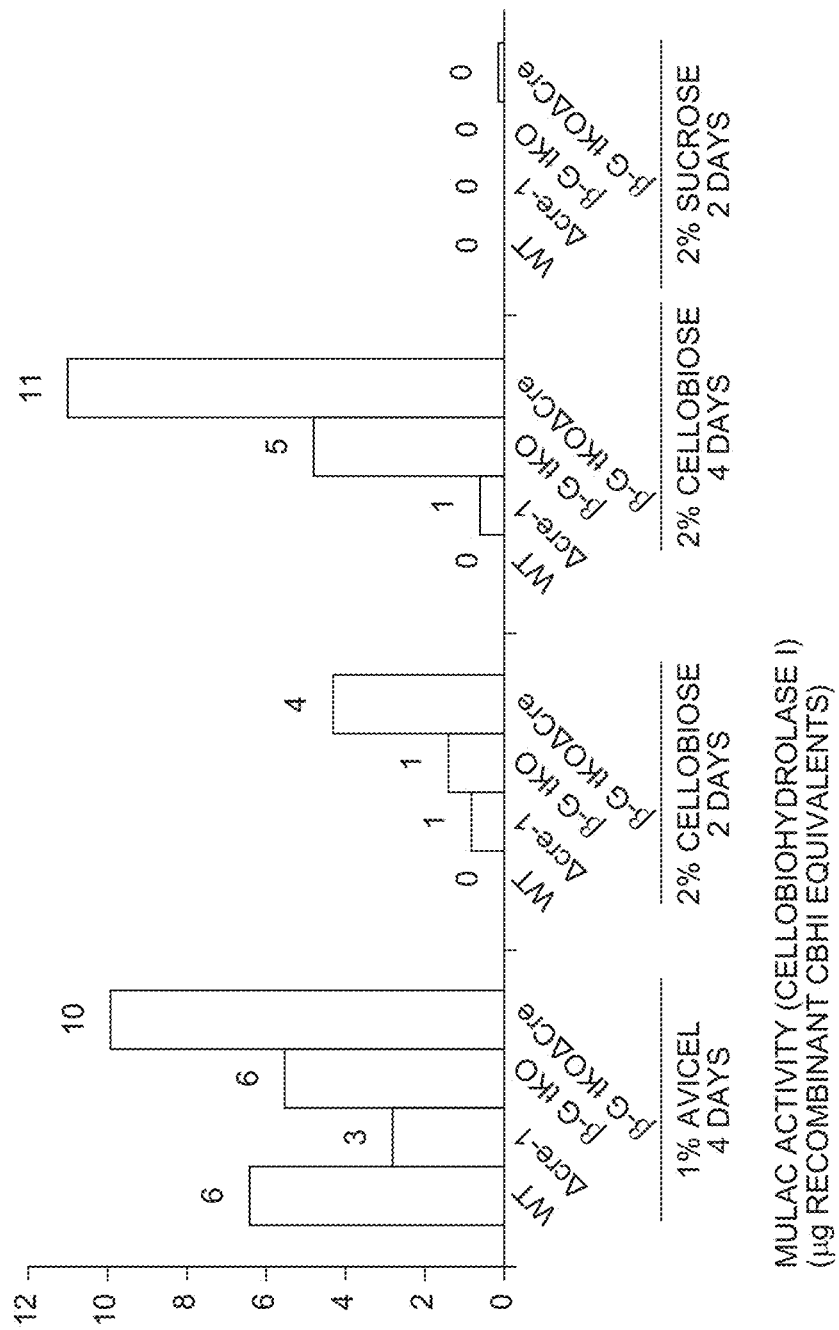
Figure 9:
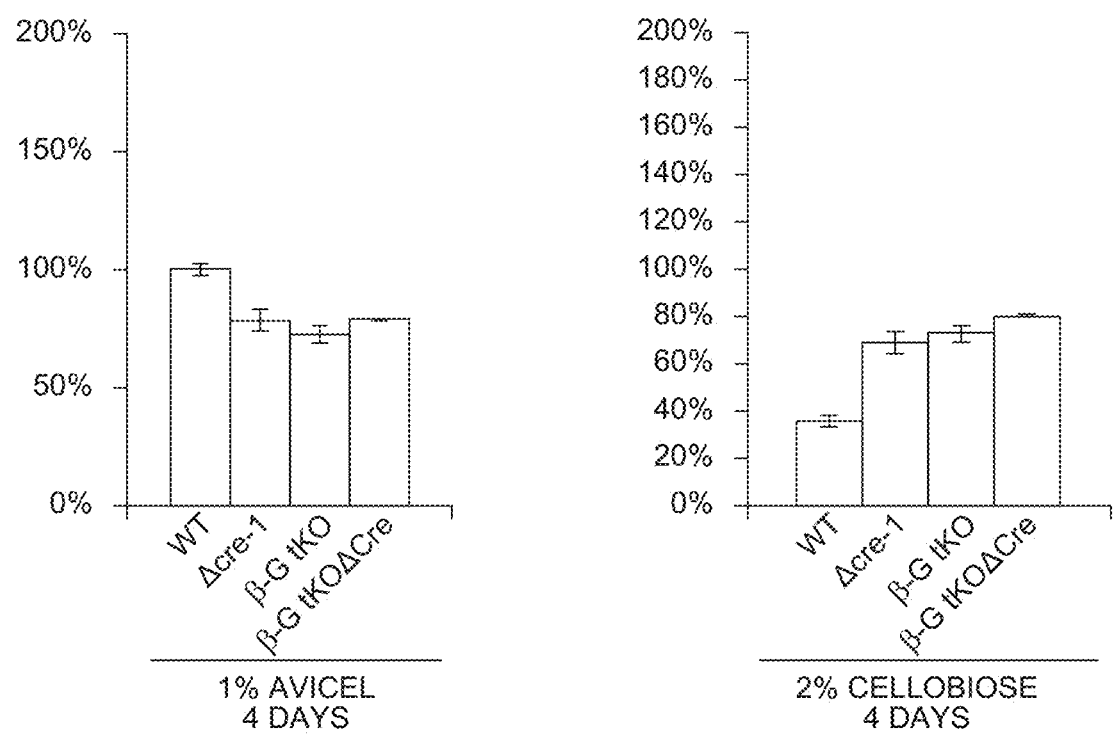
FIG. 9 compares Azo-CM-cellulose (endo-1,4-β-glucanase) activities in culture filtrates from wild type (WT), Δcre-1, Δ4952Δ8755Δ130, and Δ4952Δ8755Δ130Δcre-1. Strains were grown in 1% sucrose for 24 hrs followed by 4 days 2% sucrose, 1% Avicel®, or 2% cellobiose. The endo-1,4-β-glucanase activity is presented as a percentage of the wild type activity on Avicel® after 4 days and of activity. Note: No data is shown for sucrose cultures because Azo-CM-cellulose activity was not detectable for any of the 4 strains.

Deletion of β-Glucosidase Genes Shows Increased Cellulolytic Enzyme Production when Induced with Cellobiose The triple β-glucosidase deletion shows a very similar result to the wild type culture when induced with sucrose or Avicel®. On sucrose, there is very little secreted protein (180 µg/ml) after 2 days (FIGS. 7A-7F), and those that are secreted have no activity towards MuLac (FIGS. 8A-8B). When induced with Avicel®, by day 4 we can see a significant concentration of proteins in the supernatant (FIGS. 7A-7F). This culture supernatant has an Azo-CM-Cellulose and MuLac activity similar to that for the wild type cultures at the same time point (5.5 µg CBHI equivalent) (FIGS. 8A-8B and 9). While this deletion is similar to wild type for the sucrose and Avicel® cultures, it responds very differently to cellobiose. At two days on cellobiose, we can see MuLac activity equivalent to 1.4 µg recombinant CBHI and by 4 days, this value has significantly increased to 4.84 µg recombinant CBHI equivalent (FIG. 8B), and the Azo-CM-Cellulose activity is similar to the wild type when grown on Avicel® (FIG. 9). This specific enzyme activity indicates that in addition to inducing transcription, cellobiose can directly stimulate the secretion of active cellulases when we minimize the affect of carbon catabolite repression.

Deletion of Cre-1 Increased Cellulolytic Enzyme Production

Figure 10A:
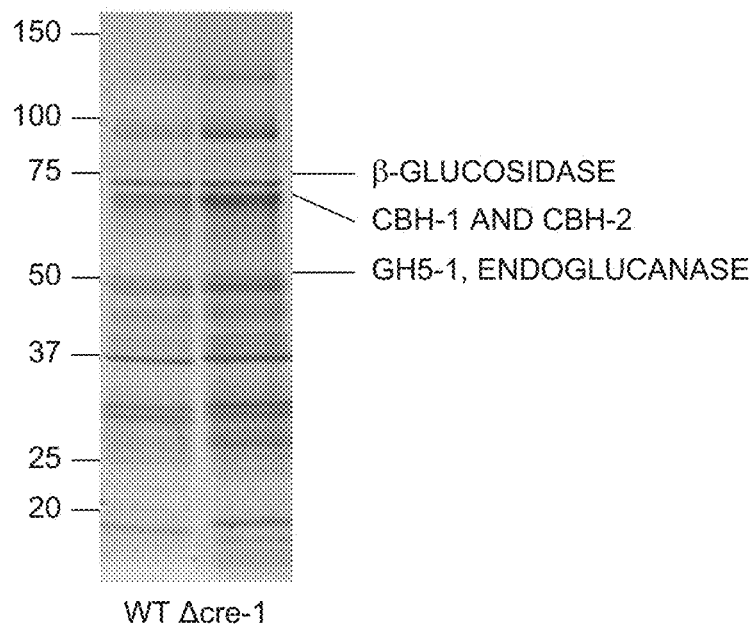
FIGS. 10A-10B compare the phenotypes of N. crassa wild type (WT) and Δcre-1 strains.
Figure 10B:
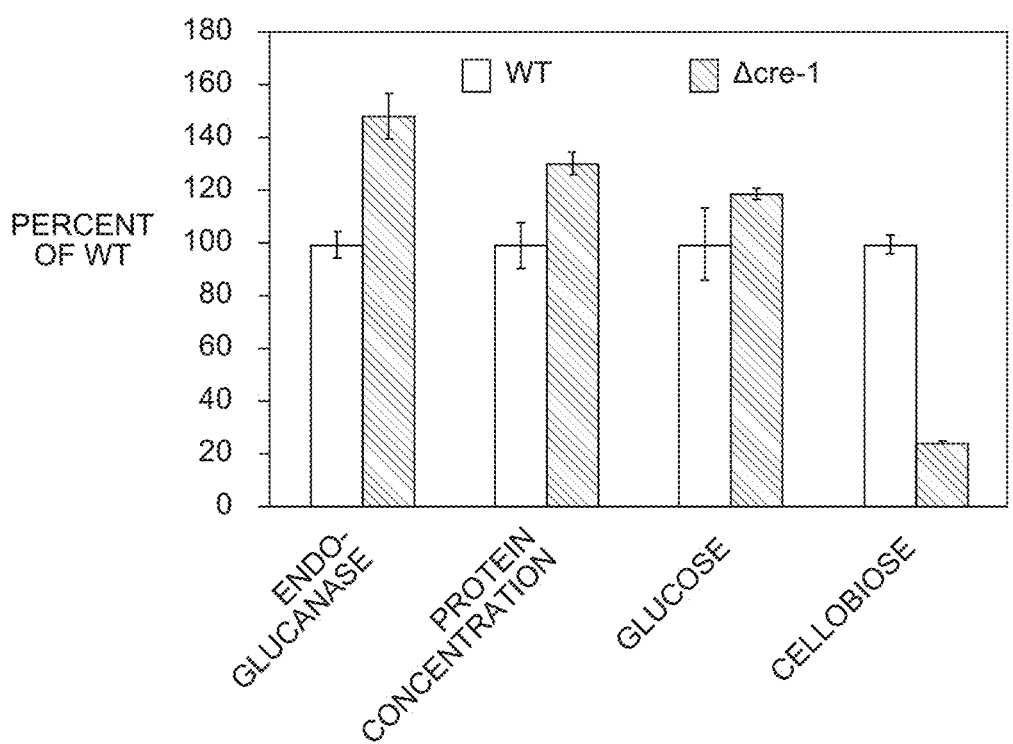
Figure 11A:
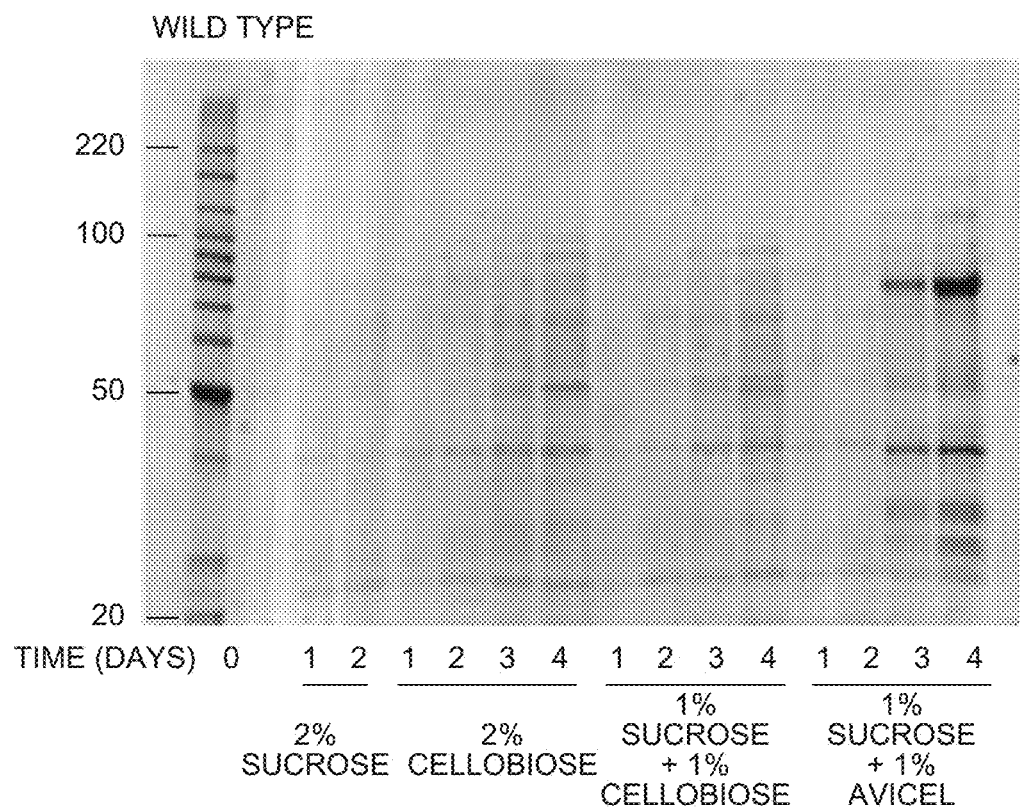
FIGS. 11A-11D show a SDS-PAGE analysis of secreted proteins in culture filtrates from wild type (WT), Δcre-1, Δ4952Δ8755Δ130, and Δ4952Δ8755Δ130Δcre-1 deletion mutants. Strains were grown in 1% sucrose for 24 hours followed by 4 days in 2% sucrose, 2% cellobiose, 1% sucrose and 1% cellobiose, or 1% sucrose and 1% Avicel® with samples taken at 24 hour time points. 15 µl filtered culture supernatant was run on a Criterion 10% Tris-HCl polyacrylamide gel and stained with Thermo Scientific GelCode Blue Stain Reagent. Note: The protein running at 72 kDa in Δcre-1 and Δ4952Δ8755Δ130Δcre-1 on sucrose has been identified using Mass Spectrometry as NCU01517 (Glucoamylase 1).
Figure 11B:
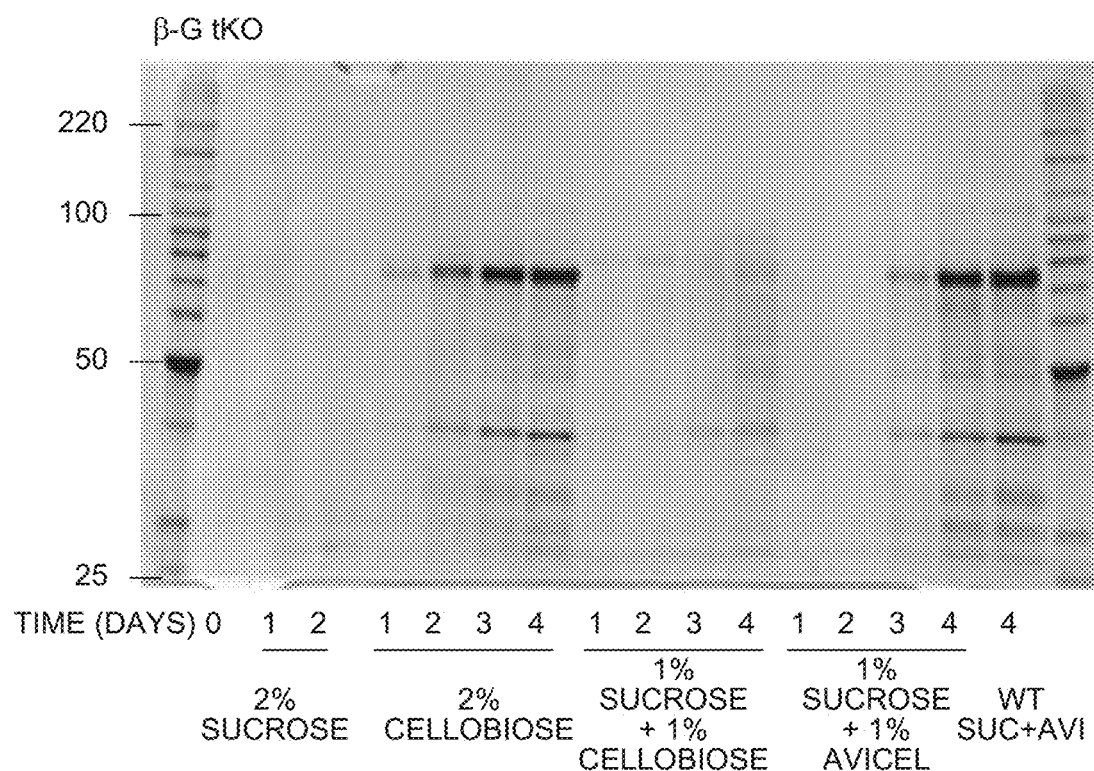
Figure 11C:
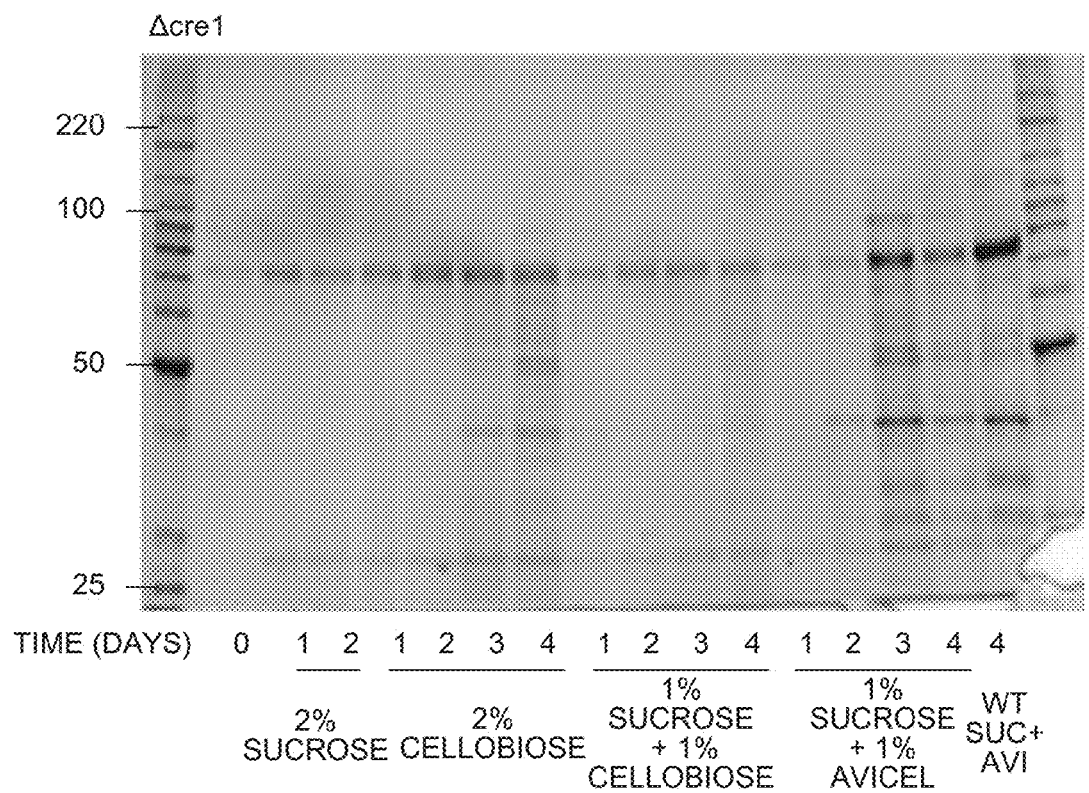
Figure 11D:
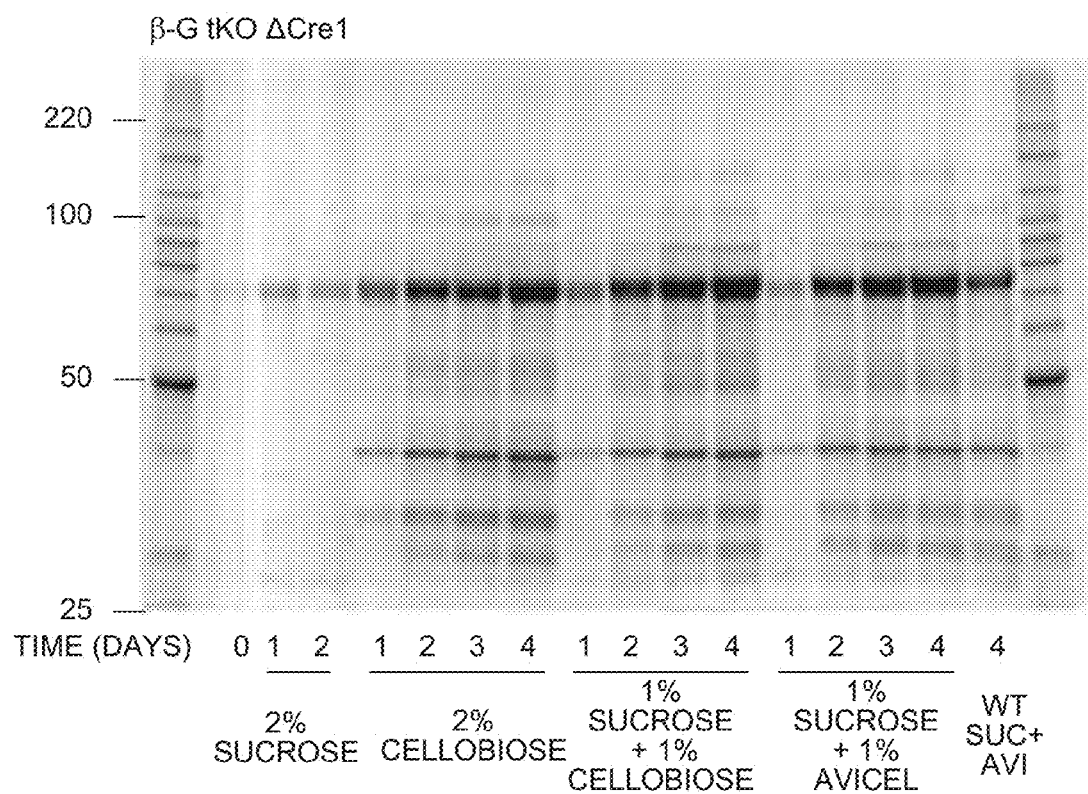

To investigate the role of CRE-1 for *N. crassa* growth on cellulolytic media the relative growth rates of Δcre-1 and wild type (WT) strains were compared on different carbon sources. When grown on 2% Avicel® medium as a sole carbon source, the Δcre-1 strain consumed Avicel® faster than WT (e.g. 3-4 days vs. 5-6 days), secreted 30% more extracellular protein and showed 50% higher endoglucanase activity (FIGS. 10A and 10B). An aggregate Avicelase assay (which measures combined β-glucosidase, endo- and exo-cellulase activity) showed 20% higher glucose concentrations in the Δcre-1 strain as compared to WT (FIG. 10B). However, less cellobiose was detected, suggesting increased secretion of β-glucosidase (which converts cellobiose into glucose; FIG. 10B) in the Δcre-1 strain.

Figure 12:
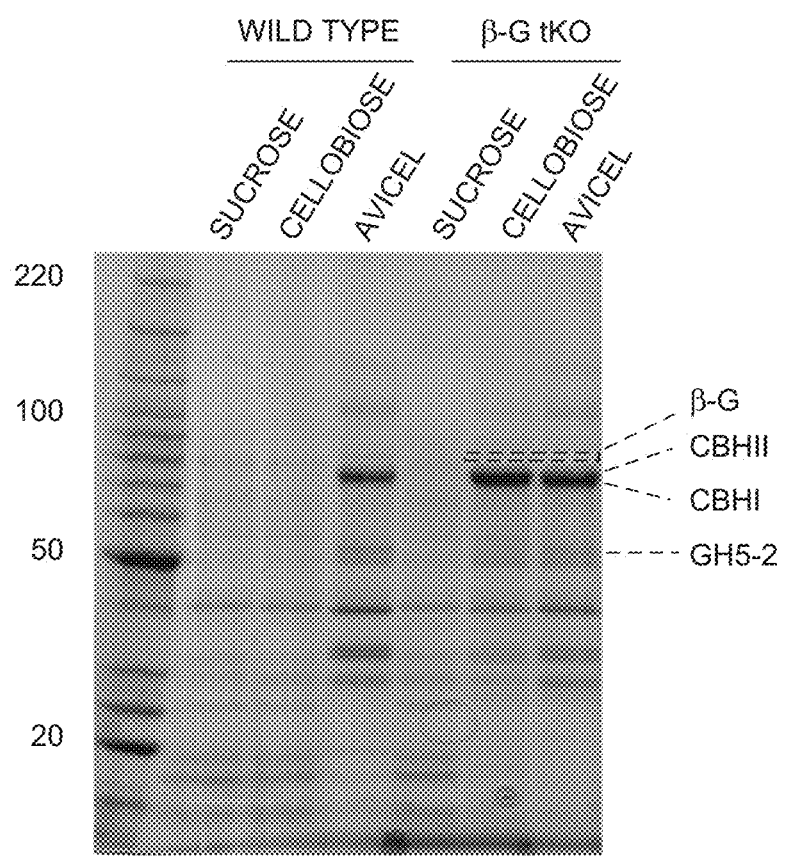
FIG. 12 shows a SDS-PAGE analysis of secreted proteins in culture filtrates from wild type N. crassa and Δ4952Δ8755Δ130 (β-G tKO). Strains were grown in 1% sucrose for 24 hrs followed by 5 days in 2% sucrose, 2% cellobiose, or 2% Avicel®. Protein bands representing cellobiohydrolase 1 (cbh-1, NCU07340), cellobiohydrolase 2 (cbh-2, NCU09680), and endoglucanase 2 (gh5-2, NCU00762) are marked. In addition, β-glucosidase (NCU04952) is marked in the wild type and its absence is outlined in the triple deletion Δ4952Δ8755Δ130.

Compared to the WT strain, Δcre-1 generally appears to produce more secreted proteins. This is evident not only in the cellobiose and Avicel® induced cultures, but also at 48 hours on sucrose (FIGS. 7A-7F and 11A-11D) where the secreted protein concentration is approximately twice that seen for WT (481 µg/ml vs. 270 µg/ml). While the Δcre-1 secretes more protein on sucrose, these proteins do not exhibit any activity towards MuLac (FIGS. 8A-8B). While the most obvious band at 70 kDa, runs at the same molecular weight as CBH-1/2, the lack of activity implies that this is either an inactive form of CBH-1/2 or a different non-cellulolytic protein. Similar to what was seen in the transcriptional studies, Δcre-1 shows a slight increase in cellulase secretion on cellobiose (653 µg/ml) (FIGS. 7A-7F), which results in a modest increase in activity towards MuLac (0.8 ug) (FIG. 8B). In addition, when induced with Avicel®, the MuLac activity at 4 days is less than the activity of wild type (2.8 ug CBHI equivalent) (FIG. 8B). However, this effect might be due to starvation as the overall protein-banding pattern is generally lighter at 4 days as compared to 3 days (FIG. 12).

Deletion of β-Glucosidase Genes and Cre-1 Shows Increased Cellulolytic Enzyme Production when Induced with Cellobiose The triple β-glucosidase/Δcre-1 deletion strain is similar to the cre-1 deletion strain in that it seems to constitutively secrete more enzymes than the wildtype and the pattern visible on a protein gel under sucrose or Avicel® induction look very similar for these two strains (FIGS. 11A-11D). The major difference between the Δcre-1 and triple β-glucosidase/Δcre-1 deletion strains is the affect of cellobiose on the activity of the secreted proteins (FIGS. 8A-8B). By four days on cellobiose, this mutant is capable of producing more than 11 µg CBHI equivalent, which is even more than is produced on Avicel® at this same timepoint (FIG. 8B). In addition, the Azo-CMC activity assay indicates that this strain produces a similar amount of endo-1,4-β-glucanase activity in either an Avicel® or cellobiose inducing culture (FIG. 9).

Example 2

The following example relates to the identification of orthologues of the *N. crassa* fl-glucosidase genes NCU00130, NCU04952, and NCU08755.
Materials and Methods BLASTp searches were conducted using the National Center for Biotechnology Information (NCBI) non-redundant amino acid database using the NCU00130, NCU04952, and NCU08755 amino acid sequences as queries. Sequence hits from the BLASTp searches were aligned in MEGA5 using ClustalW2.

Phylogenetic trees were generated using the Neighbor-Joining method (Saitou N. and Nei M., 1987). The evolutionary distances were computed using the Poisson correction method (Zuckerkandl E. and Pauling L., 1965) and are in the units of the number of amino acid substitutions per site. Evolutionary analyses were conducted in MEGA5 (Tamura K., Dudley J., Nei M., and Kumar S., 2007).
Results The results of the ClustalW amino acid sequence alignments for NCU00130, NCU04952, and NCU08755 orthologues in closely related fungi are shown in FIGS. 13AA-13E.

Figure 14:
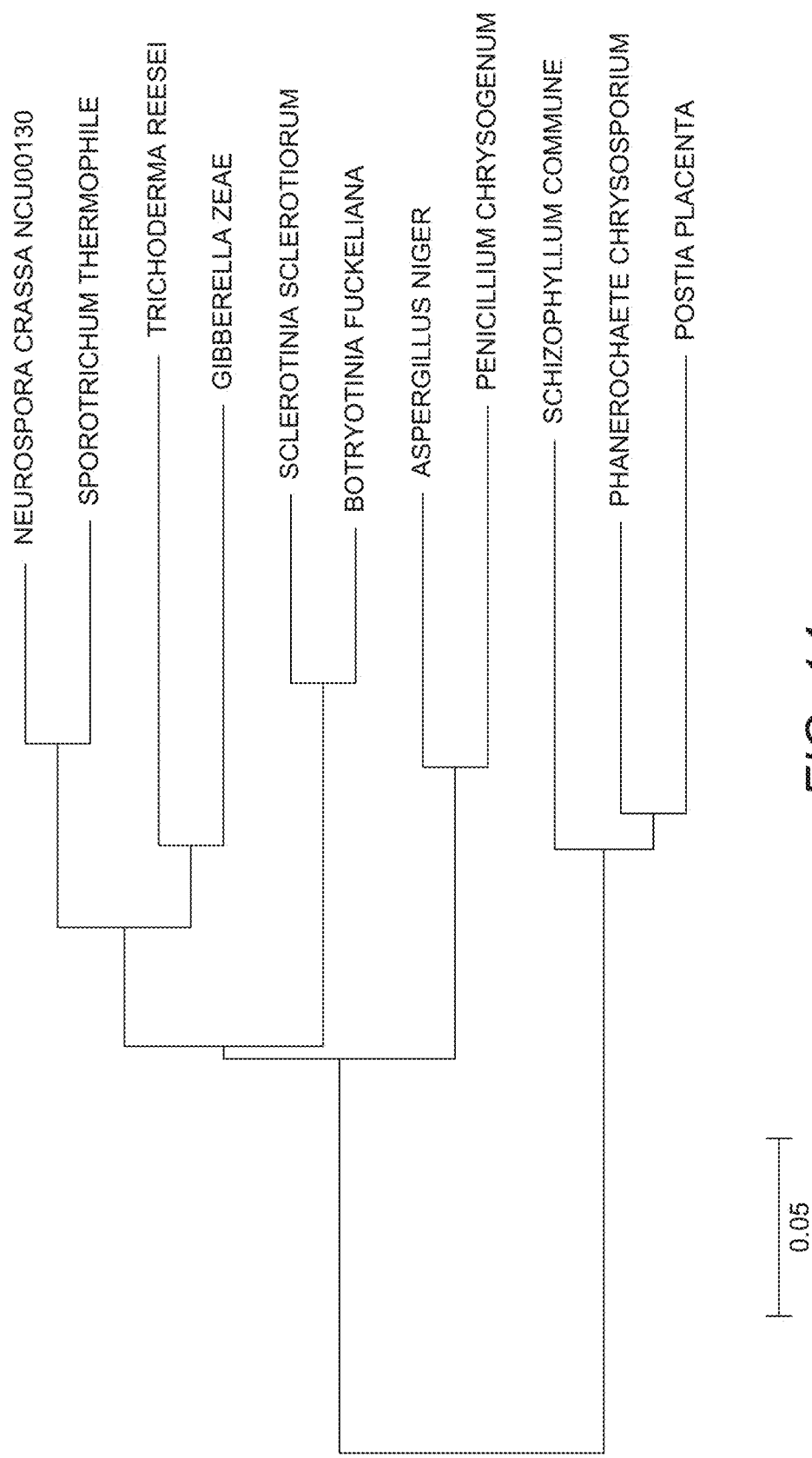
FIG. 14 shows the evolutionary relationships of β-glucosidase NCU00130 orthologues. The evolutionary history was inferred using the Neighbor-Joining method (Saitou N. and Nei M., 1987). The optimal tree with the sum of branch length=1.56132503 is shown. The tree is drawn to scale, with branch lengths in the same units as those of the evolutionary distances used to infer the phylogenetic tree. The evolutionary distances were computed using the Poisson correction method (Zuckerkandl E. and Pauling L., 1965) and are in the units of the number of amino acid substitutions per site. The analysis involved 11 amino acid sequences. All positions containing gaps and missing data were eliminated. There were a total of 447 positions in the final dataset. Evolutionary analyses were conducted in MEGA5 (Tamura K, Dudley J., Nei M., and Kumar S., 2007).

The phylogenetic tree of the β-glucosidase NCU00130 is depicted in FIG. 14.

Figure 15:
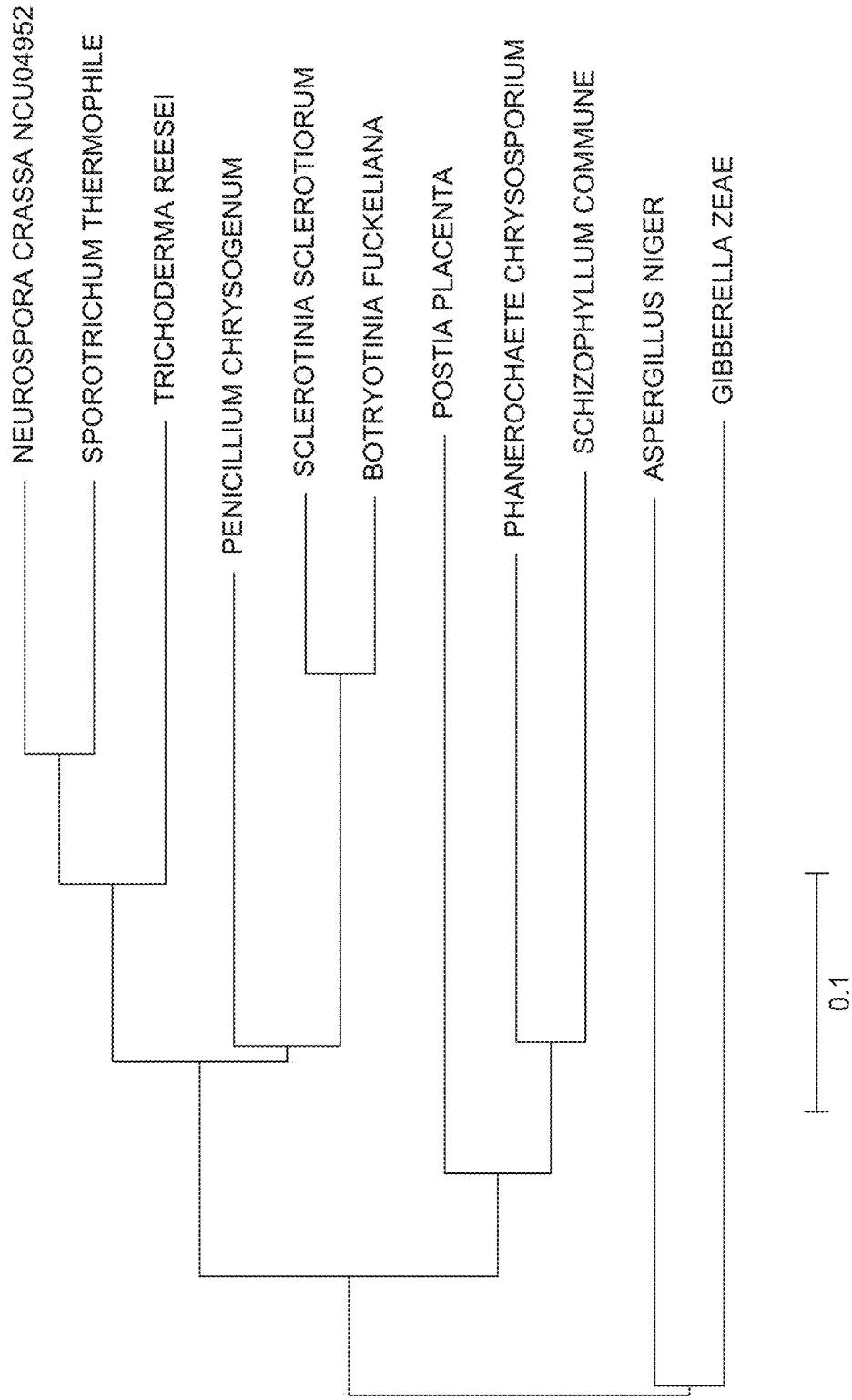
FIG. 15 shows the evolutionary relationships of β-glucosidase NCU04952 orthologues. The optimal tree with the sum of branch length=2.84018960 is shown. The analysis involved 11 amino acid sequences. There were a total of 690 positions in the final dataset.

The phylogenetic tree of the β-glucosidase NCU04952 is depicted in FIG. 15.

Figure 16:
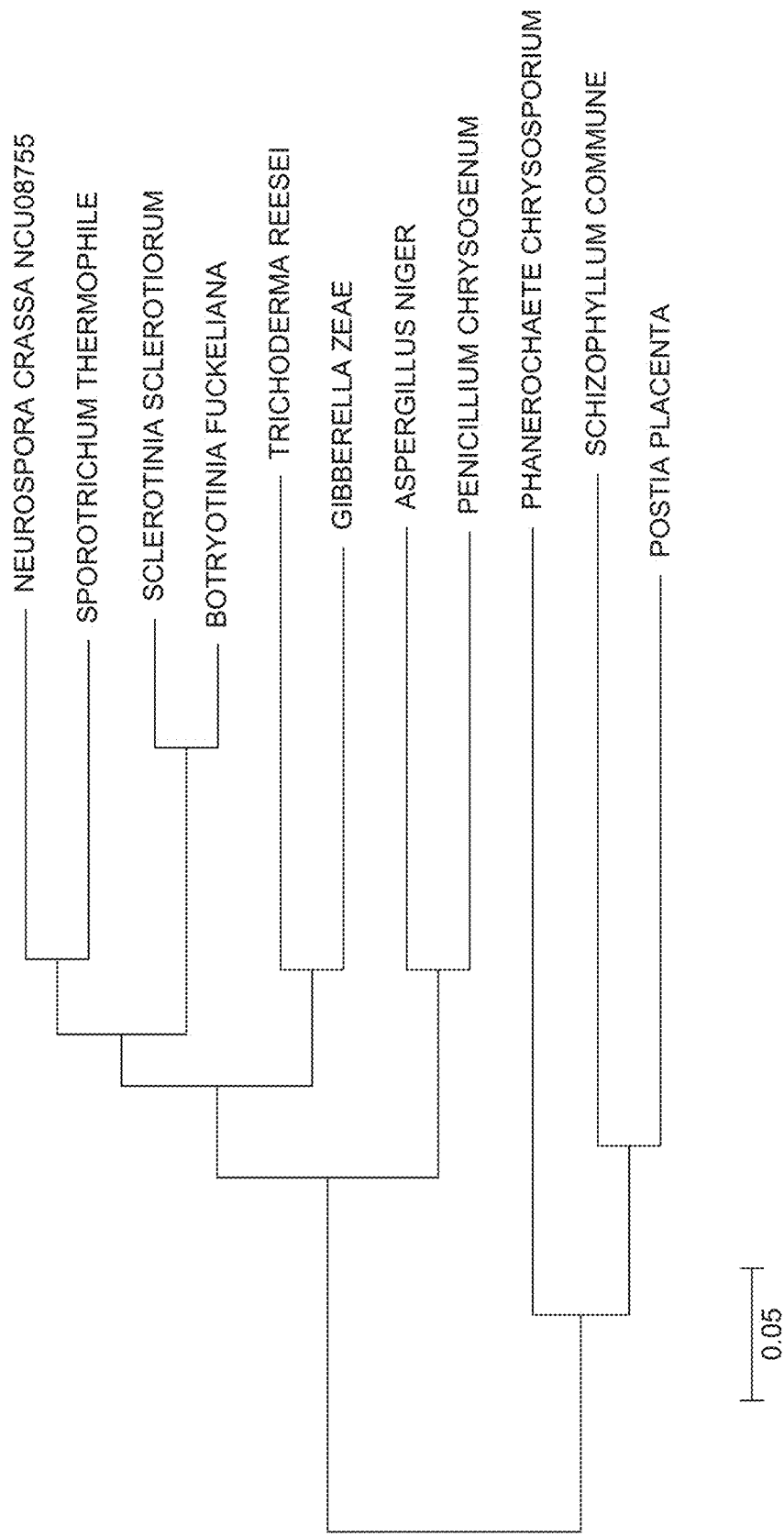
FIG. 16 shows the evolutionary relationships of β-glucosidase NCU08755 orthologues. The optimal tree with the sum of branch length=2.37353896 is shown. The analysis involved 11 amino acid sequences. There were a total of 709 positions in the final dataset.

The phylogenetic tree of the β-glucosidase NCU08755 is depicted in FIG. 16.

Example 3

The following example relates to the identification and characterization of the proteins secreted at higher levels from the triple β-glucosidase gene deletion *N. crassa* strain, and the triple β-glucosidase and cre-1 *N. crassa* deletion strain.
Materials and Methods
Strains Strains obtained from the Fungal Genetics Stock Center (FGSC) include the wild type (FGSC 2489), and deletion strains for the intracellular β-glucosidase NCU00130 (FGSC 11822 and FGSC 11823), and extracellular β-glucosidases: NCU08755 (FGSC 18387 and FGSC 18388) and NCU04952 (FGSC 13731 and FGSC 13732). The homokaryon cre-1 deletion strain (NCU08807) is described in (44). Multiple deletion strains were made by performing sequential crosses. The genotype of each multiple deletion strain was confirmed using a gene-specific primer and a common primer for the hygromycin (hph) cassette. The hph forward primer used was SEQ ID NO: 4 from Example 1. The reverser primers used for NCU00130, NCU004953, NCU08755, and NCU08807 were the same as those used for Example 1. In particular, the reverse primer for NCU00130 was SEQ ID NO: 5, the reverse primer for NCU004953 was SEQ ID NO: 6, the reverse primer for NCU08755 was SEQ ID NO: 7, and the reverse primer for NCU08807 was SEQ ID NO: 8.
Transcriptional Studies Conidia from strains were inoculated at an OD595 equal to 0.05 in 50 ml Vogel's salts (45) with 2% w/v sucrose in a 250 ml Erlenmeyer flask and grown under constant light at 200 rpm for 16 hours. Biomass was then spun at 4200 rpm for 10 minutes and washed in Vogel's salts twice to remove any excess sucrose. Biomass was then added to a new flask containing 50 ml Vogel's salts supplemented with 1% w/v sucrose, 0.2% w/v cellobiose (Sigma) or 1% w/v Avicel® PH 101 (Sigma). Cultures were induced for 4 hrs under constant light at 200 rpm. The culture biomass was then harvested by filtration over a Whatman glass microfiber filter (GF/F) on a Buchner funnel and washed with 50 ml Vogel's salts. The biomass was flash frozen in liquid nitrogen and stored at −80° C. Three independent biological duplicates (flasks) were evaluated for each time point.
RNA Isolation Total RNA from frozen samples was isolated using Zirconia/Silica beads (0.5 mm diameter; Biospec) and a Mini-Beadbeater-96 (Biospec) with 1 mL TRIzol reagent (Invitrogen) according to the manufacturer's instructions. The total RNA was further purified by digestion with TURBO DNA-free (Ambion) and an RNeasy kit (Qiagen). RNA concentration and integrity was checked by Nanodrop and agarose gel electrophoresis.

RT-PCR

Quantitative RT-PCR was performed using the EXPRESS One-Step SYBR GreenER Kit (Invitrogen) and the StepOnePlus Real-Time PCR System (Applied Biosystems). Reactions were performed in triplicate with a total reaction volume of 10 µl including 300 nM each forward and reverse primers and 75 ng template RNA. Data Analysis was performed by the StepOne Software (Applied Biosystems) using the Relative Quantitation/Comparative CT (ΔΔCT) setting. Data was normalized to the endogenous control actin with expression on sucrose as the reference sample.

The RT-PCR primers used for actin (NCU4173) were SEQ ID NO: 9 and SEQ ID NO: 10 from Example 1; the RT-PCR primers used for cbh-1 (NCU07340) were SEQ ID NO: 11 and SEQ ID NO: 12 from Example 1; the RT-PCR primers used for gh6-2 (NCU09680) were SEQ ID NO: 13 and SEQ ID NO: 14 from Example 1; and the RT-PCR primers used for gh5-1 (NCU00762) were SEQ ID NO: 15 and SEQ ID NO: 16 from Example 1 (46, 47).

mRNA Sequencing mRNA sequencing was performed using an Illumina kit (RS-100-0801) with isolated RNA. The final cDNA library was quantified by an Agilent bioanalyzer 2000 and sequenced using an Illumina Genome Analyzer-II using standard Illumina operating procedures.

Phylogenetic Analysis

GenBank accession numbers (PID), Joint Genome Institute protein ID (JGI), or Broad Institute *Fusarium* Comparative Database Genes (FGSG) numbers for B-G's used in phylogenetic analysis are as follows; NCU08755: *Myceliophthora thermophila*, JGI 80304; *Aspergillus niger*, PID 254674400; *Phanerochaete chrysosporium*, PID 19352194; *Trichoderma reesei*, JGI 121735; *Fusarium graminearum*, FGSG_06605; *Sclerotinia sclerotiorum*, PID 156051478; *Botryotinia fuceliana*, PID 154301968; *Penicillium chrysogenum*, PID 255942539; *Schizophyllum commune*, JGI 256304; *Postia placenta*, JGI 107557. NCU00130: *Myceliophthora thermophila*, JGI 115968; *Aspergillus niger*, PID 213437; *Phanerochaete chrysosporium*, PID 127920; *Trichoderma reesei*, JGI 120749; *Fusarium graminearum*, FGSG_07274; *Sclerotinia sclerotiorum*, PID 156037816; *Botryotinia fuceliana*, PID 156037816; *Penicillium chrysogenum*, PID 255941826; *Schizophyllum commune*, JGI 57050; *Postia placenta*, JGI 45922. NCU04952: *Myceliophthora thermophila*, JGI 66804; *Aspergillus terreus*, PID 115401928; *Phanerochaete chrysosporium*, PID 3320413; *Trichoderma reesei*, JGI 76672; *Sclerotinia sclerotiorum*, PID 156050519; *Botryotinia fuceliana*, PID 154293970; *Penicillium chrysogenum*, PID 255945487; *Schizophyllum commune*, PID 302694815.

All proteins used in the alignments were identified using BLASTp. Homologous proteins sequences were aligned in MEGA5 using ClustalW. Maximum Likelihood phylogeny was determined using the Poisson model to estimate distances and the Nearest-Neighborhood-Interchange (NNI) tree searching strategy with 500 bootstrap replications (48, 49).

Analysis of Differential Expression

To establish biological variation, triplicate cultures were sampled and analyzed for the WT strain on cellulose and sucrose at 4 hours after the media shift. For all other strains and conditions, a single RNAseq library was analyzed.

Sequenced libraries were mapped against predicted transcripts from the *N. crassa* OR74A genome (version 10) with Tophat (version 1.1.4) (50). Transcript abundance was estimated with Cufflinks (version 0.9.2) in FPKMs (fragments per kilobase of exon per million fragments mapped) (51) using upper quartile normalization and mapping against reference isoforms from the Broad Institute.

Hierarchical Clustering Analysis

Genes exhibiting statistically significant expression changes between strains or growth conditions were identified with Cuffdiff, using upper quartile normalization and a minimum of mapped reads per locus. These genes were then filtered to select only those exhibiting a two-fold change in estimated abundance between all biological replicates of each strain/condition tested and only those genes with an FPKM consistently above 10 in at least one strain/condition.

The hierarchical clustering analysis was performed using Cluster 3.0 (52) according to the FPKMs in the WT strain on cellulose, WT on cellobiose, mutant strains on cellobiose and mutant strains on cellulose. Prior to clustering, FPKMs were log transformed, normalized across strains/conditions on a per-gene basis and centered on the mean value across strains/conditions. The Pearson correlation coefficient (uncentered) was used as the similarity metric and average linkage as the clustering method.

Shake Flask Studies

Cultures were grown in 1% sucrose for 24 hours followed by the addition of 2% sucrose or 0.2% cellobiose. Supernatant was harvested after 24 (WT, Δ3βG and Δ3βGΔcre) or 72 hours (Δ3βG). The WT Avicel® culture was grown for 5 days on 2% Avicel®, Δ3βG was grown in 1% sucrose for 24 hours followed by 48 hours in 1% Avicel® and Δ3βGΔcre was grown in 1% sucrose for 24 hours followed by 24 hours in 1% Avicel®.

Bioreactor Studies

Cellulase production was carried out in a 3.7 L bioreactor (BioEngineering AG) at an operating volume of 1 L. The bioreactor was equipped with one 48 mm Rushton impeller and four equally spaced baffles to provide adequate mixing. Impeller speed was controlled at 200 rpm for 8 hours to allow spore germination followed by 500 rpm for the remainder of the experiment. The temperature was maintained at 25° C., and medium pH was controlled at 5.5 using 40% phosphoric acid and 1:5 diluted ammonium hydroxide. The dissolved oxygen was maintained at a level greater than 20% of the saturation value of the medium by varying the aeration rate between 0.5 and 3 VVM in response to the dissolved oxygen tension. Minimal growth medium with 1% w/v sucrose as the sole carbon source (unless otherwise noted) was inoculated with $10^9$ conidia. After 24 hours initial growth, cellulase production was induced with either cellobiose or Avicel® added to a final concentration of 0.2% w/v. Supernatant samples were collected at timepoint 0, 12 hours before induction, at induction, as well as 4, 8, 12, 24 and 36 hours post induction. Samples were spun at 4000 rpm for 5 minutes to pellet biomass and the supernatant was filtered through a 0.2 µm PES filter before being stored at −20° C. until all samples were collected.

Enzyme Activity Assays

Total secreted proteins were measured using the Bio-Rad Protein Assay kit (Bio-Rad) and visualized by running 15 µl of unconcentrated supernatant on a Criterion 4-14% Tris-HCL polyacrylamide gel and stained with Thermo Scientific GelCode Blue Stain Reagent.

Total Avicelase activity was conducted in 250 mL media bottles incubated at 50° C. on a orbital shaker at 200 rpm. Each bottle contained 1% cellulose (Avicel®) and 50 mM (pH 5.0) sodium acetate in a working volume of 50 mL. Tetracycline (10 µg/mL) was added to prevent microbial contamination. Bioreactor culture broth samples were buffer exchanged using a 10 kDa MWCO centrifugal filter to remove any soluble sugars prior to initiating hydrolysis experiments. After pre-incubating the hydrolysis mixture to 50° C., enzyme was added (1 mL filtered culture broth). Samples were taken every 4 hours for the first 12 hours and then every 12 hours thereafter for a total of 48 hours. Hydrolysis experiments were performed in triplicate.

Sugar Analysis

Sucrose, fructose, glucose and cellobiose were measured on a DIONEX ICS-3000 HPLC (Dionex Corp., Sunnyvale, Calif.) using a CarboPac PA20 Analytical Column (3×150 mm) and a CarboPac PA20 guard column (3×30 mm) at 30° C. Following injection of 25 µl of diluted samples, elution was performed with 100 mM KOH (isocratic) at 0.4 ml/min. Sugars were detected using PAD, Four-Potential Carbohydrate Waveform and Peaks were analyzed using the Chromeleon software package.

Mass Spectrometry

Acetonitrile (Fisher Optima grade, 99.9%) and formic acid (Pierce, 1 mL ampules, 99+%) purchased from Fisher Scientific (Pittsburgh, Pa.), and water purified to a resistivity of 18.2 MΩ·cm (at 25° C.) using a Milli-Q Gradient ultra-pure water purification system (Millipore, Billerica, Mass.), were used to prepare mobile phase solvents for liquid chromatography-mass spectrometry.

Trypsin-digested proteins were analyzed using an orthogonal acceleration quadrupole time-of-flight (Q-tof) mass spectrometer that was connected in-line with an ultra-performance liquid chromatograph (UPLC). Peptides were separated using a nanoAcquity UPLC (Waters, Milford, Mass.) equipped with $C_{18}$ trapping (180 µm×20 mm) and analytical (100 µm×100 mm) columns and a 10 µL sample loop. Solvent A was 99.9% water/0.1% formic acid and solvent B was 99.9% acetonitrile/0.1% formic acid (v/v). Sample solutions contained in 0.3 mL polypropylene snap-top vials sealed with septa caps (Wheaton Science, Millville, N.J.) were loaded into the nanoAcquity autosampler compartment prior to analysis. Following sample injection (10 µL), trapping was performed for 3 min with 100% A at a flow rate of 15 µL/min. The injection needle was washed with 500 µL each of solvents A and B after injection to avoid cross-contamination between samples. The elution program consisted of a linear gradient from 8% to 35% B over 30 min, a linear gradient to 95% B over 0.33 min, isocratic conditions at 95% B for 3.67 min, a linear gradient to 1% B over 0.33 min, and isocratic conditions at 1% B for 11.67 min, at a flow rate of 500 nL/min. The analytical column and sample compartment were maintained at 35° C. and 8° C., respectively.

The UPLC column exit was connected to a Universal NanoFlow Sprayer nanoelectrospray ionization (nanoESI) emitter that was mounted in the nanoflow ion source of the mass spectrometer (Q-tof Premier, Waters, Milford, Mass.). The nanoESI emitter tip was positioned approximately 3 mm from the sampling cone aperture. The nanoESI source parameters were as follows: nanoESI voltage 2.4 kV, nebulizing gas (nitrogen) pressure 0.15 mbar, sample cone voltage 35 V, extraction cone and ion guide voltages 4 V, and source block temperature 80° C. No cone gas was used. The collision cell contained argon gas at a pressure of $8\times10^{-3}$ mbar. The Tof analyzer was operated in "V" mode. Under these conditions, a mass resolving power (53) of $1.0\times10^{4}$ (measured at m/z=771) was routinely achieved, which was sufficient to resolve the isotopic distributions of the singly and multiply charged precursor and fragment ions measured in this study. Thus, an ion's mass and charge were determined independently, i.e., the ion charge was determined from the reciprocal of the spacing between adjacent isotope peaks in the m/z spectrum. External mass calibration was performed immediately prior to analysis using a solution of sodium formate. Survey scans were acquired in the positive ion mode over the range m/z=400-1500 using a 0.45 s scan integration and a 0.05 s interscan delay. In the data-dependent mode, up to five precursor ions exceeding an intensity threshold of 20 counts/second (cps) were selected from each survey scan for tandem mass spectrometry (MS/MS) analysis. Real-time deisotoping and charge state recognition were used to select 2+, 3+, and 4+ charge state precursor ions for MS/MS. Collision energies for collisionally activated dissociation (CAD) were automatically selected based on the mass and charge state of a given precursor ion. MS/MS spectra were acquired over the range m/z=100-2000 using a 0.20 s scan integration and a 0.05 s interscan delay. Ions were fragmented to achieve a minimum total ion current (TIC) of 30,000 cps in the cumulative MS/MS spectrum for a maximum of 2 s. To avoid the occurrence of redundant MS/MS measurements, real-time dynamic exclusion was used to preclude re-selection of previously analyzed precursor ions over an exclusion width of ±0.2 m/z unit for a period of 300 s.

Data resulting from LC-MS/MS analysis of trypsin-digested proteins were processed using ProteinLynx Global Server software (version 2.3, Waters), which performed background subtraction (threshold 35% and fifth order polynomial), smoothing (Savitzky-Golay, 10 times, over three channels), and centroiding (top 80% of each peak and minimum peak width at half height four channels) of mass spectra and MS/MS spectra. Processed data were searched against the *Neurospora crassa* protein database (Broad Institute, Cambridge, Mass.). The following criteria were used for the database search: precursor ion mass tolerance 100 ppm, fragment ion mass tolerance 0.15 Da, digest reagent trypsin, allowing for up to three missed cleavages, and methionine oxidation as a variable modification. The identification of at least three consecutive fragment ions from the same series, i.e., b or y-type fragment ions (54), was required for assignment of a peptide to an MS/MS spectrum. MS/MS spectra were inspected to verify the presence of fragment ions that identify the peptides. A protein was determined to be present if at least 1 peptide was detected in 2 out of 3 biological replicates (whole supernatant, PASC bound or PASC unbound)

Results

Figure 17A:
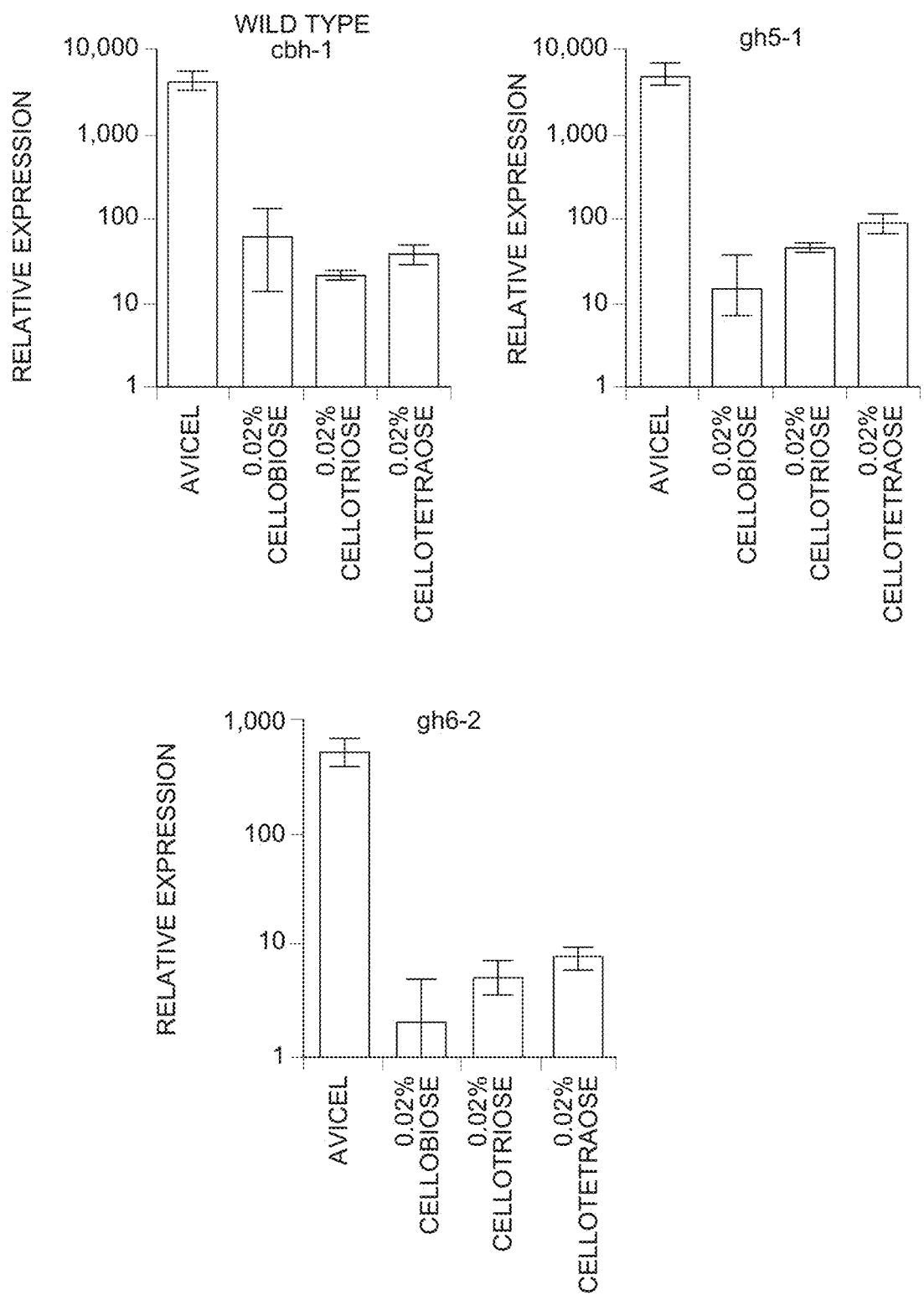
FIGS. 17A-17B show cellulase induction in WT and Δ3βG after induction with cellodextrins.

Induction of Cellulase Transcripts in Cellodextrin-Induced Cultures of *N. crassa* Lacking Three β-Glucosidase Genes Lignocellulolytic genes were not induced, nor was cellulolytic enzyme activity detected when wild-type *N. crassa* (WT) was grown on sucrose, cellobiose, cellotriose, or cellotetraose as the sole carbon source (FIG. 17A). It was believed that when *N. crassa* is grown on cellodextrins, glucose produced by action of β-glucosidase enzymes may mask its inducing capacity (FIG. 1). While the genome of *N. crassa* has at least 7 genes encoding predicted β-glucosidase enzymes, only three (NCU00130, NCU04952 and NCU08755) show a significant increase in transcription during growth on Avicel® or *Miscanthus* (20). All three of these β-glucosidases showed significant homology to both predicted and experimentally verified β-glucosidase enzymes in other filamentous fungi. Based on expression data, we believed that GH1-1 (NCU00130), GH3-3 (NCU08755), and GH3-4 (NCU04952) would be the most relevant enzymes in converting cellobiose to glucose when *N. crassa* is grown on either Avicel® or cellodextrins as sole carbon sources.

Figure 17B:
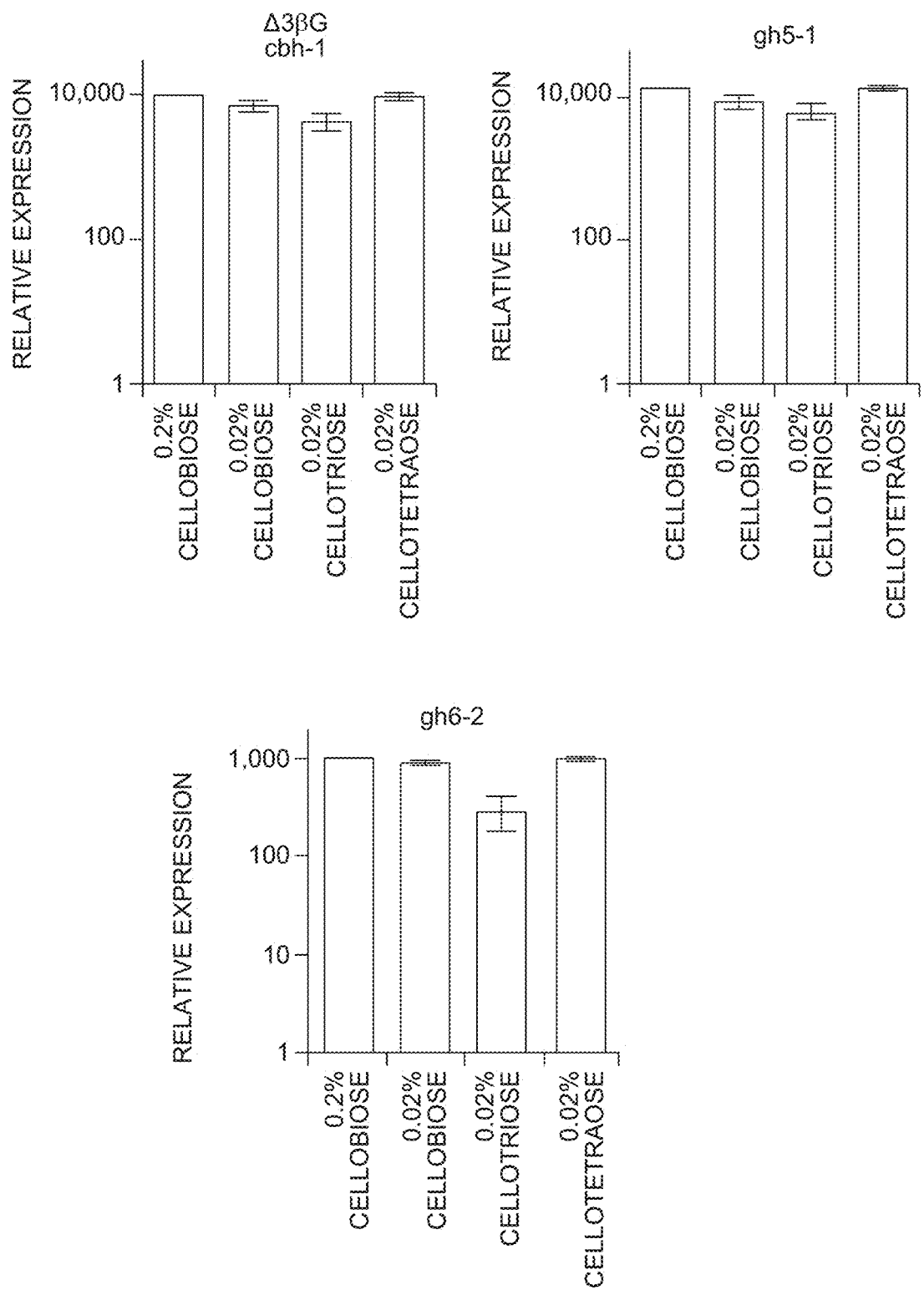
Figure 18A:
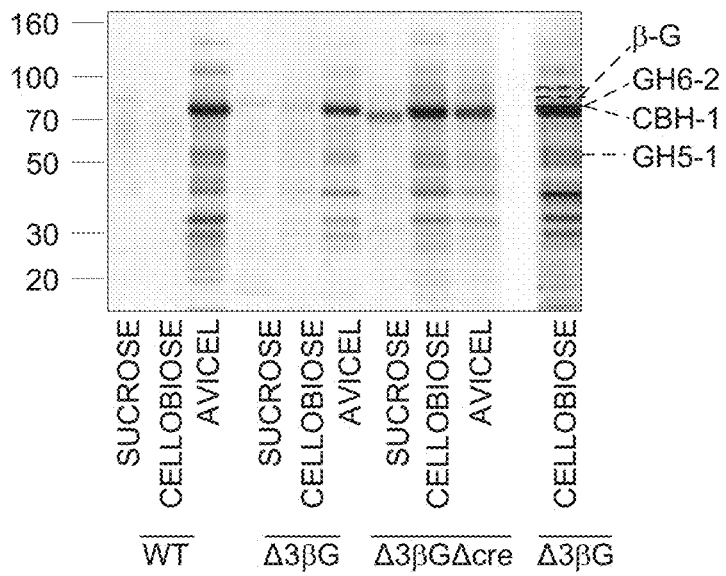
FIGS. 18A-18B show cellulase expression levels in WT and β-glucosidase deletion strains after induction with cellobiose or Avicel®.

To determine whether cellobiose induces cellulase gene expression in *N. crassa*, we tested whether the expression of three major cellulase genes (cbh-1, NCU07340; gh6-2, NCU09680 and gh5-1, NCU00762) were induced in strains carrying deletions in the β-glucosidase genes gh1-1, gh3-3 or gh3-4 via a transfer experiment. To eliminate the possibility of redundancy between the β-glucosidase enzymes, double and triple mutant strains carrying different combinations of β-glucosidase gene deletion sets were also constructed and tested. Following a 4 hr induction with 0.2% cellobiose, the individual β-glucosidase deletion strains (Δgh1-1, Δgh3-3 or Δgh3-4) did not show a significant induction of cbh-1, gh6-2, or gh5-1 expression; whereas a Δgh1-1Δgh3-3 double mutant showed some cellulase gene induction. However, a strain carrying deletions for all three β-glucosidase genes (Δgh1-1, Δgh3-3 and Δgh3-4; Δ3βG) showed similar relative expression levels of cbh-1, gh5-1 and gh6-2 when shifted to 0.2% cellobiose as did a WT culture shifted to Avicel® (FIG. 18A). In addition, the Δ3βG strain showed similar relative expression levels of cbh-1, gh5-1 and gh6-2 when shifted to cellobiose, cellotriose, or cellotetraose (FIG. 17B). The transcriptional response in the Δ3βG mutant was specific for cellobiose and was not due to starvation as the expression of cbh-1 and gh5-1 in WT and the Δ3βG strain when transferred to media lacking any carbon source showed only a small increase in transcription levels (less than 50-fold induction). These values are negligible when compared to the 20,000-fold (minimum) induction of cbh-1 and gh5-1 by Avicel® in WT *N. crassa* and in the Δ3βG strain shifted to cellobiose.

Figure 19A:
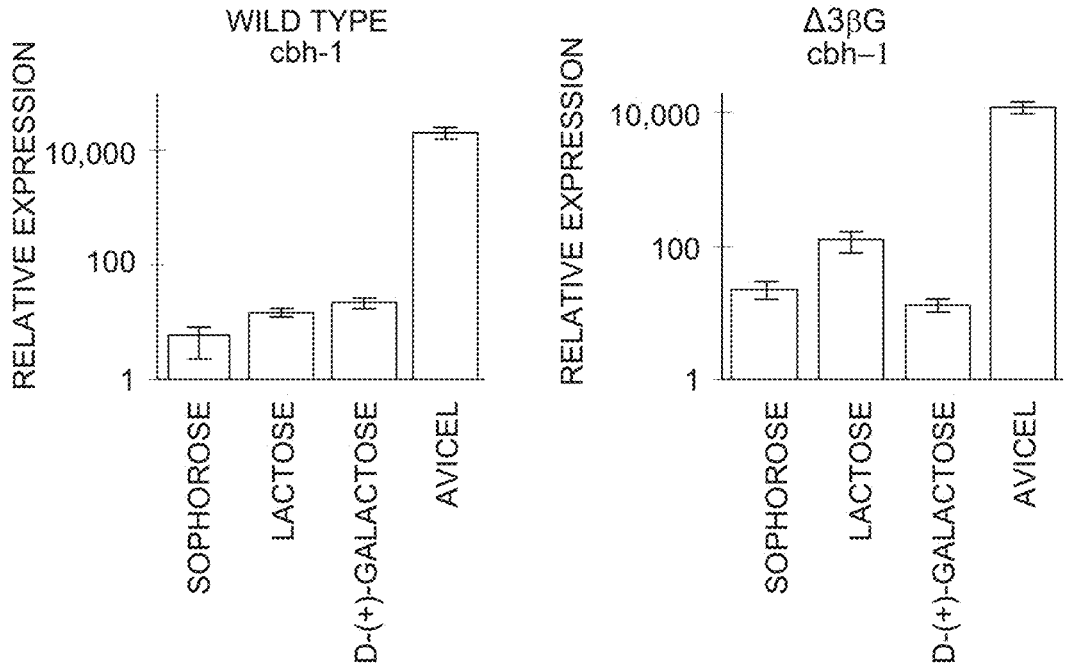
FIGS. 19A-19B show cellulase induction in WT and Δ3βG after induction with sophorose, lactose or D-(+)-galactose.
Figure 19B:
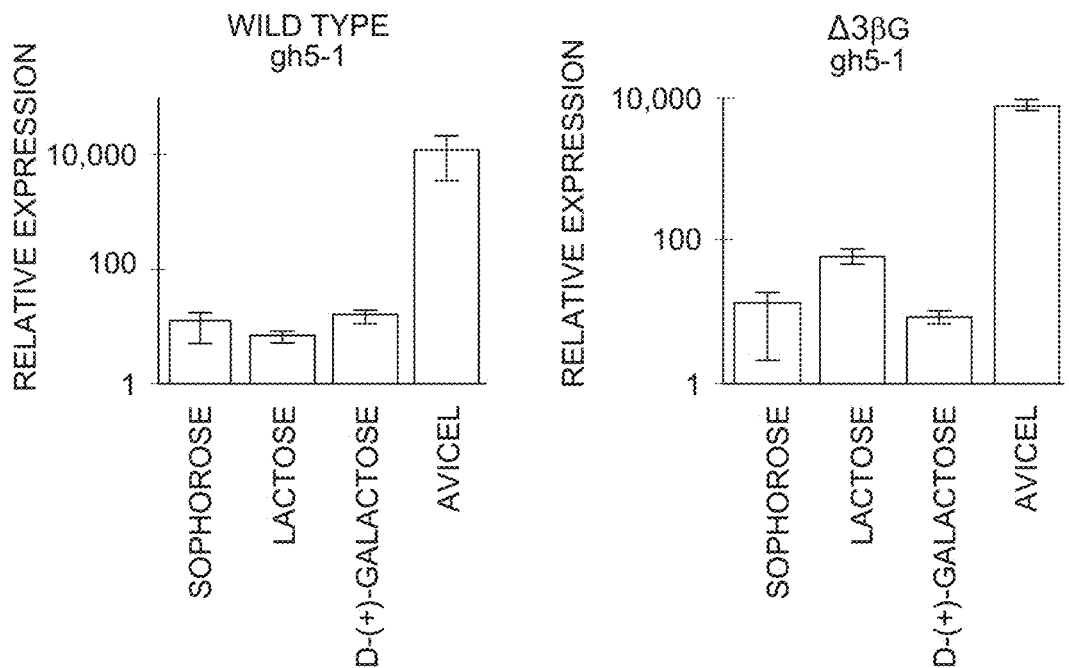

The most widely used soluble inducers of cellulases in the industrial species *T. reesei* are sophorose and lactose (25). We therefore examined whether exposure to sophorose or lactose induced cellulase gene expression in *N. crassa* using both the WT and the Δ3βG deletion strain. As observed for other filamentous fungal species (15), transfer of either WT or the Δ3βG mutant to media containing sophorose, lactose or D-(+)-galactose (a degradation product of lactose), did not significantly induce cellulase gene expression (FIGS. 19A-19B).

Carbon catabolite repression (CCR) acts in filamentous fungi to repress cellulase and hemicellulase gene expression in the presence of preferred carbon sources, such as glucose or sucrose, even when lignocellulose is present (4). The C2H2 zinc finger transcription factor CreA/CRE1/CRE-1 (26) plays a key role in CCR as strains lacking CreA/CRE1/CRE-1 in *Aspergillus* sp., *T. reesei* and *N. crassa*, respectively, produce increased amounts of both cellulases and hemicellulases when grown on cellulose or hemicellulose (21, 27, 28). Quantitative RT-PCR analysis of RNA isolated from an *N. crassa* cre-1 deletion strain (ΔNCU08807) showed that the basal expression of cbh-1 and gh5-1 increased about ten-fold relative to a WT strain. When shifted from sucrose to 0.2% cellobiose for 4 hrs, the Δcre-1 strain showed increased induction of cbh-1, gh5-1 and gh6-2 (3,000, 500, and 85-fold, respectively). However, the level of induction in the Δcre-1 mutant was significantly lower than induction levels obtained for WT exposed to Avicel® or the Δ3βG mutant exposed to cellobiose. Notably, a Δ3βG strain that also carried the Δcre-1 deletion (Δ3βGΔcre) exhibited stronger induction of cbh-1, gh5-1 and gh6-2 than either the WT strain shifted to Avicel® or the Δ3βG strain shifted to cellobiose (FIG. 18A). These data indicate that the induction of cellulase gene expression in the Δ3βG mutant when exposed to cellobiose is comparable to induction by cellulose and is not a consequence of relief from CCR.

Recapitulation of Wild-Type *N. crassa* Cellulolytic Response in the Triple β-Glucosidase Mutant on Cellobiose High throughput sequencing (RNA-Seq) was used to assess whether the full genomic response in the Δ3βG strains to cellobiose was similar to or different from a WT strain exposed to Avicel®. The full genomic pattern of gene expression changes showed that the response of the Δ3βG mutant to cellobiose closely matched that of WT induced by Avicel®, but was significantly different from the response of WT to cellobiose or when subjected to starvation. To identify which genes were significantly and specifically induced in WT *N. crassa* in response to Avicel®, a pairwise analysis was performed between expression profiles of WT transferred to Avicel® versus WT transferred to no added carbon source. These analyses identified 321 genes (including the three deleted β-glucosidase genes) that were significantly and specifically induced in WT cultures in response to Avicel® (cellulose regulon). This gene set included 16 predicted cellulase and 12 predicted hemicellulase genes. Additional genes in the cellulose regulon included 41 genes encoding proteins predicted to be active on carbohydrates by CAZy (29) and 111 genes encoding secreted proteins (signalP) (30). Of the 321 genes in the cellulose regulon, 156 encode proteins that are characterized as unclassified proteins (MIPS FunCat database) (31). Of specific interest, the orthologue for xlnR/xyr1 (NCU06971), which plays a major role in the regulation of cellulases in *Aspergilli* (32) and *T. reesei* (33), falls into the cellulose regulon. However, although NCU06971 was previously identified as a xlnR/xyr1 homolog in *N. crassa* (34), its role in plant cell wall degradation is unknown.

Figure 20A:
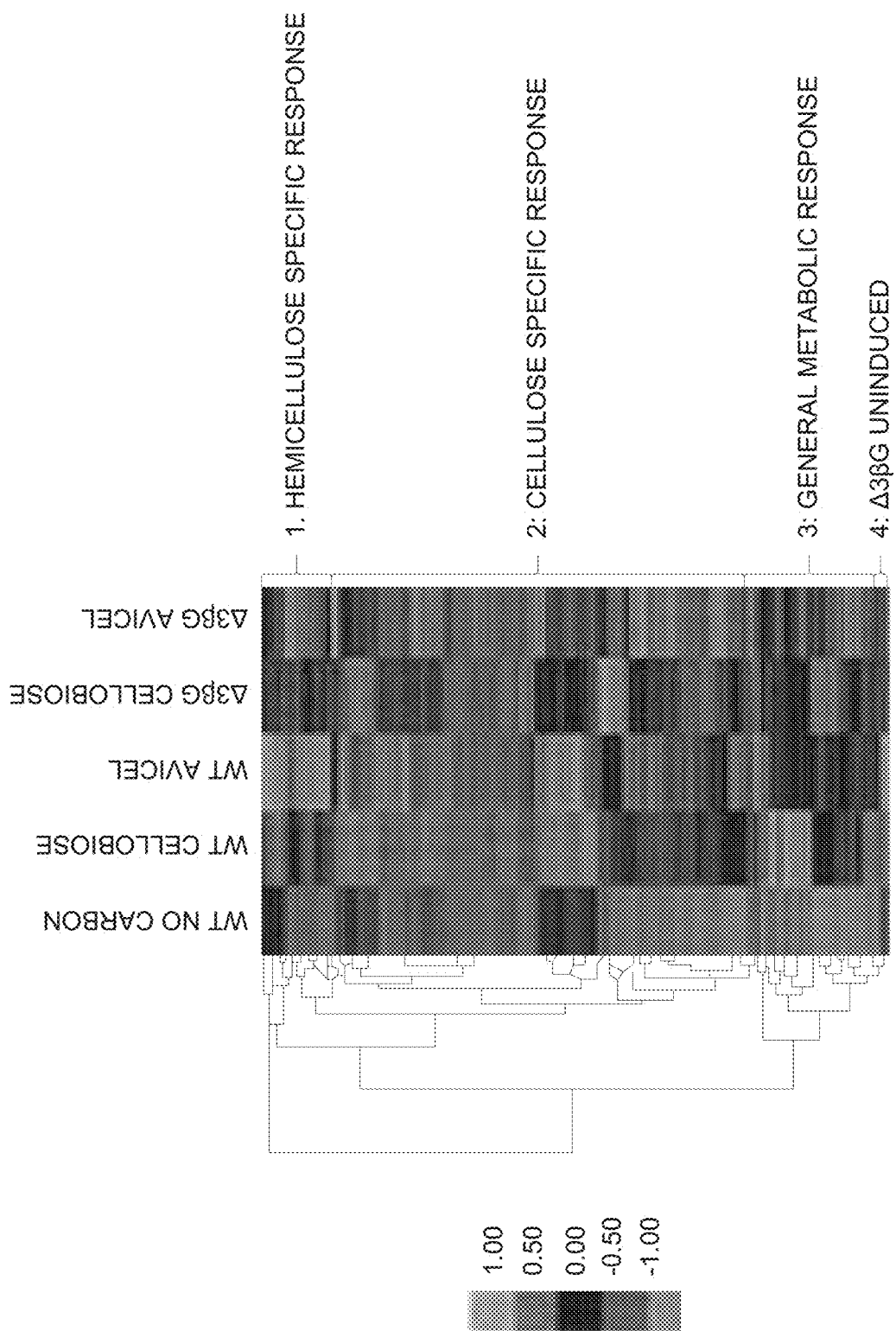
FIGS. 20A-20B show RNA sequencing of the WT and Δ3βG strains.

Hierarchical clustering of genes within the cellulose regulon from expression data of WT transferred to media containing no carbon source, cellobiose or Avicel® and the Δ3βG strain transferred to media containing cellobiose or Avicel® resulted in the identification of four distinct expression clusters (FIG. 20A). The largest cluster (cluster 2) contained 210 genes that showed high expression in the WT strain on Avicel®, as well as in the Δ3βG strain on either cellobiose or under Avicel®-induced conditions. This group of 210 genes contained all 16 predicted cellulases (NCU00762, gh5-1; NCU00836, gh61-7; NCU01050, gh61-4; NCU02240, gh61-1; NCU02344, gh61-12; NCU02916, gh61-3; NCU03328, gh61-6; NCU04854, gh7-2; NCU05057, gh7-1; NCU05121, gh45-1; NCU07190, gh6-3; NCU07340, cbh-1; NCU07760, gh61-2; NCU07898, gh61-13; NCU08760, gh61-5; NCU09680, gh6-2) as well as 3 genes identified to be accessory proteins for cellulose degradation (NCU00206, cdh-1; NCU07143, lac-2; NCU09764, CBM1 containing protein) (20, 35). This cluster also contained 9 hemicellulase genes (NCU02343, gh51-1; NCU02855, gh11-1; NCU04997, gh10-3; NCU05924, gh10-1; NCU05955, gh74-1; NCU07225, gh11-2; NCU07326, gh43-6; NCU08189, gh10-2; NCU09775, gh54-1). Of the 182 proteins remaining in this cluster, 29 are predicted to be active on carbohydrates by CAZy (29) and 76 are predicted to be secreted by signalP, with 25 genes falling into both categories. The remaining 102 genes were grouped into their predicted functional category (31) resulting in 10 genes expected to be involved in C-compound and carbohydrate metabolism; 8 genes involved in protein folding, modification, or transport; and 62 genes encoding unclassified proteins.

A small cluster of 36 genes (cluster 1) showed high expression levels in either the WT or Δ3βG deletion strain when exposed to Avicel® (FIG. 20A), but had lower expression levels in the Δ3βG deletion strain on cellobiose. This group contained a predicted β-xylosidase gene (NCU09652, gh43-5) and several other genes encoding proteins active on hemicellulose (NCU00710, acetyl xylan esterase; NCU01900, xylosidase/arabinosidase; NCU00891, xylitol dehydrogenase; and NCU08384, xylose reductase). These results suggest that these genes were induced by the 0.5-1.0% hemicellulose found in Avicel® (20) and are not part of the regulon induced by cellobiose.

Figure 20B:
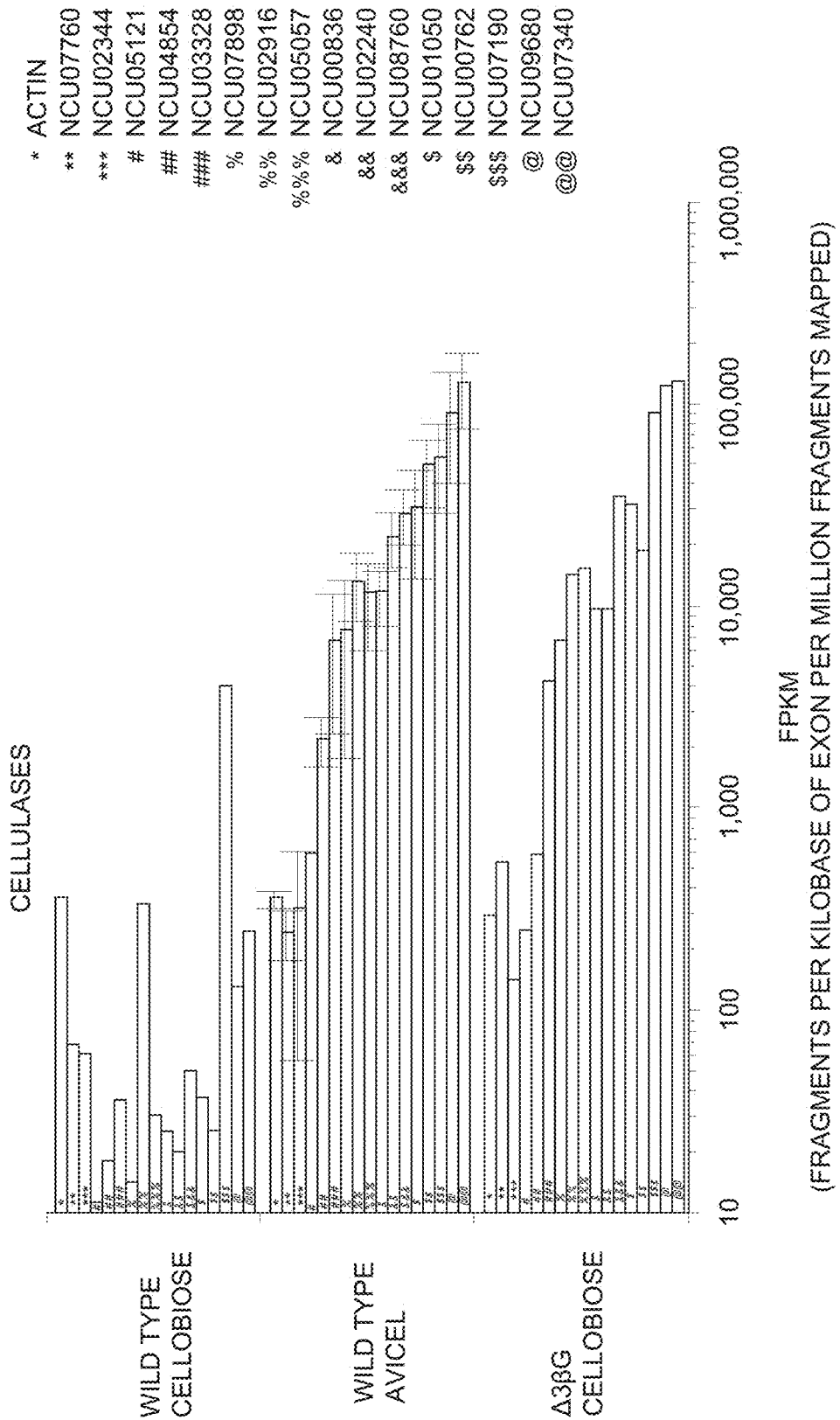

When comparing the induction of the Δ3βG strain on cellobiose versus WT on Avicel®, a striking pattern appears (FIG. 20B). Genes induced in the WT by Avicel® are very close to the value seen in the Δ3βG mutant. For example, the FPKM for cbh-1 in the WT on Avicel® is 126,816±53,016, while the FPKM in Δ3βG on cellobiose is 130,865. This pattern extends even to the lesser-induced cellulases like NCU07760 (gh61-2), which has a FPKM of 239±62 for WT on Avicel® and 538 for Δ3βG mutant on cellobiose. In contrast, some hemicellulase genes in the Δ3βG mutant were induced in response to cellobiose, but had lower expression levels than in Avicel®-induced WT or Δ3βG cultures. For example, while NCU05924 (endoxylanase, gh10-1) has 20,023±9,888 FPKMs in WT induced with Avicel®, an expression level of 10,000 FPKMs was observed in the Δ3βG mutant induced with cellobiose. These results indicate that while all of the cellulase genes are in the same regulon, the hemicellulase genes are divided into those that are coordinately regulated with cellulases and those that require additional signals for full induction.

Figure 18B:
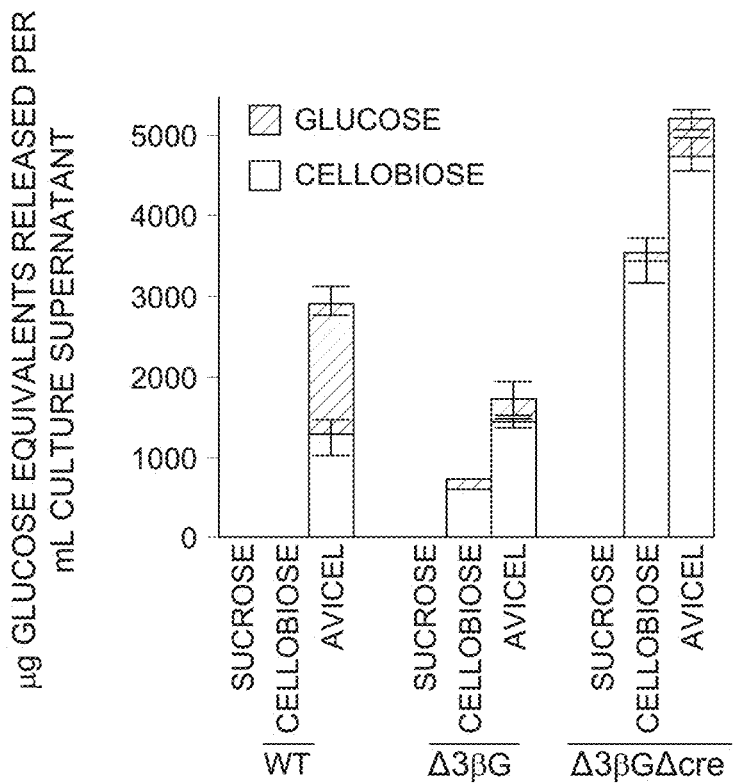

Transcription of Plant Cell Wall Degrading Enzymes in the Δ3βG Mutant Correlates with Cellulase Secretion and Activity To determine whether the transcriptional response of the Δ3βG and Δ3βGΔcre strains in response to cellobiose corresponded to an increase in functional protein, we assessed secreted proteins and cellulase activity of the Δ3βG and Δ3βGΔcre strains in response to induction with either cellobiose or Avicel® (SI Materials and Methods), as compared to WT cultures. As expected, supernatants from all sucrose-grown cultures (Δ3βG, Δ3βGΔcre and WT) were unable to produce glucose or cellobiose from crystalline cellulose in an Avicel® hydrolysis assay (Materials and Methods), while supernatants from all three Avicel®-induced cultures (Δ3βG, Δ3βGΔcre and WT) were able to degrade crystalline cellulose to cellobiose and glucose (FIG. 18C). When grown on cellobiose, the Δ3βG and Δ3βGΔcre strains displayed a secreted protein pattern similar to WT Avicel®-grown cultures (FIG. 18B) (20). Importantly, supernatants from both the Δ3βG and Δ3βGΔcre deletion strains induced by cellobiose hydrolyzed crystalline cellulose, while supernatants from WT cellobiose grown cultures did not. The Δ3βG and Δ3βGΔcre strains, which lack three β-glucosidases, produced mostly cellobiose. These data are consistent with the role of the three β-glucosidase enzymes in providing the bulk of the glucose-generating activity in WT cultures (37).

Figure 21A:
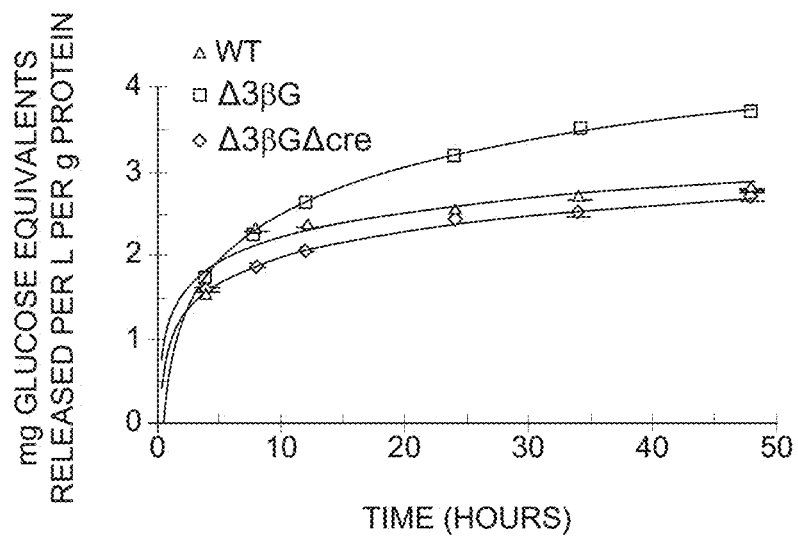
FIGS. 21A-21B show enzyme activity in WT, Δ3βG, and Δ3βGΔcre strains after induction with cellobiose or Avicel®.
Figure 21B:
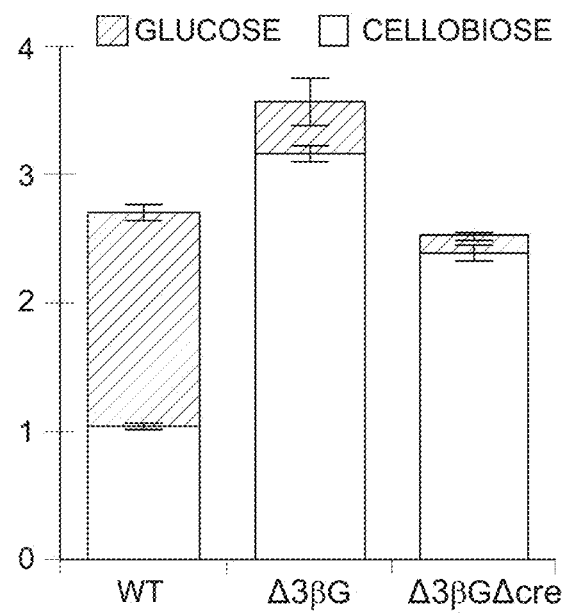

Industrial filamentous fungi are grown in submerged cultures for high-level production of a variety of products (38). We therefore examined the induction of cellulases in the Δ3βG and Δ3βGΔcre deletion strains in a controlled bioreactor process (FIGS. 7A-7D). After 24 hours growth on sucrose, WT, Δ3βG and Δ3βGΔcre produce a similar amount of biomass (~3.5 g/L) (FIGS. 7A-7C). After induction with 0.2% cellobiose, WT did not secrete a significant amount of protein (0.05 mg/mL; FIG. 7C). In contrast, the Δ3βG and Δ3βGΔcre cultures produced 0.12 mg/mL and 0.24 mg/mL protein, respectively, in the supernatant (FIGS. 7A and 7B). In addition, the cellobiose-induced Δ3βG and Δ3βGΔcre cultures showed a significant increase in endoglucanase activity over this same period of induction (FIG. 7F). Examining the aggregate Avicelase activity from the 24-hour time point indicated that the Δ3βGΔcre strain produced 60% more glucose equivalents (0.424 mg/mL) as compared to the Δ3βG strain (0.296 mg/mL) (FIG. 7E). However, when the total concentration of protein was normalized, the Δ3βGΔcre strain had less specific activity than either the WT or Δ3βG culture supernatants (FIGS. 21A-21B).

Proteomic Analysis of Secreted Proteins

Figure 22B:
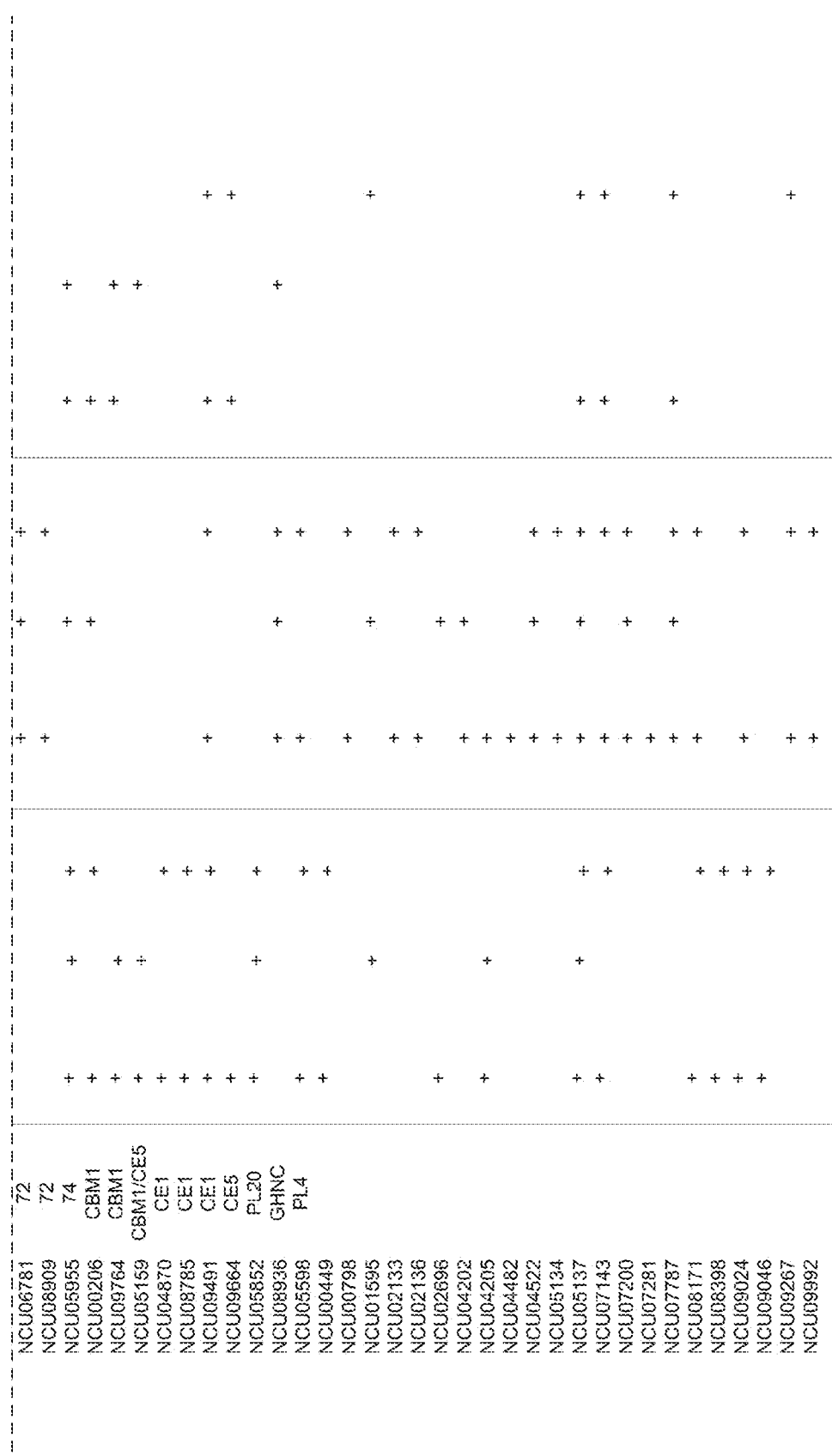

In order to compare the identity of proteins secreted by WT N. crassa grown on Avicel® versus the Δ3βG strains when induced with cellobiose, we analyzed the secretome using a shotgun proteomics approach (Table 1). There were 39 proteins identified in the WT Avicel®-grown culture supernatant. In cellobiose-grown cultures, 38 proteins were identified in the Δ3βG broth and 24 were identified in the Δ3βGΔcre broth (FIGS. 22A-22B). Using quantitative mass spectrometry it was concluded that 76% of the WT N. crassa secretome on Avicel® is composed of 6 individual proteins (35). All of these proteins were identified in the WT, Δ3βG, and Δ3βGΔcre culture broths (except for the deleted β-glucosidase, gh3-4) (Table 1). In addition to the cellulases, we identified a number of lower abundance accessory proteins which make up a total of 6.5% of the secretome (35): a cellobiose dehydrogenase (CDH-1), a type 2 lactonase (LAC-2), and two hypothetical proteins: NCU09764, a CBM1-containing protein of unknown function and NCU05137, a gene which when deleted leads to an increase in cellulase activity (20). These data indicate that, similar to the transcriptional response of the Δ3βG mutant to cellobiose, the identity of proteins secreted and the amount of protein secreted in the Δ3βG strain on cellobiose mimicked the WT N. crassa response to Avicel®.

TABLE 1

| Gene | Annotation | Wild Type | Δ3βG | Δ3βGΔcre | Secretome Percentage |
|---|---|---|---|---|---|
| Cellulases | | | | | |
| NCU07340 | CBH-1 | + | + | + | 39.5% |
| NCU09680 | GH6-2 | + | + | + | 13.4% |
| NCU07898 | GH61-2 | + | | + | 6.6% |
| NCU00762 | GH5-1 | + | + | + | 5.9% |
| NCU08760 | GH61-5 | + | + | + | 4.6% |
| NCU05057 | GH7-1 | + | + | + | 4.0% |
| NCU02240 | GH61-1 | + | | + | 3.4% |
| NCU07190 | GH6-3 | + | + | + | 3.2% |
| Accessory Proteins | | | | | |
| NCU04952 | GH3-4 | + | N/A | N/A | 3.8% |
| NCU00206 | CDH-1 | + | + | + | 2.4% |
| NCU09764 | N/A | + | + | + | 1.6% |
| NCU05137 | NCW-1 | + | + | + | 1.5% |
| NCU07143 | LAC-2 | + | + | + | 1.0% |

In Table 1, GH refers to glycoside hydrolase, and N/A refers to gene knockout. For secretome percentage, Avicel®-induced secretome was identified by AQUA Mass Spectrometry (35). Thirteen proteins represent 91% of the total secretome with all other proteins representing less than 1% of the secretome.

Example 4

The following example relates to the characterization of cellulase activity in N. crassa strains containing deletions of the N. crassa gene NCU00890 and the N. crassa gene NCU06650.

Materials and Methods

The *N. crassa* triple β-glucosidases gene deletion strain, and the *N. crassa* triple β-glucosidases gene deletion and cre-1 gene deletion strain were generated as described in Example 1.

Deletion strains for NCU06650 (FGSC 11246 and 11247) and NCU00890 (FGSC 16749) were obtained from the Fungal Genetics Stock Center (FGSC). Multiple deletion strains were generated by performing sequential crosses. The genotype of each multiple deletion strain was confirmed using a gene-specific primer and a common primer for the hygromycin (hph) cassette. The forward primer for hph was:

```
hph Middle FWD:
                                    [SEQ ID NO: 4]
5'-CGA CAG ACG TCG CGG TGA GTT CAG-3'
```

Reverse Primers were:

```
NCU06650:
                                    [SEQ ID NO: 23]
5'-CAT CTC ATA CTC CCT CAT CC-3'

NCU00890:
                                    [SEQ ID NO: 24]
5'-GGT TGT CTC GGT CGA CAT TG-3'
```

Exoglucanase (Cellobiohydrolase I) activity was measured using a 4-Methylumbelliferyl β-D-cellobioside (MuLac) assay. This assay mainly measures the activity of CBH-1 and activity is expressed as the change in fluorescence over time resulting in the slope of a best-fit line as an indication of enzyme activity. The assay was performed in a total volume of 100 μl containing 20 μl total culture supernatant and had a final concentration of 1.0 mM MuLac and 50 mM sodium acetate pH 5. The assay was performed in a Beckman Coulter Paradigm plate reader set at 40° C. with excitation/emission wavelengths of 360/465 nm with readings every 30 seconds for 10 minutes. The slope of the best-fit line represents the MuLac activity for an individual culture supernatant.

Results

Given that both NCU00890 and NCU06650 deletions have both been characterized as hypersecretors, we wanted to examine if combining these deletions with the triple β-glucosidase and cre-1 deletion strain would increase cellulase secretion. The NCU00890 geneencodes a β-mannosidase. The NCU06650 gene encodes an characterized polypeptide having closest homology to a phospholipase.

Figure 23:
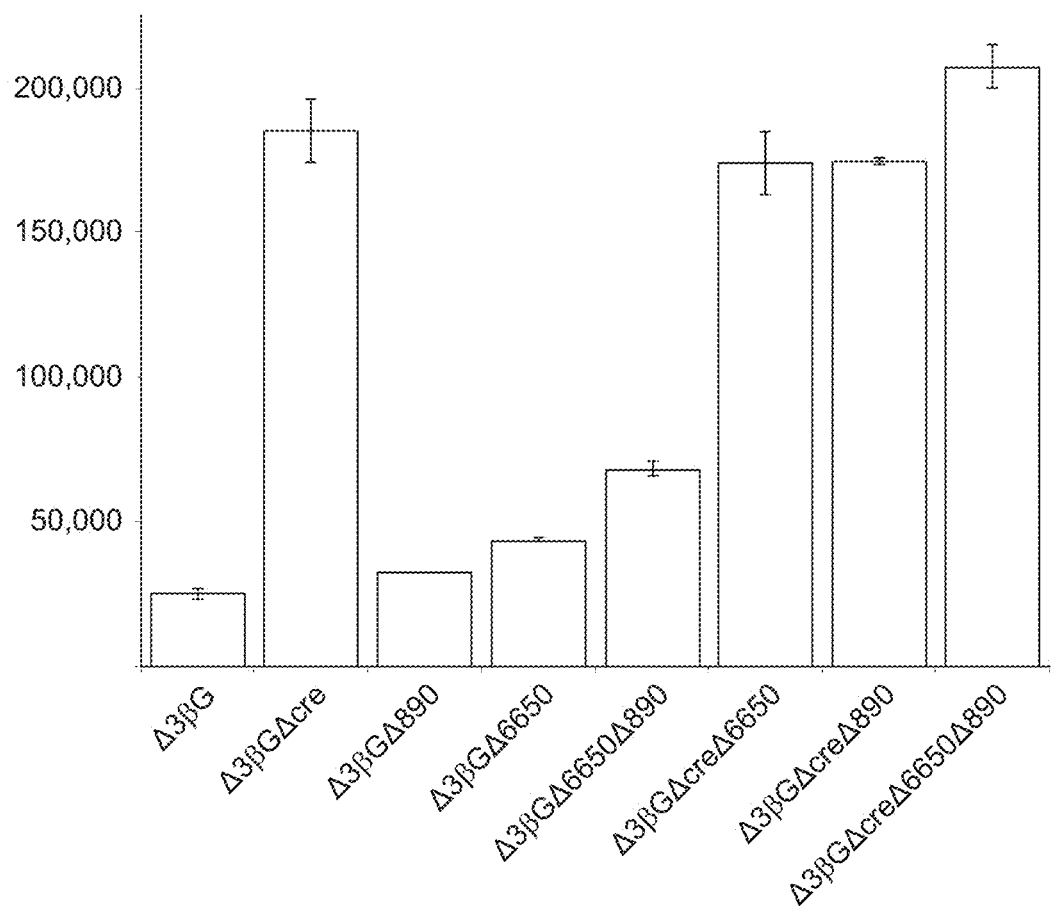
FIG. 23 compares MuLac activity (cellulase activity) in culture filtrates from Neurospora crassa strains Δ3βG, Δ3βGΔcre, Δ3βGΔ890, Δ3βGΔ6650, Δ3βGΔ6650Δ890, Δ3βGΔcreΔ6650, Δ3βGΔcreΔ890, and Δ3βGΔcreΔ6650Δ890. The strains with Δ890 have a deletion in the β-mannosidase gene NCU00890. The strains with Δ6650 have a deletion in the phospholipase gene or phospholipase-like gene NCU06650. Strains were grown in 2% sucrose for 36 hrs followed by 24 hrs in 0.2% cellobiose. Exoglucanase activity in the culture supernatant was measured using a 4-Methylumbelliferyl-β-D-cellobioside (Mu-Lac) assay. Results are shown as relative fluorescence between strains.

As shown in FIG. 23, when either the NCU00890 or the NCU06650 deletion is combined with the triple β-glucosidase deletion strain, we see a modest increase in cellobiohydrolase I activity after 24 hours induction by cellobiose. Moreover, by also including the cre-1 deletion the sextuple mutant (containing the triple β-glucosidase deletion and both the NCU00890 and the NCU06650 deletion) had even higher cellobiohydrolase I activity after 24 hours induction by cellobiose.

Homologues of the β-mannosidase gene NCU00890 were identified in *Trichoderma reesei*. The *T. reesei* homologues are found on Scaffold 10, 258215-260779, protein ID 62166; and on Scaffold 4, 877954-880802, protein ID 57857.

Additionally, a homologue of the gene NCU06650 was identified in *T. reesei*. The homologue was found on Scaffold 22, 490155-490769, protein ID 67579.

The *T. reesei* homologues were identified by performing a BLASTp search of either NCU00890 or NCU06650 using the DOE Joint Genome Institute *T. reesei* database.

REFERENCES

1. Rubin E M (2008) Genomics of cellulosic biofuels. *Nature* 454:841-845.
2. Himmel M E, et al. (2007) Biomass recalcitrance: engineering plants and enzymes for biofuels production. *Science* 315:804-807.
3. Cherry J R & Fidantsef A L (2003) Directed evolution of industrial enzymes: an update. *Curr Opin Biotechnol* 14:438-443.
4. Kubicek C P, Messner R, Gruber F, Mach R L, & Kubicek-Pranz E M (1993) The *Trichoderma* cellulase regulatory puzzle: from the interior life of a secretory fungus. *Enzyme Microb Technol* 15:90-99.
5. Vaheri M P, Vaheri M E O, & Kauppinen V S (1979) Formation and release of cellulolytic enzymes during growth of *Trichoderma reesei* on cellobiose and glycerol. *Appl Microbiol Biotechnol* 8:73-80.
6. Mandels M & Reese E T (1960) Induction of cellulase in fungi by cellobiose. *J Bacteriol* 79:816-826.
7. Vaheri M P, Vaheri M E O, & Kauppinen V S (1979) Formation and release of cellulolytic enzymes during growth of *Trichoderma reesei* on cellobiose and glycerol. *Appl Microbiol Biotechnol* 8:73-80.
8. Chikamatsu G, Shirai K, Kato M, Kobayashi T, & Tsukagoshi N (1999) Structure and expression properties of the endo-beta-1,4-glucanase A gene from the filamentous fungus *Aspergillus nidulans*. *FEMS Microbiol Lett* 175:239-245.
9. Nevalainen K M, Te'o V S, & Bergquist P L (2005) Heterologous protein expression in filamentous fungi. *Trends Biotechnol* 23:468-474.
10. Suzuki H, Igarashi K, & Samejima M (2010) Cellotriose and cellotetraose as inducers of the genes encoding cellobiohydrolases in the basidiomycete *Phanerochaete chrysosporium*. *Appl Environ Microbiol* 76:6164-6170.
11. Vaheri M, Leisola M, & Kauppinen V (1979) Transglycosylation products of cellulase system of *Trichoderma reesei*. *Biotechnol Lett* 1:41-46.
12. Mandels M, Parrish F W, & Reese E T (1962) Sophorose as an inducer of cellulase in *Trichoderma viride*. *J Bacteriol* 83:400-408.
13. Sternberg D & Mandels G R (1979) Induction of cellulolytic enzymes in *Trichoderma reesei* by sophorose. *J Bacteriol* 139:761-769.
14. Sternberg D & Mandels G R (1980) Regulation of the cellulolytic system in *Trichoderma reesei* by sophorose: induction of cellulase and repression of beta-glucosidase. *J Bacteriol* 144:1197-1199.
15. Gielkens M M, Dekkers E, Visser J, & de Graaff L H (1999) Two cellobiohydrolase-encoding genes from *Aspergillus niger* require D-xylose and the xylanolytic transcriptional activator XlnR for their expression. *Appl Environ Microbiol* 65:4340-4345.
16. Ulmer D C, Leisola M S A, & Fiechter A (1984) Possible induction of the ligninolytic system of *Phanerochaete chrysosporium*. *J Biotechnol* 1:13-24.
17. Fritscher C C (1990) Cellobiose metabolism and cellobiohydrolase I biosynthesis by *Trichoderma reesei*. *Exp Mycol* 14:405-415.
18. Reese E T, Parrish F W, & Ettlinger M (1971) Nojirimycin and d-glucono-1,5-lactone as inhibitors of carbohydrases *Carbohydrate Res* 18:381-388.

19. Woodward J & Arnold S L (1981) The inhibition of β-glucosidase activity in *Trichoderma reesei* C30 cellulase by derivatives and isomers of glucose. *Biotechnol Bioeng* 23:1553-1562.
20. Tian C, et al. (2009) Systems analysis of plant cell wall degradation by the model filamentous fungus *Neurospora crassa. Proc Natl Acad Sci USA* 106:22157-22162.
21. Sun J & Glass N L (2011) Identification of the CRE-1 cellulolytic regulon in *Neurospora crassa. PLoS One* 6:e25654.
22. Galazka J M, et al. (2010) Cellodextrin transport in yeast for improved biofuel production. *Science* 330:84-86.
23. Maddi A, Bowman S M, & Free S J (2009) Trifluoromethanesulfonic acid-based proteomic analysis of cell wall and secreted proteins of the ascomycetous fungi *Neurospora crassa* and *Candida albicans. Fungal Genet Biol* 46:768-781.
24. Bohlin C, et al. (2010) A comparative study of activity and apparent inhibition of fungal beta-glucosidases. *Biotechnol Bioeng* 107:943-952.
25. Seiboth B, Hofmann G, & Kubicek C P (2002) Lactose metabolism and cellulase production in *Hypocrea jecorina*: the gal1 gene, encoding galactose-1-phosphate uridylyltransferase, is essential for growth on galactose but not for cellulase induction. *Mol Genet Genomics* 267:124-132.
26. Portnoy T, et al. (2011) The CRE1 carbon catabolite repressor of the fungus *Trichoderma reesei*: a master regulator of carbon assimilation. *BMC Genomics* 12:269.
27. Tamayo E N, et al. (2008) CreA mediates repression of the regulatory gene xlnR which controls the production of xylanolytic enzymes in *Aspergillus nidulans. Fungal Genet Biol* 45:984-993.
28. Nakari-Setala T, et al. (2009) Genetic modification of carbon catabolite repression in *Trichoderma reesei* for improved protein production. *Appl Environ Microbiol* 75:4853-4860.
29. Cantarel B L, et al. (2009) The Carbohydrate-Active EnZymes database (CAZy): an expert resource for glycogenomics. *Nucleic Acids Res* 37:D233-238.
30. Nielsen H, Emanuelsson O, Brunak S, & von Heijne G (2007) Locating proteins in the cell using TargetP, SignalP and related tools. *Nat Protoc* 2:953-971.
31. Ruepp A, et al. (2004) The FunCat, a functional annotation scheme for systematic classification of proteins from whole genomes. *Nucleic Acids Res* 32:5539-5545.
32. Noguchi Y, et al. (2009) Genes regulated by AoXlnR, the xylanolytic and cellulolytic transcriptional regulator, in *Aspergillus oryzae. Appl Microbiol Biotechnol* 85:141-154.
33. Portnoy T, et al. (2011) Differential regulation of the cellulase transcription factors XYR1, ACE2, and ACE1 in *Trichoderma reesei* strains producing high and low levels of cellulase. *Eukaryot Cell* 10:262-271.
34. Goncalves R D, Cupertino F B, Freitas F Z, Luchessi A D, & Bertolini M C (2011) A genome-wide screen for *Neurospora crassa* transcription factors regulating glycogen metabolism. *Mol Cell Proteomics* 10:M111 007963.
35. Phillips C M, Iavarone A T, & Marletta M A (2011) A quantitative proteomic approach for cellulose degradation by *Neurospora crassa. J Proteome Res* 10:4177-4185.
36. Ilmen M, Saloheimo A, Onnela M L, & Penttila M E (1997) Regulation of cellulase gene expression in the filamentous fungus *Trichoderma reesei. Appl Environ Microbiol* 63:1298-1306.
37. Levine S E, Fox J M, Clark D S, & Blanch H W (2011) A mechanistic model for rational design of optimal cellulase mixtures. *Biotechnol Bioeng* 108:2561-2570.
38. Gibbs P A, Seviour R J, & Schmid F (2000) Growth of filamentous fungi in submerged culture: problems and possible solutions. *Crit Rev Biotechnol* 20:17-48.
39. Messner R, Gruber F, & Kubicek C P (1988) Differential regulation of synthesis of multiple forms of specific endoglucanases by *Trichoderma reesei* QM9414. *J Bacteriol* 170:3689-3693.
40. Kubicek C P, Messner R, Gruber F, Mandels M, & Kubicek-Pranz E M (1993) Triggering of cellulase biosynthesis by cellulose in *Trichoderma reesei*. Involvement of a constitutive, sophorose-inducible, glucose-inhibited betadiglucoside permease. *J Biol Chem* 268:19364-19368.
41. Ha S J, et al. (2011) Engineered *Saccharomyces cerevisiae* capable of simultaneous cellobiose and xylose fermentation. *Proc Natl Acad Sci USA* 108:504-509.
42. Langmead B, Trapnell C, Pop M, & Salzberg S L (2009) Ultrafast and memory-efficient alignment of short DNA sequences to the human genome. *Genome Biol* 10:R25.
43. Roberts A, Trapnell C, Donaghey J, Rinn J L, & Pachter L (2011) Improving RNA-Seq expression estimates by correcting for fragment bias. *Genome Biol* 12:R22.
44. Sun J & Glass N L (2011) Identification of the CRE-1 Cellulolytic Regulon in *Neurospora crassa. PLoS One* 6:e25654.
45. Vogel H (1956) A convenient growth medium for *Neurospora. Microbial Genetics Bulletin* 13:42-46.
46. Tian C, et al. (2009) Systems analysis of plant cell wall degradation by the model filamentous fungus *Neurospora crassa. Proc Natl Acad Sci USA* 106:22157-22162.
47. Dementhon K, Iyer G, & Glass N L (2006) VIB-1 is required for expression of genes necessary for programmed cell death in *Neurospora crassa. Eukaryot Cell* 5:2161-2173.
48. Hall B G (2008) *Phylogenetic trees made easy: a how-to manual* (Sinauer Associates, Sunderland, Mass.) 3rd Ed pp xiv, 233 p.
49. Tamura K, et al. (2011) MEGA5: Molecular Evolutionary Genetics Analysis using Maximum Likelihood, Evolutionary Distance, and Maximum Parsimony Methods. *Mol Biol Evol* 28:2731-2739.
50. Langmead B, Trapnell C, Pop M, & Salzberg S L (2009) Ultrafast and memory efficient-alignment of short DNA sequences to the human genome. *Genome Biol* 10:R25.
51. Roberts A, Trapnell C, Donaghey J, Rinn J L, & Pachter L (2011) Improving RNA-Seq expression estimates by correcting for fragment bias. *Genome Biol* 12:R22.
52. de Hoon M J L, Imoto S, Nolan J, & Miyano S (2004) Open source clustering software. *Bioinformatics* 20:1453-1454.
53. Marshall A G & Hendrickson C L (2008) High-resolution mass spectrometers. *Annu Rev Anal Chem (Palo Alto Calif.)* 1:579-599.
54. Roepstorff P & Fohlman J (1984) Proposal for a common nomenclature for sequence ions in mass spectra of peptides. *Biomed Mass Spectrom* 11:601.

What is claimed:

1. A method for inducing secretion of a protein, the method comprising:
   (a) providing a mutant Ascomycete or Basidiomycete fungal cell, wherein the mutant cell comprises inactivating mutations in three endogenous β-glucosidase genes: gh1-1, gh3-3 and gh3-4; and
   (b) contacting the mutant cell with cellulosic biomass, wherein the cellulosic biomass induces the mutant cell to secrete the protein,
   wherein the mutant cell is *Neurospora crassa*.

2. A method for inducing secretion of a protein, the method comprising:
   (a) providing a mutant Ascomycete or Basidiomycete fungal cell, wherein the mutant cell comprises inactivating mutations in three endogenous β-glucosidase genes: gh1-1, gh3-3 and gh3-4; and
   (b) contacting the mutant cell with cellulosic biomass, wherein the cellulosic biomass induces the mutant cell to secrete the protein,
   wherein the β-glucosidases encoded by the gh1-1, gh3-3 and gh3-4 genes are orthologues of NCU00130, NCU04952 and NCU08755, respectively, and the mutant cell and orthologues are selected from the group consisting of:

|        | Species                    | NCU00130      | NCU04952      | NCU08755          |
|--------|----------------------------|---------------|---------------|-------------------|
| (i)    | Neurospora crassa          | SEQ ID NO: 01 | SEQ ID NO: 02 | SEQ ID NO: 03     |
| (ii)   | Aspergillus niger          | SEQ ID NO: 35 | SEQ ID NO: 56 | SEQ ID NO: 27     |
| (iii)  | Phanerochaete chrysosporium| SEQ ID NO: 36 | SEQ ID NO: 57 | SEQ ID NO: 26     |
| (iv)   | Sporotrichum thermophile   | SEQ ID NO: 37 | SEQ ID NO: 58 | SEQ ID NO: 25     |
| (v)    | Trichoderma reesei         | SEQ ID NO: 38 | SEQ ID NO: 59 | SEQ ID NO: 28     |
| (vi)   | Gibberella zeae            | SEQ ID NO: 39 | SEQ ID NO: 60 | SEQ ID NO: 29     |
| (vii)  | Sclerotinia sclerotiorum   | SEQ ID NO: 40 | SEQ ID NO: 61 | SEQ ID NO: 30     |
| (viii) | Botryotinia fuckeliana     | SEQ ID NO: 41 | SEQ ID NO: 62 | SEQ ID NO: 31     |
| (ix)   | Penicillium chrysogenum    | SEQ ID NO: 42 | SEQ ID NO: 63 | SEQ ID NO: 32     |
| (x)    | Schizophyllum commune      | SEQ ID NO: 43 | SEQ ID NO: 65 | SEQ ID NO: 33 and |
| (xi)   | Postia placenta            | SEQ ID NO: 44 | SEQ ID NO: 64 | SEQ ID NO: 34.    |

3. The method of claim 1 wherein the β-glucosidases encoded by the gh1-1, gh3-3 and gh3-4 genes are orthologues of NCU00130, NCU04952 and NCU08755, respectively, and the orthologues are:

| NCU00130      | NCU04952      | NCU08755       |
|---------------|---------------|----------------|
| SEQ ID NO: 01 | SEQ ID NO: 02 | SEQ ID NO: 03. |

4. The method of claim 1, wherein the mutant cell further comprises an inactivating mutation in an endogenous catabolite repressor gene, wherein the gene is cre-1.

5. The method of claim 2, wherein the mutant cell further comprises an inactivating mutation in an endogenous catabolite repressor gene, wherein the gene is cre-1.

6. The method of claim 3, wherein the mutant cell further comprises an inactivating mutation in an endogenous catabolite repressor gene, wherein the gene is cre-1.

7. The method of claim 1, wherein the mutant cell further comprises an inactivating mutation in an endogenous β-mannosidase gene, wherein the β-mannosidase gene is NCU00890.

8. The method of claim 2, wherein the mutant cell further comprises an inactivating mutation in an endogenous β-mannosidase gene, wherein the β-mannosidase gene is NCU00890 or a homologue thereof.

9. The method of claim 3, wherein the mutant cell further comprises an inactivating mutation in an endogenous β-mannosidase gene, wherein the β-mannosidase gene is NCU00890.

10. The method of claim 1, wherein the mutant cell further comprises an inactivating mutation in an endogenous phospholipase gene, wherein the phospholipase gene is NCU06650.

11. The method of claim 2, wherein the mutant cell further comprises an inactivating mutation in an endogenous phospholipase gene, wherein the phospholipase gene is NCU06650 or a homologue thereof.

12. The method of claim 3, wherein the mutant cell further comprises an inactivating mutation in an endogenous phospholipase gene, wherein the phospholipase gene is NCU06650.

13. The method of claim 1, wherein the secreted protein is selected from the group consisting of a cellulase, a GH61 enzyme, a cellobiose dehydrogenase, a lactonase, a carbohydrate esterase, a polysaccharide lyase, and combinations thereof.

14. The method of claim 2, wherein the secreted protein is selected from the group consisting of a cellulase, a GH61 enzyme, a cellobiose dehydrogenase, a lactonase, a carbohydrate esterase, a polysaccharide lyase, and combinations thereof.

15. The method of claim 3, wherein the secreted protein is selected from the group consisting of a cellulase, a GH61 enzyme, a cellobiose dehydrogenase, a lactonase, a carbohydrate esterase, a polysaccharide lyase, and combinations thereof.

16. The method of claim 1, wherein the cellulosic biomass comprises cellodextrin.

17. The method of claim 2, wherein the cellulosic biomass comprises cellodextrin.

18. The method of claim 3, wherein the cellulosic biomass comprises cellodextrin.

19. The method of claim 1, wherein the cellulosic biomass comprises cellobiose.

20. The method of claim 2, wherein the cellulosic biomass comprises cellobiose.

21. The method of claim 3, wherein the cellulosic biomass comprises cellobiose.

22. A method for inducing secretion of a protein, the method comprising:
    (a) contacting a mutant Ascomycete or Basidiomycete fungal cell with a cellulosic biomass, wherein the cellulosic biomass induces the mutant cell to secrete the protein, wherein the mutant cell comprises inactivating mutations in three endogenous β-glucosidase genes: gh1-1, gh3-3 and gh3-4; and
    (b) detecting increased secretion of the protein, wherein the increased secretion is relative to wild-type secretion of a corresponding wild-type fungal cell,
    wherein the mutant cell is *Neurospora crassa*.

23. A method for inducing secretion of a protein, the method comprising:
    (a) contacting a mutant Ascomycete or Basidiomycete fungal cell with a cellulosic biomass, wherein the cellulosic biomass induces the mutant cell to secrete the protein, wherein the mutant cell comprises inactivating mutations in three endogenous β-glucosidase genes: gh1-1, gh3-3 and gh3-4; and
    (b) detecting increased secretion of the protein, wherein the increased secretion is relative to wild-type secretion of a corresponding wild-type fungal cell,
    wherein the β-glucosidases encoded by the gh1-1, gh3-3 and gh3-4 genes are orthologues of NCU00130, NCU04952 and NCU08755, respectively, and the mutant cell and orthologues are selected from the group consisting of:

|       | Species                     | NCU00130      | NCU04952      | NCU08755      |
|-------|-----------------------------|---------------|---------------|---------------|
| (i)   | Neurospora crassa           | SEQ ID NO: 01 | SEQ ID NO: 02 | SEQ ID NO: 03 |
| (ii)  | Aspergillus niger           | SEQ ID NO: 35 | SEQ ID NO: 56 | SEQ ID NO: 27 |
| (iii) | Phanerochaete chrysosporium | SEQ ID NO: 36 | SEQ ID NO: 57 | SEQ ID NO: 26 |
| (iv)  | Sporotrichum thermophile    | SEQ ID NO: 37 | SEQ ID NO: 58 | SEQ ID NO: 25 |

-continued

|  | Species | NCU00130 | NCU04952 | NCU08755 |
|---|---|---|---|---|
| (v) | Trichoderma reesei | SEQ ID NO: 38 | SEQ ID NO: 59 | SEQ ID NO: 28 |
| (vi) | Gibberella zeae | SEQ ID NO: 39 | SEQ ID NO: 60 | SEQ ID NO: 29 |
| (vii) | Sclerotinia sclerotiorum | SEQ ID NO: 40 | SEQ ID NO: 61 | SEQ ID NO: 30 |
| (viii) | Botryotinia fuckeliana | SEQ ID NO: 41 | SEQ ID NO: 62 | SEQ ID NO: 31 |
| (ix) | Penicillium chrysogenum | SEQ ID NO: 42 | SEQ ID NO: 63 | SEQ ID NO: 32 |
| (x) | Schizophyllum commune | SEQ ID NO: 43 | SEQ ID NO: 65 | SEQ ID NO: 33 and |
| (xi) | Postia placenta | SEQ ID NO: 44 | SEQ ID NO: 64 | SEQ ID NO: 34. |

\* \* \* \* \*

SEQUENCE LISTING

<160> NUMBER OF SEQ ID NOS: 65

<210> SEQ ID NO 1
<211> LENGTH: 476
<212> TYPE: PRT
<213> ORGANISM: Neurospora crassa

<400> SEQUENCE: 1

```
Met Ser Leu Pro Lys Asp Phe Leu Trp Gly Phe Ala Thr Ala Ala Tyr
  1               5                  10                  15

Gln Ile Glu Gly Ala Ile His Ala Asp Gly Arg Gly Pro Ser Ile Trp
             20                  25                  30

Asp Thr Phe Cys Asn Ile Pro Gly Lys Ile Ala Asp Gly Ser Ser Gly
         35                  40                  45

Ala Val Ala Cys Asp Ser Tyr Asn Arg Thr Lys Glu Asp Ile Asp Leu
     50                  55                  60

Leu Lys Ser Leu Gly Ala Thr Ala Tyr Arg Phe Ser Ile Ser Trp Ser
 65                  70                  75                  80

Arg Ile Ile Pro Val Gly Gly Arg Asn Asp Pro Ile Asn Gln Lys Gly
                 85                  90                  95

Ile Asp His Tyr Val Lys Phe Val Asp Leu Leu Glu Ala Gly Ile
            100                 105                 110

Thr Pro Phe Ile Thr Leu Phe His Trp Asp Leu Pro Asp Gly Leu Asp
            115                 120                 125

Lys Arg Tyr Gly Gly Leu Leu Asn Arg Glu Glu Phe Pro Leu Asp Phe
        130                 135                 140

Glu His Tyr Ala Arg Thr Met Phe Lys Ala Ile Pro Lys Cys Lys His
145                 150                 155                 160

Trp Ile Thr Phe Asn Glu Pro Trp Cys Ser Ser Ile Leu Gly Tyr Asn
                165                 170                 175

Ser Gly Tyr Phe Ala Pro Gly His Thr Ser Asp Arg Thr Lys Ser Pro
            180                 185                 190

Val Gly Asp Ser Ala Arg Glu Pro Trp Ile Val Gly His Asn Leu Leu
        195                 200                 205

Ile Ala His Gly Arg Ala Val Lys Val Tyr Arg Glu Asp Phe Lys Pro
    210                 215                 220

Thr Gln Gly Gly Glu Ile Gly Ile Thr Leu Asn Gly Asp Ala Thr Leu
225                 230                 235                 240

Pro Trp Asp Pro Glu Asp Pro Leu Asp Val Glu Ala Cys Asp Arg Lys
                245                 250                 255

Ile Glu Phe Ala Ile Ser Trp Phe Ala Asp Pro Ile Tyr Phe Gly Lys
            260                 265                 270

Tyr Pro Asp Ser Met Arg Lys Gln Leu Gly Asp Arg Leu Pro Glu Phe
        275                 280                 285

Thr Pro Glu Glu Val Ala Leu Val Lys Gly Ser Asn Asp Phe Tyr Gly
    290                 295                 300

Met Asn His Tyr Thr Ala Asn Tyr Ile Lys His Lys Lys Gly Val Pro
305                 310                 315                 320

Pro Glu Asp Asp Phe Leu Gly Asn Leu Glu Thr Leu Phe Tyr Asn Lys
                325                 330                 335

Lys Gly Asn Cys Ile Gly Pro Glu Thr Gln Ser Phe Trp Leu Arg Pro
            340                 345                 350

His Ala Gln Gly Phe Arg Asp Leu Leu Asn Trp Leu Ser Lys Arg Tyr
        355                 360                 365
```

```
Gly Tyr Pro Lys Ile Tyr Val Thr Glu Asn Gly Thr Ser Leu Lys Gly
    370                 375                 380

Glu Asn Ala Met Pro Leu Lys Gln Ile Val Glu Asp Phe Arg Val
385                 390                 395                 400

Lys Tyr Phe Asn Asp Tyr Val Asn Ala Met Ala Lys Ala His Ser Glu
                405                 410                 415

Asp Gly Val Asn Val Lys Gly Tyr Leu Ala Trp Ser Leu Met Asp Asn
                420                 425                 430

Phe Glu Trp Ala Glu Gly Tyr Glu Thr Arg Phe Gly Val Thr Tyr Val
            435                 440                 445

Asp Tyr Glu Asn Asp Gln Lys Arg Tyr Pro Lys Lys Ser Ala Lys Ser
450                 455                 460

Leu Lys Pro Leu Phe Asp Ser Leu Ile Lys Lys Asp
465                 470                 475

<210> SEQ ID NO 2
<211> LENGTH: 735
<212> TYPE: PRT
<213> ORGANISM: Neurospora crassa

<400> SEQUENCE: 2

Met His Leu Arg Ile Phe Ala Val Leu Ala Ala Thr Ser Leu Ala Trp
1               5                   10                  15

Ala Glu Thr Ser Glu Lys Gln Ala Arg Gln Ala Gly Ser Gly Phe Ala
                20                  25                  30

Ala Trp Asp Ala Ala Tyr Ser Gln Ala Ser Thr Ala Leu Ser Lys Leu
            35                  40                  45

Ser Gln Gln Asp Lys Val Asn Ile Val Thr Gly Val Gly Trp Asn Lys
50                  55                  60

Gly Pro Cys Val Gly Asn Thr Pro Ala Ile Ala Ser Ile Gly Tyr Pro
65                  70                  75                  80

Gln Leu Cys Leu Gln Asp Gly Pro Leu Gly Ile Arg Phe Gly Gly Ser
                85                  90                  95

Val Thr Ala Phe Thr Pro Gly Ile Gln Ala Ala Ser Thr Trp Asp Val
                100                 105                 110

Glu Leu Ile Arg Gln Arg Gly Val Tyr Leu Gly Ala Glu Ala Arg Gly
            115                 120                 125

Val Gly Val His Val Leu Leu Gly Pro Val Ala Gly Ala Leu Gly Lys
    130                 135                 140

Ile Pro Asn Gly Gly Arg Asn Trp Glu Gly Phe Gly Pro Asp Pro Tyr
145                 150                 155                 160

Leu Thr Gly Ile Ala Met Ser Glu Thr Ile Glu Gly Ile Gln Ser Asn
                165                 170                 175

Gly Val Gln Ala Cys Ala Lys His Phe Ile Leu Asn Glu Gln Glu Thr
            180                 185                 190

Asn Arg Asp Thr Ile Ser Ser Val Val Asp Asp Arg Thr Met His Glu
        195                 200                 205

Leu Tyr Leu Phe Pro Phe Ala Asp Ala Val His Ser Asn Val Ala Ser
    210                 215                 220

Val Met Cys Ser Tyr Asn Lys Val Asn Gly Thr Trp Ala Cys Glu Asn
225                 230                 235                 240

Asp Lys Ile Gln Asn Gly Leu Leu Lys Glu Leu Gly Phe Lys Gly
                245                 250                 255

Tyr Val Met Ser Asp Trp Asn Ala Gln His Thr Thr Asn Gly Ala Ala
            260                 265                 270
```

```
Asn Ser Gly Met Asp Met Thr Met Pro Gly Ser Asp Phe Asn Gly Lys
            275                 280                 285

Thr Ile Leu Trp Gly Pro Gln Leu Asn Thr Ala Val Asn Asn Gly Gln
290                 295                 300

Val Ser Lys Ala Arg Leu Asp Asp Met Ala Lys Arg Ile Leu Ala Ser
305                 310                 315                 320

Trp Tyr Leu Leu Glu Gln Asn Ser Gly Tyr Pro Ala Thr Asn Leu Lys
            325                 330                 335

Ala Asn Val Gln Gly Asn His Lys Glu Asn Val Arg Ala Val Ala Arg
                340                 345                 350

Asp Gly Ile Val Leu Leu Lys Asn Asp Asn Ile Leu Pro Leu Lys
            355                 360                 365

Lys Pro Ser Lys Leu Ala Ile Ile Gly Ser Ser Val Val Asn Pro
370                 375                 380

Ala Gly Arg Asn Ala Cys Thr Asp Arg Gly Cys Asn Thr Gly Ala Leu
385                 390                 395                 400

Gly Met Gly Trp Gly Ser Gly Thr Ala Asp Tyr Pro Tyr Phe Val Ala
                405                 410                 415

Pro Tyr Asp Ala Leu Lys Thr Arg Ala Gln Ser Asp Gly Thr Thr Val
            420                 425                 430

Asn Leu Leu Ser Ser Asp Ser Thr Ser Gly Val Ala Asn Ala Ala Ser
            435                 440                 445

Gly Ala Asp Ala Ala Leu Val Phe Ile Thr Ala Asp Ser Gly Glu Gly
450                 455                 460

Tyr Ile Thr Val Glu Gly Val Thr Gly Asp Arg Pro Asn Leu Asp Pro
465                 470                 475                 480

Trp His Asn Gly Asn Gln Leu Val Gln Ala Val Ala Gln Ala Asn Lys
                485                 490                 495

Asn Thr Ile Val Val His Ser Thr Gly Pro Ile Ile Leu Glu Thr
            500                 505                 510

Ile Leu Ala Gln Pro Gly Val Lys Ala Val Val Trp Ala Gly Leu Pro
            515                 520                 525

Ser Gln Glu Asn Gly Asn Ala Leu Val Asp Val Leu Tyr Gly Leu Val
530                 535                 540

Ser Pro Ser Gly Lys Leu Pro Tyr Thr Ile Ala Lys Ser Glu Ser Asp
545                 550                 555                 560

Tyr Gly Thr Ala Val Gln Arg Gly Gly Thr Asp Leu Phe Thr Glu Gly
                565                 570                 575

Leu Phe Ile Asp Tyr Arg His Phe Asp Lys Asn Gly Ile Ala Pro Arg
            580                 585                 590

Tyr Glu Phe Gly Phe Gly Leu Ser Tyr Thr Asn Phe Thr Tyr Ser Ser
            595                 600                 605

Leu Ser Ile Thr Ser Thr Ala Ser Ser Gly Pro Ala Ser Gly Asp Thr
            610                 615                 620

Ile Pro Gly Gly Arg Ala Asp Leu Trp Glu Thr Val Ala Thr Val Thr
625                 630                 635                 640

Ala Val Val Lys Asn Thr Gly Val Gln Gly Ala Glu Ala Pro Gln
                645                 650                 655

Leu Tyr Ile Thr Leu Pro Ser Ser Ala Pro Ser Ser Pro Lys Gln
            660                 665                 670

Leu Arg Gly Phe Ala Lys Leu Lys Leu Ala Pro Gly Glu Ser Lys Thr
            675                 680                 685
```

```
Ala Thr Phe Ile Leu Arg Arg Arg Asp Leu Ser Tyr Trp Asp Thr Gly
    690                 695                 700

Ser Gln Asn Trp Val Val Pro Ser Gly Ser Phe Gly Val Val Val Gly
705                 710                 715                 720

Ala Ser Ser Arg Asp Leu Arg Leu Asn Gly Lys Phe Asp Val Tyr
                725                 730                 735

<210> SEQ ID NO 3
<211> LENGTH: 875
<212> TYPE: PRT
<213> ORGANISM: Neurospora crassa

<400> SEQUENCE: 3

Met Lys Phe Ala Ile Pro Leu Ala Leu Leu Ala Ser Gly Asn Leu Ala
1               5                   10                  15

Leu Ala Ala Pro Glu Pro Ile His Pro Ser His Gln Gln Leu Asn Lys
            20                  25                  30

Arg Ser Leu Ala Tyr Ser Glu Pro His Tyr Pro Ser Pro Trp Met Asp
        35                  40                  45

Pro Lys Ala Ile Gly Trp Glu Glu Ala Tyr Glu Lys Ala Lys Ala Phe
    50                  55                  60

Val Ser Gln Leu Thr Leu Leu Glu Lys Val Asn Leu Thr Thr Gly Ile
65                  70                  75                  80

Gly Trp Gly Ala Glu Gln Cys Val Gly Gln Thr Gly Ala Ile Pro Arg
                85                  90                  95

Leu Gly Leu Lys Ser Met Cys Met Gln Asp Ala Pro Leu Ala Ile Arg
            100                 105                 110

Gly Thr Asp Tyr Asn Ser Val Phe Pro Ala Gly Val Thr Thr Ala Ala
        115                 120                 125

Thr Phe Asp Arg Gly Leu Met Tyr Lys Arg Gly Tyr Ala Leu Gly Gln
    130                 135                 140

Glu Ala Lys Gly Lys Gly Val Thr Val Leu Leu Gly Pro Val Ala Gly
145                 150                 155                 160

Pro Leu Gly Arg Ala Pro Glu Gly Gly Arg Asn Trp Glu Gly Phe Ser
                165                 170                 175

Thr Asp Pro Val Leu Thr Gly Ile Ala Met Ala Glu Thr Ile Lys Gly
            180                 185                 190

Thr Gln Asp Ala Gly Val Val Ala Cys Ala Lys His Phe Ile Gly Asn
        195                 200                 205

Glu Gln Glu His Phe Arg Gln Val Gly Glu Ser Gln Asp Tyr Gly Tyr
    210                 215                 220

Asn Ile Ser Glu Thr Leu Ser Ser Asn Ile Asp Asp Lys Thr Met His
225                 230                 235                 240

Glu Met Tyr Leu Trp Pro Phe Val Asp Ala Ile Arg Ala Gly Val Gly
                245                 250                 255

Ser Phe Met Cys Ala Tyr Thr Gln Ala Asn Asn Ser Tyr Ser Cys Gln
            260                 265                 270

Asn Ser Lys Leu Leu Asn Asn Leu Leu Lys Gln Glu Asn Gly Phe Gln
        275                 280                 285

Gly Phe Val Met Ser Asp Trp Gln Ala His His Ser Gly Val Ala Ser
    290                 295                 300

Ala Ala Ala Gly Leu Asp Met Ser Met Pro Gly Asp Thr Met Phe Asn
305                 310                 315                 320

Ser Gly Arg Ser Tyr Trp Gly Thr Asn Leu Thr Leu Ala Val Leu Asn
                325                 330                 335
```

```
Gly Thr Val Pro Gln Trp Arg Ile Asp Asp Met Ala Met Arg Ile Met
            340                 345                 350

Ala Ala Phe Phe Lys Val Gly Thr Val Glu Asp Gln Glu Pro Ile
            355                 360                 365

Asn Phe Ser Phe Trp Thr Leu Asp Thr Tyr Gly Pro Leu His Trp Ala
370                 375                 380

Ala Arg Lys Asp Tyr Gln Gln Ile Asn Trp His Val Asn Val Gln Gly
385                 390                 395                 400

Asp His Gly Ser Leu Ile Arg Glu Ile Ala Ala Arg Gly Thr Val Leu
                405                 410                 415

Leu Lys Asn Thr Gly Ser Leu Pro Leu Lys Pro Lys Phe Leu Ala
            420                 425                 430

Val Ile Gly Glu Asp Ala Gly Pro Asn Pro Leu Gly Pro Asn Gly Cys
            435                 440                 445

Ala Asp Asn Arg Cys Asn Asn Gly Thr Leu Gly Ile Gly Trp Gly Ser
        450                 455                 460

Gly Thr Gly Asn Phe Pro Tyr Leu Val Thr Pro Asp Gln Ala Leu Gln
465                 470                 475                 480

Ala Arg Ala Val Gln Asp Gly Ser Arg Tyr Glu Ser Val Leu Arg Asn
            485                 490                 495

His Ala Pro Thr Glu Ile Lys Ala Leu Val Ser Gln Gln Asp Ala Thr
            500                 505                 510

Ala Ile Val Phe Val Asn Ala Asn Ser Gly Glu Gly Phe Ile Glu Ile
            515                 520                 525

Asp Gly Asn Lys Gly Asp Arg Leu Asn Leu Thr Leu Trp Asn Glu Gly
530                 535                 540

Asp Ala Leu Val Lys Asn Val Ser Ser Trp Cys Asn Asn Thr Ile Val
545                 550                 555                 560

Val Leu His Thr Pro Gly Pro Val Leu Leu Thr Glu Trp Tyr Asp Asn
            565                 570                 575

Pro Asn Ile Thr Ala Ile Leu Trp Ala Gly Met Pro Gly Gln Glu Ser
            580                 585                 590

Gly Asn Ser Ile Thr Asp Val Leu Tyr Gly Arg Val Asn Pro Ser Gly
            595                 600                 605

Arg Thr Pro Phe Thr Trp Gly Ala Thr Arg Glu Ser Tyr Gly Thr Asp
610                 615                 620

Val Leu Tyr Glu Pro Asn Asn Gly Asn Glu Ala Pro Gln Leu Asp Tyr
625                 630                 635                 640

Thr Glu Gly Val Phe Ile Asp Tyr Arg His Phe Asp Lys Ala Asn Ala
            645                 650                 655

Ser Val Leu Tyr Glu Phe Gly Phe Gly Leu Ser Tyr Thr Thr Phe Glu
            660                 665                 670

Tyr Ser Asn Leu Lys Ile Glu Lys His Gln Val Gly Glu Tyr Thr Pro
675                 680                 685

Thr Thr Gly Gln Thr Glu Ala Ala Pro Thr Phe Gly Asn Phe Ser Glu
            690                 695                 700

Ser Val Glu Asp Tyr Val Phe Pro Ala Ala Glu Phe Pro Tyr Val Tyr
705                 710                 715                 720

Gln Phe Ile Tyr Pro Tyr Leu Asn Ser Thr Asp Met Ser Ala Ser Ser
            725                 730                 735

Gly Asp Ala Gln Tyr Gly Gln Thr Ala Glu Glu Phe Leu Pro Pro Lys
            740                 745                 750
```

```
Ala Asn Asp Gly Ser Ala Gln Pro Leu Leu Arg Ser Gly Leu His
            755                 760                 765

His Pro Gly Gly Asn Pro Ala Leu Tyr Asp Ile Met Tyr Thr Val Thr
    770                 775                 780

Ala Asp Ile Thr Asn Thr Gly Lys Val Ala Gly Asp Glu Val Pro Gln
785                 790                 795                 800

Leu Tyr Val Ser Leu Gly Gly Pro Glu Asp Pro Lys Val Val Leu Arg
                805                 810                 815

Gly Phe Asp Arg Leu Arg Val Glu Pro Gly Lys Val Gln Phe Lys
                820                 825                 830

Ala Val Leu Thr Arg Arg Asp Val Ser Ser Trp Asp Thr Val Lys Gln
            835                 840                 845

Asp Trp Val Ile Thr Glu Tyr Ala Lys Lys Val Tyr Val Gly Pro Ser
    850                 855                 860

Ser Arg Lys Leu Asp Leu Glu Glu Val Leu Pro
865                 870                 875
```

```
<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
cgacagacgt cgcggtgagt tcag                                          24

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
tagtgtacaa accccaagc                                                19

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
aacacacaca cacacactgg                                               20

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
acagtggagg tgagaaagg                                                19

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 8
gtacttacgc agtagcgtgg                                                       20

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
tgatcttacc gactacct                                                         18

<210> SEQ ID NO 10
<211> LENGTH: 18
<212> TYPE: DNA
<213> ORGANISM: Artificial Sequence
<220> FEATURE:
<223> OTHER INFORMATION: Synthetic Construct

<400> SEQUENCE: 10
cagagcttct ccttgatg                                                         18

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
atctgggaag cgaacaaag                                                        19

<210> SEQ ID NO 12
<211> LENGTH: 18
<212> TYPE: DNA
<213> ORGANISM: Artificial Sequence
<220> FEATURE:
<223> OTHER INFORMATION: Synthetic Construct

<400> SEQUENCE: 12
tagcggtcgt cggaatag                                                         18

<210> SEQ ID NO 13
<211> LENGTH: 18
<212> TYPE: DNA
<213> ORGANISM: Artificial Sequence
<220> FEATURE:
<223> OTHER INFORMATION: Synthetic Construct

<400> SEQUENCE: 13
cccatcacca ctactacc                                                         18

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
ccagccctga acaccaag                                                         18

<210> SEQ ID NO 15

```
<211> LENGTH: 19
<212> TYPE: DNA
<213> ORGANISM: Artificial Sequence
<220> FEATURE:
<223> OTHER INFORMATION: Synthetic Construct

<400> SEQUENCE: 15
gagttcacat tccctgaca                                                   19

<210> SEQ ID NO 16
<211> LENGTH: 18
<212> TYPE: DNA
<213> ORGANISM: Artificial Sequence
<220> FEATURE:
<223> OTHER INFORMATION: Synthetic Construct

<400> SEQUENCE: 16
cgaagccaac acggaaga                                                    18

<210> SEQ ID NO 17
<211> LENGTH: 18
<212> TYPE: DNA
<213> ORGANISM: Artificial Sequence
<220> FEATURE:
<223> OTHER INFORMATION: Synthetic Construct

<400> SEQUENCE: 17
tcaagcccgg ttactatc                                                    18

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
aacctgtcac ctgcaact                                                    18

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct

<400> SEQUENCE: 19
ctactgccat gtcctctc                                                    18

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct

<400> SEQUENCE: 20
tatcaggacc actttggctt c                                                21

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct

<400> SEQUENCE: 21
```

```
gttcggcgtt acctatgt                                                    18
```

<210> SEQ ID NO 22
<211> LENGTH: 19
<212> TYPE: DNA
<213> ORGANISM: Artificial Sequence
<220> FEATURE:
<223> OTHER INFORMATION: Synthetic Construct

<400> SEQUENCE: 22

```
agagtcaaag agcggcttc                                                   19
```

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23

```
catctcatac tccctcatcc                                                  20
```

<210> SEQ ID NO 24
<211> LENGTH: 20
<212> TYPE: DNA
<213> ORGANISM: Artificial Sequence
<220> FEATURE:
<223> OTHER INFORMATION: Synthetic Construct

<400> SEQUENCE: 24

```
ggttgtctcg gtcgacattg                                                  20
```

<210> SEQ ID NO 25
<211> LENGTH: 870
<212> TYPE: PRT
<213> ORGANISM: Sporotrichum Thermophile

<400> SEQUENCE: 25

```
Met Lys Ala Ala Ala Leu Ser Cys Leu Phe Gly Ser Thr Leu Ala Val
  1               5                  10                  15

Ala Gly Ala Ile Glu Ser Arg Lys Val His Gln Lys Pro Leu Ala Arg
                 20                  25                  30

Ser Glu Pro Phe Tyr Pro Ser Pro Trp Met Asn Pro Asn Ala Asp Gly
             35                  40                  45

Trp Ala Glu Ala Tyr Ala Gln Ala Lys Ser Phe Val Ser Gln Met Thr
         50                  55                  60

Leu Leu Glu Lys Val Asn Leu Thr Thr Gly Val Gly Trp Gly Ala Glu
 65                  70                  75                  80

Gln Cys Val Gly Gln Val Gly Ala Ile Pro Arg Leu Gly Leu Arg Ser
                 85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175
```

```
Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
            195                 200                 205

Arg Gln Val Pro Glu Ala Gln Gly Tyr Gly Tyr Asn Ile Ser Glu Thr
            210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Gln Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
            275                 280                 285

Asp Trp Gln Ala Gln His Thr Gly Ala Ala Ser Ala Val Ala Gly Leu
290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
            355                 360                 365

Asp Asp Thr Tyr Gly Pro Ile His Trp Ala Ala Lys Gln Gly Tyr Gln
370                 375                 380

Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Ser Ser Pro Asn Gly Pro Asn Gly Cys Ser Asp Arg Gly Cys Asn
            435                 440                 445

Glu Gly Thr Leu Ala Met Gly Trp Gly Ser Gly Thr Ala Asn Tyr Pro
            450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Lys Thr
                485                 490                 495

Lys Ala Leu Val Ser Gln Ala Asn Ala Thr Ala Ile Val Phe Val Asn
            500                 505                 510

Ala Asp Ser Gly Glu Gly Tyr Ile Asn Val Asp Gly Asn Glu Gly Asp
            515                 520                 525

Arg Lys Asn Leu Thr Leu Trp Asn Asn Gly Asp Thr Leu Val Lys Asn
530                 535                 540

Val Ser Ser Trp Cys Ser Asn Thr Ile Val Ile His Ser Val Gly
545                 550                 555                 560

Pro Val Leu Leu Thr Asp Trp Tyr Asp Asn Pro Asn Ile Thr Ala Ile
                565                 570                 575

Leu Trp Ala Gly Leu Pro Gly Gln Glu Ser Gly Asn Ser Ile Thr Asp
            580                 585                 590
```

Val Leu Tyr Gly Lys Val Asn Pro Ala Ala Arg Ser Pro Phe Thr Trp
                595                 600                 605

Gly Lys Thr Arg Glu Ser Tyr Gly Ala Asp Val Leu Tyr Lys Pro Asn
    610                 615                 620

Asn Gly Asn Gly Ala Pro Gln Gln Asp Phe Thr Glu Gly Val Phe Ile
625                 630                 635                 640

Asp Tyr Arg Tyr Phe Asp Lys Val Asp Asp Ser Val Ile Tyr Glu
                645                 650                 655

Phe Gly His Gly Leu Ser Tyr Thr Thr Phe Glu Tyr Ser Asn Ile Arg
                660                 665                 670

Val Val Lys Ser Asn Val Ser Glu Tyr Arg Pro Thr Thr Gly Thr Thr
                675                 680                 685

Ala Gln Ala Pro Thr Phe Gly Asn Phe Ser Thr Asp Leu Glu Asp Tyr
                690                 695                 700

Leu Phe Pro Lys Asp Glu Phe Pro Tyr Ile Tyr Gln Tyr Ile Tyr Pro
705                 710                 715                 720

Tyr Leu Asn Thr Thr Asp Pro Arg Arg Ala Ser Ala Asp Pro His Tyr
                725                 730                 735

Gly Gln Thr Ala Glu Glu Phe Leu Pro Pro His Ala Thr Asp Asp Asp
                740                 745                 750

Pro Gln Pro Leu Leu Arg Ser Ser Gly Gly Asn Ser Pro Gly Gly Asn
                755                 760                 765

Arg Gln Leu Tyr Asp Ile Val Tyr Thr Ile Thr Ala Asp Ile Thr Asn
                770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
                805                 810                 815

Arg Ile Glu Pro Gly Glu Thr Arg Gln Phe Thr Gly Arg Leu Thr Arg
                820                 825                 830

Arg Asp Leu Ser Asn Trp Asp Val Thr Val Gln Asp Trp Val Ile Ser
                835                 840                 845

Arg Tyr Pro Lys Thr Ala Tyr Val Gly Arg Ser Ser Arg Lys Leu Asp
                850                 855                 860

Leu Lys Ile Glu Leu Pro
865                 870

<210> SEQ ID NO 26
<211> LENGTH: 802
<212> TYPE: PRT
<213> ORGANISM: Phanerochaete Chrysosporium

<400> SEQUENCE: 26

Gln Ser Gly Leu Tyr Gln Gln Cys Gly Gly Ile Gly Trp Thr Gly Ala
  1               5                  10                  15

Thr Thr Cys Val Ser Gly Ala Thr Cys Thr Val Leu Asn Pro Tyr Tyr
                 20                  25                  30

Ser Gln Cys Leu Pro Gly Ala Ala Thr Thr Val Ser Ser Ser His
             35                  40                  45

Ser Ser Ser Ser Ser Val Ser Ser His Ser Ser Ala Ser Ser Ser
         50                  55                  60

Ser Ile Ser Ser Thr Thr Ser Pro Pro Ala Pro Ser Gln Thr Val
65                  70                  75                  80

Ala Asn Val Ser Pro Glu Trp Ala Ala Ala Tyr Val Lys Ala Gln Ala
                 85                  90                  95

```
Ala Val Ala Lys Leu Ser Val Thr Asp Met Val Asn Leu Ala Thr Gly
            100                 105                 110

Val Gln Trp Glu Lys Gly Pro Cys Val Gly Asn Thr Pro Ala Ile Ser
            115                 120                 125

Ser Ile Pro Gly Phe Thr Gly Leu Cys Leu Gln Asp Ser Pro Val Gly
            130                 135                 140

Val Arg Tyr Ala Asp Gly Thr Ser Val Phe Pro Pro Glu Ile Asn Val
145                 150                 155                 160

Ala Ala Thr Trp Asn Arg Thr Leu Met Arg Gln Arg Gly Ala Ala Met
                165                 170                 175

Gly Ala Glu Phe Lys Gly Lys Gly Val His Val Ala Leu Gly Pro Met
            180                 185                 190

Met Asn Leu Met Arg Val Pro Ala Ala Gly Arg Asn Trp Glu Gly Gly
            195                 200                 205

Gly Gly Asp Pro Phe Leu Ser Gly Glu Leu Ala Phe Glu Thr Ile Thr
            210                 215                 220

Gly Ile Gln Ser Ser Gly Ala Gln Ala Cys Ala Lys His Phe Ile Asn
225                 230                 235                 240

Asn Glu Gln Glu His Phe Arg Asp Ser Ser Ser Asn Val Asp Asp
                245                 250                 255

Arg Thr Glu His Glu Leu Tyr Gly His Pro Phe Leu Arg Ser Val Gln
                260                 265                 270

Ala Asn Val Ala Ser Val Met Cys Ser Tyr Asn Gln Ile Asn Gly Thr
                275                 280                 285

Phe Ser Cys Glu Asn Glu Lys Thr Leu Ser Gly Leu Leu Lys Gly Glu
            290                 295                 300

Tyr Gly Phe Gln Gly Tyr Val Met Ser Asp Trp Trp Ala Thr His Ser
305                 310                 315                 320

Gly Ala Pro Ala Val Asn Ala Gly Leu Asp Met Thr Met Pro Gly Asp
                325                 330                 335

Glu Thr Thr Asn Ser Gly Thr Thr Tyr Phe Gly Gln Asn Leu Val Asn
                340                 345                 350

Ala Val Asn Ser Gly Gln Val Ser Gln Ala Arg Ile Lys Asp Met Ala
                355                 360                 365

Thr Arg Ile Leu Ala Ala Trp Tyr Leu Leu Gly Gln Asp Gln Asn Phe
370                 375                 380

Pro Ala Val Asn Phe Asn Ser Trp Asn Ser Gly Gln Gly Gln His Val
385                 390                 395                 400

Asn Val Ser Gly Asn His Ala Ser Leu Ile Arg Thr Ile Gly Ala Ala
                405                 410                 415

Ser Gln Ile Leu Leu Lys Asn Val Asn Gly Ala Leu Pro Leu Lys Lys
            420                 425                 430

Pro Lys Thr Ile Gly Ile Ile Gly Asn Gly Ala Gly Ser Asn Pro Ser
            435                 440                 445

Gly Pro Asn Ala Phe Ser Asp Arg Ala Gly Asp Val Gly Val Leu Ala
            450                 455                 460

Leu Gly Trp Gly Ser Gly Thr Ala Asn Phe Pro Tyr Leu Val Ala Pro
465                 470                 475                 480

Val Asp Ala Ile Thr Ala Arg Ala Ser Gln Asp Gly Thr Thr Val Ser
                485                 490                 495

Ser Ser Leu Ser Asp Thr Asp Leu Thr Gly Ala Ala Asn Thr Ala Thr
            500                 505                 510
```

```
Gly Lys Asp Val Ala Met Val Phe Ile Thr Ala Asp Ser Gly Glu Gly
            515                 520                 525

Tyr Leu Thr Val Glu Gly Asn Ala Gly Asp Arg Asn Asp Leu Gln Ala
    530                 535                 540

Trp His Gly Gly Asp Ala Leu Val Gln Gln Val Ala Ser His Asn Lys
545                 550                 555                 560

Asn Thr Ile Val Val Ile Asn Ser Val Gly Pro Ile Asn Met Glu Ala
                565                 570                 575

Trp Val Asn His Pro Asn Val Thr Ala Ile Val Trp Ser Gly Leu Pro
            580                 585                 590

Gly Gln Glu Ala Gly Asn Ala Val Thr Asp Val Leu Phe Gly Ala Val
    595                 600                 605

Asn Pro Gly Gly Lys Leu Pro Phe Thr Ile Gly Lys Ser Ile Ser Asp
610                 615                 620

Tyr Ser Ala Gln Ile Ile Thr Thr Gly Ser Gly Ile Val Pro Ile Pro
625                 630                 635                 640

Tyr Asn Glu Gly Leu Phe Ile Asp Tyr Arg His Phe Asp Gln Ala Gly
                645                 650                 655

Ile Ala Pro Arg Phe Glu Phe Gly Phe Gly Leu Ser Tyr Thr Thr Phe
            660                 665                 670

Asp Tyr Ser Asn Leu Val Ile Thr Gly Ser Thr Ala Gly Gly Thr Arg
    675                 680                 685

Gln Pro Pro Gly Pro Gly Ser Ser Leu Asp Pro Trp Leu His Asp Ser
690                 695                 700

Val Val Thr Val Ser Phe Thr Leu Thr Asn Asn Gly Thr Val Asp Gly
705                 710                 715                 720

Thr Glu Val Pro Gln Leu Tyr Leu Ser Pro Pro Thr Ser Ala Lys Ser
                725                 730                 735

Ala Pro Gln Asn Leu Lys Gly Phe Asp Ser Gly Phe Leu Pro Ala Gly
            740                 745                 750

Ala Ser Thr Thr Val Ser Phe Glu Leu Ser Arg Tyr Ser Phe Ser Val
    755                 760                 765

Trp Asp Val Val Ser Gln Ser Trp Gln Ile Pro Ala Gly Val Thr Gly
770                 775                 780

Ile Ser Val Gly Ala Ser Ser Arg Asp Leu Arg Leu Lys Gly Ser Ile
785                 790                 795                 800

Thr Asn

<210> SEQ ID NO 27
<211> LENGTH: 860
<212> TYPE: PRT
<213> ORGANISM: Aspergillus Niger

<400> SEQUENCE: 27

Met Arg Phe Thr Leu Ile Glu Ala Val Ala Leu Thr Ala Val Ser Leu
1               5                   10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Glu Ala Tyr Gln Arg Ala Val
        35                  40                  45

Asp Ile Val Ser Gln Met Thr Leu Ala Glu Lys Val Asn Leu Thr Thr
    50                  55                  60

Gly Thr Gly Trp Glu Leu Glu Leu Cys Val Gly Gln Thr Gly Gly Val
65                  70                  75                  80
```

```
Pro Arg Leu Gly Ile Pro Gly Met Cys Ala Gln Asp Ser Pro Leu Gly
                85                  90                  95

Val Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
        195                 200                 205

Gly Phe Asn Ile Thr Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Phe Lys Tyr Tyr
        355                 360                 365

Tyr Val Ser Glu Gly Pro Tyr Glu Lys Val Asn Gln Phe Val Asn Val
    370                 375                 380

Gln Arg Asn His Ser Glu Leu Ile Arg Ile Gly Ala Asp Ser Thr
385                 390                 395                 400

Val Leu Leu Lys Asn Asp Gly Ala Leu Pro Leu Thr Gly Lys Glu Arg
                405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys Asn Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
```

```
              500                 505                 510
Asn Val Asp Gly Asn Leu Gly Asp Arg Arg Asn Leu Thr Leu Trp Arg
            515                 520                 525

Asn Gly Asp Asn Val Ile Lys Ala Ala Ala Ser Asn Cys Asn Asn Thr
            530                 535             540

Ile Val Ile Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
            595                 600                 605

Asp Tyr Leu Tyr Thr Glu Pro Asn Asn Gly Asn Gly Ala Pro Gln Glu
            610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Gln Val Glu Val Leu Ser Ala Pro Ala Tyr
            660                 665                 670

Glu Pro Ala Ser Gly Glu Thr Glu Ala Ala Pro Thr Phe Gly Glu Val
            675                 680                 685

Gly Asn Ala Ser Asp Tyr Leu Tyr Pro Asp Gly Leu Gln Arg Ile Thr
            690                 695                 700

Lys Phe Ile Tyr Pro Trp Leu Asn Ser Thr Asp Leu Glu Ala Ser Ser
705                 710                 715                 720

Gly Asp Ala Ser Tyr Gly Gln Asp Ala Ser Asp Tyr Leu Pro Glu Gly
            725                 730                 735

Ala Thr Asp Gly Ser Ala Gln Pro Ile Leu Pro Ala Gly Gly Gly Ala
            740                 745                 750

Gly Gly Asn Pro Arg Leu Tyr Asp Glu Leu Ile Arg Val Thr Val Thr
            755                 760                 765

Ile Lys Asn Thr Gly Lys Val Ala Gly Asp Glu Val Pro Gln Leu Tyr
            770                 775             780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Gln Trp Ser Thr Thr
                805                 810                 815

Leu Thr Arg Arg Asp Leu Ala Asn Trp Asn Val Glu Thr Gln Asp Trp
            820                 825                 830

Glu Ile Thr Ser Tyr Pro Lys Met Val Phe Val Gly Ser Ser Ser Arg
            835                 840                 845

Lys Leu Pro Leu Arg Ala Ser Leu Pro Thr Val His
            850                 855             860

<210> SEQ ID NO 28
<211> LENGTH: 874
<212> TYPE: PRT
<213> ORGANISM: Trichoderma Reesei

<400> SEQUENCE: 28

Met Lys Thr Leu Ser Val Phe Ala Ala Ala Leu Leu Ala Ala Val Ala
1               5                   10                  15
```

-continued

```
Glu Ala Asn Pro Tyr Pro Pro His Ser Asn Gln Ala Tyr Ser Pro
             20                  25                  30
Pro Phe Tyr Pro Ser Pro Trp Met Asp Pro Ser Ala Pro Gly Trp Glu
         35                  40                  45
Gln Ala Tyr Ala Gln Ala Lys Glu Phe Val Ser Gly Leu Thr Leu Leu
     50                  55                  60
Glu Lys Val Asn Leu Thr Thr Gly Val Gly Trp Met Gly Glu Lys Cys
 65                  70                  75                  80
Val Gly Asn Val Gly Thr Val Pro Arg Leu Gly Met Arg Ser Leu Cys
                 85                  90                  95
Met Gln Asp Gly Pro Leu Gly Leu Arg Phe Asn Thr Tyr Asn Ser Ala
             100                 105                 110
Phe Ser Val Gly Leu Thr Ala Ala Ala Ser Trp Ser Arg His Leu Trp
         115                 120                 125
Val Asp Arg Gly Thr Ala Leu Gly Ser Glu Ala Lys Gly Lys Gly Val
     130                 135                 140
Asp Val Leu Leu Gly Pro Val Ala Gly Pro Leu Gly Arg Asn Pro Asn
 145                 150                 155                 160
Gly Gly Arg Asn Val Glu Gly Phe Gly Ser Asp Pro Tyr Leu Ala Gly
                 165                 170                 175
Leu Ala Leu Ala Asp Thr Val Thr Gly Ile Gln Asn Ala Gly Thr Ile
             180                 185                 190
Ala Cys Ala Lys His Phe Leu Leu Asn Glu Gln Glu His Phe Arg Gln
         195                 200                 205
Val Gly Glu Ala Asn Gly Tyr Gly Tyr Pro Ile Thr Glu Ala Leu Ser
     210                 215                 220
Ser Asn Val Asp Asp Lys Thr Ile His Glu Val Tyr Gly Trp Pro Phe
 225                 230                 235                 240
Gln Asp Ala Val Lys Ala Gly Val Gly Ser Ile Met Cys Ser Tyr Asn
                 245                 250                 255
Gln Val Asn Asn Ser Tyr Ala Cys Gln Asn Ser Lys Leu Ile Asn Gly
             260                 265                 270
Leu Leu Lys Glu Glu Tyr Gly Phe Gln Gly Phe Val Met Ser Asp Trp
         275                 280                 285
Gln Ala Gln His Thr Gly Val Ala Ser Ala Val Ala Gly Leu Asp Met
     290                 295                 300
Thr Met Pro Gly Asp Thr Ala Phe Asn Thr Gly Ala Ser Tyr Phe Gly
 305                 310                 315                 320
Ser Asn Leu Thr Leu Ala Val Leu Asn Gly Thr Val Pro Glu Trp Arg
                 325                 330                 335
Ile Asp Asp Met Val Met Arg Ile Met Ala Pro Phe Phe Lys Val Gly
             340                 345                 350
Lys Thr Val Asp Ser Leu Ile Asp Thr Asn Phe Asp Ser Trp Thr Asn
         355                 360                 365
Gly Glu Tyr Gly Tyr Val Gln Ala Ala Val Asn Glu Asn Trp Glu Lys
     370                 375                 380
Val Asn Tyr Gly Val Asp Val Arg Ala Asn His Ala Asn His Ile Arg
 385                 390                 395                 400
Glu Val Gly Ala Lys Gly Thr Val Ile Phe Lys Asn Asn Gly Ile Leu
                 405                 410                 415
Pro Leu Lys Lys Pro Lys Phe Leu Thr Val Ile Gly Glu Asp Ala Gly
             420                 425                 430
Gly Asn Pro Ala Gly Pro Asn Gly Cys Gly Asp Arg Gly Cys Asp Asp
```

-continued

```
            435                 440                 445
Gly Thr Leu Ala Met Glu Trp Gly Ser Gly Thr Thr Asn Phe Pro Tyr
450                 455                 460
Leu Val Thr Pro Asp Ala Ala Leu Gln Ser Gln Ala Leu Gln Asp Gly
465                 470                 475                 480
Thr Arg Tyr Glu Ser Ile Leu Ser Asn Tyr Ala Ile Ser Gln Thr Gln
                485                 490                 495
Ala Leu Val Ser Gln Pro Asp Ala Ile Ala Ile Val Phe Ala Asn Ser
                500                 505                 510
Asp Ser Gly Glu Gly Tyr Ile Asn Val Asp Gly Asn Glu Gly Asp Arg
            515                 520                 525
Lys Asn Leu Thr Leu Trp Lys Asn Gly Asp Asp Leu Ile Lys Thr Val
530                 535                 540
Ala Ala Val Asn Pro Lys Thr Ile Val Ile His Ser Thr Gly Pro
545                 550                 555                 560
Val Ile Leu Lys Asp Tyr Ala Asn His Pro Asn Ile Ser Ala Ile Leu
                565                 570                 575
Trp Ala Gly Ala Pro Gly Gln Glu Ser Gly Asn Ser Leu Val Asp Ile
                580                 585                 590
Leu Tyr Gly Lys Gln Ser Pro Gly Arg Thr Pro Phe Thr Trp Gly Pro
            595                 600                 605
Ser Leu Glu Ser Tyr Gly Val Ser Val Met Thr Thr Pro Asn Asn Gly
            610                 615                 620
Asn Gly Ala Pro Gln Asp Asn Phe Asn Glu Gly Ala Phe Ile Asp Tyr
625                 630                 635                 640
Arg Tyr Phe Asp Lys Val Ala Pro Gly Lys Pro Arg Ser Ser Asp Lys
                645                 650                 655
Ala Pro Thr Tyr Glu Phe Gly Phe Gly Leu Ser Trp Ser Thr Phe Lys
                660                 665                 670
Phe Ser Asn Leu His Ile Gln Lys Asn Asn Val Gly Pro Met Ser Pro
            675                 680                 685
Pro Asn Gly Lys Thr Ile Ala Ala Pro Ser Leu Gly Ser Phe Ser Lys
            690                 695                 700
Asn Leu Lys Asp Tyr Gly Phe Pro Lys Asn Val Arg Arg Ile Lys Glu
705                 710                 715                 720
Phe Ile Tyr Pro Tyr Leu Ser Thr Thr Thr Ser Gly Lys Glu Ala Ser
                725                 730                 735
Gly Asp Ala His Tyr Gly Gln Thr Ala Lys Glu Phe Leu Pro Ala Gly
                740                 745                 750
Ala Leu Asp Gly Ser Pro Gln Pro Arg Ser Ala Ala Ser Gly Glu Pro
            755                 760                 765
Gly Gly Asn Arg Gln Leu Tyr Asp Ile Leu Tyr Thr Val Thr Ala Thr
            770                 775                 780
Ile Thr Asn Thr Gly Ser Val Met Asp Asp Ala Val Pro Gln Leu Tyr
785                 790                 795                 800
Leu Ser His Gly Gly Pro Asn Glu Pro Pro Lys Val Leu Arg Gly Phe
                805                 810                 815
Asp Arg Ile Glu Arg Ile Ala Pro Gly Gln Ser Val Thr Phe Lys Ala
                820                 825                 830
Asp Leu Thr Arg Arg Asp Leu Ser Asn Trp Asp Thr Lys Lys Gln Gln
            835                 840                 845
Trp Val Ile Thr Asp Tyr Pro Lys Thr Val Tyr Val Gly Ser Ser Ser
850                 855                 860
```

Arg Asp Leu Pro Leu Ser Ala Arg Leu Pro
865                 870

<210> SEQ ID NO 29
<211> LENGTH: 886
<212> TYPE: PRT
<213> ORGANISM: Gibberella Zeae

<400> SEQUENCE: 29

Met Lys Ala Asn Trp Leu Ala Ala Val Tyr Leu Ala Gly Thr
 1               5                  10                  15

Asp Ala Ala Val Pro Asp Thr Leu Ala Gly Val Asn Leu Val Ala Arg
            20                  25                  30

Asp Thr Leu Ala His Ser Pro Pro His Tyr Pro Ser Pro Trp Met Asp
        35                  40                  45

Pro Asn Ala Val Gly Trp Glu Asp Ala Tyr Ala Lys Ala Lys Asp Phe
    50                  55                  60

Val Ser Gln Met Thr Leu Leu Glu Lys Val Asn Leu Thr Thr Gly Val
65                  70                  75                  80

Gly Trp Gln Gly Glu Arg Cys Val Gly Asn Val Gly Ser Ile Pro Arg
                85                  90                  95

Leu Gly Met Arg Gly Leu Cys Leu Gln Asp Gly Pro Leu Gly Ile Arg
            100                 105                 110

Phe Ser Asp Tyr Asn Ser Ala Phe Pro Thr Gly Val Thr Ala Gly Ala
        115                 120                 125

Ser Trp Ser Lys Ala Leu Trp Tyr Glu Arg Gly Arg Leu Met Gly Thr
130                 135                 140

Glu Phe Lys Glu Lys Gly Ile Asp Ile Ala Leu Gly Pro Ala Thr Gly
145                 150                 155                 160

Pro Leu Gly Arg His Ala Ala Gly Gly Arg Asn Trp Glu Gly Phe Thr
                165                 170                 175

Val Asp Pro Tyr Ala Ala Gly His Ala Met Ala Glu Thr Val Lys Gly
            180                 185                 190

Ile Gln Asp Ser Gly Val Ile Ala Cys Ala Lys His Tyr Ile Ala Asn
        195                 200                 205

Glu Gln Glu His Phe Arg Gln Arg Gly Asp Val Met Ser Gln Lys Phe
210                 215                 220

Asn Ile Ser Glu Ser Leu Ser Ser Asn Leu Asp Asp Lys Thr Met His
225                 230                 235                 240

Glu Leu Tyr Asn Trp Pro Phe Ala Asp Ala Val Arg Ala Gly Val Gly
                245                 250                 255

Ser Ile Met Cys Ser Tyr Asn Gln Val Asn Asn Ser Tyr Ala Cys Gln
            260                 265                 270

Asn Ser Lys Leu Leu Asn Gly Ile Leu Lys Asp Glu Met Gly Phe Gln
        275                 280                 285

Gly Phe Val Met Ser Asp Trp Gln Ala Gln His Thr Gly Ala Ala Ser
290                 295                 300

Ala Val Ala Gly Leu Asp Met Thr Met Pro Gly Asp Thr Glu Phe Asn
305                 310                 315                 320

Thr Gly Phe Ser Phe Trp Gly Gly Asn Leu Thr Leu Ala Val Ile Asn
                325                 330                 335

Gly Thr Val Pro Ala Trp Arg Ile Asp Asp Met Ala Thr Arg Ile Met
            340                 345                 350

Ala Ala Phe Phe Lys Val Gly Arg Ser Val Glu Glu Glu Pro Asp Ile

```
                    355                 360                 365
Asn Phe Ser Ala Trp Thr Arg Asp Glu Tyr Gly Phe Val Gln Thr Tyr
    370                 375                 380
Ala Gln Glu Asn Arg Glu Lys Val Asn Phe Ala Val Asn Val Gln His
385                 390                 395                 400
Asp His Lys Arg His Ile Arg Glu Ala Ala Lys Gly Ser Val Val
                405                 410                 415
Leu Lys Asn Thr Gly Ser Leu Pro Leu Lys Lys Pro Gln Phe Leu Ala
            420                 425                 430
Val Ile Gly Glu Asp Ala Gly Ser Asn Pro Ala Gly Pro Asn Gly Cys
                435                 440                 445
Ala Asp Arg Gly Cys Asp Asn Gly Thr Leu Ala Met Ala Trp Gly Ser
            450                 455                 460
Gly Thr Ser Gln Phe Pro Tyr Leu Val Thr Pro Asp Gln Gly Ile Ser
465                 470                 475                 480
Leu Gln Ala Ile Gln Asp Gly Thr Arg Tyr Glu Ser Ile Leu Asn Asn
                485                 490                 495
Asn Gln Trp Pro Gln Thr Gln Ala Leu Val Ser Gln Pro Asn Val Thr
            500                 505                 510
Ala Ile Val Phe Ala Asn Ala Asp Ser Gly Glu Gly Tyr Ile Glu Val
                515                 520                 525
Asp Gly Asn Tyr Gly Asp Arg Lys Asn Leu Thr Leu Trp Lys Gln Gly
            530                 535                 540
Asp Glu Leu Ile Lys Asn Val Ser Ala Ile Cys Pro Asn Thr Ile Val
545                 550                 555                 560
Val Leu His Thr Val Gly Pro Val Leu Leu Thr Glu Trp His Asn Asn
                565                 570                 575
Pro Asn Ile Thr Ala Ile Val Trp Ala Gly Val Pro Gly Gln Glu Ser
            580                 585                 590
Gly Asn Ala Ile Ala Asp Ile Leu Tyr Gly Lys Thr Ser Pro Gly Arg
                595                 600                 605
Ser Pro Phe Thr Trp Gly Arg Thr Tyr Asp Ser Tyr Gly Thr Lys Val
            610                 615                 620
Leu Tyr Lys Ala Asn Asn Gly Glu Gly Ala Pro Gln Glu Asp Phe Val
625                 630                 635                 640
Glu Gly Asn Phe Ile Asp Tyr Arg His Phe Asp Arg Gln Ser Pro Ser
                645                 650                 655
Thr Asn Gly Lys Ser Ala Thr Asn Asp Ser Ser Ala Pro Leu Tyr Glu
            660                 665                 670
Phe Gly Phe Gly Leu Ser Trp Thr Thr Phe Glu Tyr Ser Asp Leu Lys
        675                 680                 685
Val Glu Ser Val Ser Asn Ala Ser Tyr Ser Pro Ser Val Gly Asn Thr
            690                 695                 700
Ile Pro Ala Pro Thr Tyr Gly Asn Phe Ser Lys Asn Leu Asp Asp Tyr
705                 710                 715                 720
Thr Phe Pro Ser Gly Val Arg Tyr Leu Tyr Lys Phe Ile Tyr Pro Tyr
                725                 730                 735
Leu Asn Thr Ser Ser Ser Ala Glu Lys Ala Ser Gly Asp Val Lys Gly
            740                 745                 750
Arg Phe Gly Glu Thr Gly Asp Glu Phe Leu Pro Pro Asn Ala Leu Asn
        755                 760                 765
Gly Ser Ser Gln Pro Arg Leu Pro Ser Ser Gly Ala Pro Gly Gly Asn
        770                 775                 780
```

```
Pro Gln Leu Trp Asp Ile Met Tyr Thr Val Thr Ala Thr Ile Thr Asn
785                 790                 795                 800

Thr Gly Asp Ala Thr Ser Asp Glu Val Pro Gln Leu Tyr Val Ser Leu
                805                 810                 815

Gly Gly Glu Gly Glu Pro Val Arg Val Leu Arg Gly Phe Glu Arg Leu
            820                 825                 830

Glu Asn Ile Ala Pro Gly Glu Ser Ala Thr Phe Thr Ala Gln Leu Thr
        835                 840                 845

Arg Arg Asp Leu Ser Asn Trp Asp Val Asn Val Gln Asn Trp Val Ile
    850                 855                 860

Thr Asp His Ala Lys Lys Ile Trp Val Gly Ser Ser Ser Arg Asn Leu
865                 870                 875                 880

Pro Leu Ser Ala Asp Leu
                885

<210> SEQ ID NO 30
<211> LENGTH: 891
<212> TYPE: PRT
<213> ORGANISM: Sclerotinia Sclerotiorum

<400> SEQUENCE: 30

Met Arg Tyr Ser Leu Val Val Ala Gly Leu Leu Ala Ala Ala Thr Pro
 1               5                  10                  15

Ser Gln Gln Ala Thr Thr Ser His Arg Thr Lys Gln Ser Arg Gln Ser
            20                  25                  30

Val Asn Ala Thr Tyr Pro Gly Gly Val Asp Pro Ala Ala Glu Ala Gly
        35                  40                  45

Ala Leu Phe Gly Gln Thr Ser Asp Pro Phe Tyr Pro Ser Pro Trp Met
    50                  55                  60

Ser Pro Asn Met Gly Gly Trp Glu Asp Ala Tyr Val Lys Ala Lys Asp
65                  70                  75                  80

Phe Val Ser Gln Leu Thr Leu Met Glu Lys Val Asn Leu Thr Thr Gly
                85                  90                  95

Val Gly Trp Glu Gly Glu Gln Cys Val Gly Gln Ala Gly Ser Val Pro
            100                 105                 110

Arg Leu Gly Leu Arg Ser Met Cys Met Gln Asp Ser Pro Val Gly Val
        115                 120                 125

Arg Asp Thr Asp Phe Asn Ser Val Phe Ser Ser Gly Gln Ser Val Ala
    130                 135                 140

Ala Thr Phe Asp Arg Gly Leu Met Tyr Ala Arg Gly Tyr Ala Met Gly
145                 150                 155                 160

Gln Glu His Lys Ala Lys Gly Val Thr Val Gln Leu Gly Pro Val Ala
                165                 170                 175

Gly Pro Leu Gly Arg Ser Pro Gln Gly Gly Arg Asn Trp Glu Gly Phe
            180                 185                 190

Ser Pro Asp Pro Val Leu Thr Gly Ile Gly Met Ala Glu Thr Ile Lys
        195                 200                 205

Gly Ile Gln Asp Ala Gly Ile Ile Ala Cys Ala Lys His Phe Ile Gly
    210                 215                 220

Asn Glu Gln Glu His Phe Arg Gln Ala Pro Glu Ala Ile Gly Tyr Gly
225                 230                 235                 240

Tyr Asn Ile Thr Glu Ser Ser Ser Ser Asn Ile Asp Asp Val Thr Met
                245                 250                 255

His Glu Thr Tyr Leu Trp Pro Phe Ala Asp Ala Val Arg Ala Gly Val
```

```
              260                 265                 270
Gly Ser Ile Met Cys Ser Tyr Asn Gln Val Asn Asn Ser Tyr Ser Cys
            275                 280                 285
Gln Asn Ser Lys Met Leu Asn Asn Leu Leu Lys Glu Glu Leu Gly Phe
            290                 295                 300
Gln Gly Phe Val Met Ser Asp Trp Gln Ala Gln His Ser Gly Ala Ser
305                 310                 315                 320
Ser Ala Val Ala Gly Leu Asp Met Thr Met Pro Gly Asp Thr Val Phe
                325                 330                 335
Asn Ser Gly Glu Ser Tyr Trp Gly Thr Asn Leu Thr Leu Ala Val Ile
                340                 345                 350
Asn Gly Thr Val Pro Glu Trp Arg Leu Asp Asp Met Ala Met Arg Ile
            355                 360                 365
Met Ala Ala Tyr Phe Lys Val Gly Leu Thr Leu Asp Glu Pro Glu Ile
            370                 375                 380
Asn Phe Ser Ser Trp Thr Leu Asp Thr Tyr Gly Pro Leu His Tyr Ala
385                 390                 395                 400
Ala Asn Lys Asp Val Gln Lys Ile Asn His His Val Asp Val Arg Gly
                405                 410                 415
Asp His Gly Lys Leu Ile Arg Asp Ile Gly Ala Arg Ser Thr Val Leu
                420                 425                 430
Leu Lys Asn Thr Lys Asn Ala Leu Pro Leu Ser Lys Pro Lys Phe Leu
            435                 440                 445
Ala Val Ile Gly Gln Asp Ala Gly Pro Asn Ala Tyr Gly Pro Asn Gly
            450                 455                 460
Cys Ser Asp Arg Gly Cys Asp Asn Gly Thr Leu Gly Met Ala Trp Gly
465                 470                 475                 480
Ser Gly Ser Ser Asn Phe Pro Tyr Leu Ile Thr Pro Thr Ala Leu
                485                 490                 495
Gln Asn Gln Ala Ile Ala Asp Gly Thr Val Tyr Gln Ser Ile Leu Asp
            500                 505                 510
Asn Tyr Ala Thr Ser Gln Ile Glu Ala Leu Val Ser Gln Asp Val Thr
            515                 520                 525
Ala Ile Val Phe Val Asn Ala Asn Ser Gly Glu Gly Tyr Ile Ser Val
            530                 535                 540
Asp Gly Asn Glu Gly Asp Arg Asn Asn Leu Thr Leu Trp His Ser Gly
545                 550                 555                 560
Asp Ala Leu Ile Gln Asn Val Ser Ala Ile Cys Asn Asn Thr Ile Val
                565                 570                 575
Val Ile His Ser Thr Gly Pro Thr Leu Val Gly Asp Trp Tyr Asp Asn
            580                 585                 590
Glu Asn Val Thr Ala Ile Leu Trp Ala Gly Val Pro Gly Gln Glu Ser
            595                 600                 605
Gly Asn Ser Ile Thr Asp Ile Leu Tyr Gly Lys Val Asn Pro Ala Ala
            610                 615                 620
Arg Thr Pro Phe Thr Trp Gly Pro Thr Arg Glu Ser Tyr Gly Ala Asp
625                 630                 635                 640
Val Leu Tyr Asp Ala Asn Asn Gly Glu Gly Ala Pro Gln Val Asp Phe
                645                 650                 655
Thr Glu Gly Asn Phe Ile Asp Tyr Arg Ala Phe Asp Arg Gln Asn Ile
                660                 665                 670
Asp Pro Ile Tyr Glu Phe Gly Phe Gly Leu Ser Tyr Thr Thr Phe Asp
            675                 680                 685
```

```
Tyr Ser Glu Leu Val Val Thr Lys Asn Thr Asn Ala Ser Ser Phe Tyr
        690                 695                 700

Thr Pro Ser Ser Gly Leu Thr Gln Ala Ala Pro Thr Phe Gly Asn Phe
705                 710                 715                 720

Ser Lys Asn Leu Asp Asp Tyr Leu Phe Pro Asn Gly Ser Phe Pro Tyr
                725                 730                 735

Val Tyr Gln Tyr Ile Tyr Pro Tyr Leu Asn Thr Ser Asp Ala Ala Ala
                740                 745                 750

Ala Ser Ala Asp Pro Arg Tyr Gly Gln Glu Ala Ser Glu Phe Leu Pro
        755                 760                 765

Pro Asn Ala Ala Asn Gly Ser Pro Gln Pro Ile His Ala Ala Gly Gly
770                 775                 780

Ala Pro Gly Gly Asn Pro Gln Leu Tyr Asp Val Leu Tyr Thr Val Thr
785                 790                 795                 800

Ala Gln Ile His Asn Ser Gly Asp Ile Asp Gly Glu Val Pro Gln
            805                 810                 815

Leu Tyr Ile Ser Leu Gly Gly Pro Asn Asp Pro Ala Val Val Leu Arg
                820                 825                 830

Gly Phe Glu Arg Leu Ser Ile Pro Ala Gly Ser Thr Ala Thr Phe Arg
        835                 840                 845

Ala Asp Leu Thr Arg Arg Asp Leu Ser Asn Trp Asp Thr Val Ala Gln
850                 855                 860

Asn Trp Phe Ile Ser Asp Tyr Thr Lys Lys Val Phe Val Gly Ser Ser
865                 870                 875                 880

Ser Arg Lys Leu Pro Leu Thr Gln Asp Leu Ala
                885                 890

<210> SEQ ID NO 31
<211> LENGTH: 887
<212> TYPE: PRT
<213> ORGANISM: Botryotinia Fuckeliana

<400> SEQUENCE: 31

Met Lys Ser Leu Leu Asp Leu Val Leu Val Leu Ser Gly Ile Ile Thr
1               5                   10                  15

Gly Asp Arg Lys Leu Leu Thr Leu Gly Thr Lys Ser Ser Asn Ser Thr
                20                  25                  30

Tyr Pro Gly Ala Val Asp Pro Ala Thr Asp Ser Gly Ala Val Phe Gly
            35                  40                  45

Gln Thr Ser Glu Pro Phe Tyr Pro Ser Pro Trp Met Asn Pro Asn Thr
50                  55                  60

Gly Gly Trp Glu Asp Ala Tyr Val Lys Ala Lys Asp Phe Val Ser Gln
65                  70                  75                  80

Leu Thr Leu Leu Glu Lys Val Asn Leu Thr Thr Gly Val Gly Trp Glu
                85                  90                  95

Gly Glu Gln Cys Val Gly Gln Ala Gly Ser Val Pro Arg Leu Gly Leu
            100                 105                 110

Arg Ser Met Cys Met Gln Asp Ser Pro Val Gly Val Arg Asp Thr Asp
        115                 120                 125

Phe Asn Ser Val Phe Ser Ser Gly Gln Ser Val Ala Ala Thr Phe Asp
    130                 135                 140

Arg Gly Leu Met Tyr Ala Arg Gly Tyr Ala Met Gly Gln Glu His Lys
145                 150                 155                 160

Ala Lys Gly Val Thr Val Gln Leu Gly Pro Val Ala Gly Pro Leu Gly
```

```
              165                 170                 175
Arg Ala Pro Gln Gly Gly Arg Asn Trp Glu Gly Phe Ser Pro Asp Pro
            180                 185                 190
Val Leu Thr Gly Ile Gly Ile Ala Glu Thr Ile Lys Gly Ile Gln Asp
            195                 200                 205
Ala Gly Ile Ile Ala Cys Ala Lys His Phe Ile Gly Asn Glu Gln Glu
            210                 215                 220
His Phe Arg Gln Ser Gly Glu Ser Gln Gly Phe Gly Phe Asn Ile Thr
225                 230                 235                 240
Glu Ser Ser Ser Asn Ile Asp Asp Val Thr Met His Glu Thr Tyr
                245                 250                 255
Leu Trp Pro Phe Ala Asp Ala Val Arg Ala Gly Val Gly Ser Ile Met
                260                 265                 270
Cys Ser Tyr Asn Gln Val Asn Asn Ser Tyr Ala Cys Gln Asn Ser Lys
                275                 280                 285
Met Leu Asn Asn Leu Leu Lys Asp Glu Leu Gly Phe Gln Gly Phe Val
            290                 295                 300
Met Thr Asp Trp Gln Ala Gln His Thr Gly Ala Ala Ser Ala Val Ala
305                 310                 315                 320
Gly Leu Asp Met Thr Met Pro Gly Asp Thr Leu Phe Asn Ser Gly Glu
                325                 330                 335
Ser Phe Trp Gly Thr Asn Leu Thr Leu Ala Val Ile Asn Gly Thr Val
                340                 345                 350
Pro Glu Trp Arg Ile Asp Asp Met Ala Met Arg Ile Met Ala Ala Tyr
                355                 360                 365
Phe Lys Val Gly Leu Thr Leu Asp Glu Pro Glu Ile Asn Phe Ser Ser
370                 375                 380
Trp Thr Leu Asp Thr Tyr Gly Pro Leu His Tyr Ala Ala Gly Lys Asp
385                 390                 395                 400
Val Gln Gln Ile Asn Trp His Val Asp Val Arg Gly Asp His Ala Lys
                405                 410                 415
Leu Ile Arg Asp Ile Gly Ala Arg Ser Thr Val Leu Leu Lys Asn Thr
                420                 425                 430
Asn Asn Ala Leu Pro Leu Ser Lys Pro Lys Phe Leu Ala Val Ile Gly
            435                 440                 445
Glu Asp Ala Gly Ser Ser Pro Tyr Gly Pro Asn Gly Cys Ser Asp Arg
450                 455                 460
Gly Cys Asp Asn Gly Thr Leu Gly Met Ala Trp Gly Ser Gly Ser Ala
465                 470                 475                 480
Asn Phe Pro Tyr Leu Val Thr Pro Asp Thr Ala Leu Gln Asn Gln Ala
                485                 490                 495
Ile Ala Asp Gly Thr Val Tyr Gln Ser Ile Leu Asp Asn Tyr Ala Thr
            500                 505                 510
Ala Gln Ile Glu Ala Leu Val Ser Gln Glu Val Thr Ala Ile Val Phe
            515                 520                 525
Val Asn Ala Asn Ser Gly Glu Gly Tyr Ile Ser Val Asp Gly Asn Ile
            530                 535                 540
Gly Asp Arg Asn Asn Leu Thr Leu Trp Asn Ser Gly Asp Ala Leu Ile
545                 550                 555                 560
Lys Asn Val Ser Ala Leu Cys Asn Asn Thr Ile Val Val Ile His Ser
                565                 570                 575
Thr Gly Pro Thr Leu Val Gly Asp Trp Tyr Asp Asn Glu Asn Ile Thr
            580                 585                 590
```

Ala Ile Leu Trp Ala Gly Val Pro Gly Gln Glu Ser Gly Asn Ser Ile
            595                 600                 605

Thr Asp Val Leu Tyr Gly Lys Val Asn Pro Ala Ala Arg Thr Pro Phe
    610                 615                 620

Thr Trp Gly Pro Thr Arg Glu Ser Tyr Gly Thr Asp Val Leu Tyr Glu
625                 630                 635                 640

Pro Asn Asn Gly Glu Ala Ala Pro Gln Leu Asp Phe Thr Gly Asn
                645                 650                 655

Phe Ile Asp Tyr Arg Ala Phe Asp Ala Gln Gly Ile Glu Pro Ile Tyr
                660                 665                 670

Glu Phe Gly Phe Gly Leu Ser Tyr Thr Thr Phe Asn Tyr Ser Gly Leu
            675                 680                 685

Thr Val Thr Lys Asn Ala Asn Ala Ser Ser Thr Tyr Thr Pro Ser Ser
    690                 695                 700

Gly Leu Thr Gln Ala Ala Pro Ser Phe Gly Asn Phe Ser Thr Asp Leu
705                 710                 715                 720

Asn Asp Tyr Ile Phe Pro Asn Gly Ser Phe Pro Tyr Val Tyr Gln Tyr
                725                 730                 735

Ile Tyr Pro Tyr Leu Asn Thr Ser Asp Ala Ala Ala Ser Ser Ala Asp
            740                 745                 750

Pro Asn Tyr Gly Gln Asn Ala Ser Glu Phe Leu Pro Pro Lys Ala Thr
    755                 760                 765

Asp Gly Ser Ala Gln Pro Ile Leu Ala Ala Gly Gly Ala Pro Gly Gly
                770                 775                 780

Asn Pro Ala Leu Tyr Asp Val Leu Tyr Thr Val Thr Ala Gln Ile Gln
785                 790                 795                 800

Asn Ser Gly Lys Leu Asp Gly Glu Glu Val Pro Gln Leu Tyr Val Lys
                805                 810                 815

Leu Gly Gly Pro Asn Asp Pro Leu Ile Val Leu Arg Gly Phe Glu Arg
            820                 825                 830

Leu Ser Ile Pro Ala Gly Asn Thr Thr Thr Phe Thr Ala Asp Leu Thr
    835                 840                 845

Arg Arg Asp Leu Ser Asn Trp Asp Thr Ala Ala Gln Asn Trp Phe Ile
850                 855                 860

Ser Asn Tyr Thr Lys Thr Val Tyr Val Gly Ser Ser Ser Arg Asn Leu
865                 870                 875                 880

Pro Leu Ser Gln Asp Leu Ala
                885

<210> SEQ ID NO 32
<211> LENGTH: 865
<212> TYPE: PRT
<213> ORGANISM: Penicillium Chrysogenum

<400> SEQUENCE: 32

Met Lys Phe Ala Trp Phe Glu Val Ala Ala Leu Thr Ala Ser Val Ala
  1               5                  10                  15

Asn Ala Asn Ser Leu Ala Tyr Ser Pro Pro Tyr Tyr Pro Ser Pro Trp
                 20                  25                  30

Met Thr Gly Glu Gly Asp Trp Ser Glu Ala Tyr Thr Arg Ala Val Glu
             35                  40                  45

Phe Val Ser Asn Leu Thr Leu Ala Glu Lys Val Asn Leu Thr Thr Gly
    50                  55                  60

Ser Gly Trp Met Gln Glu Ser Cys Val Gly Glu Thr Gly Gly Ile Pro

```
                65                  70                  75                  80
Arg Leu Gly Met Trp Gly Met Cys Met Gln Asp Ala Pro Leu Gly Ile
                    85                  90                  95

Arg Phe Ser Asp Tyr Asn Ser Ala Phe Pro Ala Gly Val Asn Val Ala
                100                 105                 110

Ala Ala Trp Asp Lys Arg Leu Ala Tyr Gln Arg Gly Val Ala Met Gly
                115                 120                 125

Glu Glu His Arg Asp Lys Gly Val Asp Val Gln Leu Gly Pro Val Ala
                130                 135                 140

Gly Pro Leu Gly Lys Phe Pro Asp Gly Gly Arg Asn Trp Glu Gly Phe
145                 150                 155                 160

Ser Pro Asp Pro Val Leu Thr Gly Val Met Met Ala Glu Thr Ile Lys
                165                 170                 175

Gly Met Gln Asp Ala Gly Val Ile Ala Cys Ala Lys His Phe Ile Gly
                180                 185                 190

Asn Glu Gln Glu His Phe Arg Gln Ser Gly Glu Ala Gln Gly Tyr Gly
                195                 200                 205

Tyr Asn Ile Ser Gln Ser Leu Ser Ser Asn Ile Asp Asp Lys Thr Met
                210                 215                 220

His Glu Leu Tyr Leu Trp Pro Phe Val Asp Ser Ile Arg Ala Gly Val
225                 230                 235                 240

Gly Ser Val Met Cys Ser Tyr Asn Gln Ile Asn Asn Ser Tyr Gly Cys
                245                 250                 255

Ala Asn Ser Tyr Ser Leu Asn Lys Leu Leu Lys Gly Glu Leu Gly Phe
                260                 265                 270

Gln Gly Phe Val Met Ser Asp Trp Gly Ala His His Ser Gly Val Glu
                275                 280                 285

Ser Ala Leu Ala Gly Leu Asp Met Ser Met Pro Gly Asp Val Ile Leu
                290                 295                 300

Gly Ser Pro Tyr Ser Tyr Trp Gly Thr Asn Leu Thr Ile Ser Val Leu
305                 310                 315                 320

Asn Gly Thr Met Pro Glu Trp Arg Val Asp Asp Met Ala Val Arg Ile
                325                 330                 335

Met Ser Ala Tyr Tyr Lys Val Gly Arg Asp Arg Phe Arg Thr Pro Pro
                340                 345                 350

Asn Phe Ser Ser Trp Thr Arg Asp Glu Tyr Asn Phe Gln His Ser Met
                355                 360                 365

Val Ser Glu Asp Trp Gly Lys Val Asn Glu Arg Val Asn Val Gln Arg
                370                 375                 380

Asp His Ala Gln Ile Ile Arg Lys Ile Gly Ser Asp Ser Thr Val Leu
385                 390                 395                 400

Leu Lys Asn Lys Gly Gly Ala Leu Pro Leu Thr His Asn Glu Lys Phe
                405                 410                 415

Ile Ser Ile Leu Gly Glu Asp Ala Gly Ser Asn Ala His Gly Ala Asn
                420                 425                 430

Gly Cys Asp Asp Arg Gly Cys Asp Asn Gly Thr Leu Ala Met Gly Trp
                435                 440                 445

Gly Ser Gly Thr Ala Asn Tyr Pro Tyr Leu Ile Thr Pro Glu Gln Ala
                450                 455                 460

Ile Gln Asn Glu Ala Leu Glu Tyr Ser Asn Gly Gln Thr Asn Val Phe
465                 470                 475                 480

Ala Val Thr Asp Asn Trp Ala Leu Thr Gln Met Ala Ala Leu Ala Ser
                485                 490                 495
```

```
Gln Ala Asp Val Ala Leu Val Phe Val Asn Ala Asp Ser Gly Glu Gly
            500                 505                 510

Phe Ile Asn Val Asp Gly Asn Glu Gly Asp Arg Lys Asn Leu Thr Leu
            515                 520                 525

Trp Lys Asn Gly Glu Glu Val Ile Lys Thr Ala Ser Gln His Cys Asn
530                 535                 540

Asn Thr Ile Val Ile His Ser Thr Ser Ala Val Leu Ile Ser Asp
545                 550                 555                 560

Trp Tyr Asp Asn Asp Asn Ile Thr Ala Ile Ile Trp Ala Gly Leu Pro
                565                 570                 575

Gly Gln Glu Ser Gly His Ser Leu Val Asp Val Leu Tyr Gly Arg Ile
            580                 585                 590

Asn Pro Gly Gly Lys Thr Pro Phe Thr Trp Gly Lys Thr Arg Lys Asp
            595                 600                 605

Tyr Gly Pro Pro Leu Val Thr Val Pro Asn Asn Gly Ala Asp Ala Pro
            610                 615                 620

Gln Asp Asn Phe Glu Asp Gly Val Phe Ile Asp Tyr Arg Arg Phe Asp
625                 630                 635                 640

Lys Asp Asn Ile Glu Pro Ile Tyr Glu Phe Gly Tyr Gly Leu Ser Tyr
                645                 650                 655

Thr Lys Phe Ala Phe Ser Asp Ile Lys Val Thr Pro Leu Ala Ser Ser
            660                 665                 670

Gln Arg Gly Glu Tyr Lys Ala Thr Thr Gly Lys Ser Gln Lys Ala Pro
            675                 680                 685

Val Leu Gly Glu Pro Ser Thr Val Ser Asp Asn Leu Phe Pro Glu Gly
            690                 695                 700

Ile Lys Arg Val Arg Gln Tyr Leu Tyr Pro Trp Leu Asn Ser Thr Asp
705                 710                 715                 720

Leu Arg Ala Ser Ser Gly Asp Pro Asp Tyr Gly Met Asp Ser Lys Asp
                725                 730                 735

Tyr Leu Pro Glu Gly Ala Thr Asp Gly Ser Pro Gln Asp Leu Leu Pro
            740                 745                 750

Ser Ser Gly Ser Ser Gly Gly Asn Pro Gly Leu Phe Glu Asp Leu Tyr
            755                 760                 765

Gln Val Thr Ala Thr Ile Thr Asn Thr Gly Ser Val Thr Gly Asp Glu
            770                 775                 780

Val Pro Gln Leu Tyr Leu Ser Leu Gly Gly Asn Asp Asp Pro Thr Lys
785                 790                 795                 800

Val Leu Arg Gln Phe Asp Arg Val Thr Ile Ala Pro Gly Gln Ser Leu
                805                 810                 815

Gln Trp Thr Thr Thr Leu Thr Arg Arg Asp Val Ser Asn Trp Asp Val
            820                 825                 830

Ala Ser Gln Asn Trp Val Ile Ser Gly Ala Gln Lys Lys Val Tyr Val
            835                 840                 845

Gly Asn Ser Ser Arg Lys Leu Pro Leu Ser Ala Asp Leu Pro Ser Val
            850                 855                 860

Glu
865

<210> SEQ ID NO 33
<211> LENGTH: 924
<212> TYPE: PRT
<213> ORGANISM: Schizophyllum Commune
```

<400> SEQUENCE: 33

```
Met Ala Pro Phe Lys Ser Arg Leu Leu Leu Val Leu Gly Ala Val
1               5                   10                  15

Ala Ala Ala Arg Pro Asp Val Arg Gln Val Ser Asp Ser Asp Val Gly
            20                  25                  30

Ser Ala Ala Ser Ser Ala Ala Ser Ser Ser Pro Leu Ser Ser Ala Leu
            35                  40                  45

Ser Ser Ile Ala Ser Ser Val Glu Ala Thr Ser Thr Gly Ala Thr Phe
50                  55                  60

Ala Ser Ser Ala Ala Pro Ser Ser Leu Pro Ser Ser Val Glu Gly Ser
65                  70                  75                  80

Thr Ile Ala Ser Ser Thr Ser Ala Val Ser Ser Val Thr Ser Ala
                85                  90                  95

Ala Ser Ala Ser Ile Thr Ser Ser Ala Thr Ala Ser Asn Ser Ser Glu
            100                 105                 110

Ser Ala Thr Ser Ser Ser Ala Glu Glu Ser Ser Ala Ser Ser Ala Pro
            115                 120                 125

Pro Thr Thr Val Ser His Thr Ile Pro Leu Ser Ser Tyr Ser Phe Ser
        130                 135                 140

Ala Phe Pro Ala Pro Thr Tyr Ala Pro Val Pro Gly Val Phe Pro Glu
145                 150                 155                 160

Thr Asp Pro Ser Ser Pro Pro Gly Pro Tyr Asp Gln Asp Ile Ile Pro
                165                 170                 175

Asp Phe Ser Ala Ala Trp Leu Glu Ala Trp Asp Lys Ala Gln Gln Lys
            180                 185                 190

Ile Ala Gly Tyr Thr Leu Glu Gln Lys Ile Asn Ile Ser Thr Gly Val
        195                 200                 205

Gly Trp Glu Asp Gly Arg Cys Val Gly Asn Ile Gly Ala Ile Asn Ala
210                 215                 220

Ser Asp Gly Ser Val Asp Phe Pro Gly Leu Cys Leu Glu Asp Ser Pro
225                 230                 235                 240

Leu Gly Val Arg Phe Ala Asp Phe Val Thr Ala Phe Pro Thr Ala Ile
                245                 250                 255

Asn Ala Ala Ala Thr Trp Asn Arg Gly Leu Ile Arg Leu Arg Gly Leu
            260                 265                 270

Phe Met Gly Gln Glu His Val Ala Lys Gly Val Asn Val Gln Leu Gly
        275                 280                 285

Pro Met Met Asn Ile Gly Arg Val Ala Gln Gly Gly Arg Asn Trp Glu
290                 295                 300

Gly Phe Gly Ala Asp Pro Tyr Leu Ala Gly Glu Ala Ala Tyr Glu Thr
305                 310                 315                 320

Ile Leu Gly Met Gln Glu Ala Gly Val Gln Ala Cys Ala Lys His Leu
                325                 330                 335

Ile Asn Asn Glu Gln Glu His Lys Arg Thr Thr Glu Ser Ser Asp Val
            340                 345                 350

Asp Asp Arg Thr Glu His Glu Ile Tyr Ala His Pro Phe Leu Arg Ser
        355                 360                 365

Ile Met Ala Gly Val Ala Ser Ile Met Cys Ser Tyr Asn Ala Ile Asn
370                 375                 380

Gly Thr Tyr Ala Cys Glu Asn Asp Lys Ile Leu Asn Asp Val Val Lys
385                 390                 395                 400

Arg Glu Tyr Gly Phe Gln Gly Tyr Ile Met Ser Asp Trp Gly Ala Thr
                405                 410                 415
```

```
Met Ser Ala Ile Ser Pro Ile Ala Gly Leu Asp Met Thr Met Pro Gly
            420                 425                 430

Asp Ala Gln Leu Gly Gly Ile Gly Trp Tyr Glu Thr Leu Leu Glu Tyr
            435                 440                 445

Val His Asn Gly Thr Ile Pro Glu Ser Arg Ile Asp Asp Met Ala Thr
450                 455                 460

Arg Ile Leu Ala Gly Trp Tyr Leu Leu Lys Gln Asp Asp Pro Ser Phe
465                 470                 475                 480

Pro Thr Ala Asn Phe Asp Ala Phe Leu Pro Glu Asn Gln Ala Thr Asn
            485                 490                 495

Asp His Val Asp Ala Gln Asp Glu Glu His Thr Ser Leu Val Arg Asn
            500                 505                 510

Met Gly Ala Ala Ser Ile Val Leu Leu Lys Asn Glu Arg Asp Ala Leu
            515                 520                 525

Pro Leu His Lys Pro Arg Ala Leu Leu Leu Ala Gly Ser Asp Ala Gly
            530                 535                 540

Pro Gly Arg Ala Gly Pro Asn Gln Phe Ala Asp Gln Gly Gly Ser Asp
545                 550                 555                 560

Gly Val Leu Ala Met Gly Trp Gly Ser Gly Thr Ala Asn Phe Thr Tyr
            565                 570                 575

Leu Val Thr Pro Leu Glu Ala Ile Gln Arg Arg Ala Arg Lys Asp Arg
            580                 585                 590

Thr Ser Val Ser Trp Leu Leu Asp Asp Phe Asp Leu Pro Leu Ala Gly
            595                 600                 605

Asn Met Ala Lys Arg Val Glu Thr Met Ala Pro Gly Arg Asn Ala Ala
            610                 615                 620

Ile Val Phe Val Asn Ser Asp Ser Gly Glu Gln Tyr Ile Thr Val Asp
625                 630                 635                 640

Gly Asn Glu Gly Asp Arg Lys Asn Leu Thr Ala Trp His Gly Gly Asp
            645                 650                 655

Asp Leu Ile Leu Ala Val Ala Ala Gln Asn Asn Asn Thr Ile Val Val
            660                 665                 670

Val His Ser Val Gly Pro Leu Ile Leu Glu Pro Trp Ile Asp His Glu
            675                 680                 685

Asn Val Thr Ala Val Leu Trp Ala Gly Val Pro Gly Asn Glu Ala Gly
            690                 695                 700

Asn Ser Leu Ala Asp Val Leu Tyr Gly Arg Trp Asn Pro Ser Gly Arg
705                 710                 715                 720

Leu Pro Tyr Thr Ile Ala Lys Ser Leu Glu Asp Tyr Gly Thr Gly Leu
            725                 730                 735

Ile Leu Gly Gly Thr Asn Glu Asp Phe Leu Asn Ile Pro Tyr Thr Glu
            740                 745                 750

Gly Leu Phe Val Asp Tyr Arg Arg Phe Asp Tyr Phe Asn Ile Thr Pro
            755                 760                 765

Arg Phe Glu Phe Gly Phe Gly Leu Ser Tyr Thr Asp Phe Glu Tyr Ser
            770                 775                 780

Asn Leu Val Ile Ser Ala Val Asp Ala Pro Asp Gly Thr Asp Gln Asp
785                 790                 795                 800

Leu Ala Asp Ala Trp Ala Thr Gly Val Ala Ser Pro Ile Ala Glu Gly
            805                 810                 815

Ser Ser Thr Ala Leu Trp Leu His Arg Pro Ala Phe Thr Val Glu Phe
            820                 825                 830
```

-continued

Asp Val Thr Asn Ser Gly Asp Leu Phe Gly Gly Glu Ile Pro Gln Leu
                835                 840                 845

Tyr Val Asn Pro Pro Asp Gly Ser Gly Glu Pro Pro Ser Val Leu Lys
    850                 855                 860

Gly Phe Thr Asn Val Glu Ala Leu Pro Gly Glu Thr Lys His Val Ser
865                 870                 875                 880

Leu Pro Leu Ser Arg Tyr Asp Leu Ser Ile Trp Asp Val Val Gln Gln
                885                 890                 895

Gly Trp Ala Lys Pro Asn Gly Thr Ile Gly Ile Thr Val Gly Ala Ser
            900                 905                 910

Ser Arg Asp Gly Arg Leu Ser Ala Glu Val Pro Leu
            915                 920

<210> SEQ ID NO 34
<211> LENGTH: 776
<212> TYPE: PRT
<213> ORGANISM: Postia Placenta

<400> SEQUENCE: 34

Met Tyr Lys Leu Ala Pro Ser Ala Leu Leu Trp Arg Asp Ser Gly Thr
1               5                   10                  15

Pro Val Leu Gly Gln His Gln Gly Cys Thr Leu Pro Arg Phe Val Met
                20                  25                  30

Leu Leu Ala Gly Asn Ala Trp Ala Glu Ala Tyr Ala Lys Ala Glu Ala
            35                  40                  45

Phe Val Ala Gly Leu Thr Leu Glu Gln Lys Val Asn Val Ser Thr Gly
        50                  55                  60

Val Tyr Trp Glu Gln Gly Leu Cys Val Gly Asn Ile Gly Glu Val Ala
65                  70                  75                  80

Asp Leu Arg Gly Leu Cys Leu Gln Asp Ser Pro Leu Gly Val Arg Tyr
                85                  90                  95

Thr Asp Tyr Asn Thr Ala Phe Pro Ala Gly Ile Ser Thr Ala Ala Thr
                100                 105                 110

Phe Asn Arg Thr Met Met Arg Leu Arg Gly Gln Gln Met Gly Glu Glu
            115                 120                 125

Phe Arg Gly Lys Gly Val Asn Val Ala Leu Gly Pro Met Met Asn Met
        130                 135                 140

Gly Arg Val Ala Gln Ala Gly Arg Asn Trp Glu Gly Phe Gly Thr Asp
145                 150                 155                 160

Pro Phe Leu Ser Gly Glu Ala Ala Tyr Glu Thr Thr Leu Gly Leu Gln
                165                 170                 175

Ser Ala Gly Val Gln Ala Cys Ala Lys His Tyr Ile Asp Tyr Glu Gln
                180                 185                 190

Glu Tyr Lys Arg Thr Gln Glu Ser Ser Glu Val Asp Asp Arg Thr Gln
            195                 200                 205

His Glu Ile Tyr Leu Lys Pro Phe Leu Arg Ala Val Met Ala Gly Thr
        210                 215                 220

Ala Ser Val Met Cys Ser Tyr Asn Met Ile Asn Asp Thr Tyr Ser Cys
225                 230                 235                 240

Glu Asn Asp Arg Thr Leu Asn Gln Leu Leu Lys Gly Glu Leu Gly Phe
                245                 250                 255

Arg Gly Tyr Val Met Ser Asp Trp Gly Ala Gln Glu Ser Thr Leu Ser
                260                 265                 270

Ala Met Ala Gly Leu Asp Met Ser Met Pro Gly Asp Ile Thr Leu Gly
            275                 280                 285

```
Ser Gly Asn Ser Trp Trp Gly Pro Asn Leu Thr Ala Phe Val Glu Asn
    290                 295                 300
Gly Thr Ile Pro Leu Ser Arg Met Asp Asp Met Ala Thr Arg Ile Met
305                 310                 315                 320
Ala Ser Tyr Tyr Leu Leu Gly Gln Asp Gln Asp Tyr Pro Asn Asp Gly
                325                 330                 335
Arg Leu Ile Pro Asn Ala Val Ser Phe Asn Ala Phe Asn Gln Tyr Asp
                340                 345                 350
Gln Val His Asn Leu His Ile Asp Val Gln Ala Asp His Tyr Gln Ile
                355                 360                 365
Val Arg Glu Ile Gly His Ala Gly Ala Val Leu Leu Lys Asn Thr Asn
    370                 375                 380
Gly Ala Leu Pro Leu Asn Ala Pro Arg Asn Val Val Leu Ile Gly Ser
385                 390                 395                 400
Asp Ala Gly Asn Gly Ala Met Gly Ala Asn Gly Tyr Thr Asp Arg Gly
                405                 410                 415
Gly Asp Asp Gly Ile Leu Gly Met Gly Trp Gly Ser Gly Thr Asp Asn
                420                 425                 430
Tyr Pro Tyr Leu Ile Ser Pro Met Asp Ala Met Gln Val Arg Ala Arg
                435                 440                 445
Gln Asp Gly Thr Thr Leu Met Asn Trp Tyr Tyr Asp Trp Asp Thr Glu
    450                 455                 460
Gly Ala Ala Thr Ala Ala Ile Gln Phe Glu Ala Ala Ile Val Phe Val
465                 470                 475                 480
Asn Ser Asp Ser Gly Glu Gly Tyr Ile Glu Val Asp Gly Asn Leu Gly
                485                 490                 495
Asp Arg Asn Asn Leu Thr Leu Trp His Asn Ala Asp Asn Leu Ile Thr
    500                 505                 510
Ala Val Ala Ser Gln Asn Asn Thr Ile Val Val Ala His Ser Val
    515                 520                 525
Gly Pro Ser Ile Ile Asp Ser Trp Val Glu Asn Pro Asn Val Thr Ala
    530                 535                 540
Ile Ile Trp Ala Gly Val Ala Gly Gln Glu Ala Gly Asn Ala Ile Val
545                 550                 555                 560
Asp Val Leu Tyr Gly Asp Tyr Asn Pro Ser Gly Arg Leu Pro Tyr Thr
                565                 570                 575
Ile Ala Lys Arg Leu Glu Asp Tyr Gly Val Phe Leu Thr Leu Gly Gly
                580                 585                 590
Asn Gly Ser Thr Ile Leu Ser Val Pro Tyr Thr Glu Gly Leu Phe Tyr
    595                 600                 605
Asp Tyr Arg His Phe Asp Glu Tyr Asn Ile Thr Pro Arg Tyr Glu Phe
    610                 615                 620
Gly Tyr Gly Leu Ser Tyr Thr Thr Phe Glu Tyr Tyr Asn Leu Ala Thr
625                 630                 635                 640
Ser Ile Val Pro Gln Tyr Asp Pro Thr Asp Tyr Ala Leu Glu Ala Ala
                645                 650                 655
Trp Ala Ala Gly Val Pro Thr Pro Gln Gly Glu Gly Ser Ser Val Ala
                660                 665                 670
Leu Trp Leu His Arg Pro Phe Val Gln Val Ser Phe Glu Val Gln Asn
    675                 680                 685
Thr Gly Ala Val Ala Gly Thr Glu Ile Pro Gln Val Tyr Val His Phe
    690                 695                 700
```

```
Pro Thr Gly Ile Gly Glu Pro Ser Trp Leu Lys Gly Phe Asp Ala
705                 710                 715                 720

Val Tyr Ile Glu Pro Gly Glu Val Thr Val Thr Val Thr Ile Ser
            725                 730                 735

Arg Tyr Asp Leu Ser Ile Trp Asp Val Val Ala Gln Gly Trp Val Lys
            740                 745                 750

Pro Ala Gly Glu Ile Thr Phe Ser Val Gly Ala Ser Ser Arg Asp Phe
            755                 760                 765

Arg Leu Gln Gly Tyr Ile Pro Ile
            770                 775

<210> SEQ ID NO 35
<211> LENGTH: 483
<212> TYPE: PRT
<213> ORGANISM: Aspergillus Niger

<400> SEQUENCE: 35

Met Gly Ser Ala Thr Ala Ser Thr Leu Pro Pro Asp Phe Leu Trp Gly
1               5                   10                  15

Phe Ala Thr Ala Ser Tyr Gln Ile Glu Gly Ala Val Thr Glu Asp Gly
                20                  25                  30

Arg Gly Pro Ser Ile Trp Asp Thr Phe Cys Lys Ile Pro Gly Lys Ile
            35                  40                  45

Ala Gly Gly Ala Asn Gly Asp Val Ala Cys Asp Ser Tyr His Arg Thr
50                  55                  60

Ala Glu Asp Ile Ala Leu Leu Lys Glu Cys Gly Ala Gln Ala Tyr Arg
65                  70                  75                  80

Phe Ser Ile Ser Trp Ser Arg Ile Ile Pro Leu Gly Gly Arg Asn Asp
                85                  90                  95

Pro Ile Asn Asp Lys Gly Val Gln His Tyr Val Lys Phe Val Asp Asp
            100                 105                 110

Leu Leu Ala Ala Gly Ile Thr Pro Leu Val Thr Leu Phe His Trp Asp
            115                 120                 125

Leu Pro Asp Ala Leu Asp Lys Arg Tyr Gly Gly Leu Leu Asn Lys Glu
130                 135                 140

Glu Phe Val Ala Asp Phe Ala Asn Tyr Ala Arg Val Met Phe Arg Ala
145                 150                 155                 160

Leu Gly Ser Lys Val Lys His Trp Ile Thr Phe Asn Glu Pro Trp Cys
                165                 170                 175

Ser Ser Val Leu Gly Tyr Asn Val Gly Gln Phe Ala Pro Gly Arg Thr
            180                 185                 190

Ser Asp Arg Ser Lys Ser Ala Glu Gly Asp Ser Ser Arg Glu Cys Trp
            195                 200                 205

Ile Val Gly His Asn Ile Leu Val Ala His Gly Ala Ala Val Lys Ile
210                 215                 220

Tyr Arg Glu Glu Phe Lys Ser Arg Asp Gly Gly Glu Ile Gly Ile Thr
225                 230                 235                 240

Leu Asn Gly Asp Trp Ala Glu Pro Trp Asp Pro Glu Asn Pro Ala Asp
                245                 250                 255

Ile Glu Ala Cys Asp Arg Lys Ile Glu Phe Ala Ile Ser Trp Phe Ala
            260                 265                 270

Asp Pro Ile Tyr His Gly Arg Tyr Pro Asp Ser Met Ile Lys Gln Leu
            275                 280                 285

Gly Asp Arg Leu Pro Ser Trp Thr Ala Glu Asp Ile Ala Leu Val His
290                 295                 300
```

```
Gly Ser Asn Asp Phe Tyr Gly Met Asn His Tyr Cys Ala Asn Tyr Ile
305                 310                 315                 320

Lys Ala Lys Thr Gly Glu Ala Asp Pro Asn Asp Thr Ala Gly Asn Leu
            325                 330                 335

Glu Ile Leu Leu Lys Asn Lys Lys Gly Glu Phe Ile Gly Pro Glu Thr
        340                 345                 350

Gln Ser Ala Trp Leu Arg Pro Tyr Ala Leu Gly Phe Arg Lys Leu Leu
    355                 360                 365

Lys Trp Leu Ser Asp Arg Tyr Gly Gln Pro Lys Ile Tyr Val Thr Glu
370                 375                 380

Asn Gly Thr Ser Leu Lys Gly Glu Asn Asp Leu Pro Val Glu Glu Leu
385                 390                 395                 400

Leu Lys Asp Glu Phe Arg Thr Gln Tyr Phe Arg Asp Tyr Ile Ala Ala
                405                 410                 415

Met Ala Asp Ala Tyr Thr Leu Asp Gly Val Asn Val Arg Ala Tyr Met
            420                 425                 430

Ala Trp Ser Leu Met Asp Asn Phe Glu Trp Ala Glu Gly Tyr Glu Thr
        435                 440                 445

Arg Phe Gly Ser Thr Tyr Val Asp Tyr Glu His Gly Gln Lys Arg Ile
    450                 455                 460

Pro Lys Asp Ser Ala Lys Gln Ile Gly Gln Ile Phe Ser Gln Tyr Ile
465                 470                 475                 480

Glu Lys Lys

<210> SEQ ID NO 36
<211> LENGTH: 540
<212> TYPE: PRT
<213> ORGANISM: Phanerochaete Chrysosporium

<400> SEQUENCE: 36

Met Ser Ala Ser Ala Ala Pro Pro Asn Lys Leu Pro Ala Asp Phe Leu
1               5                   10                  15

Trp Gly Phe Ala Thr Ala Ser Phe Gln Ile Glu Gly Ala Thr Asp Val
            20                  25                  30

Asp Gly Arg Gly Lys Ser Ile Trp Asp Phe Ser Lys Ile Pro Gly
        35                  40                  45

Lys Thr Leu Asp Gly Lys Asn Gly Asp Val Ala Thr Asp Ser Tyr Asn
50                  55                  60

Arg Trp Arg Glu Asp Val Asp Leu Leu Val Gln Tyr Gly Val Lys Ser
65                  70                  75                  80

Tyr Arg Phe Ser Ile Ser Trp Ser Arg Ile Ile Pro Leu Gly Arg
            85                  90                  95

Asn Asp Pro Val Asn Glu Ala Gly Ile Lys Phe Tyr Ser Asp Leu Ile
            100                 105                 110

Asp Ala Leu Leu Glu Arg Gly Ile Val Pro Phe Val Thr Leu Tyr His
            115                 120                 125

Trp Asp Leu Pro Gln Ala Leu His Asp Arg Tyr Leu Gly Trp Leu Asn
            130                 135                 140

Lys Asp Glu Ile Val Gln Asp Tyr Val Arg Tyr Ala Gly Val Cys Phe
145                 150                 155                 160

Glu Arg Phe Gly Asp Arg Val Lys His Trp Leu Thr Met Asn Glu Pro
                165                 170                 175

Trp Cys Ile Ser Ile Leu Gly Tyr Gly Arg Gly Val Phe Ala Pro Gly
            180                 185                 190
```

Arg Ser Ser Asp Arg Met Arg Ser Pro Glu Gly Asp Ser Ser Thr Glu
            195                 200                 205

Pro Trp Ile Val Gly His Ser Val Ile Leu Ala His Ala Tyr Ala Val
        210                 215                 220

Lys Leu Tyr Arg Glu Gln Phe Lys Ala Asn Arg Gly Gly Gln Ile Gly
225                 230                 235                 240

Ile Thr Leu Asn Gly Asp Trp Ala Met Pro Tyr Asp Ser Pro Gln
                245                 250                 255

Asn Ile Glu Ala Ala Gln His Ala Leu Asp Val Ala Ile Gly Trp Phe
                260                 265                 270

Ala Asp Pro Ile Tyr Leu Gly Gln Tyr Pro Ala Tyr Met Lys Glu Met
            275                 280                 285

Leu Gly Asp Arg Leu Pro Glu Phe Thr Pro Glu Glu Leu Ala Val Val
        290                 295                 300

Lys Gly Ser Ser Asp Phe Tyr Gly Met Asn Thr Tyr Thr Thr Asn Leu
305                 310                 315                 320

Cys Lys Ala Gly Gly Glu Asp Glu Phe Gln Gly Asn Val Glu Tyr Thr
                325                 330                 335

Phe Thr Arg Pro Asp Gly Thr Gln Leu Gly Thr Ala Ala His Cys Ser
            340                 345                 350

Trp Leu Gln Asp Tyr Ala Pro Gly Phe Arg Asp Leu Leu Asn Tyr Leu
        355                 360                 365

Tyr Lys Arg Tyr Arg Lys Pro Ile Tyr Val Thr Glu Asn Gly Phe Ala
370                 375                 380

Val Lys Asp Glu Asn Ser Lys Pro Leu Glu Glu Ala Leu Lys Asp Asp
385                 390                 395                 400

Asp Arg Val His Tyr Tyr Gln Gly Val Thr Asp Ser Leu Leu Ala Ala
                405                 410                 415

Val Lys Glu Asp Gly Val Asp Val Arg Gly Tyr Phe Gly Trp Ser Leu
            420                 425                 430

Leu Asp Asn Phe Glu Trp Ala Asp Gly Tyr Ile Thr Arg Phe Gly Val
        435                 440                 445

Thr Tyr Val Asp Tyr Asp Thr Gln Lys Arg Tyr Pro Lys Asp Ser Gly
        450                 455                 460

Lys Phe Leu Ser Gln Trp Phe Pro Ala His Ile Ala Glu Ser Pro Lys
465                 470                 475                 480

Pro Ala Ala Glu Thr Lys Lys Ala Ala Thr Pro Ser Pro Leu Lys Pro
                485                 490                 495

His Gly Ala Ile Ser Asn Gly Val Ser Lys Lys Ser Ser Ala Thr Lys
            500                 505                 510

Glu Pro Lys Ser Ala Ser Arg Lys Lys Gly Arg Lys Ala Pro Phe Ala
        515                 520                 525

Arg Phe Thr Ala Tyr Ile Ser Ala Phe Leu Gly Leu
        530                 535                 540

<210> SEQ ID NO 37
<211> LENGTH: 476
<212> TYPE: PRT
<213> ORGANISM: Sporotrichum Thermophile

<400> SEQUENCE: 37

Met Ser Leu Pro Lys Asp Phe Lys Trp Gly Phe Ala Thr Ala Ser Tyr
1               5                   10                  15

Gln Ile Glu Gly Ser Val Asn Glu Asp Gly Arg Gly Pro Ser Ile Trp

```
                20                  25                  30
Asp Thr Phe Cys Ala Ile Pro Gly Lys Ile Ala Asp Gly Ser Ser Gly
                35                  40                  45

Ala Val Ala Cys Asp Ser Tyr Lys Arg Thr Lys Glu Asp Ile Glu Leu
 50                  55                  60

Leu Lys Ser Ile Gly Ala Lys Ala Tyr Arg Phe Ser Ile Ala Trp Ser
 65                  70                  75                  80

Arg Val Ile Pro Leu Gly Gly Arg Asn Asp Pro Ile Asn Gln Lys Gly
                85                  90                  95

Leu Asp His Tyr Val Lys Phe Val Asp Asp Leu Val Glu Ala Gly Ile
                100                 105                 110

Glu Pro Phe Ile Thr Leu Ser His Trp Asp Leu Pro Asp Ala Leu Glu
                115                 120                 125

Lys Arg Tyr Gly Gly Tyr Leu Asn Lys Glu Glu Phe Ala Ala Asp Phe
                130                 135                 140

Glu Asn Tyr Ala Arg Val Met Phe Lys Ala Ile Pro Lys Cys Lys His
145                 150                 155                 160

Trp Ile Thr Phe Asn Glu Pro Trp Cys Thr Ser Ile Leu Gly Tyr Asn
                165                 170                 175

Thr Gly Tyr Phe Ala Pro Gly Arg Thr Ser Asp Arg Ser Lys Ser Pro
                180                 185                 190

Val Gly Asp Ser Ala Arg Glu Pro Trp Ile Val Gly His Asn Ile Leu
                195                 200                 205

Ile Ala His Gly Arg Ala Val Lys Ala Tyr Arg Glu Asp Phe Lys Pro
                210                 215                 220

Thr Gln Gly Gly Glu Ile Gly Ile Thr Leu Asn Gly Asp Ala Thr Leu
225                 230                 235                 240

Pro Trp Asp Pro Glu Asp Pro Ala Asp Val Glu Ala Cys Asp Arg Lys
                245                 250                 255

Ile Glu Phe Ala Ile Ser Trp Phe Ala Asp Pro Ile Tyr Phe Gly Glu
                260                 265                 270

Tyr Pro Ala Ser Met Arg Lys Gln Leu Gly Asp Arg Leu Pro Lys Phe
                275                 280                 285

Thr Ala Glu Glu Val Ala Leu Val Lys Gly Ser Asn Asp Phe Tyr Gly
                290                 295                 300

Met Asn His Tyr Thr Ala Asn Tyr Ile Lys His Lys Lys Gly Val Pro
305                 310                 315                 320

Pro Glu Asp Asp Phe Leu Gly Asn Leu Glu Thr Leu Phe Tyr Asn Lys
                325                 330                 335

Asn Ala Asp Cys Ile Gly Pro Glu Thr Gln Ser Phe Trp Leu Arg Pro
                340                 345                 350

His Pro Gln Gly Phe Arg Asp Leu Leu Asn Trp Leu Ser Lys Arg Tyr
                355                 360                 365

Gly Tyr Pro Lys Ile Tyr Val Thr Glu Asn Gly Thr Ser Leu Lys Gly
                370                 375                 380

Glu Asn Asp Met Pro Leu Glu Gln Ile Leu Glu Asp Phe Arg Val
385                 390                 395                 400

Lys Tyr Phe His Asp Tyr Val His Ala Met Lys Ala Ser Ala Glu
                405                 410                 415

Asp Gly Val Asn Val Gln Gly Tyr Leu Ala Trp Ser Leu Met Asp Asn
                420                 425                 430

Phe Glu Trp Ala Glu Gly Tyr Glu Thr Arg Phe Gly Val Thr Tyr Val
                435                 440                 445
```

Asp Tyr Ala Asn Asp Gln Lys Arg Tyr Pro Lys Lys Ser Ala Lys Ser
            450                 455                 460

Leu Lys Pro Leu Phe Asp Ser Leu Ile Arg Lys Glu
465                 470                 475

<210> SEQ ID NO 38
<211> LENGTH: 466
<212> TYPE: PRT
<213> ORGANISM: Trichoderma Reesei

<400> SEQUENCE: 38

Met Leu Pro Lys Asp Phe Gln Trp Gly Phe Ala Thr Ala Ala Tyr Gln
1               5                   10                  15

Ile Glu Gly Ala Val Asp Gln Asp Gly Arg Gly Pro Ser Ile Trp Asp
            20                  25                  30

Thr Phe Cys Ala Gln Pro Gly Lys Ile Ala Asp Gly Ser Ser Gly Val
        35                  40                  45

Thr Ala Cys Asp Ser Tyr Asn Arg Thr Ala Glu Asp Ile Ala Leu Leu
    50                  55                  60

Lys Ser Leu Gly Ala Lys Ser Tyr Arg Phe Ser Ile Ser Trp Ser Arg
65                  70                  75                  80

Ile Ile Pro Glu Gly Gly Arg Gly Asp Ala Val Asn Gln Ala Gly Ile
                85                  90                  95

Asp His Tyr Val Lys Phe Val Asp Leu Leu Asp Ala Gly Ile Thr
            100                 105                 110

Pro Phe Ile Thr Leu Phe His Trp Asp Leu Pro Glu Gly Leu His Gln
        115                 120                 125

Arg Tyr Gly Gly Leu Leu Asn Arg Thr Glu Phe Pro Leu Asp Phe Glu
    130                 135                 140

Asn Tyr Ala Arg Val Met Phe Arg Ala Leu Pro Lys Val Arg Asn Trp
145                 150                 155                 160

Ile Thr Phe Asn Glu Pro Leu Cys Ser Ala Ile Pro Gly Tyr Gly Ser
                165                 170                 175

Gly Thr Phe Ala Pro Gly Arg Gln Ser Thr Ser Glu Pro Trp Thr Val
            180                 185                 190

Gly His Asn Ile Leu Val Ala His Gly Arg Ala Val Lys Ala Tyr Arg
        195                 200                 205

Asp Asp Phe Lys Pro Ala Ser Gly Asp Gly Gln Ile Gly Ile Val Leu
    210                 215                 220

Asn Gly Asp Phe Thr Tyr Pro Trp Asp Ala Ala Asp Pro Ala Asp Lys
225                 230                 235                 240

Glu Ala Ala Glu Arg Arg Leu Glu Phe Phe Thr Ala Trp Phe Ala Asp
                245                 250                 255

Pro Ile Tyr Leu Gly Asp Tyr Pro Ala Ser Met Arg Lys Gln Leu Gly
            260                 265                 270

Asp Arg Leu Pro Thr Phe Thr Pro Glu Glu Arg Ala Leu Val His Gly
        275                 280                 285

Ser Asn Asp Phe Tyr Gly Met Asn His Tyr Thr Ser Asn Tyr Ile Arg
    290                 295                 300

His Arg Ser Ser Pro Ala Ser Ala Asp Asp Thr Val Gly Asn Val Asp
305                 310                 315                 320

Val Leu Phe Thr Asn Lys Gln Gly Asn Cys Ile Gly Pro Glu Thr Gln
                325                 330                 335

Ser Pro Trp Leu Arg Pro Cys Ala Ala Gly Phe Arg Asp Phe Leu Val

```
              340                 345                 350
Trp Ile Ser Lys Arg Tyr Gly Tyr Pro Pro Ile Tyr Val Thr Glu Asn
            355                 360                 365

Gly Thr Ser Ile Lys Gly Glu Ser Asp Leu Pro Lys Glu Lys Ile Leu
370                 375                 380

Glu Asp Asp Phe Arg Val Lys Tyr Tyr Asn Glu Tyr Ile Arg Ala Met
385                 390                 395                 400

Val Thr Ala Val Glu Leu Asp Gly Val Asn Val Lys Gly Tyr Phe Ala
                405                 410                 415

Trp Ser Leu Met Asp Asn Phe Glu Trp Ala Asp Gly Tyr Val Thr Arg
            420                 425                 430

Phe Gly Val Thr Tyr Val Asp Tyr Glu Asn Gly Gln Lys Arg Phe Pro
        435                 440                 445

Lys Lys Ser Ala Lys Ser Leu Lys Pro Leu Phe Asp Glu Leu Ile Ala
    450                 455                 460

Ala Ala
465

<210> SEQ ID NO 39
<211> LENGTH: 491
<212> TYPE: PRT
<213> ORGANISM: Gibberella Zeae

<400> SEQUENCE: 39

Met Ser Leu Pro Ala Asp Phe Lys Trp Gly Phe Ala Thr Ala Ser Tyr
1               5                   10                  15

Gln Ile Glu Gly Ala Ile Asp Lys Asp Gly Arg Gly Pro Ala Asn Trp
            20                  25                  30

Asp Thr Phe Cys Ala Gln Ala Gly Lys Ile Ala Asp Gly Ser Ser Gly
        35                  40                  45

Val Thr Ala Cys Asp Ser Tyr Asn Arg Thr Ala Glu Asp Ile Ser Leu
    50                  55                  60

Leu Lys Ser Leu Gly Ser Lys Ala Tyr Arg Phe Ser Ile Cys Trp Ser
65                  70                  75                  80

Arg Ile Ile Pro Leu Gly Gly Arg Asn Asp Pro Ile Asn Gln Ala Gly
                85                  90                  95

Ile Asp His Tyr Arg Lys Phe Val Asp Asp Leu Leu Asp Ala Gly Ile
            100                 105                 110

Thr Pro Phe Ile Thr Leu Phe His Trp Asp Val Pro Asp Glu Leu Asp
        115                 120                 125

Arg Arg Tyr Gly Gly Leu Met Asn Arg Glu Glu Phe Pro Leu Asp Tyr
    130                 135                 140

Glu Arg Tyr Ala Arg Val Met Phe Glu Ala Ile Pro Arg Cys Lys Asn
145                 150                 155                 160

Trp Ile Thr His Asn Glu Pro Trp Cys Ser Ala Ile Leu Gly Tyr Ser
                165                 170                 175

Thr Gly Ser Asn Ala Pro Gly Arg Cys Ser Asp Arg Asn Lys Ser Asp
            180                 185                 190

Val Gly Asp Ser Ser Thr Glu Pro Trp Ile Val Gly His Asn Leu Leu
        195                 200                 205

Val Ala His Gly Arg Ala Val Lys Ile Tyr Arg Glu Glu Phe Lys Pro
    210                 215                 220

Lys Asn Gly Gly Glu Ile Gly Ile Thr Leu Asn Gly Asp Ala Thr Tyr
225                 230                 235                 240
```

```
Pro Trp Asp Pro Lys Asp Pro Arg Asp Ile Glu Ala Ala Glu Arg Lys
                245                 250                 255

Ile Glu Phe Ala Ile Ser Trp Phe Ala Asp Pro Ile Tyr Phe Gly Asp
            260                 265                 270

Tyr Pro Ala Ser Met Arg Ala Gln Leu Gly Asp Arg Leu Pro Thr Phe
        275                 280                 285

Thr Pro Glu Glu Lys Ala Leu Val Leu Gly Ser Asn Asp Phe Tyr Gly
    290                 295                 300

Met Asn His Tyr Thr Ala Asn Tyr Val Lys His Arg Glu Gly Glu Ala
305                 310                 315                 320

Ala Pro Glu Asp Phe Val Gly Asn Leu Glu Leu His Phe Trp Asn His
                325                 330                 335

Arg Gly Asp Cys Ile Gly Glu Thr Gln Ser Thr Trp Leu Arg Pro
            340                 345                 350

Cys Ala Gln Gly Phe Arg Asp Leu Leu Val Trp Ile Ser Lys Arg Tyr
        355                 360                 365

Gly Phe Pro Arg Met Tyr Val Thr Glu Asn Gly Thr Ser Ile Lys Gly
    370                 375                 380

Glu Asn Asp Met Pro Arg Glu Lys Ile Leu Gln Asp Phe Arg Val
385                 390                 395                 400

Gln Tyr Tyr Asp Asp Tyr Val Arg Ala Met Ala Asp Ala Ser Arg Leu
                405                 410                 415

Asp Gly Val Asp Ile His Gly Tyr Phe Ala Trp Ser Leu Leu Asp Asn
            420                 425                 430

Phe Glu Trp Ala Glu Gly Tyr Glu Thr Arg Phe Gly Val Thr Tyr Val
        435                 440                 445

Asp Tyr Glu Asn Asp Gln Lys Arg Tyr Pro Lys Lys Ser Ala Gln His
    450                 455                 460

Leu Lys Pro Leu Phe Asp Ser Leu Ile Lys Lys Glu Glu Asn Gly Leu
465                 470                 475                 480

Asn Gly Val Gly Lys Val Lys Ala Gly Gln Thr
                485                 490

<210> SEQ ID NO 40
<211> LENGTH: 478
<212> TYPE: PRT
<213> ORGANISM: Sclerotinia Sclerotiorum

<400> SEQUENCE: 40

Met Ser Lys Ala Val Leu Pro Lys Asp Phe Ile Trp Gly Phe Ala Thr
1

```
Ala Leu Asp Lys Arg Tyr Gly Leu Leu Asn Lys Glu Glu Phe Val
        130                 135                 140

Lys Asp Tyr Ala Arg Tyr Ala Arg Val Leu Phe Glu Ala Leu Pro Lys
145                 150                 155                 160

Val Lys Asn Trp Ile Thr Phe Asn Glu Pro Trp Cys Ser Ser Ile Leu
                165                 170                 175

Gly Tyr Ser Thr Gly Leu Phe Ala Pro Gly His Thr Ser Asn Lys Leu
            180                 185                 190

Arg Ser Gln Ile Gly Asp Ser Ser Thr Glu Pro Trp Thr Val Gly His
        195                 200                 205

Asn Ile Leu Val Ala His Gly Ala Ala Val Lys Ile Tyr Arg Glu Glu
210                 215                 220

Phe Lys Ala Lys Asp Gly Gly Gln Ile Gly Ile Thr Leu Asn Gly Asp
225                 230                 235                 240

Ala Val Tyr Pro Trp Asp Pro Glu Gly Pro Lys Asp Val Glu Ala Ala
                245                 250                 255

Glu Arg Lys Leu Glu Phe Ser Ile Ala Trp Phe Ala Asp Pro Ile Tyr
            260                 265                 270

His Gly Lys Tyr Pro Asp Ser Met Arg Lys Gln Leu Gly Asp Arg Leu
        275                 280                 285

Pro Ser Phe Thr Asp Glu Glu Val Ala Leu Val Lys Gly Ser Asn Asp
290                 295                 300

Phe Tyr Gly Met Asn His Tyr Thr Ala Asn Tyr Ile Arg His Arg Thr
305                 310                 315                 320

Thr Glu Pro Glu Leu Asn Asp Tyr Ile Gly Asn Leu Asp Thr Ser Phe
                325                 330                 335

Glu Asn Lys Lys Gly Asp Asn Ile Gly Pro Val Thr Gln Ser Val Trp
            340                 345                 350

Leu Arg Pro Asn Pro Gln Gly Phe His Asp Leu Ile Leu Trp Ile Ser
        355                 360                 365

Lys Arg Tyr Gly Phe Pro Pro Ile Tyr Ile Thr Glu Asn Gly Thr Ser
370                 375                 380

Ile Leu Asn Glu Asn Asp Leu Pro Tyr Pro Gln Ile Leu Lys Asp Thr
385                 390                 395                 400

Phe Arg Ala Asp Tyr Phe Arg Asn Tyr Ile Arg Ala Met Ala Gln Ala
                405                 410                 415

Val Glu Asp Gly Ala Asn Val Arg Gly Tyr Leu Gly Trp Ser Leu Met
            420                 425                 430

Asp Asn Phe Glu Trp Ala Glu Gly Tyr Glu Thr Arg Phe Gly Val Thr
        435                 440                 445

Tyr Val Asp Tyr Glu Gly Gly Gln Arg Arg Glu Ala Lys Glu Ser Ala
450                 455                 460

Leu Val Leu Lys Pro Leu Phe Glu Glu Leu Ile Lys Lys Glu
465                 470                 475

<210> SEQ ID NO 41
<211> LENGTH: 478
<212> TYPE: PRT
<213> ORGANISM: Botryotinia Fuckeliana

<400> SEQUENCE: 41

Met Ser Lys Ala Val Leu Pro Lys Asp Phe Thr Trp Gly Phe Ala Thr
1               5                   10                  15

Ala Ser Tyr Gln Ile Glu Gly Ala Pro Glu Glu Asp Gly Arg Gly Pro
```

-continued

```
                20                  25                  30
Ser Ile Trp Asp Thr Phe Cys Lys Ile Pro Gly Lys Ile Ala Asp Gly
                35                  40                  45

Ser Ser Gly Asp Val Ala Cys Asp Ser Tyr His Arg Val Ser Glu Asp
                50                  55                  60

Ile Ala Leu Leu Lys Leu Thr Gly Ala Lys Ala Tyr Arg Phe Ser Ile
 65                  70                  75                  80

Ser Trp Ser Arg Ile Ile Pro Leu Gly Arg Asn Asp Pro Val Asn
                    85                  90                  95

Glu Lys Gly Ile Ala Tyr Tyr Ala Lys Leu Val Asp Asp Leu Leu Lys
                100                 105                 110

Glu Gly Ile Thr Pro Phe Val Thr Leu Phe His Trp Asp Leu Pro Asp
                115                 120                 125

Asn Leu Asp Lys Arg Tyr Gly Gly Leu Leu Asn Lys Glu Glu Phe Val
                130                 135                 140

Lys Asp Tyr Ala His Tyr Ala Arg Val Leu Phe Lys Ala Tyr Pro Lys
145                 150                 155                 160

Val Lys Asn Trp Ile Thr Phe Asn Glu Pro Trp Cys Ser Ser Ile Leu
                    165                 170                 175

Gly Tyr Ser Thr Gly Leu Phe Ala Pro Gly His Thr Ser Asp Arg Ser
                180                 185                 190

Lys Ser Ala Val Gly Asp Ser Ser Arg Glu Pro Trp Thr Val Gly His
                195                 200                 205

Asn Ile Leu Ile Ala His Gly Ala Ala Val Lys Ile Tyr Arg Glu Glu
                210                 215                 220

Phe Lys Ala Lys Asp Gly Gly Gln Ile Gly Ile Thr Leu Asn Gly Asp
225                 230                 235                 240

Gly Val Tyr Pro Trp Asp Ala Ser Asp Pro Lys Asp Val Glu Ala Ala
                    245                 250                 255

Glu Arg Lys Leu Glu Phe Ser Ile Ser Trp Phe Ala Asp Pro Ile Tyr
                260                 265                 270

His Gly Lys Tyr Pro Asp Ser Met Arg Ala Gln Leu Gly Asp Arg Leu
                275                 280                 285

Pro Thr Phe Thr Asp Asp Glu Val Ala Leu Val Lys Gly Ser Asn Asp
                290                 295                 300

Phe Tyr Gly Met Asn His Tyr Thr Ala Asn Tyr Ile Arg His Lys Lys
305                 310                 315                 320

Thr Glu Pro Glu Glu Asp Asp Phe Ala Gly Asn Leu Glu Leu Leu Phe
                    325                 330                 335

Glu Asn Lys Gln Gly Asp Asn Ile Gly Pro Glu Thr Gln Ser Val Trp
                340                 345                 350

Leu Arg Pro Asn Pro Gln Gly Phe His Asp Leu Ile Leu Trp Leu Ser
                355                 360                 365

Lys Arg Tyr Gly Phe Pro Thr Ile Tyr Ile Thr Glu Asn Gly Thr Ser
                370                 375                 380

Leu Leu Arg Glu Asn Asp Ile Pro Tyr Pro Asp Ile Leu Lys Asp Thr
385                 390                 395                 400

Phe Arg Ala Asp Tyr Phe Arg Asp Tyr Ile Arg Ala Met Ala Ser Ala
                    405                 410                 415

Val Glu Lys Gly Ala Asp Val Arg Gly Tyr Leu Gly Trp Ser Leu Met
                420                 425                 430

Asp Asn Phe Glu Trp Ala Glu Gly Tyr Glu Thr Arg Phe Gly Val Thr
                435                 440                 445
```

Tyr Val Asp Tyr Glu Gly Gly Gln Arg Arg Glu Pro Lys Glu Ser Ala
            450                 455                 460

Leu Ala Leu Lys Pro Leu Phe Glu Glu Leu Ile Lys Lys Glu
465                 470                 475

<210> SEQ ID NO 42
<211> LENGTH: 483
<212> TYPE: PRT
<213> ORGANISM: Penicillium Chrysogenum

<400> SEQUENCE: 42

Met Gly Ser Thr Glu Gln Ser Thr Leu Pro Ser Asp Phe Leu Trp Gly
 1               5                  10                  15

Phe Ala Thr Ala Ala Tyr Gln Ile Glu Gly Gly Val Asn Asp Asp Gly
            20                  25                  30

Arg Ala Pro Ser Ile Trp Asp Thr Phe Cys Lys Ile Pro Gly Lys Ile
        35                  40                  45

Ala Gly Gly Gly Thr Gly Asp Val Ala Cys Asp Ser Tyr His Arg Thr
    50                  55                  60

His Glu Asp Ile Ala Leu Leu Lys Glu Cys Gly Ala Gln Ala Tyr Arg
65                  70                  75                  80

Phe Ser Leu Ser Trp Ser Arg Ile Ile Pro Leu Gly Gly Arg Asn Asp
                85                  90                  95

Pro Ile Asn Lys Lys Gly Ile Glu Phe Tyr Gln Lys Phe Val Asp Asp
            100                 105                 110

Leu Ile Asp Ala Gly Ile Thr Pro Met Ile Thr Leu Tyr His Trp Asp
        115                 120                 125

Leu Pro Asp Glu Leu Asp Lys Arg Tyr Gly Gly Pro Leu Asn Lys Glu
    130                 135                 140

Glu Phe Val Ala Asp Phe Ala Arg Tyr Ala Arg Val Val Phe Glu Ala
145                 150                 155                 160

Phe Gly Ser Lys Val Lys His Trp Ile Thr Phe Asn Glu Pro Trp Cys
                165                 170                 175

Val Ser Val Leu Gly Tyr Asn Asn Gly Ser Phe Ala Pro Gly His Thr
            180                 185                 190

Ser Asp Arg Ile Lys Ser Pro Val Gly Asp Ser Ser Thr Glu Pro Trp
        195                 200                 205

Ile Val Ser His Ser Leu Leu Val Ala His Gly Ala Ala Val Lys Ile
    210                 215                 220

Tyr Arg Asp Glu Phe Lys Glu Arg Asn Gly Gly Glu Ile Gly Ile Thr
225                 230                 235                 240

Leu Asn Gly Asp Trp Ala Glu Pro Trp Asp Pro Glu Asn Pro Ala Asp
                245                 250                 255

Val Glu Ala Cys Asp Arg Lys Ile Glu Phe Ala Ile Ser Trp Phe Ala
            260                 265                 270

Asp Pro Ile Tyr His Gly Lys Tyr Pro Asp Ser Met Ile Lys Gln Leu
        275                 280                 285

Gly Asp Arg Leu Pro Thr Trp Thr Pro Glu Asp Ile Ala Leu Val Lys
    290                 295                 300

Gly Ser Asn Asp Phe Tyr Gly Met Asn His Tyr Cys Ala Asn Phe Ile
305                 310                 315                 320

Arg Ala Lys Thr Gly Glu Pro Asp Ile Asn Asp Ile Ala Gly Asn Leu
                325                 330                 335

Glu Leu Leu Leu Glu Asp Lys Asn Gly Val Ser Val Gly Pro Ile Thr

```
            340                 345                 350
Gln Ser Pro Trp Leu Arg Pro Ser Ala Ile Gly Phe Arg Lys Leu Leu
            355                 360                 365

Lys Trp Leu Ser Glu Arg Tyr Gly Tyr Pro Lys Ile Tyr Val Thr Glu
370                 375                 380

Asn Gly Thr Ser Val Leu Gly Glu Asn Asp Met Pro Leu Glu Glu Leu
385                 390                 395                 400

Leu Asn Asp Glu Phe Arg Val Gln Tyr Phe Arg Asp Tyr Ile Gly Ala
                405                 410                 415

Met Ala Asp Ala Tyr Thr His Asp Gly Val Asn Val Arg Ala Tyr Met
            420                 425                 430

Ala Trp Ser Leu Met Asp Asn Phe Glu Trp Ala Glu Gly Tyr Glu Thr
            435                 440                 445

Arg Phe Gly Val Thr Phe Val Asp Tyr Glu Asn Asp Gln Lys Arg Ile
            450                 455                 460

Pro Lys Lys Ser Ala Lys Glu Ile Ser Gln Ile Phe Asp Arg Leu Ile
465                 470                 475                 480

Glu Lys Ala

<210> SEQ ID NO 43
<211> LENGTH: 471
<212> TYPE: PRT
<213> ORGANISM: Schizophyllum Commune

<400> SEQUENCE: 43

Met Ala Ala Thr Thr Val Gln Lys Lys Leu Pro Lys Asp Phe Ile Trp
1               5                   10                  15

Gly Phe Ala Thr Ala Ser Phe Gln Ile Glu Gly Ser Thr Asp Val Asp
            20                  25                  30

Gly Arg Gly Lys Ser Ile Trp Asp Asp Tyr Ser Arg Thr Pro Gly Lys
        35                  40                  45

Thr Leu Asp Gly Arg Asn Gly Asp Val Ala Thr Asp Ser Tyr Lys Arg
    50                  55                  60

Trp Lys Glu Asp Leu Asp Leu Leu Ala Ser Tyr His Val Lys Ser Tyr
65                  70                  75                  80

Arg Phe Ser Ile Ala Trp Ser Arg Ile Ile Pro Leu Gly Gly Arg Asp
                85                  90                  95

Asp Pro Ile Asn Pro Ala Gly Ile Lys Phe Tyr Ser Asp Leu Ile Asp
            100                 105                 110

Gly Leu Leu Glu Arg Gly Ile Ile Pro Phe Val Thr Leu Tyr His Trp
        115                 120                 125

Asp Leu Pro Gln Gly Leu His Asp Arg Tyr Gly Gly Trp Leu Asn Lys
    130                 135                 140

Asp Glu Ile Val Lys Asp Tyr Thr Asn Tyr Ala Arg Val Cys Phe Glu
145                 150                 155                 160

Asn Phe Gly Asp Arg Val Lys Tyr Trp Leu Thr Met Asn Glu Pro Trp
                165                 170                 175

Cys Ile Ser Ile Leu Gly Tyr Gly Arg Gly Val Phe Ala Pro Gly Arg
            180                 185                 190

Ser Ser Asp Arg Phe Arg Ser Ala Glu Gly Asp Ser Ser Thr Glu Pro
        195                 200                 205

Trp Ile Val Gly His Asn Val Ile Leu Ser His Ala Asn Ala Val Lys
    210                 215                 220

Leu Tyr Arg Asp Glu Phe Lys Ser Arg Gln Gly Gly Gln Ile Gly Val
```

```
                225                 230                 235                 240
        Thr Leu Asn Gly Asp Met Glu Leu Pro Trp Asp Asp Ser Pro Glu Asn
                        245                 250                 255

Ile Ala Ala Ala Gln His Ala Leu Asp Phe Ala Ile Gly Trp Phe Ala
                        260                 265                 270

Asp Pro Ile Tyr Leu Gly His Tyr Pro Glu Tyr Met Arg Gly Val Leu
                        275                 280                 285

Gly Asp Arg Leu Pro Thr Phe Thr Pro Glu Glu Trp Glu Val Val Lys
                290                 295                 300

Gly Ser Ser Asp Phe Tyr Gly Met Asn Thr Tyr Thr Thr Asn Leu Ala
        305                 310                 315                 320

Arg Ala Gly Gly Asp Asp Glu Phe Gln Gly Leu Val Asp Tyr Thr Phe
                        325                 330                 335

Thr Arg Pro Asp Gly Thr Gln Leu Gly Thr Gln Ala His Cys Ala Trp
                        340                 345                 350

Leu Gln Asp Tyr Pro Glu Gly Phe Arg Gln Leu Leu Asn Tyr Leu Tyr
                        355                 360                 365

Lys Arg Tyr Lys Leu Pro Ile Tyr Val Thr Glu Asn Gly Phe Ala Val
                370                 375                 380

Lys Asp Glu Asp Ser Met Pro Lys Glu Gln Ala Ile Lys Asp Thr Asp
        385                 390                 395                 400

Arg Val Asn Tyr Phe Arg Gly Asn Thr Lys Ala Ile Leu Asp Ala Val
                        405                 410                 415

Asn Glu Asp Gly Val Asp Val Arg Ala Tyr Phe Pro Trp Ser Leu Leu
                        420                 425                 430

Asp Asn Phe Glu Trp Ala Asp Gly Tyr Val Thr Arg Phe Gly Cys Thr
                        435                 440                 445

Tyr Val Asp Tyr Glu Thr Gln Glu Arg Thr Pro Lys Asp Ser Ala Lys
                450                 455                 460

Phe Leu Val Gln Val Arg Ser
        465                 470

<210> SEQ ID NO 44
<211> LENGTH: 501
<212> TYPE: PRT
<213> ORGANISM: Postia Placenta

<400> SEQUENCE: 44

Met Ala Asn Lys Ile Ser Ser Arg Leu Pro Lys Asp Phe Leu Trp Gly
        1               5                   10                  15

Phe Ala Thr Ala Ser Phe Gln Ile Glu Gly Ser Thr Gln Val Asp Gly
                        20                  25                  30

Arg Gly Lys Ser Ile Trp Asp Asp Phe Ser Lys Lys Pro Gly Lys Thr
                    35                  40                  45

Leu Asp Gly Arg Asp Gly Asp Val Ala Thr Asp Ser Tyr Arg Leu Trp
                50                  55                  60

Lys Asp Asp Leu Asp Leu Leu Val Ser Tyr Gly Val Lys Ser Tyr Arg
        65                  70                  75                  80

Phe Ser Ile Ala Trp Ser Arg Ile Ile Pro Leu Gly Gly Arg Asn Asp
                        85                  90                  95

Pro Val Asn Glu Ala Gly Ile Arg Phe Tyr Ser Asn Leu Ile Asp Asn
                        100                 105                 110

Leu Leu Ala Arg Gly Ile Ile Pro Phe Val Thr Leu Tyr His Trp Asp
                    115                 120                 125
```

```
Leu Pro Gln Gly Leu Glu Asp Arg Tyr Gly Gly Trp Leu Asn Lys Glu
130                 135                 140

Glu Ile Val Lys Asp Tyr Val Asn Tyr Ala Lys Ile Cys Phe Glu Arg
145                 150                 155                 160

Phe Gly Asn Arg Val Lys Asn Trp Leu Thr Phe Asn Glu Pro Trp Cys
                165                 170                 175

Ile Ser Val His Gly Tyr Gly His Gly Val Phe Ala Pro Gly Arg Ser
                180                 185                 190

Ser Asp Arg Thr Arg Cys Pro Glu Gly Asp Thr Ser Thr Glu Pro Trp
                195                 200                 205

Leu Val Gly His Asn Val Ile Leu Ala His Ala Tyr Ala Ser Lys Leu
210                 215                 220

Tyr Arg Glu Glu Phe Lys Gln Ala Gln Gly Gly Gln Ile Gly Ile Thr
225                 230                 235                 240

Leu Asn Gly Asp Trp Ala Leu Pro Tyr Asp Ser Pro Glu Ser Ala
                245                 250                 255

Ser Arg Gly Ser Asp Ala Asp Leu Leu Thr Phe Ala Asp Pro Ile Tyr
                260                 265                 270

Leu Gly His Tyr Pro Glu Tyr Leu Lys Glu Met Leu Gly Ser Arg Leu
                275                 280                 285

Pro Thr Phe Thr Ala Glu Glu Leu His Val Val Lys Gly Ser Ser Glu
290                 295                 300

Phe Tyr Gly Met Asn Thr Tyr Thr Thr Asn Leu Cys Met Ala Gly Gly
305                 310                 315                 320

Asp Asn Glu Phe Gln Gly Lys Val Lys Tyr Thr Phe Thr Arg Pro Asp
                325                 330                 335

Gly Thr Gln Leu Gly Thr Gln Ala His Cys Ala Trp Leu Gln Asp Tyr
                340                 345                 350

Ala Pro Gly Phe Arg Gln Leu Leu Asn Tyr Leu Tyr Lys Arg Tyr Arg
                355                 360                 365

Lys Pro Ile Tyr Val Thr Glu Asn Gly Phe Ala Val Lys Asp Glu Asn
370                 375                 380

Asn Lys Pro Val Glu Glu Ala Leu Ser Asp Tyr Asp Arg Val His Tyr
385                 390                 395                 400

Phe Gln Gly Thr Thr Ser Ser Leu Leu Ser Ala Val Val Glu Asp Gly
                405                 410                 415

Val Asp Ile Arg Gly Tyr Phe Ala Trp Ser Leu Met Asp Asn Phe Glu
                420                 425                 430

Trp Ala Asp Gly Tyr Val Thr Arg Phe Gly Val Thr Tyr Val Asp Tyr
                435                 440                 445

Glu Thr Gln Lys Arg Tyr Pro Lys Asp Ser Ala Arg Phe Val Cys Gln
450                 455                 460

Trp Phe Lys Glu Asn Ile Glu Lys Asp Glu Ser Ser Glu Ser Ala Ala
465                 470                 475                 480

Gly Pro Ser Ala Pro Val Ser Lys Leu Ala Asp Ala His Leu Ile
                485                 490                 495

Asp Ala Val Arg Ala
                500

<210> SEQ ID NO 45
<211> LENGTH: 551
<212> TYPE: PRT
<213> ORGANISM: Aspergillus Niger

<400> SEQUENCE: 45
```

```
Trp Ala Glu Ala Tyr Gln Arg Ala Val Asp Ile Val Ser Gln Met Thr
  1               5                  10                  15

Leu Ala Glu Lys Val Asn Leu Thr Thr Gly Thr Gly Trp Glu Leu Glu
             20                  25                  30

Leu Cys Val Gly Gln Thr Gly Gly Val Pro Arg Leu Gly Ile Pro Gly
             35                  40                  45

Met Cys Ala Gln Asp Ser Pro Leu Gly Val Arg Asp Ser Asp Tyr Asn
         50                  55                  60

Ser Ala Phe Pro Ala Gly Val Asn Val Ala Ala Thr Trp Asp Lys Asn
 65                  70                  75                  80

Leu Ala Tyr Leu Arg Gly Gln Ala Met Gly Gln Glu Phe Ser Asp Lys
                 85                  90                  95

Gly Ala Asp Ile Gln Leu Gly Pro Ala Ala Gly Pro Leu Gly Arg Ser
                100                 105                 110

Pro Asp Gly Gly Arg Asn Trp Glu Gly Phe Ser Pro Asp Pro Ala Leu
             115                 120                 125

Ser Gly Val Leu Phe Ala Glu Thr Ile Lys Gly Ile Gln Asp Ala Gly
         130                 135                 140

Val Val Ala Thr Ala Lys His Tyr Ile Ala Tyr Glu Gln Glu His Phe
145                 150                 155                 160

Arg Gln Ala Pro Glu Ala Gln Gly Tyr Gly Phe Asn Ile Thr Glu Ser
                165                 170                 175

Gly Ser Ala Asn Leu Asp Asp Lys Thr Met His Glu Leu Tyr Leu Trp
                180                 185                 190

Pro Phe Ala Asp Ala Ile Arg Ala Gly Ala Gly Ala Val Met Cys Ser
             195                 200                 205

Tyr Asn Gln Ile Asn Asn Ser Tyr Gly Cys Gln Asn Ser Tyr Thr Leu
         210                 215                 220

Asn Lys Leu Leu Lys Ala Glu Leu Gly Phe Gln Gly Phe Val Met Ser
225                 230                 235                 240

Asp Trp Ala Ala His His Ala Gly Val Ser Gly Ala Leu Ala Gly Leu
                245                 250                 255

Asp Met Ser Met Pro Gly Asp Val Asp Tyr Asp Ser Gly Thr Ser Tyr
             260                 265                 270

Trp Gly Thr Asn Leu Thr Ile Ser Val Leu Asn Gly Thr Val Pro Gln
         275                 280                 285

Trp Arg Val Asp Asp Met Ala Val Arg Ile Met Ala Ala Tyr Tyr Lys
290                 295                 300

Val Gly Arg Asp Arg Leu Trp Thr Pro Pro Asn Phe Ser Ser Trp Thr
305                 310                 315                 320

Arg Asp Glu Tyr Gly Phe Lys Tyr Tyr Tyr Val Ser Glu Gly Pro Tyr
                325                 330                 335

Glu Lys Val Asn Gln Phe Val Asn Val Gln Arg Asn His Ser Glu Leu
             340                 345                 350

Ile Arg Arg Ile Gly Ala Asp Ser Thr Val Leu Leu Lys Asn Asp Asp
             355                 360                 365

Gly Ala Leu Pro Leu Thr Gly Lys Glu Arg Leu Val Ala Leu Ile Gly
         370                 375                 380

Glu Asp Ala Gly Ser Asn Pro Tyr Gly Ala Asn Gly Cys Ser Asp Arg
385                 390                 395                 400

Gly Cys Asp Asn Gly Thr Leu Ala Met Gly Trp Gly Ser Gly Thr Ala
                405                 410                 415
```

Asn Phe Pro Tyr Leu Val Thr Pro Glu Gln Ala Ile Ser Asn Glu Val
            420                 425                 430

Leu Lys Asn Lys Asn Gly Val Phe Thr Ala Thr Asp Asn Trp Ala Ile
        435                 440                 445

Asp Gln Ile Glu Ala Leu Ala Lys Thr Ala Ser Val Ser Leu Val Phe
    450                 455                 460

Val Asn Ala Asp Ser Gly Glu Gly Tyr Ile Asn Val Asp Gly Asn Leu
465                 470                 475                 480

Gly Asp Arg Arg Asn Leu Thr Leu Trp Arg Asn Gly Asp Asn Val Ile
            485                 490                 495

Lys Ala Ala Ser Asn Cys Asn Asn Thr Ile Val Ile Ile His Ser
        500                 505                 510

Val Gly Pro Val Leu Val Asn Glu Trp Tyr Asp Asn Pro Asn Val Thr
            515                 520                 525

Ala Ile Leu Trp Gly Gly Leu Pro Gly Gln Glu Ser Gly Asn Ser Leu
        530                 535                 540

Ala Asp Val Leu Tyr Gly Arg
545                 550

<210> SEQ ID NO 46
<211> LENGTH: 823
<212> TYPE: PRT
<213> ORGANISM: Phanerochaete Chrysosporium

<400> SEQUENCE: 46

Met Gly Leu Thr Leu Val Val Leu Leu His Leu Ala Leu Gly Leu Leu
1               5                   10                  15

Thr Gly Val Gln Ala Gln Ser Gly Leu Tyr Gln Gln Cys Gly Gly Ile
            20                  25                  30

Gly Trp Thr Gly Ala Thr Thr Cys Val Ser Gly Ala Thr Cys Thr Val
        35                  40                  45

Leu Asn Pro Tyr Tyr Ser Gln Cys Leu Pro Gly Ala Ala Thr Thr Ser
    50                  55                  60

Val Ser Ser Ser His Ser Ser Ser Ser Val Ser Ser His Ser Ser
65                  70                  75                  80

Ser Glu Ser Ser Ser Ser Ile Ser Ser Thr Ser Thr Ser Pro Pro Ala
            85                  90                  95

Pro Ser Gln Thr Val Ala Asn Val Ser Pro Glu Trp Ala Ala Ala Tyr
        100                 105                 110

Val Lys Ala Gln Ala Ala Val Ala Lys Leu Ser Val Thr Asp Met Val
    115                 120                 125

Asn Leu Ala Thr Gly Val Gln Trp Gln Lys Gly Pro Cys Val Gly Asn
130                 135                 140

Thr Pro Ala Ile Ser Ser Ile Pro Gly Phe Thr Gly Leu Cys Leu Gln
145                 150                 155                 160

Asp Ser Pro Val Gly Val Arg Tyr Ala Asp Gly Thr Ser Val Phe Pro
            165                 170                 175

Pro Glu Ile Asn Val Ala Ala Thr Trp Asn Arg Thr Leu Met Arg Gln
        180                 185                 190

Arg Gly Ala Ala Met Gly Ala Glu Phe Lys Gly Lys Gly Val His Val
    195                 200                 205

Ala Leu Gly Pro Met Met Asn Leu Met Arg Val Pro Ala Ala Gly Arg
        210                 215                 220

Asn Trp Glu Gly Gly Gly Gly Asp Pro Phe Leu Ser Gly Glu Val Ala
225                 230                 235                 240

-continued

```
Phe Glu Thr Ile Ser Gly Ile Gln Ser Ser Gly Ala Gln Ala Cys Ala
            245                 250                 255

Lys His Phe Ile Asn Asn Glu Gln Glu His Phe Arg Asp Ser Ser Ser
            260                 265                 270

Ser Asn Val Asp Asp Arg Thr Glu His Glu Leu Tyr Gly His Pro Phe
            275                 280                 285

Leu Arg Ser Val Gln Ala Asn Val Ala Ser Val Met Cys Ser Tyr Asn
            290                 295                 300

Gln Ile Asn Gly Thr Phe Ser Cys Glu Asn Glu Lys Thr Leu Ser Gly
305                 310                 315                 320

Leu Leu Lys Gly Glu Tyr Gly Phe Gln Gly Tyr Val Met Ser Asp Trp
                325                 330                 335

Trp Ala Thr His Ser Gly Ala Pro Ala Val Asn Ala Gly Leu Asp Met
                340                 345                 350

Thr Met Pro Gly Asp Glu Thr Leu Ser Ser Gly Thr Thr Tyr Phe Gly
                355                 360                 365

Gln Asn Leu Val Asn Ala Val Asn Ser Gly Gln Val Ser Gln Ala Arg
            370                 375                 380

Val Lys Asp Met Ala Thr Arg Ile Leu Ala Ala Trp Tyr Leu Leu Gly
385                 390                 395                 400

Gln Asp Gln Asn Phe Pro Ala Val Asn Phe Asn Ser Trp Asn Ser Gly
                405                 410                 415

Gln Gly Gln His Val Asn Val Ser Gly Asn His Ala Ser Leu Ile Arg
                420                 425                 430

Thr Ile Gly Ala Ala Ser Gln Ile Leu Leu Lys Asn Ala Asn Gly Ala
                435                 440                 445

Leu Pro Leu Lys Lys Pro Lys Thr Ile Gly Ile Gly Asn Gly Ala
450                 455                 460

Gly Ser Asn Pro Asn Gly Pro Asn Ala Phe Ser Asp Arg Ala Gly Asp
465                 470                 475                 480

Val Gly Val Leu Ala Leu Gly Trp Gly Ser Gly Thr Ala Asn Phe Pro
                485                 490                 495

Tyr Leu Val Ala Pro Val Asp Ala Ile Thr Ala Arg Ala Ser Gln Asp
                500                 505                 510

Gly Thr Thr Val Ser Ser Ser Leu Ser Asp Thr Asp Leu Thr Gly Ala
            515                 520                 525

Ala Asn Thr Ala Thr Gly Lys Asp Val Ala Met Val Phe Ile Thr Ala
530                 535                 540

Asp Ser Gly Glu Gly Tyr Leu Thr Val Glu Gly Asn Ala Gly Asp Arg
545                 550                 555                 560

Asn Asp Leu Gln Ala Trp His Gly Gly Asp Ala Leu Val Gln Gln Val
                565                 570                 575

Ala Ser His Asn Lys Asn Thr Ile Val Val Ile Asn Ser Val Gly Pro
                580                 585                 590

Ile Asn Met Glu Ala Trp Val Asn His Pro Asn Val Thr Ala Ile Val
                595                 600                 605

Trp Ser Gly Leu Pro Gly Gln Glu Ala Gly Asn Ala Val Thr Asp Val
                610                 615                 620

Leu Phe Gly Ala Val Asn Pro Gly Gly Lys Leu Pro Phe Thr Ile Gly
625                 630                 635                 640

Lys Ser Ile Ser Asp Tyr Ser Ala Gln Ile Ile Thr Thr Gly Ser Gly
                645                 650                 655
```

```
Ile Val Pro Ile Pro Tyr Asn Glu Gly Leu Phe Ile Asp Tyr Arg His
            660                 665                 670

Phe Asp Gln Ala Gly Ile Ala Pro Arg Phe Glu Phe Gly Phe Gly Leu
            675                 680                 685

Ser Tyr Thr Thr Phe Asp Tyr Ser Asn Leu Val Ile Thr Gly Ser Thr
            690                 695                 700

Ala Gly Gly Thr Arg Gln Pro Pro Gly Pro Gly Ser Ser Leu Asp Pro
705                 710                 715                 720

Trp Leu His Asp Ser Val Val Thr Val Ser Phe Thr Leu Thr Asn Asn
                725                 730                 735

Gly Thr Val Asp Gly Thr Glu Val Pro Gln Leu Tyr Leu Ser Pro Pro
                740                 745                 750

Ala Ser Ala Lys Ser Ala Pro Gln Asn Leu Lys Gly Phe Asp Ser Val
            755                 760                 765

Phe Leu Pro Ala Gly Ala Ser Thr Thr Val Ser Phe Glu Leu Ser Arg
            770                 775                 780

Tyr Ser Phe Ser Val Trp Asp Val Val Ser Gln Ser Trp Gln Ile Pro
785                 790                 795                 800

Ala Gly Val Thr Gly Ile Ser Val Gly Ala Ser Ser Arg Asp Leu Arg
                805                 810                 815

Leu Lys Gly Ser Ile Thr Asn
                820

<210> SEQ ID NO 47
<211> LENGTH: 733
<212> TYPE: PRT
<213> ORGANISM: Sporotrichum Thermophile

<400> SEQUENCE: 47

Met Thr Leu Gln Ala Phe Ala Leu Leu Ala Ala Ala Leu Val Arg
  1               5                  10                  15

Gly Glu Thr Pro Thr Lys Val Pro Arg Asp Ala Pro Arg Gly Ala Ala
                 20                  25                  30

Ala Trp Glu Ala Ala His Ser Ser Ala Ala Ala Leu Gly Lys Leu
             35                  40                  45

Ser Gln Gln Asp Lys Ile Asn Ile Val Thr Gly Val Gly Trp Asn Lys
 50                  55                  60

Gly Pro Cys Val Gly Asn Thr Pro Ala Ile Ser Ser Ile Asn Tyr Pro
 65                  70                  75                  80

Gln Leu Cys Leu Gln Asp Gly Pro Leu Gly Val Arg Phe Gly Ser Ser
                 85                  90                  95

Ile Thr Ala Phe Thr Pro Gly Ile Gln Ala Ala Ser Thr Trp Asp Val
            100                 105                 110

Asp Leu Ile Arg Gln Arg Gly Glu Tyr Met Gly Ala Glu Phe Lys Gly
            115                 120                 125

Cys Gly Ile His Val Gln Leu Gly Pro Val Ala Gly Pro Leu Gly Lys
            130                 135                 140

Val Pro Gln Gly Gly Arg Asn Trp Glu Gly Phe Gly Val Asp Pro Tyr
145                 150                 155                 160

Leu Thr Gly Ile Ala Met Ala Glu Thr Ile Glu Gly Ile Gln Ser Ala
                165                 170                 175

Gly Val Gln Ala Thr Ala Lys His Tyr Ile Leu Asn Glu Gln Glu Leu
            180                 185                 190

Asn Arg Glu Thr Met Ser Ser Asn Val Asp Asp Arg Thr Leu His Glu
            195                 200                 205
```

```
Leu Tyr Leu Trp Pro Phe Ala Asp Ala Val His Ser Asn Val Ala Ser
    210                 215                 220

Val Met Cys Ser Tyr Asn Lys Ile Asn Gly Thr Trp Ala Cys Glu Asn
225                 230                 235                 240

Asp Arg Val Leu Asn Val Ile Leu Lys Gln Glu Leu Gly Phe Pro Gly
                245                 250                 255

Tyr Val Met Ser Asp Trp Asn Ala Gln His Ser Thr Asp Asp Ala Ala
            260                 265                 270

Asn His Gly Met Asp Met Thr Met Pro Gly Ser Asp Phe Asn Gly Gly
        275                 280                 285

Thr Ile Leu Trp Gly Pro Gln Leu Asp Ser Ala Val Asn Ser Gly Arg
    290                 295                 300

Val Pro Lys Ser Arg Leu Asp Asp Met Val Glu Arg Ile Leu Ala Ala
305                 310                 315                 320

Trp Tyr Leu Leu Gly Gln Asp Ser Asn Tyr Pro Ala Ile Asn Ile Gly
                325                 330                 335

Ala Asn Val Gln Gly Asn His Lys Glu Asn Val Arg Ala Val Ala Arg
            340                 345                 350

Asp Gly Ile Val Leu Leu Lys Asn Asp Gly Ile Leu Pro Leu Lys
        355                 360                 365

Lys Pro Ala Lys Leu Ala Leu Ile Gly Ser Ala Ala Val Val Asn Pro
370                 375                 380

Gln Gly Leu Asn Ser Cys Gln Asp Gln Gly Cys Asn Lys Gly Ala Leu
385                 390                 395                 400

Gly Met Gly Trp Gly Ser Gly Ala Val Asn Tyr Pro Tyr Phe Val Ala
                405                 410                 415

Pro Tyr Asp Ala Leu Lys Ala Arg Ala Gln Glu Asp Gly Thr Thr Val
            420                 425                 430

Ser Leu His Asn Ser Asp Ser Thr Ser Gly Val Ala Asn Val Ala Ser
        435                 440                 445

Asp Ala Asp Ala Ala Ile Val Val Ile Thr Ala Asp Ser Gly Glu Gly
    450                 455                 460

Tyr Ile Thr Val Glu Gly Ala Ala Gly Asp Arg Leu Asn Leu Asp Pro
465                 470                 475                 480

Trp His Asn Gly Asn Glu Leu Val Lys Ala Val Ala Ala Ala Asn Lys
                485                 490                 495

Asn Thr Ile Val Val His Ser Val Gly Pro Ile Ile Leu Glu Thr
            500                 505                 510

Ile Leu Ala Thr Glu Gly Val Lys Ala Ile Val Trp Ala Gly Leu Pro
    515                 520                 525

Ser Gln Glu Asn Gly Asn Ala Leu Val Asp Ile Leu Tyr Gly Leu Ala
530                 535                 540

Ser Pro Ser Gly Lys Leu Val Tyr Thr Ile Ala Lys Arg Glu Gln Asp
545                 550                 555                 560

Tyr Gly Thr Ala Val Val Arg Gly Asp Asp Thr Phe Pro Glu Gly Leu
                565                 570                 575

Phe Val Asp Tyr Arg His Phe Asp Lys Glu Asn Ile Glu Pro Arg Tyr
            580                 585                 590

Glu Phe Gly Phe Gly Leu Ser Tyr Thr Asn Phe Thr Tyr Ala Asp Leu
        595                 600                 605

Glu Leu Thr Ser Thr Ala Thr Ala Gly Pro Ala Thr Gly Glu Thr Ile
    610                 615                 620
```

-continued

Pro Gly Gly Ala Ala Asp Leu Trp Glu Glu Val Ala Thr Val Thr Ala
625                 630                 635                 640

Thr Ile Thr Asn Ser Gly Gly Val Asp Gly Ala Glu Val Ala Gln Leu
            645                 650                 655

Tyr Leu Thr Leu Pro Ser Ser Ala Pro Ala Thr Pro Pro Lys Gln Leu
            660                 665                 670

Arg Gly Phe Ala Lys Leu Lys Leu Ala Ala Gly Ala Ser Gly Thr Ala
            675                 680                 685

Thr Phe Ser Leu Arg Arg Arg Asp Leu Ser Tyr Trp Asp Thr Gly Arg
            690                 695                 700

Gly Gln Trp Val Val Pro Glu Gly Glu Phe Gly Val Ser Val Gly Ala
705                 710                 715                 720

Ser Ser Arg Asp Ile Arg Leu Thr Gly Ser Phe Arg Val
            725                 730

<210> SEQ ID NO 48
<211> LENGTH: 744
<212> TYPE: PRT
<213> ORGANISM: Trichoderma Reesei

<400> SEQUENCE: 48

Met Arg Tyr Arg Thr Ala Ala Leu Ala Leu Ala Thr Gly Pro Phe
1               5                   10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
            35                  40                  45

Ala Ala Leu Ala Lys Leu Asn Leu Gln Asp Lys Val Gly Ile Val Ser
50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
            100                 105                 110

Ala Ser Thr Trp Asp Val Asn Leu Ile Arg Glu Arg Gly Gln Phe Ile
            115                 120                 125

Gly Glu Glu Val Lys Ala Ser Gly Ile His Val Ile Leu Gly Pro Val
130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
            180                 185                 190

Leu Asn Glu Gln Glu Leu Asn Arg Glu Thr Ile Ser Ser Asn Pro Asp
            195                 200                 205

Asp Arg Thr Leu His Glu Leu Tyr Thr Trp Pro Phe Ala Asp Ala Val
210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asn Ala Gln His
            260                 265                 270

-continued

```
Thr Thr Val Gln Ser Ala Asn Ser Gly Leu Asp Met Ser Met Pro Gly
        275                 280                 285

Thr Asp Phe Asn Gly Asn Asn Arg Leu Trp Gly Pro Ala Leu Thr Asn
    290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
            340                 345                 350

Asn Val Arg Ala Ile Ala Arg Asp Gly Ile Val Leu Leu Lys Asn Asp
            355                 360                 365

Ala Asn Ile Leu Pro Leu Lys Lys Pro Ala Ser Ile Ala Val Val Gly
    370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
            420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val
        515                 520                 525

Lys Ala Val Val Trp Ala Gly Leu Pro Ser Gln Glu Ser Gly Asn Ala
    530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
            595                 600                 605

Ser Tyr Thr Lys Phe Asn Tyr Ser Arg Leu Ser Val Leu Ser Thr Ala
    610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
    675                 680                 685
```

```
Asn Leu Thr Pro Gly Gln Ser Gly Thr Ala Thr Phe Asn Ile Arg Arg
    690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740

<210> SEQ ID NO 49
<211> LENGTH: 813
<212> TYPE: PRT
<213> ORGANISM: Gibberella Zeae

<400> SEQUENCE: 49

Met Ala Ser Leu Arg Ser Val Leu Val Ser Gly Leu Leu Ala Thr Gly
1               5                   10                  15

Val Ser Ala Gln Asn Phe Gly Gly Ser Ala Arg Asp Glu Glu Ala Phe
            20                  25                  30

Ser Trp Val Gln Pro Lys Asn Thr Thr Ile Leu Gly Gln Tyr Gly His
        35                  40                  45

Ser Pro His Tyr Asn Ser Thr Tyr Ala Thr Gly Lys Gly Trp Glu Glu
    50                  55                  60

Gly Phe Ala Lys Ala Lys Glu Phe Leu Ala Lys Leu Thr Leu Glu Glu
65                  70                  75                  80

Lys Ala Asp Met Val Thr Gly Thr Pro Gly Pro Cys Val Gly Asn Ile
                85                  90                  95

Ile Ala Ile Pro Arg Leu Gly Phe Lys Gly Leu Cys Leu His Asp Gly
            100                 105                 110

Pro Leu Ala Ile Arg Val Ala Asp Tyr Ala Ser Val Phe Ser Ala Gly
        115                 120                 125

Val Ser Ala Ala Ser Ser Trp Asp Lys Asp Leu Leu Tyr Gln Arg Gly
    130                 135                 140

Leu Ala Leu Gly Gln Glu Phe Lys Ala Lys Gly Ala His Ile Leu Leu
145                 150                 155                 160

Gly Pro Val Ala Gly Pro Leu Gly Arg Ser Ala Tyr Ser Gly Arg Asn
                165                 170                 175

Trp Glu Gly Phe Ser Pro Asp Pro Tyr Leu Thr Gly Val Ala Met Glu
            180                 185                 190

His Thr Ile Asn Gly His Gln Asp Ala Gly Val Gln Ala Thr Ala Lys
        195                 200                 205

His Phe Ile Gly Asn Glu Gln Glu Val Met Arg Asn Pro Thr Phe Lys
    210                 215                 220

Lys Asp Gly Tyr Val Gly Glu Val Asp Glu Ala Leu Ser Ser Asn
225                 230                 235                 240

Met Asp Asp Arg Thr Met His Glu Leu Tyr Leu Trp Pro Phe Ala Asn
                245                 250                 255

Ala Ala His Ala Lys Ala Ser Ser Phe Met Cys Ala Tyr Gln Arg Leu
            260                 265                 270

Asn Gly Ser Tyr Ser Cys Gln Asn Ser Lys Leu Leu Asn Gly Ile Leu
        275                 280                 285

Arg Asp Glu Leu Gly Phe Gln Gly Tyr Val Met Ser Asp Trp Gly Gly
    290                 295                 300

Thr His Ala Gly Val Ala Thr Ile Glu Ser Gly Leu Asp Met Asp Met
305                 310                 315                 320
```

-continued

```
Pro Gly Gly Ile Gly Ala Tyr Gly Met Asp Phe Lys Ala Gly Ser Phe
            325                 330                 335

Phe Gly Gly Asn Leu Thr Arg Ala Val Thr Asn Gly Thr Leu Glu Glu
            340                 345                 350

Ala Arg Val Asp Asp Met Ile Met Arg Ile Met Thr Pro Tyr Phe Trp
            355                 360                 365

Leu Gly Gln Asp Lys Glu Asp Tyr Pro Ser Val Asp Glu Ser Ser Ala
    370                 375                 380

Asp Leu Asn Thr Phe Ser Pro Arg Lys Thr Trp Leu Lys Glu Phe Asn
385                 390                 395                 400

Phe Thr Gly Thr Arg Ser Arg Asp Val Arg Gly Asp His Gly Ala Leu
            405                 410                 415

Ile Arg Lys His Gly Ala Glu Ser Thr Val Leu Leu Lys Asn Glu Asn
            420                 425                 430

Asn Ala Leu Pro Leu Lys Lys Pro Lys Ser Ile Ala Val Phe Gly Asn
            435                 440                 445

Asp Ala Gly Asp Ile Thr Glu Gly Phe Tyr Asn Gln Gln Asp Phe Glu
    450                 455                 460

Phe Gly Asn Leu Val Val Gly Gly Ser Gly Thr Gly Arg Leu Thr
465                 470                 475                 480

Tyr Leu Val Ser Pro Leu Thr Ala Ile Asn Ala Arg Ala Lys Gln Asp
            485                 490                 495

Gly Thr Leu Val Gln Gln Trp Met Asn Asn Thr Leu Ile Thr Thr Ser
            500                 505                 510

Asn Val Thr Asp Leu Trp Ile Pro Ala Leu Pro Asp Val Cys Leu Val
            515                 520                 525

Phe Leu Lys Thr Trp Ala Thr Glu Gly Ala Asp Arg Gly His Leu Ser
    530                 535                 540

Val Asp Trp Asn Gly Asp Glu Val Val Leu Ser Val Ala Lys Ser Cys
545                 550                 555                 560

Asn Asn Thr Val Val Val Thr His Ser Ser Gly Ile Asn Thr Leu Pro
            565                 570                 575

Trp Ala Asp His Pro Asn Val Thr Ala Ile Leu Ala Ala His Tyr Pro
            580                 585                 590

Gly Glu Glu Ser Gly Asn Ser Leu Val Asp Leu Leu Tyr Gly Asp Val
            595                 600                 605

Asn Pro Ser Gly Arg Leu Pro Tyr Thr Ile Ala Leu Asn Gly Thr Asp
    610                 615                 620

Tyr Asn Ala Pro Pro Thr Thr Ala Ile Asn Thr Thr Gly Thr Asp Asp
625                 630                 635                 640

Trp Gln Ser Trp Phe Asp Glu Lys Leu Glu Ile Asp Tyr Arg Tyr Phe
            645                 650                 655

Asp Ala Gln Asn Met Ser Val Arg Tyr Glu Phe Gly Phe Gly Leu Ser
            660                 665                 670

Tyr Ser Thr Phe Glu Ile Ser Asp Ile Ser Ala Glu Pro Leu Ala Asp
            675                 680                 685

Asp Ile Thr Ala Met Pro Glu Ala Leu Pro Val Gln Pro Gly Gly Asn
    690                 695                 700

Pro Ala Leu Trp Glu Ser Ile Tyr Asn Val Thr Val Ser Val Ala Asn
705                 710                 715                 720

Ser Gly Lys Val Asp Gly Ala Thr Val Pro Gln Leu Tyr Val Ser Phe
            725                 730                 735
```

```
Pro Glu Ser Ala Pro Lys Gly Thr Pro Lys Gln Leu Arg Gly Phe
            740                 745                 750

Glu Lys Val Phe Leu Glu Ala Gly Glu Ser Lys Ser Val Ser Phe Glu
        755                 760                 765

Leu Met Arg Arg Asp Leu Ser Tyr Trp Asp Ile Ile Ser Gln Gln Trp
    770                 775                 780

Val Ile Pro Glu Gly Glu Phe Thr Ile Arg Val Gly Phe Ser Ser Arg
785                 790                 795                 800

Thr Leu Lys Glu Glu Thr Lys Val Thr Leu Val Lys Ala
                805                 810

<210> SEQ ID NO 50
<211> LENGTH: 833
<212> TYPE: PRT
<213> ORGANISM: Sclerotinia Sclerotiorum

<400> SEQUENCE: 50

Met Ala Ile Pro Tyr Val Glu Val Glu Trp Ser Glu Arg Asp Thr Lys
  1               5                  10                  15

Met Gln Val Leu Ser Le

```
Ala Val Asn Ala Gly Thr Val Pro Gln Thr Arg Leu Asp Asp Met Ala
305                 310                 315                 320

Leu Arg Ile Leu Ala Ser Trp Tyr Phe Leu Gly Gln Asp Thr Asn Tyr
            325                 330                 335

Pro Val Val Thr Gly Trp Ser Ser Trp Asn Gly Gly Val Gly Gly Pro
                340                 345                 350

Asn Val Ser Ser Asp His Asn Thr Val Ala Arg Ala Ile Ala Arg Asp
                355                 360                 365

Gly Ile Val Leu Leu Lys Asn Thr Asn Asn Ala Leu Pro Leu Lys Lys
                370                 375                 380

Pro Ala Ser Leu Ala Ile Ile Gly Gln Asp Ala Ile Val Asn Pro Ala
385                 390                 395                 400

Gly Ala Asn Ser Cys Thr Asp Arg Gly Cys Asp Thr Gly Thr Leu Ala
                405                 410                 415

Met Gly Trp Gly Ser Gly Thr Ala Asp Phe Pro Tyr Leu Val Ala Pro
                420                 425                 430

Tyr Asp Ala Ile Lys Ala Arg Ala Ala Ala Asp Gly Thr Thr Val Thr
            435                 440                 445

Leu Ser Asn Thr Asp Ser Thr Ser Thr Gly Ala Ser Val Ala Ser Ala
            450                 455                 460

Ala Ala Thr Ala Ile Val Phe Ile Asn Ser Asp Ser Gly Glu Glu Tyr
465                 470                 475                 480

Ile Thr Val Glu Gly Ala Ala Gly Asp Arg Ile Asn Leu Asp Pro Trp
                485                 490                 495

His Asn Gly Asn Ser Leu Val Ser Ala Ile Ala Ala Val Asn Lys Asn
                500                 505                 510

Thr Ile Val Val Ile His Ser Val Gly Pro Leu Ile Leu Glu Ser Ile
            515                 520                 525

Leu Ala Leu Pro Asn Val Ile Ala Ile Ile Trp Ala Gly Leu Pro Gly
530                 535                 540

Gln Glu Ser Gly Asn Ala Leu Val Asp Ile Leu Tyr Gly Ser Val Ser
545                 550                 555                 560

Pro Ser Gly Lys Leu Pro Phe Thr Ile Ala Lys Thr Gln Ser Asp Tyr
                565                 570                 575

Gly Thr Ala Ile Ala Asn Gly Asp Asp Asn Tyr Ser Glu Gly Leu Phe
                580                 585                 590

Ile Asp Tyr Arg His Phe Asp Gln Ala Gly Leu Thr Pro Arg Tyr Glu
            595                 600                 605

Phe Gly Tyr Gly Leu Ser Tyr Ser Ser Phe Ser Tyr Ser Asn Leu Ile
            610                 615                 620

Leu Ser Ser Ile Ser Ser Ser Thr Gly Asn Asn Ala Leu Leu Pro
625                 630                 635                 640

Gly Gly Lys Ser Asn Leu Phe Asp Ile Ile Ala Thr Val Ser Ile Thr
                645                 650                 655

Leu Ser Asn Ser Gly Ser Val Pro Ala Ala Glu Ile Ala Gln Leu Tyr
            660                 665                 670

Ile Gly Phe Pro Asp Ser Val Pro Gly Thr Pro Leu Arg Gln Leu Arg
            675                 680                 685

Gly Phe Lys Lys Ile Ser Leu Glu Ala Gly Ala Lys Ser Ser Leu Met
            690                 695                 700

Phe Glu Leu Arg Arg Lys Asp Leu Ser Tyr Trp Asp Ala Gly Ser Gln
705                 710                 715                 720
```

Met Trp Val Leu Pro Val Gly Tyr Phe Gly Val Trp Val Gly Ala Ser
            725                 730                 735

Ser Arg Asp Leu Arg Leu Glu Gly Val Leu Ser Ala Ser Ser Gly Ser
            740                 745                 750

Ser Ser Ile Ser Ser Pro Thr Thr Ser Val Ser Ser Ser Thr Ser Lys
            755                 760                 765

Thr Thr Thr Thr Pro Thr Thr Pro Gln Pro Ser Thr Ser Ser Ser Ser
            770                 775                 780

Thr Thr Thr Thr Thr Ser Pro Thr Thr Pro Thr Gly Pro Thr Gln Thr
785                 790                 795                 800

Leu Tyr Gly Gln Cys Gly Gly Ile Gly Tyr Thr Gly Pro Thr Ile Cys
            805                 810                 815

Ala Ser Gly Ser Cys Lys Phe Thr Asn Thr Tyr Tyr Ser Gln Cys Leu
            820                 825                 830

Pro

<210> SEQ ID NO 51
<211> LENGTH: 869
<212> TYPE: PRT
<213> ORGANISM: Botryotinia Fuckeliana

<400> SEQUENCE: 51

Met Tyr Phe Ser Ser Phe Val Leu Leu Ala Leu Ser Thr Pro Ile His
1               5                   10                  15

Ala Ala Ala Gly Asp Gly Asp Trp Asn Ala Tyr Thr Lys Ala Lys
            20                  25                  30

Thr Thr Leu Ala Lys Leu Thr Asn Ala Asn Lys Val Thr Leu Val Thr
            35                  40                  45

Gly Val Gly Trp Glu Lys Gly Pro Cys Val Gly Asn Thr Ala Ala Ile
    50                  55                  60

Pro Ser Ile Gly Trp Pro Ala Phe Cys Leu Gln Asp Gly Pro Leu Gly
65                  70                  75                  80

Val Arg Tyr Ala Gln Lys Val Thr Ala Phe Pro Ala Gly Ile Thr Thr
                85                  90                  95

Gly Ser Thr Trp Asp Thr Glu Leu Met Tyr Ala Arg Gly Asn Ala Leu
            100                 105                 110

Gly Ala Glu Ala Lys Ala Leu Gly Val His Asn Gln Leu Gly Pro Val
        115                 120                 125

Ala Gly Pro Leu Gly Lys Ile Pro Val Ala Gly Arg Asn Trp Glu Gly
    130                 135                 140

Phe Ser Asn Asp Pro Tyr Leu Ser Gly Val Ala Met Ala Asn Thr Val
145                 150                 155                 160

Glu Gly Met Gln Ala Ala Gly Val Gln Ala Cys Ala Lys His Tyr Leu
                165                 170                 175

Gly Asn Glu Gln Glu Phe Asn Arg Gly Thr Met Ser Ser Asn Ile Val
            180                 185                 190

Asp Arg Val Asn His Glu Leu Tyr Leu Trp Pro Phe Ala Glu Ala Val
        195                 200                 205

Lys Ala Asn Val Ala Ser Val Met Cys Ser Tyr Asn Arg Phe Asn Ser
    210                 215                 220

Thr Tyr Ala Cys Glu Asn Gln Ala Leu Leu Thr Gly Leu Leu Lys Asn
225                 230                 235                 240

Glu Leu Asp Phe Gln Gly Tyr Val Val Ser Asp Trp Ala Ala Gln Lys
                245                 250                 255

```
Thr Thr Thr Gly Ser Ala Asn Ala Gly Met Asp Met Ala Met Pro Gly
            260                 265                 270

Asp Asn Phe Gly Asp Asn Asn Phe Ile Trp Gly Thr Asn Leu Leu Asn
        275                 280                 285

Ala Val Thr Ala Gly Thr Val Pro Gln Thr Arg Leu Asp Asp Met Ala
    290                 295                 300

Thr Arg Ile Leu Ala Ala Trp Tyr Phe Leu Ala Gln Asp Thr Asn Tyr
305                 310                 315                 320

Pro Ala Val Thr Gly Trp Thr Ser Trp Asn Gly Gly Val Gly Gly Pro
                325                 330                 335

Asn Val Ser Ser Thr His Asn Thr Val Ala Arg Ala Ile Ala Arg Asp
            340                 345                 350

Gly Ile Val Leu Leu Lys Asn Thr Asn Asn Ala Leu Pro Leu Lys Lys
        355                 360                 365

Pro Val Ser Leu Ala Leu Ile Gly Gln Asp Ala Ile Val Asn Pro Ala
    370                 375                 380

Gly Ala Asn Ala Cys Ile Asp Arg Gly Cys Asp Val Gly Thr Leu Ala
385                 390                 395                 400

Met Gly Trp Gly Ser Gly Thr Ala Asp Phe Pro Tyr Leu Val Ala Pro
                405                 410                 415

Tyr Asp Ala Leu Lys Val Lys Ala Ala Ala Asp Gly Thr Thr Leu Thr
            420                 425                 430

Leu Ser Asn Thr Asp Ser Thr Ser Thr Gly Ala Ser Val Ala Ser Ala
        435                 440                 445

Ala Ala Thr Ala Ile Val Phe Ile Asn Ser Asp Ala Gly Glu Glu Tyr
    450                 455                 460

Ile Thr Val Glu Gly Ala Lys Gly Asp Arg Ile Asn Leu Asp Pro Trp
465                 470                 475                 480

His Ser Gly Asn Ala Leu Val Ala Ala Val Ala Ala Val Asn Lys Asn
                485                 490                 495

Thr Ile Val Val Ile His Ser Val Gly Pro Leu Ile Leu Glu Ser Ile
            500                 505                 510

Leu Ala Leu Pro Asn Val Ile Ala Ile Val Trp Ala Gly Leu Pro Gly
        515                 520                 525

Gln Glu Ser Gly Asn Ala Leu Val Asp Ile Leu Tyr Gly Ser Val Ser
    530                 535                 540

Pro Ser Gly Lys Leu Pro Tyr Thr Ile Ala Lys Thr Gln Ala Asp Tyr
545                 550                 555                 560

Gly Thr Ala Ile Ala Ser Gly Asp Asp Ser Tyr Ala Glu Gly Leu Phe
                565                 570                 575

Ile Asp Tyr Arg His Phe Asp Gln Ser Ser Ile Val Pro Arg Tyr Glu
            580                 585                 590

Phe Gly Phe Gly Leu Ser Tyr Thr Thr Phe Ser Tyr Ser Asn Leu Val
        595                 600                 605

Leu Ser Ser Ile Ser Thr Thr Pro Gly Asn Ser Gly Ile Leu Pro Gly
    610                 615                 620

Gly Lys Ala Asn Leu Tyr Asp Ser Ile Ala Thr Val Ser Val Ser Val
625                 630                 635                 640

Thr Asn Asn Gly Thr Ile Pro Gly Ala Glu Val Ala Gln Leu Tyr Ile
                645                 650                 655

Gly Phe Pro Asn Ser Ile Pro Asn Thr Pro Pro Lys Gln Leu Arg Gly
            660                 665                 670

Phe Lys Lys Val Asn Leu Ala Ala Gly Val Ala Asn Ser Ile Thr Phe
```

```
              675                 680                 685
Ser Leu Arg Arg Lys Asp Leu Ser Tyr Trp Asp Thr Thr Gln Ser
    690                 695                 700

Trp Ile Leu Pro Ser Gly Thr Phe Asn Val Tyr Val Gly Ser Ser
705                 710                 715                 720

Arg Asp Ile Arg Leu Ser Gly Thr Phe Leu Ser Ser Gly Ala Gly Ser
                725                 730                 735

Gly Ser Pro Ser Ser Thr Ser Ser Ser Ile Ser Ser Thr Met
            740                 745                 750

Thr Ser Leu Ser Ser Thr Ser Leu Thr Thr Ser Ile Ser Val Pro Thr
        755                 760                 765

Leu Thr Thr Lys Thr Ser Thr Thr Ser Ile Ala Ser Ala Thr Thr Ser
    770                 775                 780

Ala Thr Gly Ala Leu Gln Thr Leu Tyr Gly Gln Cys Gly Gly Asn Gly
785                 790                 795                 800

Tyr Thr Gly Pro Thr Val Asn Val Tyr Leu Asp Asp Gly Trp Lys Phe
                805                 810                 815

Gly Val Lys Gly Glu Lys Glu Lys Arg Lys Arg Lys Arg Gly
            820                 825                 830

Trp Asn Gly Asp Gly Asp Gly Asp Gly Glu Asp Val Gly Leu
        835                 840                 845

Gly Leu Ser Leu Arg Arg Trp Ser Ala Tyr Leu Phe Ser Asp Ile Leu
850                 855                 860

Lys Glu Leu Arg Ile
865

<210> SEQ ID NO 52
<211> LENGTH: 736
<212> TYPE: PRT
<213> ORGANISM: Penicillium Chrysogenum

<400> SEQUENCE: 52

Met Gln Asn Leu Leu Val Ser Ala Leu Ala Leu Ser Ala Ala Ala Asp
  1               5                  10                  15

Ala Tyr Gly Ala Gly Ala Ala Gly Trp Asp Ala Ala Tyr Ser Lys Ala
                20                  25                  30

Gln Ala Ala Leu Leu Lys Leu Asn Gln Thr Glu Lys Val Gly Ile Ala
            35                  40                  45

Thr Gly Val Gly Trp Glu Gly Gly Pro Cys Val Gly Asn Thr Tyr Ala
        50                  55                  60

Pro Ser Ser Ile Asp Tyr Pro Ser Leu Cys Leu Gln Asp Ser Pro Leu
 65                  70                  75                  80

Gly Ile Arg Tyr Ala Asn Pro Val Thr Ala Phe Pro Ala Gly Ile Asn
                85                  90                  95

Ala Gly Ala Thr Trp Asp Arg Ser Leu Leu Tyr Ala Arg Gly Ala Ala
            100                 105                 110

Met Gly Gln Glu Ala Lys Gly Leu Gly Val His Val Gln Leu Gly Pro
        115                 120                 125

Ser Ala Gly Pro Leu Gly Lys Asn Pro Asp Gly Gly Arg Asn Trp Glu
    130                 135                 140

Gly Phe Ser Val Asp Pro Tyr Leu Ala Gly Val Gly Met Glu Glu Thr
145                 150                 155                 160

Ile Gln Gly Met Gln Asp Ser Gly Val Gln Ala Cys Ala Lys His Trp
                165                 170                 175
```

-continued

```
Leu Gly Asn Glu Gln Glu His Asn Arg Glu Thr Met Ser Ser Asn Ile
            180                 185                 190

Gly Asp Arg Ala Thr His Glu Leu Tyr Leu Trp Pro Phe Met Asn Ala
        195                 200                 205

Val Lys Ala Asn Val Ala Ser Val Met Cys Ser Tyr Asn Lys Leu Asn
    210                 215                 220

Gly Thr Trp Ala Cys Glu Ser Asp Ala Val Leu Asn Asp Leu Leu Lys
225                 230                 235                 240

Asp Glu Leu Gly Phe Pro Gly Tyr Val Met Ser Asp Trp Asn Ala Gln
                245                 250                 255

His Thr Gly Val Asn Ser Ala Leu Ala Gly Leu Asp Met Thr Met Pro
            260                 265                 270

Gly Ser Asp Phe Asn Lys Pro Pro Gly Ser Ile Phe Trp Gly Pro Asn
        275                 280                 285

Leu Val Glu Ala Val Thr Asn Gly Ser Val Pro Gln Ser Arg Leu Asp
    290                 295                 300

Asp Met Ala Thr Arg Ile Leu Ala Ser Trp Tyr Leu Leu Gly Gln Asp
305                 310                 315                 320

Gln Gly Tyr Pro Glu Val Thr Phe Ser Ser Trp Asn Gly Gly Lys Ala
                325                 330                 335

Thr Val Asp Val Thr Ala Asp His Ala Ser Val Val Arg Thr Val Ala
            340                 345                 350

Arg Asp Ser Ile Val Leu Leu Lys Asn Gln Glu His Ala Leu Pro Leu
        355                 360                 365

Arg Lys Pro Lys Ser Leu Ala Ile Ile Gly Gln Asp Ala Ile Val Asn
    370                 375                 380

Pro Asp Gly Pro Asn Ala Cys Val Asp Arg Gly Cys Asn Thr Gly Thr
385                 390                 395                 400

Leu Ala Met Gly Trp Gly Ser Gly Thr Ala Glu Phe Pro Tyr Leu Ile
                405                 410                 415

Ala Pro Leu Asp Ala Ile Lys Val Gln Ala Gln Lys Asp Gly Thr Lys
            420                 425                 430

Ile Val Glu Ser Thr Thr Asp Ser Thr Ala Ala Ala Ser Ala Ala
        435                 440                 445

Ala Ala Ala Asp Thr Ala Val Val Phe Ile Asn Ala Asp Ala Gly Glu
    450                 455                 460

Gly Tyr Leu Thr Val Glu Gly Asn Ala Gly Asp Arg Asn Asn Leu Asp
465                 470                 475                 480

Pro Trp His Asn Gly Asn Glu Leu Val Lys Ser Val Ala Ala Ala Asn
                485                 490                 495

Lys Asn Val Ile Val Val His Ser Val Gly Pro Ile Ile Leu Glu
            500                 505                 510

Thr Ile Leu Ala Gln Pro Ser Val Lys Ala Ile Val Trp Ala Gly Leu
        515                 520                 525

Pro Gly Gln Glu Ser Gly Asn Ala Leu Val Asp Val Met Tyr Gly Thr
    530                 535                 540

Thr Ser Pro Ser Gly Lys Leu Pro Tyr Thr Ile Ala Lys Gln Pro Ser
545                 550                 555                 560

Asp Tyr Gly Ala Gly Trp Asn Ser Ala Leu Val Asp Asn Phe Val Glu
                565                 570                 575

Asp Leu Phe Ile Asp Tyr Arg His Phe Asp Lys Asn Gly Ile Ala Pro
            580                 585                 590

Arg Tyr Glu Phe Gly Tyr Gly Leu Ser Tyr Thr Thr Phe Asn Tyr Ser
```

```
            595                 600                 605
Gly Leu Ala Val Ser Val Ser Ala Thr Ala Gly Pro Ser Asn Gly Pro
        610                 615                 620
Ile Val Pro Gly Gly Ala Glu Glu Leu Phe Gln Ser Val Gly Thr Ile
625                 630                 635                 640
Ser Val Ile Val Glu Asn Thr Gly Glu Val Ala Gly Ala Glu Val Ala
            645                 650                 655
Gln Leu Tyr Leu Gly Leu Pro Asp Ser Val Leu Ser Thr Pro Pro Lys
        660                 665                 670
Gln Leu Arg Gly Phe Gln Lys Leu Asn Leu Gln Pro Gly Glu Gln Gly
        675                 680                 685
Thr Ala Thr Phe Glu Leu Thr Arg Arg Asp Leu Ser Tyr Trp Asp Val
        690                 695                 700
Gln Thr Gln Lys Trp Val Val Pro Ser Gly Thr Phe Thr Val Tyr Val
705                 710                 715                 720
Gly Ala Ser Ser Arg Asp Ile His Gly Glu Gly Lys Phe Thr Val Ala
            725                 730                 735

<210> SEQ ID NO 53
<211> LENGTH: 776
<212> TYPE: PRT
<213> ORGANISM: Postia Placentae

<400> SEQUENCE: 53

Met Tyr Lys Leu Ala Pro Ser Ala Leu Leu Trp Arg Asp Ser Gly Thr
1               5                   10                  15
Pro Val Leu Gly Gln His Gln Gly Cys Thr Leu Pro Arg Phe Val Met
            20                  25                  30
Leu Leu Ala Gly Asn Ala Trp Ala Glu Ala Tyr Ala Lys Ala Glu Ala
        35                  40                  45
Phe Val Ala Gly Leu Thr Leu Glu Gln Lys Val Asn Val Ser Thr Gly
    50                  55                  60
Val Tyr Trp Glu Gln Gly Leu Cys Val Gly Asn Ile Gly Glu Val Ala
65                  70                  75                  80
Asp Leu Arg Gly Leu Cys Leu Gln Asp Ser Pro Leu Gly Val Arg Tyr
                85                  90                  95
Thr Asp Tyr Asn Thr Ala Phe Pro Ala Gly Ile Ser Thr Ala Ala Thr
            100                 105                 110
Phe Asn Arg Thr Met Met Arg Leu Arg Gly Gln Gln Met Gly Glu Glu
        115                 120                 125
Phe Arg Gly Lys Gly Val Asn Val Ala Leu Gly Pro Met Met Asn Met
    130                 135                 140
Gly Arg Val Ala Gln Ala Gly Arg Asn Trp Glu Gly Phe Gly Thr Asp
145                 150                 155                 160
Pro Phe Leu Ser Gly Glu Ala Ala Tyr Glu Thr Thr Leu Gly Leu Gln
                165                 170                 175
Ser Ala Gly Val Gln Ala Cys Ala Lys His Tyr Ile Asp Tyr Glu Gln
            180                 185                 190
Glu Tyr Lys Arg Thr Gln Glu Ser Ser Glu Val Asp Asp Arg Thr Gln
        195                 200                 205
His Glu Ile Tyr Leu Lys Pro Phe Leu Arg Ala Val Met Ala Gly Thr
    210                 215                 220
Ala Ser Val Met Cys Ser Tyr Asn Met Ile Asn Asp Thr Tyr Ser Cys
225                 230                 235                 240
```

```
Glu Asn Asp Arg Thr Leu Asn Gln Leu Leu Lys Gly Glu Leu Gly Phe
                245                 250                 255

Arg Gly Tyr Val Met Ser Asp Trp Gly Ala Gln Glu Ser Thr Leu Ser
            260                 265                 270

Ala Met Ala Gly Leu Asp Met Ser Met Pro Gly Asp Ile Thr Leu Gly
        275                 280                 285

Ser Gly Asn Ser Trp Trp Gly Pro Asn Leu Thr Ala Phe Val Glu Asn
    290                 295                 300

Gly Thr Ile Pro Leu Ser Arg Met Asp Asp Met Ala Thr Arg Ile Met
305                 310                 315                 320

Ala Ser Tyr Tyr Leu Leu Gly Gln Asp Gln Asp Tyr Pro Asn Asp Gly
                325                 330                 335

Arg Leu Ile Pro Asn Ala Val Ser Phe Asn Ala Phe Asn Gln Tyr Asp
            340                 345                 350

Gln Val His Asn Leu His Ile Asp Val Gln Ala Asp His Tyr Gln Ile
        355                 360                 365

Val Arg Glu Ile Gly His Ala Gly Ala Val Leu Leu Lys Asn Thr Asn
    370                 375                 380

Gly Ala Leu Pro Leu Asn Ala Pro Arg Asn Val Val Leu Ile Gly Ser
385                 390                 395                 400

Asp Ala Gly Asn Gly Ala Met Gly Ala Asn Gly Tyr Thr Asp Arg Gly
                405                 410                 415

Gly Asp Asp Gly Ile Leu Gly Met Gly Trp Gly Ser Gly Thr Asp Asn
            420                 425                 430

Tyr Pro Tyr Leu Ile Ser Pro Met Asp Ala Met Gln Val Arg Ala Arg
        435                 440                 445

Gln Asp Gly Thr Thr Leu Met Asn Trp Tyr Tyr Asp Trp Asp Thr Glu
    450                 455                 460

Gly Ala Ala Thr Ala Ala Ile Gln Phe Glu Ala Ala Ile Val Phe Val
465                 470                 475                 480

Asn Ser Asp Ser Gly Glu Gly Tyr Ile Glu Val Asp Gly Asn Leu Gly
                485                 490                 495

Asp Arg Asn Asn Leu Thr Leu Trp His Asn Ala Asp Asn Leu Ile Thr
            500                 505                 510

Ala Val Ala Ser Gln Asn Asn Asn Thr Ile Val Val Ala His Ser Val
        515                 520                 525

Gly Pro Ser Ile Ile Asp Ser Trp Val Glu Asn Pro Asn Val Thr Ala
    530                 535                 540

Ile Ile Trp Ala Gly Val Ala Gly Gln Glu Ala Gly Asn Ala Ile Val
545                 550                 555                 560

Asp Val Leu Tyr Gly Asp Tyr Asn Pro Ser Gly Arg Leu Pro Tyr Thr
                565                 570                 575

Ile Ala Lys Arg Leu Glu Asp Tyr Gly Val Phe Leu Thr Leu Gly Gly
            580                 585                 590

Asn Gly Ser Thr Ile Leu Ser Val Pro Tyr Thr Glu Gly Leu Phe Tyr
        595                 600                 605

Asp Tyr Arg His Phe Asp Glu Tyr Asn Ile Thr Pro Arg Tyr Glu Phe
    610                 615                 620

Gly Tyr Gly Leu Ser Tyr Thr Thr Phe Glu Tyr Tyr Asn Leu Ala Thr
625                 630                 635                 640

Ser Ile Val Pro Gln Tyr Asp Pro Thr Asp Tyr Ala Leu Glu Ala Ala
                645                 650                 655

Trp Ala Ala Gly Val Pro Thr Pro Gln Gly Glu Gly Ser Ser Val Ala
```

```
                    660                 665                 670
Leu Trp Leu His Arg Pro Phe Val Gln Val Ser Phe Glu Val Gln Asn
                675                 680                 685

Thr Gly Ala Val Ala Gly Thr Glu Ile Pro Gln Val Tyr Val His Phe
            690                 695                 700

Pro Thr Gly Ile Gly Glu Pro Pro Ser Trp Leu Lys Gly Phe Asp Ala
705                 710                 715                 720

Val Tyr Ile Glu Pro Gly Glu Val Thr Thr Val Thr Val Thr Ile Ser
                725                 730                 735

Arg Tyr Asp Leu Ser Ile Trp Asp Val Val Ala Gln Gly Trp Val Lys
                740                 745                 750

Pro Ala Gly Glu Ile Thr Phe Ser Val Gly Ala Ser Ser Arg Asp Phe
            755                 760                 765

Arg Leu Gln Gly Tyr Ile Pro Ile
            770                 775

<210> SEQ ID NO 54
<211> LENGTH: 734
<212> TYPE: PRT
<213> ORGANISM: Schizophyllum Commune

<400> SEQUENCE: 54

Met Val Gly Gly Ile Arg Gln Gly Glu Thr Pro Pro Ala Ser Ser Gly
 1               5                  10                  15

Ser Leu Leu Tyr Thr Phe His Gln Ala Ser Asp Ala Val Ala Gln Leu
                20                  25                  30

Ser Leu Gln Glu Lys Val Asp Ile Ala Thr Gly Ile Gly Trp Met Asn
            35                  40                  45

Gly Pro Cys Val Gly Asn Thr Pro Ala Val Pro Thr Ile Asp Tyr Pro
 50                  55                  60

Ser Leu Cys Leu Gln Asp Ser Pro Met Gly Val Arg Tyr Ala Ser Glu
65                  70                  75                  80

Val Ser Ala Phe Pro Ala Gly Val Asn Thr Ala Ala Thr Phe Asn Arg
                85                  90                  95

Thr Leu Ile Arg Ala Arg Gly Val Ala Leu Gly Glu Glu Phe Arg Gly
            100                 105                 110

Lys Gly Ile His Val Tyr Leu Gly Pro Asp Met Asn Ile Met Arg Thr
        115                 120                 125

Ala Ala Gly Gly Arg Asn Trp Glu Gly Phe Gly Ala Asp Pro Tyr Leu
130                 135                 140

Ser Gly Glu Ala Ser Tyr Glu Thr Ile Ile Gly Val Gln Ser Val Gly
145                 150                 155                 160

Val Gln Gly Ser Ala Lys His Phe Ile Asn Asn Asp Gln Glu His Phe
                165                 170                 175

Arg Glu Ser Ser Ser Ser Asn Val Asp Asp Arg Ala Gln His Glu Ile
            180                 185                 190

Tyr Leu Ala Pro Phe Leu Lys Ser Ala Gln Ala Asn Val Ala Ser Phe
        195                 200                 205

Met Cys Ser Tyr Ser Ala Val Asn Gly Ser Trp Ser Cys Glu Asn Asp
    210                 215                 220

Lys Met Leu Asn Asp Ile Val Lys Gly Glu Trp Gly Tyr Pro Gly Tyr
225                 230                 235                 240

Ile Gln Ser Asp Trp Gly Ala Thr His Ser Thr Leu Ala Val Asn Phe
                245                 250                 255
```

-continued

Gly Leu Asp Met Thr Met Pro Gly Asp Ile Thr Phe Gly Ser Asn Thr
             260                 265                 270

Thr Tyr Phe Gly Gln Ala Leu Ile Asp Ala Val Asn Ser Gly Asp Val
         275                 280                 285

Pro Glu Asp Arg Val Ser Asp Met Ala Leu Arg Ile Leu Ala Ala Trp
     290                 295                 300

Tyr Leu Leu Gly Gln Asp Glu Gly Tyr Pro Glu Thr Asn Ile Trp Ala
305                 310                 315                 320

Trp Asp Leu Asn Asp Pro Arg Asn Leu His Val Asp Val Gln Ala Asp
                 325                 330                 335

His Gly Ser Leu Ile Arg Glu Ile Ala Asp Ala Ser Thr Ile Leu Leu
             340                 345                 350

Lys Asn Glu Asn Gly Thr Leu Pro Leu Ser Ala Pro Gly Ser Ile Ala
         355                 360                 365

Ile Ile Gly Asn Gly Ala Gly Asn Asn Ser Gln Gly Ile Asn Gly Cys
     370                 375                 380

Val Asp Arg Ser Cys Asp Asp Gly Val Leu Ala Val Gly Trp Gly Ser
385                 390                 395                 400

Gly Thr Ala Glu Phe Pro Tyr Leu Ile Thr Pro Leu Asp Ala Ile Thr
                 405                 410                 415

Ala Arg Ala Gln Glu Asp Gly Thr Thr Ile Thr Ser Ser Leu Ser Asp
             420                 425                 430

Ser Asp Thr Ala Arg Ala Ala Gln Ile Ala Ala Ala Asp Val Ala
         435                 440                 445

Ile Val Phe Ile Ser Ser Asp Ser Gly Glu Gly Tyr Leu Thr Val Glu
     450                 455                 460

Gly Asn Ala Gly Asp Arg Asn Asp Leu Leu Ala Trp His Asp Gly Asp
465                 470                 475                 480

Ala Leu Val Gln Ala Val Ala Asp Ala Asn Glu Asn Thr Ile Val Ala
                 485                 490                 495

Val Asn Thr Val Gly Ala Ile Ile Thr Glu Ala Trp Ile Glu His Pro
             500                 505                 510

Asn Val Lys Ala Val Val Trp Ser Gly Leu Pro Gly Gln Glu Ala Gly
         515                 520                 525

Asn Ser Val Ala Asp Ile Leu Tyr Gly Ala Tyr Asn Pro Ser Gly Arg
     530                 535                 540

Leu Pro Tyr Thr Ile Ala Lys Ser Ala Asp Asp Tyr Pro Ala Gln Val
545                 550                 555                 560

Leu Tyr Glu Ser Ser Ala Gln Val Pro Asp Ile Asp Tyr Ser Glu Gly
                 565                 570                 575

Leu Leu Val Asp Tyr Arg His Phe Asp Ala Asn Gly Ile Glu Pro Arg
             580                 585                 590

Tyr Glu Phe Gly Phe Gly Leu Ser Tyr Thr Thr Phe Glu Tyr Asp Asn
         595                 600                 605

Leu Ala Ile Glu Gly Ser Ala Ser Asp Gln Ser Pro Pro Thr Gly
     610                 615                 620

Pro Gly Ser Ser Leu Asp Pro Trp Leu His Glu Pro Val Val Thr Val
625                 630                 635                 640

Thr Phe Thr Val Glu Asn Thr Gly Glu Val Ala Gly His Glu Ile Pro
                 645                 650                 655

Gln Leu Tyr Val Thr Phe Pro Glu Ser Ala Gly Ser Ala Pro Leu Asn
             660                 665                 670

Leu Lys Gly Phe Glu Ser Val Phe Val Ala Pro Gly Glu Thr Ala Asp

```
                675                 680                 685
Val Ser Leu Ser Leu Thr Arg Tyr Asp Leu Ser Ile Trp Asp Val Val
    690                 695                 700
Ser Gln Ser Trp Val Val Pro Ser Gly Asp Ala Thr Ile Ser Ile Gly
705                 710                 715                 720
Ala Ser Ser Arg Asp Ile Arg Leu Thr Gly Thr Val Thr Asn
                725                 730

<210> SEQ ID NO 55
<211> LENGTH: 735
<212> TYPE: PRT
<213> ORGANISM: Neurospora crassa

<400> SEQUENCE: 55

Met His Leu Arg Ile Phe Ala Val Leu Ala Thr Ser Leu Ala Trp
1               5                   10                  15
Ala Glu Thr Ser Glu Lys Gln Ala Arg Gln Ala Gly Ser Gly Phe Ala
                20                  25                  30
Ala Trp Asp Ala Ala Tyr Ser Gln Ala Ser Thr Ala Leu Ser Lys Leu
            35                  40                  45
Ser Gln Gln Asp Lys Val Asn Ile Val Thr Gly Val Gly Trp Asn Lys
        50                  55                  60
Gly Pro Cys Val Gly Asn Thr Pro Ala Ile Ala Ser Ile Gly Tyr Pro
65                  70                  75                  80
Gln Leu Cys Leu Gln Asp Gly Pro Leu Gly Ile Arg Phe Gly Gly Ser
                85                  90                  95
Val Thr Ala Phe Thr Pro Gly Ile Gln Ala Ala Ser Thr Trp Asp Val
            100                 105                 110
Glu Leu Ile Arg Gln Arg Gly Val Tyr Leu Gly Ala Glu Ala Arg Gly
        115                 120                 125
Val Gly Val His Val Leu Leu Gly Pro Val Ala Gly Ala Leu Gly Lys
130                 135                 140
Ile Pro Asn Gly Gly Arg Asn Trp Glu Gly Phe Gly Pro Asp Pro Tyr
145                 150                 155                 160
Leu Thr Gly Ile Ala Met Ser Glu Thr Ile Glu Gly Ile Gln Ser Asn
                165                 170                 175
Gly Val Gln Ala Cys Ala Lys His Phe Ile Leu Asn Glu Gln Glu Thr
            180                 185                 190
Asn Arg Asp Thr Ile Ser Ser Val Asp Asp Arg Thr Met His Glu
        195                 200                 205
Leu Tyr Leu Phe Pro Phe Ala Asp Ala Val His Ser Asn Val Ala Ser
210                 215                 220
Val Met Cys Ser Tyr Asn Lys Val Asn Gly Thr Trp Ala Cys Glu Asn
225                 230                 235                 240
Asp Lys Ile Gln Asn Gly Leu Leu Lys Lys Glu Leu Gly Phe Lys Gly
                245                 250                 255
Tyr Val Met Ser Asp Trp Asn Ala Gln His Thr Thr Asn Gly Ala Ala
            260                 265                 270
Asn Ser Gly Met Asp Met Thr Met Pro Gly Ser Asp Phe Asn Gly Lys
        275                 280                 285
Thr Ile Leu Trp Gly Pro Gln Leu Asn Thr Ala Val Asn Asn Gly Gln
        290                 295                 300
Val Ser Lys Ala Arg Leu Asp Asp Met Ala Lys Arg Ile Leu Ala Ser
305                 310                 315                 320
```

-continued

```
Trp Tyr Leu Leu Glu Gln Asn Ser Gly Tyr Pro Ala Thr Asn Leu Lys
            325                 330                 335
Ala Asn Val Gln Gly Asn His Lys Glu Asn Val Arg Ala Val Ala Arg
        340                 345                 350
Asp Gly Ile Val Leu Leu Lys Asn Asp Asn Ile Leu Pro Leu Lys
    355                 360                 365
Lys Pro Ser Lys Leu Ala Ile Ile Gly Ser Ser Val Val Asn Pro
370                 375                 380
Ala Gly Arg Asn Ala Cys Thr Asp Arg Gly Cys Asn Thr Gly Ala Leu
385                 390                 395                 400
Gly Met Gly Trp Gly Ser Gly Thr Ala Asp Tyr Pro Tyr Phe Val Ala
                405                 410                 415
Pro Tyr Asp Ala Leu Lys Thr Arg Ala Gln Ser Asp Gly Thr Thr Val
            420                 425                 430
Asn Leu Leu Ser Ser Asp Ser Thr Ser Gly Val Ala Asn Ala Ala Ser
        435                 440                 445
Gly Ala Asp Ala Ala Leu Val Phe Ile Thr Ala Asp Ser Gly Glu Gly
    450                 455                 460
Tyr Ile Thr Val Glu Gly Val Thr Gly Asp Arg Pro Asn Leu Asp Pro
465                 470                 475                 480
Trp His Asn Gly Asn Gln Leu Val Gln Ala Val Ala Gln Ala Asn Lys
                485                 490                 495
Asn Thr Ile Val Val His Ser Thr Gly Pro Ile Ile Leu Glu Thr
            500                 505                 510
Ile Leu Ala Gln Pro Gly Val Lys Ala Val Trp Ala Gly Leu Pro
        515                 520                 525
Ser Gln Glu Asn Gly Asn Ala Leu Val Asp Val Leu Tyr Gly Leu Val
545                 535                 540
Ser Pro Ser Gly Lys Leu Pro Tyr Thr Ile Ala Lys Ser Glu Ser Asp
545                 550                 555                 560
Tyr Gly Thr Ala Val Gln Arg Gly Gly Thr Asp Leu Phe Thr Glu Gly
                565                 570                 575
Leu Phe Ile Asp Tyr Arg His Phe Asp Lys Asn Gly Ile Ala Pro Arg
            580                 585                 590
Tyr Glu Phe Gly Phe Gly Leu Ser Tyr Thr Asn Phe Thr Tyr Ser Ser
        595                 600                 605
Leu Ser Ile Thr Ser Thr Ala Ser Ser Gly Pro Ala Ser Gly Asp Thr
    610                 615                 620
Ile Pro Gly Gly Arg Ala Asp Leu Trp Glu Thr Val Ala Thr Val Thr
625                 630                 635                 640
Ala Val Val Lys Asn Thr Gly Val Gln Gly Ala Glu Ala Pro Gln
                645                 650                 655
Leu Tyr Ile Thr Leu Pro Ser Ser Ala Pro Ser Ser Pro Pro Lys Gln
            660                 665                 670
Leu Arg Gly Phe Ala Lys Leu Lys Leu Ala Pro Gly Glu Ser Lys Thr
        675                 680                 685
Ala Thr Phe Ile Leu Arg Arg Arg Asp Leu Ser Tyr Trp Asp Thr Gly
    690                 695                 700
Ser Gln Asn Trp Val Val Pro Ser Gly Ser Phe Gly Val Val Val Gly
705                 710                 715                 720
Ala Ser Ser Arg Asp Leu Arg Leu Asn Gly Lys Phe Asp Val Tyr
                725                 730                 735
```

```
<210> SEQ ID NO 56
<211> LENGTH: 860
<212> TYPE: PRT
<213> ORGANISM: Aspergillus Niger

<400> SEQUENCE: 56

Met Arg Phe Thr Leu Ile Glu Ala Val Ala Leu Thr Ala Val Ser Leu
 1               5                  10                  15

Ala Ser Ala Asp Glu Leu Ala Tyr Ser Pro Pro Tyr Tyr Pro Ser Pro
            20                  25                  30

Trp Ala Asn Gly Gln Gly Asp Trp Ala Glu Ala Tyr Gln Arg Ala Val
        35                  40                  45

Asp Ile Val Ser Gln Met Thr Leu Ala Glu Lys Val Asn Leu Thr Thr
    50                  55                  60

Gly Thr Gly Trp Glu Leu Glu Leu Cys Val Gly Gln Thr Gly Gly Val
65                  70                  75                  80

Pro Arg Leu Gly Ile Pro Gly Met Cys Ala Gln Asp Ser Pro Leu Gly
                85                  90                  95

Val Arg Asp Ser Asp Tyr Asn Ser Ala Phe Pro Ala Gly Val Asn Val
            100                 105                 110

Ala Ala Thr Trp Asp Lys Asn Leu Ala Tyr Leu Arg Gly Gln Ala Met
        115                 120                 125

Gly Gln Glu Phe Ser Asp Lys Gly Ala Asp Ile Gln Leu Gly Pro Ala
    130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Ser Gly Val Leu Phe Ala Glu Thr Ile
                165                 170                 175

Lys Gly Ile Gln Asp Ala Gly Val Val Ala Thr Ala Lys His Tyr Ile
            180                 185                 190

Ala Tyr Glu Gln Glu His Phe Arg Gln Ala Pro Glu Ala Gln Gly Tyr
        195                 200                 205

Gly Phe Asn Ile Thr Glu Ser Gly Ser Ala Asn Leu Asp Asp Lys Thr
    210                 215                 220

Met His Glu Leu Tyr Leu Trp Pro Phe Ala Asp Ala Ile Arg Ala Gly
225                 230                 235                 240

Ala Gly Ala Val Met Cys Ser Tyr Asn Gln Ile Asn Asn Ser Tyr Gly
                245                 250                 255

Cys Gln Asn Ser Tyr Thr Leu Asn Lys Leu Leu Lys Ala Glu Leu Gly
            260                 265                 270

Phe Gln Gly Phe Val Met Ser Asp Trp Ala Ala His His Ala Gly Val
        275                 280                 285

Ser Gly Ala Leu Ala Gly Leu Asp Met Ser Met Pro Gly Asp Val Asp
    290                 295                 300

Tyr Asp Ser Gly Thr Ser Tyr Trp Gly Thr Asn Leu Thr Ile Ser Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Trp Thr Pro
            340                 345                 350

Pro Asn Phe Ser Ser Trp Thr Arg Asp Glu Tyr Gly Phe Lys Tyr Tyr
        355                 360                 365

Tyr Val Ser Glu Gly Pro Tyr Glu Lys Val Asn Gln Phe Val Asn Val
    370                 375                 380
```

```
Gln Arg Asn His Ser Glu Leu Ile Arg Arg Ile Gly Ala Asp Ser Thr
385                 390                 395                 400

Val Leu Leu Lys Asn Asp Gly Ala Leu Pro Leu Thr Gly Lys Glu Arg
            405                 410                 415

Leu Val Ala Leu Ile Gly Glu Asp Ala Gly Ser Asn Pro Tyr Gly Ala
            420                 425                 430

Asn Gly Cys Ser Asp Arg Gly Cys Asp Asn Gly Thr Leu Ala Met Gly
        435                 440                 445

Trp Gly Ser Gly Thr Ala Asn Phe Pro Tyr Leu Val Thr Pro Glu Gln
    450                 455                 460

Ala Ile Ser Asn Glu Val Leu Lys Asn Lys Asn Gly Val Phe Thr Ala
465                 470                 475                 480

Thr Asp Asn Trp Ala Ile Asp Gln Ile Glu Ala Leu Ala Lys Thr Ala
                485                 490                 495

Ser Val Ser Leu Val Phe Val Asn Ala Asp Ser Gly Glu Gly Tyr Ile
            500                 505                 510

Asn Val Asp Gly Asn Leu Gly Asp Arg Arg Asn Leu Thr Leu Trp Arg
        515                 520                 525

Asn Gly Asp Asn Val Ile Lys Ala Ala Ala Ser Asn Cys Asn Asn Thr
    530                 535                 540

Ile Val Ile Ile His Ser Val Gly Pro Val Leu Val Asn Glu Trp Tyr
545                 550                 555                 560

Asp Asn Pro Asn Val Thr Ala Ile Leu Trp Gly Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gln
        595                 600                 605

Asp Tyr Leu Tyr Thr Glu Pro Asn Asn Gly Asn Gly Ala Pro Gln Glu
    610                 615                 620

Asp Phe Val Glu Gly Val Phe Ile Asp Tyr Arg Gly Phe Asp Lys Arg
625                 630                 635                 640

Asn Glu Thr Pro Ile Tyr Glu Phe Gly Tyr Gly Leu Ser Tyr Thr Thr
                645                 650                 655

Phe Asn Tyr Ser Asn Leu Gln Val Glu Val Leu Ser Ala Pro Ala Tyr
            660                 665                 670

Glu Pro Ala Ser Gly Glu Thr Glu Ala Ala Pro Thr Phe Gly Glu Val
        675                 680                 685

Gly Asn Ala Ser Asp Tyr Leu Tyr Pro Asp Gly Leu Gln Arg Ile Thr
    690                 695                 700

Lys Phe Ile Tyr Pro Trp Leu Asn Ser Thr Asp Leu Glu Ala Ser Ser
705                 710                 715                 720

Gly Asp Ala Ser Tyr Gly Gln Asp Ala Ser Asp Tyr Leu Pro Glu Gly
                725                 730                 735

Ala Thr Asp Gly Ser Ala Gln Pro Ile Leu Pro Ala Gly Gly Gly Ala
            740                 745                 750

Gly Gly Asn Pro Arg Leu Tyr Asp Glu Leu Ile Arg Val Thr Val Thr
        755                 760                 765

Ile Lys Asn Thr Gly Lys Val Ala Gly Asp Glu Val Pro Gln Leu Tyr
    770                 775                 780

Val Ser Leu Gly Gly Pro Asn Glu Pro Lys Ile Val Leu Arg Gln Phe
785                 790                 795                 800

Glu Arg Ile Thr Leu Gln Pro Ser Glu Glu Thr Gln Trp Ser Thr Thr
```

```
                    805                 810                 815
Leu Thr Arg Arg Asp Leu Ala Asn Trp Asn Val Glu Thr Gln Asp Trp
            820                 825                 830

Glu Ile Thr Ser Tyr Pro Lys Met Val Phe Val Gly Ser Ser Ser Arg
            835                 840                 845

Lys Leu Pro Leu Arg Ala Ser Leu Pro Thr Val His
            850                 855                 860

<210> SEQ ID NO 57
<211> LENGTH: 823
<212> TYPE: PRT
<213> ORGANISM: Phanerochaete Chrysosporium

<400> SEQUENCE: 57

Met Gly Leu Thr Leu Val Val Leu Leu His Leu Ala Leu Gly Leu Leu
 1               5                  10                  15

Thr Gly Val Gln Ala Gln Ser Gly Leu Tyr Gln Gln Cys Gly Gly Ile
             20                  25                  30

Gly Trp Thr Gly Ala Thr Thr Cys Val Ser Gly Ala Thr Cys Thr Val
         35                  40                  45

Leu Asn Pro Tyr Tyr Ser Gln Cys Leu Pro Gly Ala Ala Thr Thr Ser
     50                  55                  60

Val Ser Ser His Ser Ser Ser Ser Val Ser Ser His Ser Ser
 65                  70                  75                  80

Ser Glu Ser Ser Ser Ser Ile Ser Ser Thr Ser Thr Ser Pro Pro Ala
                 85                  90                  95

Pro Ser Gln Thr Val Ala Asn Val Ser Pro Glu Trp Ala Ala Ala Tyr
            100                 105                 110

Val Lys Ala Gln Ala Ala Val Ala Lys Leu Ser Val Thr Asp Met Val
        115                 120                 125

Asn Leu Ala Thr Gly Val Gln Trp Gln Lys Gly Pro Cys Val Gly Asn
    130                 135                 140

Thr Pro Ala Ile Ser Ser Ile Pro Gly Phe Thr Gly Leu Cys Leu Gln
145                 150                 155                 160

Asp Ser Pro Val Gly Val Arg Tyr Ala Asp Gly Thr Ser Val Phe Pro
                165                 170                 175

Pro Glu Ile Asn Val Ala Ala Thr Trp Asn Arg Thr Leu Met Arg Gln
            180                 185                 190

Arg Gly Ala Ala Met Gly Ala Glu Phe Lys Gly Lys Gly Val His Val
        195                 200                 205

Ala Leu Gly Pro Met Met Asn Leu Met Arg Val Pro Ala Ala Gly Arg
    210                 215                 220

Asn Trp Glu Gly Gly Gly Asp Pro Phe Leu Ser Gly Glu Val Ala
225                 230                 235                 240

Phe Glu Thr Ile Ser Gly Ile Gln Ser Ser Gly Ala Gln Ala Cys Ala
                245                 250                 255

Lys His Phe Ile Asn Asn Glu Gln Glu His Phe Arg Asp Ser Ser Ser
            260                 265                 270

Ser Asn Val Asp Asp Arg Thr Glu His Glu Leu Tyr Gly His Pro Phe
        275                 280                 285

Leu Arg Ser Val Gln Ala Asn Val Ala Ser Val Met Cys Ser Tyr Asn
    290                 295                 300

Gln Ile Asn Gly Thr Phe Ser Cys Glu Asn Glu Lys Thr Leu Ser Gly
305                 310                 315                 320
```

Leu Leu Lys Gly Glu Tyr Gly Phe Gln Gly Tyr Val Met Ser Asp Trp
                325                 330                 335

Trp Ala Thr His Ser Gly Ala Pro Ala Val Asn Ala Gly Leu Asp Met
            340                 345                 350

Thr Met Pro Gly Asp Glu Thr Leu Ser Ser Gly Thr Thr Tyr Phe Gly
        355                 360                 365

Gln Asn Leu Val Asn Ala Val Asn Ser Gly Gln Val Ser Gln Ala Arg
    370                 375                 380

Val Lys Asp Met Ala Thr Arg Ile Leu Ala Ala Trp Tyr Leu Leu Gly
385                 390                 395                 400

Gln Asp Gln Asn Phe Pro Ala Val Asn Phe Asn Ser Trp Asn Ser Gly
                405                 410                 415

Gln Gly Gln His Val Asn Val Ser Gly Asn His Ala Ser Leu Ile Arg
            420                 425                 430

Thr Ile Gly Ala Ala Ser Gln Ile Leu Leu Lys Asn Ala Asn Gly Ala
        435                 440                 445

Leu Pro Leu Lys Lys Pro Lys Thr Ile Gly Ile Gly Asn Gly Ala
    450                 455                 460

Gly Ser Asn Pro Asn Gly Pro Asn Ala Phe Ser Asp Arg Ala Gly Asp
465                 470                 475                 480

Val Gly Val Leu Ala Leu Gly Trp Gly Ser Gly Thr Ala Asn Phe Pro
                485                 490                 495

Tyr Leu Val Ala Pro Val Asp Ala Ile Thr Ala Arg Ala Ser Gln Asp
            500                 505                 510

Gly Thr Thr Val Ser Ser Ser Leu Ser Asp Thr Asp Leu Thr Gly Ala
        515                 520                 525

Ala Asn Thr Ala Thr Gly Lys Asp Val Ala Met Val Phe Ile Thr Ala
    530                 535                 540

Asp Ser Gly Glu Gly Tyr Leu Thr Val Glu Gly Asn Ala Gly Asp Arg
545                 550                 555                 560

Asn Asp Leu Gln Ala Trp His Gly Gly Asp Ala Leu Val Gln Gln Val
                565                 570                 575

Ala Ser His Asn Lys Asn Thr Ile Val Val Ile Asn Ser Val Gly Pro
            580                 585                 590

Ile Asn Met Glu Ala Trp Val Asn His Pro Asn Val Thr Ala Ile Val
        595                 600                 605

Trp Ser Gly Leu Pro Gly Gln Glu Ala Gly Asn Ala Val Thr Asp Val
    610                 615                 620

Leu Phe Gly Ala Val Asn Pro Gly Gly Lys Leu Pro Phe Thr Ile Gly
625                 630                 635                 640

Lys Ser Ile Ser Asp Tyr Ser Ala Gln Ile Ile Thr Thr Gly Ser Gly
                645                 650                 655

Ile Val Pro Ile Pro Tyr Asn Glu Gly Leu Phe Ile Asp Tyr Arg His
            660                 665                 670

Phe Asp Gln Ala Gly Ile Ala Pro Arg Phe Glu Phe Gly Phe Gly Leu
        675                 680                 685

Ser Tyr Thr Thr Phe Asp Tyr Ser Asn Leu Val Ile Thr Gly Ser Thr
    690                 695                 700

Ala Gly Gly Thr Arg Gln Pro Gly Pro Gly Ser Ser Leu Asp Pro
705                 710                 715                 720

Trp Leu His Asp Ser Val Val Thr Val Ser Phe Thr Leu Thr Asn Asn
                725                 730                 735

Gly Thr Val Asp Gly Thr Glu Val Pro Gln Leu Tyr Leu Ser Pro Pro

```
                    740                 745                 750
Ala Ser Ala Lys Ser Ala Pro Gln Asn Leu Lys Gly Phe Asp Ser Val
                755                 760                 765

Phe Leu Pro Ala Gly Ala Ser Thr Val Ser Phe Glu Leu Ser Arg
        770                 775                 780

Tyr Ser Phe Ser Val Trp Asp Val Val Ser Gln Ser Trp Gln Ile Pro
785                 790                 795                 800

Ala Gly Val Thr Gly Ile Ser Val Gly Ala Ser Ser Arg Asp Leu Arg
                805                 810                 815

Leu Lys Gly Ser Ile Thr Asn
            820

<210> SEQ ID NO 58
<211> LENGTH: 733
<212> TYPE: PRT
<213> ORGANISM: Sporotrichum Thermophile

<400> SEQUENCE: 58

Met Thr Leu Gln Ala Phe Ala Leu Leu Ala Ala Ala Leu Val Arg
1               5                  10                  15

Gly Glu Thr Pro Thr Lys Val Pro Arg Asp Ala Pro Arg Gly Ala Ala
                20                  25                  30

Ala Trp Glu Ala Ala His Ser Ser Ala Ala Ala Leu Gly Lys Leu
        35                  40                  45

Ser Gln Gln Asp Lys Ile Asn Ile Val Thr Gly Val Gly Trp Asn Lys
    50                  55                  60

Gly Pro Cys Val Gly Asn Thr Pro Ala Ile Ser Ser Ile Asn Tyr Pro
65                  70                  75                  80

Gln Leu Cys Leu Gln Asp Gly Pro Leu Gly Val Arg Phe Gly Ser Ser
                85                  90                  95

Ile Thr Ala Phe Thr Pro Gly Ile Gln Ala Ala Ser Thr Trp Asp Val
                100                 105                 110

Asp Leu Ile Arg Gln Arg Gly Glu Tyr Met Gly Ala Glu Phe Lys Gly
            115                 120                 125

Cys Gly Ile His Val Gln Leu Gly Pro Val Ala Gly Pro Leu Gly Lys
        130                 135                 140

Val Pro Gln Gly Gly Arg Asn Trp Glu Gly Phe Gly Val Asp Pro Tyr
145                 150                 155                 160

Leu Thr Gly Ile Ala Met Ala Glu Thr Ile Glu Gly Ile Gln Ser Ala
                165                 170                 175

Gly Val Gln Ala Thr Ala Lys His Tyr Ile Leu Asn Glu Gln Glu Leu
            180                 185                 190

Asn Arg Glu Thr Met Ser Ser Asn Val Asp Asp Arg Thr Leu His Glu
        195                 200                 205

Leu Tyr Leu Trp Pro Phe Ala Asp Ala Val His Ser Asn Val Ala Ser
    210                 215                 220

Val Met Cys Ser Tyr Asn Lys Ile Asn Gly Thr Trp Ala Cys Glu Asn
225                 230                 235                 240

Asp Arg Val Leu Asn Val Ile Leu Lys Gln Glu Leu Gly Phe Pro Gly
                245                 250                 255

Tyr Val Met Ser Asp Trp Asn Ala Gln His Ser Thr Asp Asp Ala Ala
            260                 265                 270

Asn His Gly Met Asp Met Thr Met Pro Gly Ser Asp Phe Asn Gly Gly
        275                 280                 285
```

```
Thr Ile Leu Trp Gly Pro Gln Leu Asp Ser Ala Val Asn Ser Gly Arg
    290                 295                 300

Val Pro Lys Ser Arg Leu Asp Asp Met Val Glu Arg Ile Leu Ala Ala
305                 310                 315                 320

Trp Tyr Leu Leu Gly Gln Asp Ser Asn Tyr Pro Ala Ile Asn Ile Gly
                325                 330                 335

Ala Asn Val Gln Gly Asn His Lys Glu Asn Val Arg Ala Val Ala Arg
                340                 345                 350

Asp Gly Ile Val Leu Leu Lys Asn Asp Asp Gly Ile Leu Pro Leu Lys
                355                 360                 365

Lys Pro Ala Lys Leu Ala Leu Ile Gly Ser Ala Ala Val Val Asn Pro
370                 375                 380

Gln Gly Leu Asn Ser Cys Gln Asp Gln Gly Cys Asn Lys Gly Ala Leu
385                 390                 395                 400

Gly Met Gly Trp Gly Ser Gly Ala Val Asn Tyr Pro Tyr Phe Val Ala
                405                 410                 415

Pro Tyr Asp Ala Leu Lys Ala Arg Ala Gln Glu Asp Gly Thr Thr Val
                420                 425                 430

Ser Leu His Asn Ser Asp Ser Thr Ser Gly Val Ala Asn Val Ala Ser
                435                 440                 445

Asp Ala Asp Ala Ala Ile Val Ile Thr Ala Asp Ser Gly Glu Gly
    450                 455                 460

Tyr Ile Thr Val Glu Gly Ala Ala Gly Asp Arg Leu Asn Leu Asp Pro
465                 470                 475                 480

Trp His Asn Gly Asn Glu Leu Val Lys Ala Val Ala Ala Asn Lys
                485                 490                 495

Asn Thr Ile Val Val His Ser Val Gly Pro Ile Ile Leu Glu Thr
                500                 505                 510

Ile Leu Ala Thr Glu Gly Val Lys Ala Ile Val Trp Ala Gly Leu Pro
        515                 520                 525

Ser Gln Glu Asn Gly Asn Ala Leu Val Asp Ile Leu Tyr Gly Leu Ala
    530                 535                 540

Ser Pro Ser Gly Lys Leu Val Tyr Thr Ile Ala Lys Arg Glu Gln Asp
545                 550                 555                 560

Tyr Gly Thr Ala Val Val Arg Gly Asp Asp Thr Phe Pro Glu Gly Leu
                565                 570                 575

Phe Val Asp Tyr Arg His Phe Asp Lys Glu Asn Ile Glu Pro Arg Tyr
                580                 585                 590

Glu Phe Gly Phe Gly Leu Ser Tyr Thr Asn Phe Thr Tyr Ala Asp Leu
                595                 600                 605

Glu Leu Thr Ser Thr Ala Thr Ala Gly Pro Ala Thr Gly Glu Thr Ile
    610                 615                 620

Pro Gly Gly Ala Ala Asp Leu Trp Glu Glu Val Ala Thr Val Thr Ala
625                 630                 635                 640

Thr Ile Thr Asn Ser Gly Gly Val Asp Gly Ala Glu Val Ala Gln Leu
                645                 650                 655

Tyr Leu Thr Leu Pro Ser Ser Ala Pro Ala Thr Pro Lys Gln Leu
    660                 665                 670

Arg Gly Phe Ala Lys Leu Lys Leu Ala Ala Gly Ala Ser Gly Thr Ala
                675                 680                 685

Thr Phe Ser Leu Arg Arg Arg Asp Leu Ser Tyr Trp Asp Thr Gly Arg
    690                 695                 700

Gly Gln Trp Val Val Pro Glu Gly Glu Phe Gly Val Ser Val Gly Ala
```

```
                705                 710                 715                 720
Ser Ser Arg Asp Ile Arg Leu Thr Gly Ser Phe Arg Val
                    725                 730

<210> SEQ ID NO 59
<211> LENGTH: 744
<212> TYPE: PRT
<213> ORGANISM: Trichoderma Reesei

<400> SEQUENCE: 59

Met Arg Tyr Arg Thr Ala Ala Leu Ala Leu Ala Thr Gly Pro Phe
 1               5                  10                  15

Ala Arg Ala Asp Ser His Ser Thr Ser Gly Ala Ser Ala Glu Ala Val
                20                  25                  30

Val Pro Pro Ala Gly Thr Pro Trp Gly Thr Ala Tyr Asp Lys Ala Lys
                35                  40                  45

Ala Ala Leu Ala Lys Leu Asn Leu Gln Asp Lys Val Gly Ile Val Ser
                50                  55                  60

Gly Val Gly Trp Asn Gly Gly Pro Cys Val Gly Asn Thr Ser Pro Ala
65                  70                  75                  80

Ser Lys Ile Ser Tyr Pro Ser Leu Cys Leu Gln Asp Gly Pro Leu Gly
                85                  90                  95

Val Arg Tyr Ser Thr Gly Ser Thr Ala Phe Thr Pro Gly Val Gln Ala
                100                 105                 110

Ala Ser Thr Trp Asp Val Asn Leu Ile Arg Glu Arg Gly Gln Phe Ile
                115                 120                 125

Gly Glu Glu Val Lys Ala Ser Gly Ile His Val Ile Leu Gly Pro Val
                130                 135                 140

Ala Gly Pro Leu Gly Lys Thr Pro Gln Gly Gly Arg Asn Trp Glu Gly
145                 150                 155                 160

Phe Gly Val Asp Pro Tyr Leu Thr Gly Ile Ala Met Gly Gln Thr Ile
                165                 170                 175

Asn Gly Ile Gln Ser Val Gly Val Gln Ala Thr Ala Lys His Tyr Ile
                180                 185                 190

Leu Asn Glu Gln Glu Leu Asn Arg Glu Thr Ile Ser Ser Asn Pro Asp
                195                 200                 205

Asp Arg Thr Leu His Glu Leu Tyr Thr Trp Pro Phe Ala Asp Ala Val
                210                 215                 220

Gln Ala Asn Val Ala Ser Val Met Cys Ser Tyr Asn Lys Val Asn Thr
225                 230                 235                 240

Thr Trp Ala Cys Glu Asp Gln Tyr Thr Leu Gln Thr Val Leu Lys Asp
                245                 250                 255

Gln Leu Gly Phe Pro Gly Tyr Val Met Thr Asp Trp Asp Ala Gln His
                260                 265                 270

Thr Thr Val Gln Ser Ala Asn Ser Gly Leu Asp Met Ser Met Pro Gly
                275                 280                 285

Thr Asp Phe Asn Gly Asn Asn Arg Leu Trp Gly Pro Ala Leu Thr Asn
                290                 295                 300

Ala Val Asn Ser Asn Gln Val Pro Thr Ser Arg Val Asp Asp Met Val
305                 310                 315                 320

Thr Arg Ile Leu Ala Ala Trp Tyr Leu Thr Gly Gln Asp Gln Ala Gly
                325                 330                 335

Tyr Pro Ser Phe Asn Ile Ser Arg Asn Val Gln Gly Asn His Lys Thr
                340                 345                 350
```

```
Asn Val Arg Ala Ile Ala Arg Asp Gly Ile Val Leu Lys Asn Asp
        355                 360                 365

Ala Asn Ile Leu Pro Leu Lys Lys Pro Ala Ser Ile Ala Val Val Gly
370                 375                 380

Ser Ala Ala Ile Ile Gly Asn His Ala Arg Asn Ser Pro Ser Cys Asn
385                 390                 395                 400

Asp Lys Gly Cys Asp Asp Gly Ala Leu Gly Met Gly Trp Gly Ser Gly
                405                 410                 415

Ala Val Asn Tyr Pro Tyr Phe Val Ala Pro Tyr Asp Ala Ile Asn Thr
                420                 425                 430

Arg Ala Ser Ser Gln Gly Thr Gln Val Thr Leu Ser Asn Thr Asp Asn
            435                 440                 445

Thr Ser Ser Gly Ala Ser Ala Ala Arg Gly Lys Asp Val Ala Ile Val
    450                 455                 460

Phe Ile Thr Ala Asp Ser Gly Glu Gly Tyr Ile Thr Val Glu Gly Asn
465                 470                 475                 480

Ala Gly Asp Arg Asn Asn Leu Asp Pro Trp His Asn Gly Asn Ala Leu
                485                 490                 495

Val Gln Ala Val Ala Gly Ala Asn Ser Asn Val Ile Val Val His
            500                 505                 510

Ser Val Gly Ala Ile Ile Leu Glu Gln Ile Leu Ala Leu Pro Gln Val
    515                 520                 525

Lys Ala Val Val Trp Ala Gly Leu Pro Ser Gln Glu Ser Gly Asn Ala
530                 535                 540

Leu Val Asp Val Leu Trp Gly Asp Val Ser Pro Ser Gly Lys Leu Val
545                 550                 555                 560

Tyr Thr Ile Ala Lys Ser Pro Asn Asp Tyr Asn Thr Arg Ile Val Ser
                565                 570                 575

Gly Gly Ser Asp Ser Phe Ser Glu Gly Leu Phe Ile Asp Tyr Lys His
            580                 585                 590

Phe Asp Asp Ala Asn Ile Thr Pro Arg Tyr Glu Phe Gly Tyr Gly Leu
    595                 600                 605

Ser Tyr Thr Lys Phe Asn Tyr Ser Arg Leu Ser Val Leu Ser Thr Ala
610                 615                 620

Lys Ser Gly Pro Ala Thr Gly Ala Val Val Pro Gly Gly Pro Ser Asp
625                 630                 635                 640

Leu Phe Gln Asn Val Ala Thr Val Thr Val Asp Ile Ala Asn Ser Gly
                645                 650                 655

Gln Val Thr Gly Ala Glu Val Ala Gln Leu Tyr Ile Thr Tyr Pro Ser
            660                 665                 670

Ser Ala Pro Arg Thr Pro Pro Lys Gln Leu Arg Gly Phe Ala Lys Leu
    675                 680                 685

Asn Leu Thr Pro Gly Gln Ser Gly Thr Ala Thr Phe Asn Ile Arg Arg
690                 695                 700

Arg Asp Leu Ser Tyr Trp Asp Thr Ala Ser Gln Lys Trp Val Val Pro
705                 710                 715                 720

Ser Gly Ser Phe Gly Ile Ser Val Gly Ala Ser Ser Arg Asp Ile Arg
                725                 730                 735

Leu Thr Ser Thr Leu Ser Val Ala
            740
```

<210> SEQ ID NO 60
<211> LENGTH: 813
<212> TYPE: PRT

<213> ORGANISM: Gibberella Zeae

<400> SEQUENCE: 60

```
Met Ala Ser Leu Arg Ser Val Leu Val Ser Gly Leu Leu Ala Thr Gly
1               5                   10                  15

Val Ser Ala Gln Asn Phe Gly Gly Ser Ala Arg Asp Glu Glu Ala Phe
            20                  25                  30

Ser Trp Val Gln Pro Lys Asn Thr Thr Ile Leu Gly Gln Tyr Gly His
        35                  40                  45

Ser Pro His Tyr Asn Ser Thr Tyr Ala Thr Gly Lys Gly Trp Glu Glu
    50                  55                  60

Gly Phe Ala Lys Ala Lys Glu Phe Leu Ala Lys Leu Thr Leu Glu Glu
65                  70                  75                  80

Lys Ala Asp Met Val Thr Gly Thr Pro Gly Pro Cys Val Gly Asn Ile
                85                  90                  95

Ile Ala Ile Pro Arg Leu Gly Phe Lys Gly Leu Cys Leu His Asp Gly
            100                 105                 110

Pro Leu Ala Ile Arg Val Ala Asp Tyr Ala Ser Val Phe Ser Ala Gly
        115                 120                 125

Val Ser Ala Ala Ser Ser Trp Asp Lys Asp Leu Leu Tyr Gln Arg Gly
    130                 135                 140

Leu Ala Leu Gly Gln Glu Phe Lys Ala Lys Gly Ala His Ile Leu Leu
145                 150                 155                 160

Gly Pro Val Ala Gly Pro Leu Gly Arg Ser Ala Tyr Ser Gly Arg Asn
                165                 170                 175

Trp Glu Gly Phe Ser Pro Asp Pro Tyr Leu Thr Gly Val Ala Met Glu
            180                 185                 190

His Thr Ile Asn Gly His Gln Asp Ala Gly Val Gln Ala Thr Ala Lys
        195                 200                 205

His Phe Ile Gly Asn Glu Gln Glu Val Met Arg Asn Pro Thr Phe Lys
    210                 215                 220

Lys Asp Gly Tyr Val Gly Glu Val Asp Glu Glu Ala Leu Ser Ser Asn
225                 230                 235                 240

Met Asp Asp Arg Thr Met His Glu Leu Tyr Leu Trp Pro Phe Ala Asn
                245                 250                 255

Ala Ala His Ala Lys Ala Ser Ser Phe Met Cys Ala Tyr Gln Arg Leu
            260                 265                 270

Asn Gly Ser Tyr Ser Cys Gln Asn Ser Lys Leu Leu Asn Gly Ile Leu
        275                 280                 285

Arg Asp Glu Leu Gly Phe Gln Gly Tyr Val Met Ser Asp Trp Gly Gly
    290                 295                 300

Thr His Ala Gly Val Ala Thr Ile Glu Ser Gly Leu Asp Met Asp Met
305                 310                 315                 320

Pro Gly Gly Ile Gly Ala Tyr Gly Met Asp Phe Lys Ala Gly Ser Phe
                325                 330                 335

Phe Gly Gly Asn Leu Thr Arg Ala Val Thr Asn Gly Thr Leu Glu Glu
            340                 345                 350

Ala Arg Val Asp Asp Met Ile Met Arg Ile Met Thr Pro Tyr Phe Trp
        355                 360                 365

Leu Gly Gln Asp Lys Glu Asp Tyr Pro Ser Val Asp Glu Ser Ser Ala
    370                 375                 380

Asp Leu Asn Thr Phe Ser Pro Arg Lys Thr Trp Leu Lys Glu Phe Asn
385                 390                 395                 400
```

```
Phe Thr Gly Thr Arg Ser Arg Asp Val Arg Gly Asp His Gly Ala Leu
                405                 410                 415
Ile Arg Lys His Gly Ala Glu Ser Thr Val Leu Leu Lys Asn Glu Asn
            420                 425                 430
Asn Ala Leu Pro Leu Lys Lys Pro Lys Ser Ile Ala Val Phe Gly Asn
        435                 440                 445
Asp Ala Gly Asp Ile Thr Glu Gly Phe Tyr Asn Gln Gln Asp Phe Glu
    450                 455                 460
Phe Gly Asn Leu Val Val Gly Gly Gly Ser Gly Thr Gly Arg Leu Thr
465                 470                 475                 480
Tyr Leu Val Ser Pro Leu Thr Ala Ile Asn Ala Arg Ala Lys Gln Asp
                485                 490                 495
Gly Thr Leu Val Gln Gln Trp Met Asn Asn Thr Leu Ile Thr Thr Ser
            500                 505                 510
Asn Val Thr Asp Leu Trp Ile Pro Ala Leu Pro Asp Val Cys Leu Val
        515                 520                 525
Phe Leu Lys Thr Trp Ala Thr Glu Gly Ala Asp Arg Gly His Leu Ser
    530                 535                 540
Val Asp Trp Asn Gly Asp Glu Val Val Leu Ser Val Ala Lys Ser Cys
545                 550                 555                 560
Asn Asn Thr Val Val Val Thr His Ser Ser Gly Ile Asn Thr Leu Pro
                565                 570                 575
Trp Ala Asp His Pro Asn Val Thr Ala Ile Leu Ala Ala His Tyr Pro
            580                 585                 590
Gly Glu Glu Ser Gly Asn Ser Leu Val Asp Leu Leu Tyr Gly Asp Val
        595                 600                 605
Asn Pro Ser Gly Arg Leu Pro Tyr Thr Ile Ala Leu Asn Gly Thr Asp
    610                 615                 620
Tyr Asn Ala Pro Pro Thr Thr Ala Ile Asn Thr Thr Gly Thr Asp Asp
625                 630                 635                 640
Trp Gln Ser Trp Phe Asp Glu Lys Leu Glu Ile Asp Tyr Arg Tyr Phe
                645                 650                 655
Asp Ala Gln Asn Met Ser Val Arg Tyr Glu Phe Gly Phe Gly Leu Ser
            660                 665                 670
Tyr Ser Thr Phe Glu Ile Ser Asp Ile Ser Ala Glu Pro Leu Ala Asp
        675                 680                 685
Asp Ile Thr Ala Met Pro Glu Ala Leu Pro Val Gln Pro Gly Gly Asn
    690                 695                 700
Pro Ala Leu Trp Glu Ser Ile Tyr Asn Val Thr Val Ser Val Ala Asn
705                 710                 715                 720
Ser Gly Lys Val Asp Gly Ala Thr Val Pro Gln Leu Tyr Val Ser Phe
                725                 730                 735
Pro Glu Ser Ala Pro Lys Gly Thr Pro Pro Lys Gln Leu Arg Gly Phe
            740                 745                 750
Glu Lys Val Phe Leu Glu Ala Gly Glu Ser Lys Ser Val Ser Phe Glu
        755                 760                 765
Leu Met Arg Arg Asp Leu Ser Tyr Trp Asp Ile Ile Ser Gln Gln Trp
    770                 775                 780
Val Ile Pro Glu Gly Glu Phe Thr Ile Arg Val Gly Phe Ser Ser Arg
785                 790                 795                 800
Asn Leu Lys Glu Glu Thr Lys Val Thr Leu Val Lys Ala
                805                 810
```

```
<210> SEQ ID NO 61
<211> LENGTH: 833
<212> TYPE: PRT
<213> ORGANISM: Sclerotinia Sclerot

```
Pro Ala Ser Leu Ala Ile Ile Gly Gln Asp Ala Ile Val Asn Pro Ala
385                 390                 395                 400

Gly Ala Asn Ser Cys Thr Asp Arg Gly Cys Asp Thr Gly Thr Leu Ala
            405                 410                 415

Met Gly Trp Gly Ser Gly Thr Ala Asp Phe Pro Tyr Leu Val Ala Pro
        420                 425                 430

Tyr Asp Ala Ile Lys Ala Arg Ala Ala Asp Gly Thr Thr Val Thr
    435                 440                 445

Leu Ser Asn Thr Asp Ser Thr Ser Thr Gly Ala Ser Val Ala Ser Ala
    450                 455                 460

Ala Ala Thr Ala Ile Val Phe Ile Asn Ser Asp Ser Gly Glu Glu Tyr
465                 470                 475                 480

Ile Thr Val Glu Gly Ala Ala Gly Asp Arg Ile Asn Leu Asp Pro Trp
                485                 490                 495

His Asn Gly Asn Ser Leu Val Ser Ala Ile Ala Ala Val Asn Lys Asn
            500                 505                 510

Thr Ile Val Val Ile His Ser Val Gly Pro Leu Ile Leu Glu Ser Ile
    515                 520                 525

Leu Ala Leu Pro Asn Val Ile Ala Ile Ile Trp Ala Gly Leu Pro Gly
530                 535                 540

Gln Glu Ser Gly Asn Ala Leu Val Asp Ile Leu Tyr Gly Ser Val Ser
545                 550                 555                 560

Pro Ser Gly Lys Leu Pro Phe Thr Ile Ala Lys Thr Gln Ser Asp Tyr
                565                 570                 575

Gly Thr Ala Ile Ala Asn Gly Asp Asp Asn Tyr Ser Glu Gly Leu Phe
            580                 585                 590

Ile Asp Tyr Arg His Phe Asp Gln Ala Gly Leu Thr Pro Arg Tyr Glu
        595                 600                 605

Phe Gly Tyr Gly Leu Ser Tyr Ser Ser Phe Ser Tyr Ser Asn Leu Ile
        610                 615                 620

Leu Ser Ser Ile Ser Ser Ser Thr Gly Asn Asn Ala Leu Leu Pro
625                 630                 635                 640

Gly Gly Lys Ser Asn Leu Phe Asp Ile Ile Ala Thr Val Ser Ile Thr
            645                 650                 655

Leu Ser Asn Ser Gly Ser Val Pro Ala Ala Glu Ile Ala Gln Leu Tyr
            660                 665                 670

Ile Gly Phe Pro Asp Ser Val Pro Gly Thr Pro Leu Arg Gln Leu Arg
        675                 680                 685

Gly Phe Lys Lys Ile Ser Leu Glu Ala Gly Ala Lys Ser Ser Leu Met
        690                 695                 700

Phe Glu Leu Arg Arg Lys Asp Leu Ser Tyr Trp Asp Ala Gly Ser Gln
705                 710                 715                 720

Met Trp Val Leu Pro Val Gly Tyr Phe Gly Val Trp Val Gly Ala Ser
                725                 730                 735

Ser Arg Asp Leu Arg Leu Glu Gly Val Leu Ser Ala Ser Ser Gly Ser
            740                 745                 750

Ser Ser Ile Ser Ser Pro Thr Thr Ser Val Ser Ser Thr Ser Lys
    755                 760                 765

Thr Thr Thr Thr Pro Thr Thr Pro Gln Pro Ser Thr Ser Ser Ser Ser
    770                 775                 780

Thr Thr Thr Thr Thr Ser Pro Thr Thr Pro Thr Gly Pro Thr Gln Thr
785                 790                 795                 800

Leu Tyr Gly Gln Cys Gly Gly Ile Gly Tyr Thr Gly Pro Thr Ile Cys
```

-continued

```
                805                 810                 815
Ala Ser Gly Ser Cys Lys Phe Thr Asn Thr Tyr Tyr Ser Gln Cys Leu
                820                 825                 830
Pro

<210> SEQ ID NO 62
<211> LENGTH: 821
<212> TYPE: PRT
<213> ORGANISM: Botryotinia Fuckeliana

<400> SEQUENCE: 62

Met Tyr Phe Ser Ser Phe Val Leu Leu Ala Leu Ser Thr Pro Ile His
 1               5                  10                  15

Ala Ala Ala Gly Asp Gly Asp Trp Asn Ala Ala Tyr Thr Lys Ala Lys
                20                  25                  30

Thr Thr Leu Ala Lys Leu Thr Asn Ala Asn Lys Val Thr Leu Val Thr
         35                  40                  45

Gly Val Gly Trp Glu Lys Gly Pro Cys Val Gly Asn Thr Ala Ala Ile
 50                  55                  60

Pro Ser Ile Gly Trp Pro Ala Phe Cys Leu Gln Asp Gly Pro Leu Gly
65                   70                  75                  80

Val Arg Tyr Ala Gln Lys Val Thr Ala Phe Pro Ala Gly Ile Thr Thr
                85                  90                  95

Gly Ser Thr Trp Asp Thr Glu Leu Met Tyr Ala Arg Gly Asn Ala Leu
            100                 105                 110

Gly Ala Glu Ala Lys Ala Leu Gly Val His Asn Gln Leu Gly Pro Val
        115                 120                 125

Ala Gly Pro Leu Gly Lys Ile Pro Val Ala Gly Arg Asn Trp Glu Gly
    130                 135                 140

Phe Ser Asn Asp Pro Tyr Leu Ser Gly Val Ala Met Ala Asn Thr Val
145                 150                 155                 160

Glu Gly Met Gln Ala Ala Gly Val Gln Ala Cys Ala Lys His Tyr Leu
                165                 170                 175

Gly Asn Glu Gln Glu Phe Asn Arg Gly Thr Met Ser Ser Asn Ile Val
            180                 185                 190

Asp Arg Val Asn His Glu Leu Tyr Leu Trp Pro Phe Ala Glu Ala Val
        195                 200                 205

Lys Ala Asn Val Ala Ser Val Met Cys Ser Tyr Asn Arg Phe Asn Ser
    210                 215                 220

Thr Tyr Ala Cys Glu Asn Gln Ala Leu Leu Thr Gly Leu Leu Lys Asn
225                 230                 235                 240

Glu Leu Asp Phe Gln Gly Tyr Val Val Ser Asp Trp Ala Ala Gln Lys
                245                 250                 255

Thr Thr Thr Gly Ser Ala Asn Ala Gly Met Asp Met Ala Met Pro Gly
            260                 265                 270

Asp Asn Phe Gly Asp Asn Asn Phe Ile Trp Gly Thr Asn Leu Leu Asn
        275                 280                 285

Ala Val Thr Ala Gly Thr Val Pro Gln Thr Arg Leu Asp Asp Met Ala
    290                 295                 300

Thr Arg Ile Leu Ala Ala Trp Tyr Phe Leu Gly Gln Asp Thr Asn Tyr
305                 310                 315                 320

Pro Ala Val Thr Gly Trp Thr Ser Trp Asn Gly Gly Val Gly Gly Pro
                325                 330                 335

Asn Val Ser Ser Thr His Asn Thr Val Ala Arg Ala Ile Ala Arg Asp
```

```
                340                 345                 350
Gly Ile Val Leu Leu Lys Asn Thr Asn Asn Ala Leu Pro Leu Lys Lys
                355                 360                 365

Pro Val Ser Leu Ala Leu Ile Gly Gln Asp Ala Ile Val Asn Pro Ala
            370                 375                 380

Gly Ala Asn Ala Cys Thr Asp Arg Gly Cys Asp Val Gly Thr Leu Ala
385                 390                 395                 400

Met Gly Trp Gly Ser Gly Thr Ala Asp Phe Pro Tyr Leu Val Ala Pro
                405                 410                 415

Tyr Asp Ala Leu Lys Val Lys Ala Ala Ala Asp Gly Thr Thr Leu Thr
            420                 425                 430

Leu Ser Asn Thr Asp Ser Thr Ser Thr Gly Ala Ser Val Ala Ser Ala
            435                 440                 445

Ala Ala Thr Ala Ile Val Phe Ile Asn Ser Asp Ala Gly Glu Glu Tyr
450                 455                 460

Ile Thr Val Glu Gly Ala Lys Gly Asp Arg Ile Asn Leu Asp Pro Trp
465                 470                 475                 480

His Ser Gly Asn Ala Leu Val Ala Ala Val Ala Val Asn Lys Asn
                485                 490                 495

Thr Ile Val Val Ile His Ser Val Gly Pro Leu Ile Leu Glu Ser Ile
                500                 505                 510

Leu Ala Leu Pro Asn Val Ile Ala Ile Val Trp Ala Gly Leu Pro Gly
            515                 520                 525

Gln Glu Ser Gly Asn Ala Leu Val Asp Ile Leu Tyr Gly Ser Val Ser
            530                 535                 540

Pro Ser Gly Lys Leu Pro Tyr Thr Ile Ala Lys Thr Gln Ala Asp Tyr
545                 550                 555                 560

Gly Thr Ala Ile Ala Ser Gly Asp Asp Ser Tyr Ala Glu Gly Leu Phe
                565                 570                 575

Ile Asp Tyr Arg His Phe Asp Gln Ser Ser Ile Val Pro Arg Tyr Glu
            580                 585                 590

Phe Gly Phe Gly Leu Ser Tyr Thr Thr Phe Ser Tyr Ser Asn Leu Val
            595                 600                 605

Leu Ser Ser Ile Ser Thr Thr Pro Gly Asn Ser Gly Ile Leu Pro Gly
            610                 615                 620

Gly Lys Ala Asn Leu Tyr Asp Ser Ile Ala Thr Val Ser Val Ser Val
625                 630                 635                 640

Thr Asn Asn Gly Thr Ile Pro Gly Ala Glu Val Ala Gln Leu Tyr Ile
                645                 650                 655

Gly Phe Pro Asn Ser Ile Pro Asn Thr Pro Lys Gln Leu Arg Gly
                660                 665                 670

Phe Lys Lys Ile Asn Leu Ala Ala Gly Val Ala Asn Ser Ile Thr Phe
            675                 680                 685

Ser Leu Arg Arg Lys Asp Leu Ser Tyr Trp Asp Thr Thr Thr Gln Ser
            690                 695                 700

Trp Ile Leu Pro Ser Gly Thr Phe Asn Val Tyr Val Gly Ser Ser Ser
705                 710                 715                 720

Arg Asp Ile Arg Leu Ser Gly Thr Phe Leu Ser Ser Gly Ala Gly Ser
                725                 730                 735

Gly Ser Pro Ser Ser Thr Ser Ser Ser Ile Ser Ser Ser Thr Met
            740                 745                 750

Thr Ser Leu Ser Ser Thr Ser Leu Thr Thr Ser Thr Ser Val Pro Thr
            755                 760                 765
```

```
Leu Thr Thr Lys Thr Ser Thr Thr Ser Ile Ala Ser Thr Thr Thr Ser
        770                 775                 780

Ala Thr Gly Ala Leu Gln Thr Leu Tyr Gly Gln Cys Gly Gly Asn Gly
785                 790                 795                 800

Tyr Thr Gly Pro Thr Val Cys Ala Ser Gly Ser Cys Lys Val Ser Asn
                805                 810                 815

Ala Tyr Tyr Ser Glu
                820

<210> SEQ ID NO 63
<211> LENGTH: 736
<212> TYPE: PRT
<213> ORGANISM: Penicillium Chrysogenum

<400> SEQUENCE: 63

Met Gln Asn Leu Leu Val Ser Ala Leu Ala Leu Ser Ala Ala Ala Asp
  1               5                  10                  15

Ala Tyr Gly Ala Gly Ala Gly Trp Asp Ala Ala Tyr Ser Lys Ala
                 20                  25                  30

Gln Ala Ala Leu Leu Lys Leu Asn Gln Thr Glu Lys Val Gly Ile Ala
             35                  40                  45

Thr Gly Val Gly Trp Glu Gly Gly Pro Cys Val Gly Asn Thr Tyr Ala
         50                  55                  60

Pro Ser Ser Ile Asp Tyr Pro Ser Leu Cys Leu Gln Asp Ser Pro Leu
 65                  70                  75                  80

Gly Ile Arg Tyr Ala Asn Pro Val Thr Ala Phe Pro Ala Gly Ile Asn
                 85                  90                  95

Ala Gly Ala Thr Trp Asp Arg Ser Leu Leu Tyr Ala Arg Gly Ala Ala
            100                 105                 110

Met Gly Gln Glu Ala Lys Gly Leu Gly Val His Val Gln Leu Gly Pro
        115                 120                 125

Ser Ala Gly Pro Leu Gly Lys Asn Pro Asp Gly Gly Arg Asn Trp Glu
    130                 135                 140

Gly Phe Ser Val Asp Pro Tyr Leu Ala Gly Val Gly Met Glu Glu Thr
145                 150                 155                 160

Ile Gln Gly Met Gln Asp Ser Gly Val Gln Ala Cys Ala Lys His Trp
                165                 170                 175

Leu Gly Asn Glu Gln Glu His Asn Arg Glu Thr Met Ser Ser Asn Ile
            180                 185                 190

Gly Asp Arg Ala Thr His Glu Leu Tyr Leu Trp Pro Phe Met Asn Ala
        195                 200                 205

Val Lys Ala Asn Val Ala Ser Val Met Cys Ser Tyr Asn Lys Leu Asn
    210                 215                 220

Gly Thr Trp Ala Cys Glu Ser Asp Ala Val Leu Asn Asp Leu Leu Lys
225                 230                 235                 240

Asp Glu Leu Gly Phe Pro Gly Tyr Val Met Ser Asp Trp Asn Ala Gln
                245                 250                 255

His Thr Gly Val Asn Ser Ala Leu Ala Gly Leu Asp Met Thr Met Pro
            260                 265                 270

Gly Ser Asp Phe Asn Lys Pro Gly Ser Ile Phe Trp Gly Pro Asn
        275                 280                 285

Leu Val Glu Ala Val Thr Asn Gly Ser Val Pro Gln Ser Arg Leu Asp
    290                 295                 300

Asp Met Ala Thr Arg Ile Leu Ala Ser Trp Tyr Leu Leu Gly Gln Asp
```

```
            305                 310                 315                 320
        Gln Gly Tyr Pro Glu Val Thr Phe Ser Ser Trp Asn Gly Gly Lys Ala
                        325                 330                 335

Thr Val Asp Val Thr Ala Asp His Ala Ser Val Arg Thr Val Ala
                        340                 345                 350

Arg Asp Ser Ile Val Leu Leu Lys Asn Gln Glu His Ala Leu Pro Leu
                        355                 360                 365

Arg Lys Pro Lys Ser Leu Ala Ile Ile Gly Gln Asp Ala Ile Val Asn
                    370                 375                 380

Pro Asp Gly Pro Asn Ala Cys Val Asp Arg Gly Cys Asn Thr Gly Thr
        385                 390                 395                 400

Leu Ala Met Gly Trp Gly Ser Gly Thr Ala Glu Phe Pro Tyr Leu Ile
                            405                 410                 415

Ala Pro Leu Asp Ala Ile Lys Val Gln Ala Gln Lys Asp Gly Thr Lys
                        420                 425                 430

Ile Val Glu Ser Thr Thr Asp Ser Thr Thr Ala Ala Ala Ser Ala Ala
                    435                 440                 445

Ala Ala Ala Asp Thr Ala Val Val Phe Ile Asn Ala Asp Ala Gly Glu
                    450                 455                 460

Gly Tyr Leu Thr Val Glu Gly Asn Ala Gly Asp Arg Asn Asn Leu Asp
        465                 470                 475                 480

Pro Trp His Asn Gly Asn Glu Leu Val Lys Ser Val Ala Ala Ala Asn
                            485                 490                 495

Lys Asn Val Ile Val Val Val His Ser Val Gly Pro Ile Ile Leu Glu
                        500                 505                 510

Thr Ile Leu Ala Gln Pro Ser Val Lys Ala Ile Val Trp Ala Gly Leu
                    515                 520                 525

Pro Gly Gln Glu Ser Gly Asn Ala Leu Val Asp Val Met Tyr Gly Thr
                    530                 535                 540

Thr Ser Pro Ser Gly Lys Leu Pro Tyr Thr Ile Ala Lys Gln Pro Ser
        545                 550                 555                 560

Asp Tyr Gly Ala Gly Trp Asn Ser Ala Leu Val Asp Asn Phe Val Glu
                            565                 570                 575

Asp Leu Phe Ile Asp Tyr Arg His Phe Asp Lys Asn Gly Ile Ala Pro
                        580                 585                 590

Arg Tyr Glu Phe Gly Tyr Gly Leu Ser Tyr Thr Thr Phe Asn Tyr Ser
                    595                 600                 605

Gly Leu Ala Val Ser Val Ser Ala Thr Ala Gly Pro Ser Asn Gly Pro
                    610                 615                 620

Ile Val Pro Gly Gly Ala Glu Glu Leu Phe Gln Ser Val Gly Thr Ile
        625                 630                 635                 640

Ser Val Ile Val Glu Asn Thr Gly Glu Val Ala Gly Ala Glu Val Ala
                            645                 650                 655

Gln Leu Tyr Leu Gly Leu Pro Asp Ser Val Leu Ser Thr Pro Pro Lys
                        660                 665                 670

Gln Leu Arg Gly Phe Gln Lys Leu Asn Leu Gln Pro Gly Glu Gln Gly
                    675                 680                 685

Thr Ala Thr Phe Glu Leu Thr Arg Arg Asp Leu Ser Tyr Trp Asp Val
                    690                 695                 700

Gln Thr Gln Lys Trp Val Val Pro Ser Gly Thr Phe Thr Val Tyr Val
        705                 710                 715                 720

Gly Ala Ser Ser Arg Asp Ile His Gly Glu Gly Lys Phe Thr Val Ala
                            725                 730                 735
```

<210> SEQ ID NO 64
<211> LENGTH: 776
<212> TYPE: PRT
<213> ORGANISM: Postia Placenta

<400> SEQUENCE: 64

```
Met Tyr Lys Leu Ala Pro Ser Ala Leu Leu Trp Arg Asp Ser Gly Thr
 1               5                  10                  15

Pro Val Leu Gly Gln His Gln Gly Cys Thr Leu Pro Arg Phe Val Met
             20                  25                  30

Leu Leu Ala Gly Asn Ala Trp Ala Glu Ala Tyr Ala Lys Ala Glu Ala
         35                  40                  45

Phe Val Ala Gly Leu Thr Leu Glu Gln Lys Val Asn Val Ser Thr Gly
     50                  55                  60

Val Tyr Trp Glu Gln Gly Leu Cys Val Gly Asn Ile Gly Glu Val Ala
 65                  70                  75                  80

Asp Leu Arg Gly Leu Cys Leu Gln Asp Ser Pro Leu Gly Val Arg Tyr
                 85                  90                  95

Thr Asp Tyr Asn Thr Ala Phe Pro Ala Gly Ile Ser Thr Ala Ala Thr
            100                 105                 110

Phe Asn Arg Thr Met Met Arg Leu Arg Gly Gln Gln Met Gly Glu Glu
        115                 120                 125

Phe Arg Gly Lys Gly Val Asn Val Ala Leu Gly Pro Met Met Asn Met
    130                 135                 140

Gly Arg Val Ala Gln Ala Gly Arg Asn Trp Glu Gly Phe Gly Thr Asp
145                 150                 155                 160

Pro Phe Leu Ser Gly Glu Ala Ala Tyr Glu Thr Thr Leu Gly Leu Gln
                165                 170                 175

Ser Ala Gly Val Gln Ala Cys Ala Lys His Tyr Ile Asp Tyr Glu Gln
            180                 185                 190

Glu Tyr Lys Arg Thr Gln Glu Ser Ser Glu Val Asp Asp Arg Thr Gln
        195                 200                 205

His Glu Ile Tyr Leu Lys Pro Phe Leu Arg Ala Val Met Ala Gly Thr
    210                 215                 220

Ala Ser Val Met Cys Ser Tyr Asn Met Ile Asn Asp Thr Tyr Ser Cys
225                 230                 235                 240

Glu Asn Asp Arg Thr Leu Asn Gln Leu Leu Lys Gly Glu Leu Gly Phe
                245                 250                 255

Arg Gly Tyr Val Met Ser Asp Trp Gly Ala Gln Glu Ser Thr Leu Ser
            260                 265                 270

Ala Met Ala Gly Leu Asp Met Ser Met Pro Gly Asp Ile Thr Leu Gly
        275                 280                 285

Ser Gly Asn Ser Trp Trp Gly Pro Asn Leu Thr Ala Phe Val Glu Asn
    290                 295                 300

Gly Thr Ile Pro Leu Ser Arg Met Asp Asp Met Ala Thr Arg Ile Met
305                 310                 315                 320

Ala Ser Tyr Tyr Leu Leu Gly Gln Asp Gln Asp Tyr Pro Asn Asp Gly
                325                 330                 335

Arg Leu Ile Pro Asn Ala Val Ser Phe Asn Ala Phe Asn Gln Tyr Asp
            340                 345                 350

Gln Val His Asn Leu His Ile Asp Val Gln Ala Asp His Tyr Gln Ile
        355                 360                 365

Val Arg Glu Ile Gly His Ala Gly Ala Val Leu Leu Lys Asn Thr Asn
```

```
                    370                 375                 380
Gly Ala Leu Pro Leu Asn Ala Pro Arg Asn Val Val Leu Ile Gly Ser
385                 390                 395                 400

Asp Ala Gly Asn Gly Ala Met Gly Ala Asn Gly Tyr Thr Asp Arg Gly
                405                 410                 415

Gly Asp Asp Gly Ile Leu Gly Met Gly Trp Gly Ser Gly Thr Asp Asn
            420                 425                 430

Tyr Pro Tyr Leu Ile Ser Pro Met Asp Ala Met Gln Val Arg Ala Arg
        435                 440                 445

Gln Asp Gly Thr Thr Leu Met Asn Trp Tyr Tyr Asp Trp Asp Thr Glu
    450                 455                 460

Gly Ala Ala Thr Ala Ala Ile Gln Phe Glu Ala Ala Ile Val Phe Val
465                 470                 475                 480

Asn Ser Asp Ser Gly Glu Gly Tyr Ile Glu Val Asp Gly Asn Leu Gly
                485                 490                 495

Asp Arg Asn Asn Leu Thr Leu Trp His Asn Ala Asp Asn Leu Ile Thr
            500                 505                 510

Ala Val Ala Ser Gln Asn Asn Thr Ile Val Val Ala His Ser Val
        515                 520                 525

Gly Pro Ser Ile Ile Asp Ser Trp Val Glu Asn Pro Asn Val Thr Ala
    530                 535                 540

Ile Ile Trp Ala Gly Val Ala Gly Gln Glu Ala Gly Asn Ala Ile Val
545                 550                 555                 560

Asp Val Leu Tyr Gly Asp Tyr Asn Pro Ser Gly Arg Leu Pro Tyr Thr
                565                 570                 575

Ile Ala Lys Arg Leu Glu Asp Tyr Gly Val Phe Leu Thr Leu Gly Gly
            580                 585                 590

Asn Gly Ser Thr Ile Leu Ser Val Pro Tyr Thr Glu Gly Leu Phe Tyr
        595                 600                 605

Asp Tyr Arg His Phe Asp Glu Tyr Asn Ile Thr Pro Arg Tyr Glu Phe
    610                 615                 620

Gly Tyr Gly Leu Ser Tyr Thr Thr Phe Glu Tyr Tyr Asn Leu Ala Thr
625                 630                 635                 640

Ser Ile Val Pro Gln Tyr Asp Pro Thr Asp Tyr Ala Leu Glu Ala Ala
                645                 650                 655

Trp Ala Ala Gly Val Pro Thr Pro Gln Gly Glu Gly Ser Ser Val Ala
            660                 665                 670

Leu Trp Leu His Arg Pro Phe Val Gln Val Ser Phe Glu Val Gln Asn
        675                 680                 685

Thr Gly Ala Val Ala Gly Thr Glu Ile Pro Gln Val Tyr Val His Phe
    690                 695                 700

Pro Thr Gly Ile Gly Glu Pro Ser Trp Leu Lys Gly Phe Asp Ala
705                 710                 715                 720

Val Tyr Ile Glu Pro Gly Glu Val Thr Val Thr Val Thr Ile Ser
                725                 730                 735

Arg Tyr Asp Leu Ser Ile Trp Asp Val Val Ala Gln Gly Trp Val Lys
            740                 745                 750

Pro Ala Gly Glu Ile Thr Phe Ser Val Gly Ala Ser Ser Arg Asp Phe
        755                 760                 765

Arg Leu Gln Gly Tyr Ile Pro Ile
    770                 775

<210> SEQ ID NO 65
```

<211> LENGTH: 734
<212> TYPE: PRT
<213> ORGANISM: Schizophyllum Commune

<400> SEQUENCE: 65

```
Met Val Gly Gly Ile Arg Gln Gly Glu Thr Pro Pro Ala Ser Ser Gly
1               5                   10                  15

Ser Leu Leu Tyr Thr Phe His Gln Ala Ser Asp Ala Val Ala Gln Leu
            20                  25                  30

Ser Leu Gln Glu Lys Val Asp Ile Ala Thr Gly Ile Gly Trp Met Asn
        35                  40                  45

Gly Pro Cys Val Gly Asn Thr Pro Ala Val Pro Thr Ile Asp Tyr Pro
    50                  55                  60

Ser Leu Cys Leu Gln Asp Ser Pro Met Gly Val Arg Tyr Ala Ser Glu
65                  70                  75                  80

Val Ser Ala Phe Pro Ala Gly Val Asn Thr Ala Ala Thr Phe Asn Arg
                85                  90                  95

Thr Leu Ile Arg Ala Arg Gly Val Ala Leu Gly Glu Glu Phe Arg Gly
            100                 105                 110

Lys Gly Ile His Val Tyr Leu Gly Pro Asp Met Asn Ile Met Arg Thr
        115                 120                 125

Ala Ala Gly Gly Arg Asn Trp Glu Gly Phe Gly Ala Asp Pro Tyr Leu
    130                 135                 140

Ser Gly Glu Ala Ser Tyr Glu Thr Ile Ile Gly Val Gln Ser Val Gly
145                 150                 155                 160

Val Gln Gly Ser Ala Lys His Phe Ile Asn Asn Asp Gln Glu His Phe
                165                 170                 175

Arg Glu Ser Ser Ser Asn Val Asp Asp Arg Ala Gln His Glu Ile
            180                 185                 190

Tyr Leu Ala Pro Phe Leu Lys Ser Ala Gln Ala Asn Val Ala Ser Phe
        195                 200                 205

Met Cys Ser Tyr Ser Ala Val Asn Gly Ser Trp Ser Cys Glu Asn Asp
    210                 215                 220

Lys Met Leu Asn Asp Ile Val Lys Gly Glu Trp Gly Tyr Pro Gly Tyr
225                 230                 235                 240

Ile Gln Ser Asp Trp Gly Ala Thr His Ser Thr Leu Ala Val Asn Phe
                245                 250                 255

Gly Leu Asp Met Thr Met Pro Gly Asp Ile Thr Phe Gly Ser Asn Thr
            260                 265                 270

Thr Tyr Phe Gly Gln Ala Leu Ile Asp Ala Val Asn Ser Gly Asp Val
        275                 280                 285

Pro Glu Asp Arg Val Ser Asp Met Ala Leu Arg Ile Leu Ala Ala Trp
    290                 295                 300

Tyr Leu Leu Gly Gln Asp Glu Gly Tyr Pro Glu Thr Asn Ile Trp Ala
305                 310                 315                 320

Trp Asp Leu Asn Asp Pro Arg Asn Leu His Val Asp Val Gln Ala Asp
                325                 330                 335

His Gly Ser Leu Ile Arg Glu Ile Ala Asp Ala Ser Thr Ile Leu Leu
            340                 345                 350

Lys Asn Glu Asn Gly Thr Leu Pro Leu Ser Ala Pro Gly Ser Ile Ala
        355                 360                 365

Ile Ile Gly Asn Gly Ala Gly Asn Asn Ser Gln Gly Ile Asn Gly Cys
    370                 375                 380

Val Asp Arg Ser Cys Asp Asp Gly Val Leu Ala Val Gly Trp Gly Ser
```

-continued

```
385                 390                 395                 400
Gly Thr Ala Glu Phe Pro Tyr Leu Ile Thr Pro Leu Asp Ala Ile Thr
                405                 410                 415

Ala Arg Ala Gln Glu Asp Gly Thr Thr Ile Thr Ser Ser Leu Ser Asp
                420                 425                 430

Ser Asp Thr Ala Arg Ala Ala Gln Ile Ala Ala Ala Ala Asp Val Ala
                435                 440                 445

Ile Val Phe Ile Ser Ser Asp Ser Gly Glu Gly Tyr Leu Thr Val Glu
                450                 455                 460

Gly Asn Ala Gly Asp Arg Asn Asp Leu Leu Ala Trp His Asp Gly Asp
465                 470                 475                 480

Ala Leu Val Gln Ala Val Ala Asp Ala Asn Glu Asn Thr Ile Val Ala
                485                 490                 495

Val Asn Thr Val Gly Ala Ile Ile Thr Glu Ala Trp Ile Glu His Pro
                500                 505                 510

Asn Val Lys Ala Val Val Trp Ser Gly Leu Pro Gly Gln Glu Ala Gly
                515                 520                 525

Asn Ser Val Ala Asp Ile Leu Tyr Gly Ala Tyr Asn Pro Ser Gly Arg
530                 535                 540

Leu Pro Tyr Thr Ile Ala Lys Ser Ala Asp Asp Tyr Pro Ala Gln Val
545                 550                 555                 560

Leu Tyr Glu Ser Ser Ala Gln Val Pro Asp Ile Asp Tyr Ser Glu Gly
                565                 570                 575

Leu Leu Val Asp Tyr Arg His Phe Asp Ala Asn Gly Ile Glu Pro Arg
                580                 585                 590

Tyr Glu Phe Gly Phe Gly Leu Ser Tyr Thr Thr Phe Glu Tyr Asp Asn
                595                 600                 605

Leu Ala Ile Glu Gly Ser Ala Ala Ser Asp Gln Ser Pro Pro Thr Gly
        610                 615                 620

Pro Gly Ser Ser Leu Asp Pro Trp Leu His Glu Pro Val Val Thr Val
625                 630                 635                 640

Thr Phe Thr Val Glu Asn Thr Gly Glu Val Ala Gly His Glu Ile Pro
                645                 650                 655

Gln Leu Tyr Val Thr Phe Pro Glu Ser Ala Gly Ser Ala Pro Leu Asn
                660                 665                 670

Leu Lys Gly Phe Glu Ser Val Phe Val Ala Pro Gly Glu Thr Ala Asp
                675                 680                 685

Val Ser Leu Ser Leu Thr Arg Tyr Asp Leu Ser Ile Trp Asp Val Val
        690                 695                 700

Ser Gln Ser Trp Val Val Pro Ser Gly Asp Ala Thr Ile Ser Ile Gly
705                 710                 715                 720

Ala Ser Ser Arg Asp Ile Arg Leu Thr Gly Thr Val Thr Asn
                725                 730
```